US012630830B2

(12) United States Patent
Chesnut et al.

(10) Patent No.: US 12,630,830 B2
(45) Date of Patent: May 19, 2026

(54) GENE EDITING TOOLS

(71) Applicant: LIFE TECHNOLOGIES CORPORATION, Carlsbad, CA (US)

(72) Inventors: Jonathan Chesnut, Carlsbad, CA (US); Alicia Ihlan, San Diego, CA (US); Robert Potter, San Marcos, CA (US); Youngzee Song, Carlsbad, CA (US)

(73) Assignee: Life Technologies Corporation, Carlsbad, CA (US)

( * ) Notice: Subject to any disclaimer, the term of this patent is extended or adjusted under 35 U.S.C. 154(b) by 846 days.

(21) Appl. No.: 17/931,858

(22) Filed: Sep. 13, 2022

(65) Prior Publication Data

US 2023/0242922 A1 Aug. 3, 2023

Related U.S. Application Data

(60) Provisional application No. 63/340,894, filed on May 11, 2022, provisional application No. 63/253,973, filed on Oct. 8, 2021, provisional application No. 63/243,292, filed on Sep. 13, 2021.

(51) Int. Cl.
*C12N 9/22* (2006.01)
*C12N 15/62* (2006.01)
*C12N 15/90* (2006.01)

(52) U.S. Cl.
CPC ............... *C12N 15/62* (2013.01); *C12N 9/22* (2013.01); *C12N 15/907* (2013.01); *C07K 2319/81* (2013.01)

(58) Field of Classification Search
CPC ...... C12N 9/22; C12N 15/62; C07K 2319/81; C07K 2319/80
See application file for complete search history.

(56) References Cited

FOREIGN PATENT DOCUMENTS

WO WO-2012015938 A2 2/2012
WO WO-2017106528 A2 6/2017
WO WO-2018039448 A1 3/2018
WO WO-2019126589 A1 6/2019
WO WO-2019157324 A1 8/2019
WO WO-2020006132 A1 1/2020

OTHER PUBLICATIONS

Medvecky M., et al., "Hypothetical Protein [Cloacibacillus sp. An23]," DATABASE RefSeq (Online) NCBI; Jun. 1, 2017, XP093009785, retrieved from EBI Database accession No. WP_087364206, 1 page.

PCT/US2022/076352, International Search Report and Written Opinion, Feb. 28, 2023, 15 pages.

*Primary Examiner* — Evelyn Y Pyla
*Assistant Examiner* — Katherine R Small

(57) ABSTRACT

The present disclosure relates to recombinant nucleases, recombinant nucleases operatively linked to nucleic acid binding domains, and methods of making and using them.

14 Claims, 41 Drawing Sheets

Specification includes a Sequence Listing.

% identity

| AN# | | 6 | 67 | 70 | 77 | 90 | 111 | 131 | 140 | 159 | 162 | 197 |
|---|---|---|---|---|---|---|---|---|---|---|---|---|
| Fok1 | | 55 | 52 | 48 | 42 | 43 | 38 | 38 | 38 | 34 | 34 | 22 |
| Clo51 | | 57 | 57 | 52 | 48 | 41 | 49 | 48 | 49 | 39 | 39 | 24 |

% identity

| | | | | | | | |
|---|---|---|---|---|---|---|---|
| Fok1 | | 49 | 50 | 43 | 48 | 38 | 39 |
| Clo51 | | 55 | 53 | 40 | 53 | 49 | 49 |

% identity

| | | | | | | | | | | | | | | |
|---|---|---|---|---|---|---|---|---|---|---|---|---|---|---|
| Fok1 | | 45 | 50 | 70 | 69 | 40 | 55 | 50 | 57 | 42 | 37 | 41 | 45 | 57 |
| Clo51 | | 45 | 52 | 51 | 51 | 48 | 57 | 60 | 57 | 44 | 42 | 46 | 49 | 54 |

| % identity | 65 | 66 | 67 | 68 | 69 | 70 | 71 | 72 | 73 | 74 | 75 | 76 | 77 | 78 | 79 | 80 | 81 | 82 | 83 | 84 | 85 | 86 | 87 | 88 | 89 | 90 |
|---|---|---|---|---|---|---|---|---|---|---|---|---|---|---|---|---|---|---|---|---|---|---|---|---|---|---|
| | | | | | | | | | | | | | | | | | | | | | | | | | Fok1 | |
| Fok1 | 70 | 72 | 52 | 49 | 50 | 48 | 46 | 45 | 45 | 43 | 44 | 44 | 42 | 44 | 43 | 42 | 43 | 43 | 42 | 43 | 41 | 41 | 42 | 40 | 41 | 43 |
| Clo51 | 51 | 54 | 57 | 90 | 60 | 52 | 51 | 49 | 48 | 57 | 48 | 49 | 48 | 46 | 46 | 50 | 44 | 43 | 46 | 41 | 42 | 42 | 49 | 44 | 47 | 41 |

| | | | | | | | | | | | | | | | | | | | | | | | |
|---|---|---|---|---|---|---|---|---|---|---|---|---|---|---|---|---|---|---|---|---|---|---|---|
| 91 | 92 | 93 | 94 | 95 | 96 | 97 | 98 | 99 | 100 | 101 | 102 | 103 | 104 | 105 | 106 | 107 | 108 | 109 | 110 | 111 | 112 | 113 | 114 |
| | | | | | | | | | | | | | | | | | | | | | | | |
| 43 | 40 | 43 | 42 | 43 | 45 | 41 | 42 | 40 | 42 | 45 | 45 | 41 | 45 | 39 | 38 | 39 | 40 | 40 | 39 | 38 | 39 | 40 | 39 |
| 41 | 43 | 42 | 44 | 40 | 45 | 45 | 44 | 38 | 40 | 46 | 45 | 44 | 46 | 46 | 50 | 45 | 48 | 48 | 44 | 49 | 47 | 48 | 40 |

B

C

| %identity | 115 | 116 | 117 | 118 | 119 | 120 | 121 | 122 | 123 | 124 | 125 | 126 | 127 | 128 | 129 | 130 | 131 | 132 | 133 | 134 | 135 | 136 | 137 |
|---|---|---|---|---|---|---|---|---|---|---|---|---|---|---|---|---|---|---|---|---|---|---|---|
| | | | | | | | | | | | | | | | | | | | | | | | |
| Fok1 | 41 | 42 | 40 | 37 | 39 | 41 | 39 | 39 | 38 | 38 | 38 | 37 | 39 | 39 | 39 | 38 | 38 | 38 | 38 | 38 | 38 | 38 | 37 |
| Clo51 | 47 | 41 | 48 | 40 | 49 | 42 | 43 | 48 | 49 | 44 | 49 | 38 | 49 | 48 | 40 | 39 | 48 | 43 | 48 | 43 | 40 | 48 | 41 |

| 138 | 139 | 140 | 141 | 142 | 143 | 144 | 145 | 146 | 147 | 148 | 149 | 150 | 151 | 152 | 153 | 154 | 155 | 156 | 157 | 158 | 159 | 160 | 161 | 162 | 163 | 164 |
|---|---|---|---|---|---|---|---|---|---|---|---|---|---|---|---|---|---|---|---|---|---|---|---|---|---|---|
| | Fok1 | | | | | | | | | | | | | | | | | | | | | | | | | |
| 38 | 38 | 38 | 38 | 38 | 38 | 37 | 36 | 34 | 35 | 37 | 36 | 36 | 38 | 34 | 33 | 32 | 34 | 36 | 33 | 33 | 34 | 29 | 34 | 34 | 35 | 34 |
| 43 | 42 | 49 | 44 | 42 | 42 | 43 | 45 | 34 | 37 | 40 | 39 | 40 | 45 | 37 | 35 | 36 | 46 | 35 | 38 | 38 | 39 | 30 | 40 | 39 | 38 | 39 |

C

D

| % identity | 165 | 166 | 167 | 168 | 169 | 170 | 171 | 172 | 173 | 174 | 175 | 176 | 177 | 178 | 179 | 180 | 181 |
|---|---|---|---|---|---|---|---|---|---|---|---|---|---|---|---|---|---|
| | Fok1 | | | | | | | | | | | | | | | | |
| Fok1 | 34 | 35 | 34 | 35 | 34 | 34 | 35 | 34 | 30 | 31 | 31 | 26 | 27 | 25 | <20 | 26 | 36 |
| Clo51 | 32 | 40 | 40 | 37 | 38 | 39 | 38 | 37 | 36 | 31 | 30 | 25 | 29 | 30 | <20 | 24 | 44 |

| | | | | | | | | | | | | | | | | | | | | | | | | |
|---|---|---|---|---|---|---|---|---|---|---|---|---|---|---|---|---|---|---|---|---|---|---|---|---|
| 182 | 183 | 184 | 185 | 186 | 187 | 188 | 189 | 190 | 191 | 192 | 193 | 194 | 195 | 196 | 197 | 198 | 199 | 200 | 201 | 202 | 203 | 204 | 205 | 206 |
| | | | | | | | | | Clo51 | | | | | | | | | | | | | AN3 | | |
| 40 | 29 | 25 | 25 | 24 | 24 | 29 | 24 | 26 | 30 | 23 | 22 | 23 | 27 | 29 | 22 | 22 | 21 | 21 | 25 | 34 | 32 | 24 | 26 | 23 |
| 40 | 30 | 28 | 31 | 30 | 29 | 31 | 28 | 28 | 30 | 28 | 30 | 27 | 27 | 29 | 24 | 24 | 25 | 25 | 30 | 28 | 25 | 24 | 29 | 27 |

% identity

| AN# | | 6 | 67 | 70 | 77 | 90 | 111 | 131 | 140 | 159 | 162 | 197 |
|---|---|---|---|---|---|---|---|---|---|---|---|---|
| Fok1 | | 55 | 52 | 48 | 42 | 43 | 38 | 38 | 38 | 34 | 34 | 22 |
| Clo51 | | 57 | 57 | 52 | 48 | 41 | 49 | 48 | 49 | 39 | 39 | 24 |

| Donor | AAVS1 AN197 | AAVS1 Fok1 |
|---|---|---|
| Donor S | 92% | 90% |
| Donor M | 95% | 93% |

| AN197 | AN6 | AN159 | Fok1 | Neg. Ctrl |
|---|---|---|---|---|
| 90.6% | 64.0% | 80.3% | 95.9% | 8.19% |

TCR KO (%)

| Donor | Fok1 | AN197 | CRIPSR | Neg. ctrl |
|---|---|---|---|---|
| Donor A | 94.8% | 94.6% | 94.1% | 9.8% |
| Donor B | 92.8% | 91.6% | 88.8% | 20% |

TALEN AN197
+300 ng dsDNA

Non-edited
Tcells

Editing of NK Cells

TALEN AN197

CRISPR/Cas9

Editing of iPSC

GENE EDITING TOOLS

CROSS-REFERENCE TO RELATED APPLICATIONS

This application claims the benefit of priority under 35 U.S.C. § 119(e) to U.S. Provisional Application No. 63/243,292, filed Sep. 13, 2021, U.S. Provisional Application No. 63/253,973, filed Oct. 8, 2021, and U.S. Provisional Application No. 63/340,894, filed May 11, 2022, the entire contents thereof are hereby expressly incorporated by reference as though fully set forth herein.

SEQUENCE LISTING

The instant application contains a Sequence Listing which has been submitted electronically in ST.26 XML format and is hereby incorporated by reference in its entirety. Said XML document, created on Sep. 13, 2022, is named TP109206WO1_SL.XML and is 425,000 bytes in size.

FIELD OF THE INVENTION

The present disclosure relates to compositions including recombinant nucleases, recombinant nucleases operatively linked to nucleic acid binding domains, and methods of making and using them.

BACKGROUND

The recent advances in TALENs or CRISPR-mediated genome editing tools enable researchers to introduce double-strand breaks (DSBs) in mammalian genome efficiently. The DSBs are then mostly repaired by either the non-homologous end joining (NHEJ) pathway or the homology-directed repair (HDR) pathway. In mammalian cells, the NHEJ pathway is predominant and error-prone. However, the HDR pathway allows for precise genome editing via the use of sister chromatids or exogenous DNA molecules.

TALE (transcription activator-like effector) proteins, also referred to herein as "TAL proteins", have a DNA binding domain (DBD) comprising an array of motifs of roughly 30-40 (e.g., 33-35) amino acid repeats that can be modified to bind to a sequence of interest. When a nuclease is fused to the TALE DBD, the resulting fusion protein (called TALEN) can efficiently target and/or process nucleic acids to affect genome editing within a cell.

Transcription activator-like (TAL) effectors represent a class of DNA binding proteins secreted by plant-pathogenic bacteria of the species, such as *Xanthomonas* and *Ralstonia*, via their type III secretion system upon infection of plant cells. Natural TAL effectors specifically have been shown to bind to plant promoter sequences thereby modulating gene expression and activating effector-specific host genes to facilitate bacterial propagation (Römer, P., et al., Plant pathogen recognition mediated by promoter activation of the pepper Bs3 resistance gene. Science 318, 645-648 (2007); Boch, J. & Bonas, U. *Xanthomonas* AvrBs3 family-type III effectors: discovery and function. Annu. Rev. Phytopathol. 48, 419-436 (2010); Kay, S., et al. U. A bacterial effector acts as a plant transcription factor and induces a cell size regulator. Science 318, 648-651 (2007); Kay, S. & Bonas, U. How *Xanthomonas* type III effectors manipulate the host plant. Curr. Opin. Microbiol. 12, 37-43 (2009).) Natural TAL effectors are generally characterized by a central repeat domain and a carboxyl-terminal nuclear localization signal sequence (NLS) and a transcriptional activation domain (AD). The central repeat domain typically consists of a variable amount of between 1.5 and 33.5 amino acid repeats that are usually 33-35 residues in length except for a generally shorter carboxyl-terminal repeat referred to as half-repeat. The repeats are mostly identical but differ in certain hypervariable residues. DNA recognition specificity of TAL effectors is mediated by hypervariable residues typically at positions 12 and 13 of each repeat—the so-called repeat variable diresidue (RVD) wherein each RVD targets a specific nucleotide in a given DNA sequence. Thus, the sequential order of repeats in a TAL protein tends to correlate with a defined linear order of nucleotides in a given DNA sequence. The underlying RVD code of some naturally occurring TAL effectors has been identified, allowing prediction of the sequential repeat order required to bind to a given DNA sequence (Boch, J. et al. Breaking the code of DNA binding specificity of TAL-type III effectors. Science 326, 1509-1512 (2009); Moscou, M. J. & Bogdanove, A. J. A simple cipher governs DNA recognition by TAL effectors. Science 326, 1501 (2009)). Further, TAL effectors generated with new repeat combinations have been shown to bind to target sequences predicted by this code. It has been shown that the target DNA sequence generally start with a 5' thymine base to be recognized by the TAL protein.

The modular structure of TALEs allows for combination of the DNA binding domain with effector molecules such as nucleases. In particular, TAL effector nucleases allow for the development of new genome engineering tools.

There exists a substantial need for efficient systems and techniques for modifying genomes.

SUMMARY

The instant technology generally relates to compositions and methods of uses of alternative nucleases (ANs) described herein.

In one aspect, the present disclosure provides a recombinant protein comprising a cleavage domain, wherein the cleavage domain comprises an amino acid sequence having at least 70%, 75%, 80%, 85%, 90%, 91%, 92%, 93%, 94%, 95%, 96%, 97%, 98%, 99%, or 100% sequence identity with the amino acid sequence of any one of SEQ ID NOs: 3 to 259, 282, and 296-299, or functional fragments thereof. In some embodiments, the cleavage domain comprises an amino acid sequence having at least 70%, 75%, 80%, 85%, 90%, 91%, 92%, 93%, 94%, 95%, 96%, 97%, 98%, 99%, or 100% sequence identity with the amino acid sequence of any one of SEQ ID NO: 200, 282 and 296-299, or a functional fragment thereof. In some embodiments, the recombinant protein further includes a nucleic acid binding domain operatively linked thereto. In embodiments, the nucleic acid binding domain is operatively linked to the recombinant protein via a covalent linkage. In embodiments, the nucleic acid binding domain is operatively linked to the recombinant protein via a non-covalent linkage. In embodiments, the recombinant protein is a fusion protein.

In embodiments wherein the recombinant proteins provided herein include a nucleic acid binding domain operatively linked to the cleavage domain, the nucleic acid binding domain described herein is a zinc finger nucleic acid binding domain. In other embodiments, the nucleic acid binding domain described herein is a transcription activator-like effector (TALE) deoxyribonucleic acid binding domain (DBD). In some embodiments, the TALE DBD is a T-less TALE DBD. In some embodiments, the TALE is derived from *Xanthomonas, Ralstonia*, or *Burkholderia*.

In some embodiments, the nucleic acid binding domain specifically binds to a target nucleic acid sequence in a nucleic acid molecule. In some embodiments, the target nucleic acid includes a first and a second target half site, wherein the nucleic acid binding domain specifically binds to a target half site.

In some embodiments, the cleavage domain cleaves the nucleic acid molecule at a cleavage site within the target nucleic acid sequence when a first and second nucleic acid binding domain (within a first and a second recombinant protein) bind to the first and second target half site, respectively.

In some embodiments, the nucleic acid binding domain comprises one or more repeat units. In some embodiments, each of the one or more repeat units is 30 amino acids to 45 amino acids in length, and wherein each repeat unit recognizes a nucleotide base. In some embodiments, each of the one or more repeat units is 32 amino acids to 40 amino acids in length. In some embodiments, at least one repeat unit is a non-naturally occurring repeat unit.

In some embodiments, the nucleic acid binding domain binds to a DNA target sequence. In some embodiments, the nucleic acid binding domain binds to a DNA target sequence and the cleavage domain cleaves DNA.

In another aspect, the present disclosure provides a nucleic acid encoding the recombinant protein described herein, such as an RNA (e.g., an mRNA, self-replicating RNA, o-RNA, or the like) or a DNA (e.g., a dsDNA within vector, or the like).

In another aspect, the present disclosure provides a vector comprising the nucleic acid described herein.

In another aspect, the present disclosure provides a cell comprising the recombinant protein, the nucleic acid, or the vector described herein.

In some embodiments, the cell is a prokaryotic cell. In some embodiments, the cell is a eukaryotic cell. In some embodiments, the cell is a plant cell, a yeast cell, an insect cell, or a mammalian cell.

In some embodiments, the cell further comprises a donor nucleic acid, such as a donor DNA and/or a donor RNA.

In some embodiments, the cell is genetically modified.

In another aspect, the present disclosure provides a method of modifying a genome comprising contacting a cell with the recombinant protein described herein (e.g., that includes a recombinant nuclease as provided herein operatively linked to a nucleic acid binding domain).

In another aspect, the present disclosure provides a method of genetically altering a cell, comprising contacting the cell with a recombinant protein (including a recombinant nuclease operably linked to a nucleic acid binding domain) described herein under conditions such that the recombinant protein binds a target DNA sequence in the cell (e.g., such that a first target half site and a second target half site are bound by a first DNA binding domain and a second DNA binding domain of first and second recombinant proteins provided herein, respectively). In some embodiments, the first and second target half sites are bound by a homodimer comprising two identical recombinant proteins (e.g., two identical recombinant nucleases operably liked to a nucleic acid binding domain) as described herein. In some embodiments, the first and second target half sites are bound by a heterodimer comprising different first and second recombinant proteins as described herein.

In another aspect, the present disclosure provides a method of modifying a genome comprising contacting a cell with the nucleic acid or the vector described herein.

In another aspect, the present disclosure provides a method of genetically altering a cell, comprising contacting the cell with the nucleic acid or the vector described herein under conditions such that the recombinant protein (e.g., that includes a recombinant nuclease operatively linked to a nucleic acid binding domain) is expressed and binds a target sequence in the cell.

In some embodiments, the nucleic acid or vector comprises RNA. In some embodiments, the nucleic acid or vector comprises DNA.

In another aspect, the present disclosure provides a method for modifying the genome of a cell, the method comprising: introducing into the cell a recombinant protein described herein (e.g., including a recombinant nuclease as provided herein operatively linked to a nucleic acid binding domain), or a nucleic acid encoding a recombinant protein described herein, where the recombinant protein binds to a target site within the cell's genome (e.g., a target site comprising a first and a second target half site, wherein the nucleic acid binding domain of the recombinant protein specifically binds to a target half site sequence), and wherein binding of recombinant proteins as described herein to the target site (e.g., to the first and second target half sites) results in cleavage of the genome of the cell at a cleavage site within the target site.

In some embodiments, the method further comprises introducing into the cell a donor nucleic acid, such that at least a portion of the donor nucleic acid is inserted into the genome of the cell at a cleavage site that has been cleaved by a recombinant protein as described herein.

In some embodiments, two or more recombinant proteins (e.g., each including a recombinant nuclease operably linked to a nucleic acid binding domain) or two or more nucleic acids encoding the two or more recombinant proteins are introduced into the cell, wherein the first and second recombinant proteins form homo and/or heterodimers and/or both homo and heterodimers within the cell. In some embodiments, the introduction of the recombinant proteins or the nucleic acids encoding the recombinant proteins results in cleavage of the genome within first and second target sites.

In some embodiments, modification the genome of a cell comprises double stranded cleavage of a cleavage site within the target nucleic acid.

In some embodiments, the target site is a chromosomal locus.

In some embodiments, the genetic modification comprises a knock-in or insertion of one or more nucleotides. In some embodiments, the genetic modification comprises a knock-out or deletion of one or more nucleotides. In some embodiments, the genetic modification comprises a mutation or alternation of one or more nucleotides.

In another aspect, the present disclosure provides a non-naturally occurring nucleic acid encoding an amino acid sequence having at least 70%, 75%, 80%, 85%, 90%, 91%, 92%, 93%, 94%, 95%, 96%, 97%, 98%, 99%, or 100% sequence identity with the amino acid sequence of any one of SEQ ID NOs: 3 to 259, 282, and 296-299. In some embodiments, the non-naturally occurring nucleic acid encodes an amino acid sequence having at least 80% sequence identity with the amino acid sequence of any one of SEQ ID NOs: 3 to 259, 282, and 296-299, or a functional fragment thereof. In some embodiments, the non-naturally occurring nucleic acid encodes an amino acid sequence having at least 90% sequence identity with the amino acid sequence of any one of SEQ ID NOs: 3 to 259, 282, and 296-299, or a functional fragment thereof. In some embodiments, the non-naturally occurring nucleic acid encodes an amino acid sequence of any one of SEQ ID NOs: 3 to 259, 282, and 296-299, or a functional fragment thereof.

In another aspect, the present disclosure provides a kit comprising a first recombinant protein described herein or a first nucleic acid described herein, and at least one reagent for making or using the recombinant protein.

In some embodiments, the kit includes a vector comprising the nucleic acid described herein.

In some embodiments, the kit further includes a second recombinant protein or a second nucleic acid, as described herein. In some embodiments, the first and second recombinant proteins bind to a first and second target half site, respectively, and form a homodimer. In some embodiments, the first and second recombinant proteins bind to a first and second target half site, respectively, and form a heterodimer.

In some embodiments, the at least one additional reagent is selected from a transfection reagent, a DNA cloning reagent, primers to the first and/or second nucleic acid, a control nucleic acid, a third nucleic acid encoding a reporter, and/or a vector.

In another aspect, the present disclosure provides a method of treating a disease or disorder treatable by genetic modification, the method comprising contacting a cell with a recombinant protein described herein, or a nucleic acid encoding a recombinant proteins described herein, under conditions such that the recombinant protein is expressed and binds to and cleaves a target DNA sequence in the cell at a cleavage site, thereby genetically modifying the cell.

In some embodiments, the method further comprises introducing into the cell a donor DNA, such that at least a portion of the donor DNA is inserted into the genome of the cell at the cleavage site of the target DNA sequence in the cell.

In some embodiments, modification the genome of a cell comprises double stranded cleavage of a target site, e.g., within the cell's genome. In some embodiments, modification of the genome of a cell comprises nicking one strand of a target site, e.g., within the cell's genome In some embodiments, the genetic modification comprises a knock-in. In some embodiments, the genetic modification comprises a knock-out. In some embodiments, the genetic modification comprises a mutation.

In some embodiments, the method further comprises administering the cell to a patient.

In some embodiments, the recombinant protein or nucleic acid is administered to a patient.

In some embodiments, the disease or disorder described herein is cancer, beta-thalassemia, sickle cell disease, hemophilia, blindness, Leber congenital amaurosis, human immune deficiency syndrome (HIV), cystic fibrosis, Duchenne's muscular dystrophy, Huntington's disease, familial hypercholesterolemia, Alzheimer's disease, retinitis pigmentosa, retinal dystrophy, diabetes, autism spectrum disorder, hypertrophic cardiomyopathy, or Tay-Sachs disease.

In certain embodiments, the disease or disorder described herein is a blood cancer. In some embodiments, the disease or disorder described herein is a leukemia, lymphoma, myeloma, or myelodysplasia, including without limitation B-cell leukemias, B-cell acute lymphoblastic leukemia, B-cell lymphomas, B-cell non-Hodgkin's lymphoma, follicular lymphoma, mantle cell lymphoma, T-cell lymphomas, Hodgkin's lymphoma and multiple myeloma. In certain embodiments, the disease or disorder described herein is a solid tumor cancer such as, without limitation, lung cancer, ovarian cancer, cervical cancer, liver cancer, glioma, glioblastoma, prostate cancer, renal cancer pancreatic cancer, gastric cancer, breast cancer, colorectal cancer, melanomas or sarcomas.

In some embodiments, the recombinant protein described herein, when provided to a group of cells (e.g., immune cells, such as T cells), is capable of maintaining or increasing the amount of CD8+ cells in the group of cells. In some embodiments, the recombinant protein described herein, when treated to a group of cells (e.g., immune cells, such as T cells), is capable of maintaining or increasing the ratio of CD8+ vs. CD4+ cells in the group of cells. In some embodiments, the recombinant protein described herein, when provided to a group of cells (e.g., immune cells, such as T cells), is capable of maintaining or increasing the amount of CD8+ cells in the group of cells to at least 110%, 120%, 130%, 140%, 150%, 160%, 170%, 180%, 190%, 200%, 250%, 300%, 350%, 400%, 450%, 500%, or more than the amount of CD8+ cells in the group of naïve cells or cells treated with a CRISPR-based genome editing tool targeting the same locus, respectively.

In another aspect, the present disclosure provides a composition comprising a recombinant protein as described herein for treating a group of cells or a subject to maintain or increase the amount of CD8+ cells and/or the ratio of CD8+ cells vs. CD4+ cells in the group of cells or the subject.

In another aspect, the present disclosure provides a method of maintaining or increasing the amount of CD8+ cells and/or the ratio of CD8+ cells vs. CD4+ cells in a group of cells or a subject, the method comprising treating the group of cells or the subject a composition comprising a recombinant protein as described herein.

BRIEF DESCRIPTION OF THE DRAWINGS

FIG. 12F depicts a positive control (activated T cells, no stain). FIG. 12G is a bar graph showing the efficiency of TCR knock-out (% TCR knock-out) from FIGS. 12A-D.

FIGS. 17A-17D and 17F shows agarose gels depicting a GCD assay at targets TIM3 (FIG. 17A), B2M (FIG. 17B), LAG3 (FIG. 17C), PD-1 (FIG. 17D) and AAVS1 (FIG. 17F). FIG. 17E is a bar graph showing the editing efficiency from FIGS. 17A-D and 17F. All targets showed higher than 80% editing efficiency detected by GCD.

FIG. 24C and FIG. 24D show graphs depicting relative iPSC cell number 24 hour and 96 hours after editing, respectively.

FIG. 26A is a graph depicting the editing efficiencies at AAVS1 and FIG. 26B is a graph depicting the editing efficiencies at B 2M1.

FIG. 27A is a graph depicting the editing efficiencies at TRAC48 and FIG. 27B is a graph depicting the editing efficiencies at C2TA.

DETAILED DESCRIPTION

Figure 1:
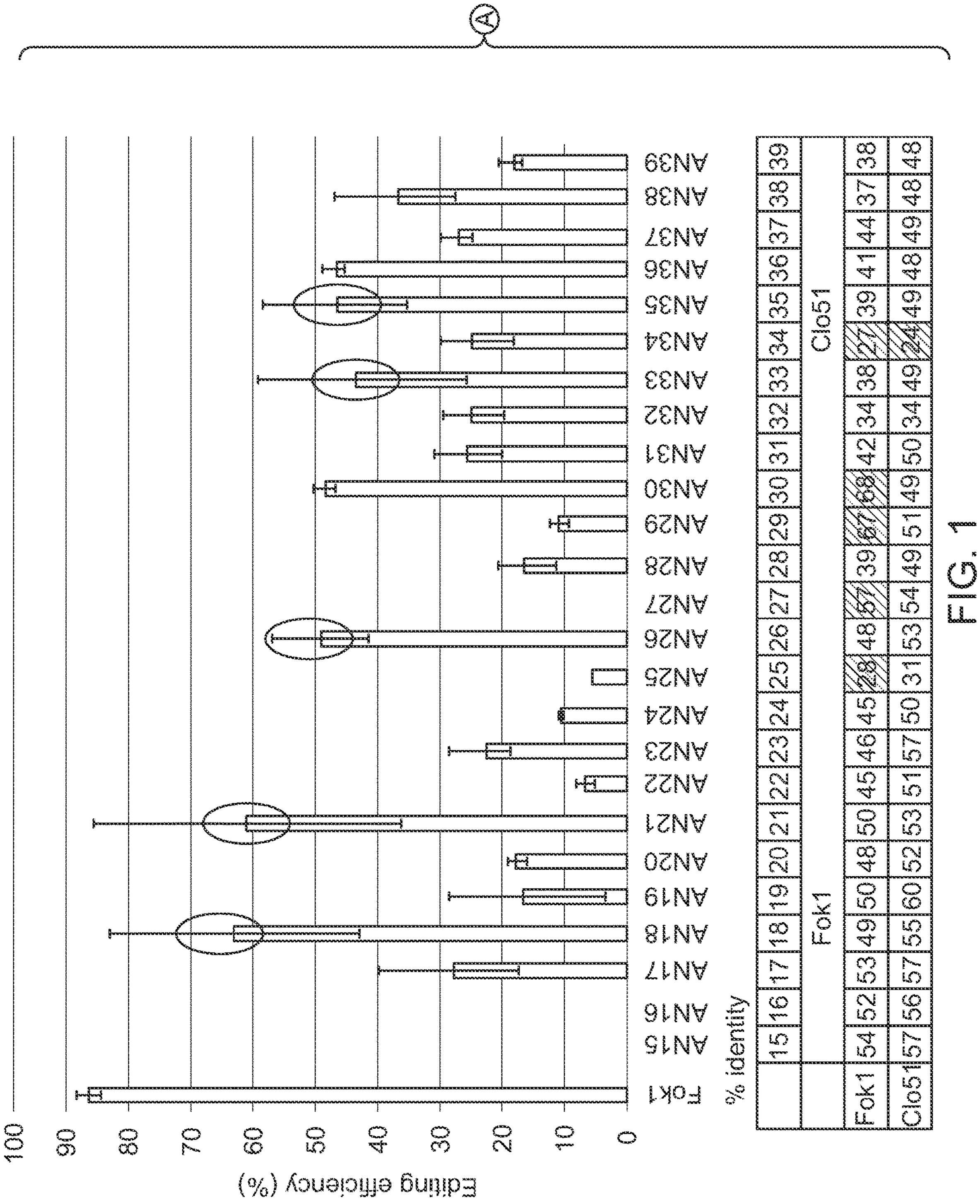
FIG. 1 is a bar graph showing gene editing efficiency of a set of alternative nucleases screened at AAVS1 in HEK293FT cells, as determined by genomic cleavage detection assay (GCD), as described in Example 1 and Example 2. 100 ng of each mRNA (encoding a first and a second recombinant protein) as described herein (200 ng per recombinant protein pair) was used and transfected into cells using the Neon electroporator. Transfections were performed in duplicate and the editing efficiency was averaged. Percent identity of each alternative nuclease to FokI or Clo51 is displayed under the bar graph.
Figure 1:
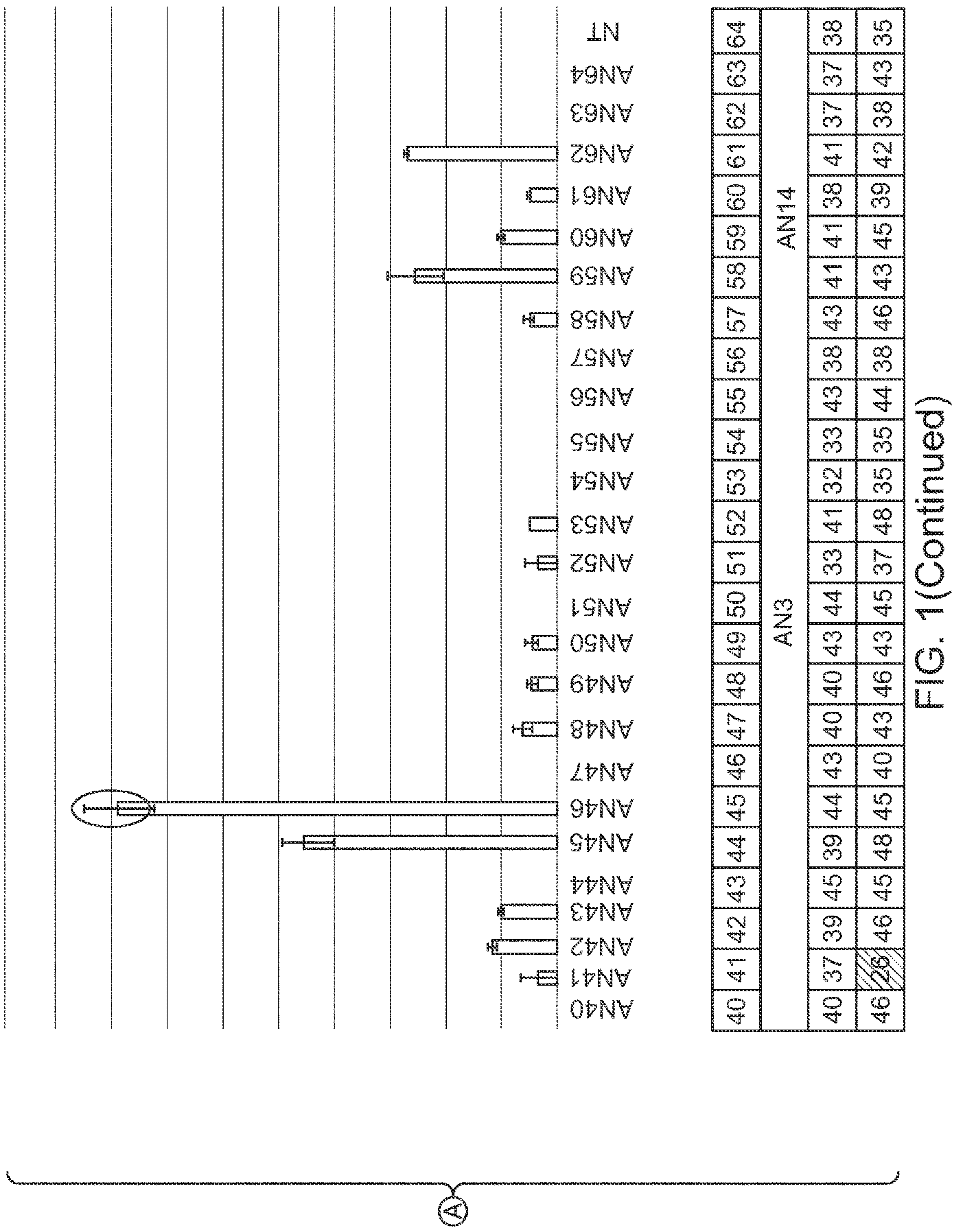

After reading this description it will become apparent to one skilled in the art how to implement the present disclosure in various alternative embodiments and alternative applications. However, all the various embodiments of the present invention will not be described herein. It will be understood that the embodiments presented here are presented by way of an example only, and not limitation. As such, this detailed description of various alternative embodiments should not be construed to limit the scope or breadth of the present disclosure as set forth herein.

Before the present technology is disclosed and described, it is to be understood that the aspects described below are not limited to specific compositions, methods of preparing such compositions, or uses thereof as such may, of course, vary. It is also to be understood that the terminology used herein is for the purpose of describing particular aspects only and is not intended to be limiting.

The detailed description divided into various sections only for the reader's convenience and disclosure found in any section may be combined with that in another section. Titles or subtitles may be used in the specification for the convenience of a reader, which are not intended to influence the scope of the present disclosure.

Definitions

Unless defined otherwise, all technical and scientific terms used herein have the same meaning as commonly understood by one of ordinary skill in the art to which this disclosure belongs. In this specification and in the claims that follow, reference will be made to a number of terms that shall be defined to have the following meanings:

The terminology used herein is for the purpose of describing particular embodiments only and is not intended to be limiting. As used herein, the singular forms "a", "an" and "the" are intended to include the plural forms as well, unless the context clearly indicates otherwise.

"Optional" or "optionally" means that the subsequently described event or circumstance can or cannot occur, and that the description includes instances where the event or circumstance occurs and instances where it does not.

The term "about" when used before a numerical designation, e.g., temperature, time, amount, concentration, and such other, including a range, indicates approximations which may vary by (+) or (−) 10%, 5%, 1%, or any subrange or subvalue there between. Preferably, the term "about" when used with regard to an amount means that the amount may vary by +/−10%.

"Comprising" or "comprises" is intended to mean that the compositions and methods include the recited elements, but not excluding others. "Consisting essentially of" when used to define compositions and methods, shall mean excluding other elements of any essential significance to the combination for the stated purpose. Thus, a composition consisting essentially of the elements as defined herein would not exclude other materials or steps that do not materially affect the basic and novel characteristic(s) of the claimed invention." Consisting of shall mean excluding more than trace elements of other ingredients and substantial method steps. Embodiments defined by each of these transition terms are within the scope of this disclosure.

As used herein "TAL effector" or "TAL effector protein" as provided herein refers to a protein including more than one TAL repeat and capable of binding to nucleic acid in a sequence specific manner. In embodiments, TAL effector protein includes at least six (e.g., at least 8, at least 10, at least 12, at least 15, at least 17, from about 6 to about 25, from about 6 to about 35, from about 8 to about 25, from about 10 to about 25, from about 12 to about 25, from about 8 to about 22, from about 10 to about 22, from about 12 to about 22, from about 6 to about 20, from about 8 to about 20, from about 10 to about 22, from about 12 to about 20, from about 6 to about 18, from about 10 to about 18, from about 12 to about 18, etc.) TAL repeats. In embodiments, the TAL effector protein includes 18 or 24 or 17.5 or 23.5 TAL nucleic acid binding cassettes. In embodiments, the TAL effector protein includes 15.5, 16.5, 17.5, 18.5, 19.5, 20.5, 21.5, 22.5 or 24.5 TAL nucleic acid binding cassettes. A TAL effector protein includes at least one polypeptide region which flanks the region containing the TAL repeats. In embodiments, flanking regions are present at the amino and/or the carboxyl termini of the TAL repeats. As used herein, the term "TALEN" refers to a TAL effector protein associated with a nuclease domain.

As used herein, the term "operatively linked" is used in connection with two or more components, in which the components linked such that both components function normally and allow the possibility that at least one of the components can mediate a function that is exerted upon at least one of the other components. By way of illustration, a polypeptide comprising a nucleic acid binding domain a DNA binding domain) and a cleavage domain are "operatively linked" When the domains retain their nucleic acid and binding functions, respectively, e.g., upon covalent or non-covalent linkage to each other.

As used herein the term "homologous recombination" or "homology-directed repair" (or "HDR") refers to a mechanism of genetic recombination in which two DNA strands comprising similar nucleotide sequences exchange genetic material. Cells use homologous recombination during meiosis, where it serves to rearrange DNA to create an entirely unique set of haploid chromosomes, but also for the repair of damaged DNA, in particular for the repair of double strand breaks. The mechanism of homologous recombination is well known to the skilled person and has been described, for example by Paques and Haber (Paques F, Haber J E.; Microbial. Mal. Biol. Rev. 63:349-404 (1999)). In aspects, homologous recombination is enabled by the presence of said first and said second flanking element being placed upstream (5') and downstream (3'), respectively, of said donor DNA sequence each of which being homologous to a continuous DNA sequence within said target sequence. As used herein the term "HDR-mediated genome editing" refers to genome editing that occurs through a HDR mechanism.

A "functional fragment" of a protein, polypeptide or nucleic acid is a protein, polypeptide or nucleic acid whose sequence is not identical to the full-length protein, polypeptide or nucleic acid, yet retains the same function as the full-length protein, polypeptide or nucleic acid. A functional fragment can possess more, fewer, or the same number of residues as the corresponding native molecule, and/or can contain one or more amino acid or nucleotide substitutions. Methods for determining the function of a nucleic acid (e.g., coding function, ability to hybridize to another nucleic acid) are well-known in the art. Similarly, methods for determining protein function are well-known. For example, the DNA-binding function of a polypeptide can be determined, for example, by filter-binding, electrophoretic mobility-shift, or immunoprecipitation assays. DNA cleavage can be assayed by gel electrophoresis, See Ausubel et al., supra. The ability of a protein to interact with another protein can be determined, for example, by co-immunoprecipitation, two-hybrid assays or complementation, both genetic and biochemical. See, for example, Fields et al. (1989) *Nature* 340:245-246; U.S. Pat. No. 5,585,245 and PCT WO 98/44350.

As used herein, "transcription activator-like effectors" (TALEs) refer to proteins composed of more than one TAL repeat and is capable of binding to nucleic acid in a sequence specific manner. TALEs represent a class of DNA binding proteins secreted by plant-pathogenic bacteria of the species, such as *Xanthomonas* and *Ralstonia*, via their type III secretion system upon infection of plant cells. Natural TALEs specifically have been shown to bind to plant promoter sequences thereby modulating gene expression and activating effector-specific host genes to facilitate bacterial propagation (Römer, P., et al., Science 318:645-648 (2007); Boch, J., et al., *Annu. Rev. Phytopathol.* 48:419-436 (2010); Kay, S., et al., *Science* 3/8:648-651 (2007); Kay, S., et al., Curr. Opin. Microbiol. 12:37-43 (2009)).

Natural TALEs are generally characterized by a central repeat domain and a carboxyl-terminal nuclear localization signal sequence (NLS) and a transcriptional activation domain (AD). The central repeat domain typically consists of a variable amount of between 1.5 and 33.5 amino acid repeats that are usually 33-35 residues in length except for a generally shorter carboxyl-terminal repeat referred to as half-repeat. The repeats are mostly identical but differ in certain hypervariable residues. DNA recognition specificity of TALEs is mediated by hypervariable residues typically at positions 12 and 13 of each repeat—the so-called repeat variable diresidue (RVD) wherein each RVD targets a specific nucleotide in a given DNA sequence. Thus, the sequential order of repeats in a TAL protein tends to correlate with a defined linear order of nucleotides in a given DNA sequence. The underlying RVD code of some naturally occurring TALEs has been identified, allowing prediction of the sequential repeat order required to bind to a given DNA sequence (Boch, J., et al., Science 326:1509-1512 (2009); Moscou, M. J., et al., Science 326:1501 (2009)). Further, TAL effectors generated with new repeat combinations have been shown to bind to target sequences predicted by this code. It has been shown that the target DNA sequence generally start with a 5' thymine base to be recognized by the TAL protein.

The modular structure of TALEs and ZFN's allows for combination of the DNA binding domain with effector molecules such as nucleases. For example, TALE nucleases allow for the development of new genome engineering tools.

TALEs used in some embodiments may generate DS breaks or may have a combined action for the generation of DS breaks. For example, TAL-FokI nuclease fusions can be designed to bind at or near a target locus and form double-stranded nucleic acid cutting activity by the association of two FokI domains.

In some embodiments, TALEs will contain greater than or equal to 6 (e.g., greater than or equal to 8, 10, 12, 15, or 17, or from 6 to 25, 6 to 35, 8 to 25, 10 to 25, 12 to 25, 8 to 22, 10 to 22, 12 to 22, 6 to 20, 8 to 20, 10 to 22, 12 to 20, 6 to 18, 10 to 18, 12 to 18, etc.) TAL repeats. In some embodiments, a TALE may contain 18 or 24 or 17.5 or 23.5 TAL nucleic acid binding cassettes. In additional embodiments, a TALE may contain 15.5, 16.5, 17.5, 18.5, 19.5, 20.5, 21.5, 22.5 or 24.5 TAL nucleic acid binding cassettes. TALEs will generally have at least one polypeptide region which flanks the region containing the TALE repeats. In many embodiments, flanking regions will be present at both the amino and carboxyl termini of the TAL repeats. Exemplary TALEs are set out in U.S. Pat. Publ. No. 2013/0274129 A1, the disclosure of which is incorporated herein by reference, and may be modified forms on naturally occurring proteins found in bacteria of the genera *Burkholderia*, Xanthamonas and *Ralstonia.*

In some embodiments, the recombinant proteins provided herein will contain nuclear localization signals (NLS) that allow them to be transported to the nucleus. For example, in some embodiments, the recombinant proteins include 1, 2, 3, 4, or more NLS's. In some embodiments, the recombinant proteins include one or more NLS's at the amino-terminus of the protein. In some embodiments, the recombinant proteins include one or more NLS's at the carboxy-terminus of the protein. In some embodiments, the recombinant proteins include one or more NLS's at the amino terminus of the protein, and one or more NLS's at the carboxy terminus of the protein. In some embodiments, the recombinant proteins include an NLS that is internal (i.e., not at the amino or carboxy-terminus) of the protein. Preferably, the recombinant fusion proteins provided herein include an NLS between a nucleic acid binding domain and cleavage domain, and a NLS at the carboxy-terminus of the cleavage domain. In some embodiments, the recombinant fusion proteins provided herein include an NLS between a nucleic acid binding domain and cleavage domain, an NLS at the amino-terminus of the recombinant protein (e.g., at the amino terminus of the nucleic acid binding domain) and an NLS at the carboxy-terminus of the recombinant protein (e.g., at the carboxy terminus of the cleavage domain).

In some embodiments, the recombinant proteins provided herein are operatively linked to a TALE DBD. The TALE DBD can include one or more non-canonical RVDs. Non-canonical RVD's useful in the recombinant proteins provided herein include, but are not limited to, those described in U.S. Pat. No. 8,586,526 and, U.S. Pat. No. 9,522,938. U.S. Patent Publication 20130196373, and the like.

The terms "polypeptide," "peptide" and "protein" are used interchangeably herein to refer to a polymer of amino acid residues, wherein the polymer may in embodiments be conjugated to a moiety that does not consist of amino acids. The terms apply to amino acid polymers in which one or more amino acid residue is an artificial chemical mimetic of a corresponding naturally occurring amino acid, as well as to naturally occurring amino acid polymers and non-naturally occurring amino acid polymers.

As may be used herein, the terms "nucleic acid," "nucleic acid molecule," "nucleic acid oligomer," "oligonucleotide," "nucleic acid sequence," "nucleic acid fragment" and "polynucleotide" are used interchangeably and are intended to include, but are not limited to, a polymeric form of nucleotides covalently linked together that may have various lengths, either deoxyribonucleotides or ribonucleotides, or analogs, derivatives or modifications thereof. Different polynucleotides may have different three-dimensional structures, and may perform various functions, known or unknown. Non-limiting examples of polynucleotides include a gene, a gene fragment, an exon, an intron, intergenic DNA (including, without limitation, heterochromatic DNA), messenger RNA (mRNA), transfer RNA, ribosomal RNA, a ribozyme, cDNA, a recombinant polynucleotide, a branched polynucleotide, a plasmid, a vector, isolated DNA of a sequence, isolated RNA of a sequence, a nucleic acid probe, and a primer. Polynucleotides useful in the methods of the disclosure may comprise natural nucleic acid sequences and variants thereof, artificial nucleic acid sequences, or a combination of such sequences.

A polynucleotide is typically composed of a specific sequence of four nucleotide bases: adenine (A); cytosine (C); guanine (G); and thymine (T) (uracil (U) for thymine (T) when the polynucleotide is RNA). Thus, the term "polynucleotide sequence" is the alphabetical representation of a polynucleotide molecule; alternatively, the term may be applied to the polynucleotide molecule itself. This alphabetical representation can be input into databases in a computer having a central processing unit and used for bioinformatics applications such as functional genomics and homology searching. Polynucleotides may optionally include one or more non-standard nucleotide(s), nucleotide analog(s) and/or modified nucleotides.

"Conservatively modified variants" applies to both amino acid and nucleic acid sequences. With respect to particular nucleic acid sequences, "conservatively modified variants" refers to those nucleic acids that encode identical or essentially identical amino acid sequences. Because of the degeneracy of the genetic code, a number of nucleic acid sequences will encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the disclosure.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K);

5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

"Percentage of sequence identity" is determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site www.ncbi.nlm.nih.gov/BLAST/or the like). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length.

The term "functional fragment" in reference to a protein, polypeptide, or nucleic acid means a protein polypeptide or nucleic acid whose sequence is not identical to the full-length protein, polypeptide or nucleic acid, yet retains (at least partially), the same function as the full-length protein, polypeptide or nucleic acid. Function can be determined by well known methods. For example, nuclease activity can be determined by a genomic cleavage detection assay as described herein. The nucleic acid binding function of a polypeptide can be determined by art-accepted methods such as mobility shift assays, immunoprecipitation assays, or the like.

The term "expression" of a polypeptide includes any step involved in the production of the polypeptide including, but not limited to, transcription, post-transcriptional modification, translation, post-translational modification, and secretion. Expression can be detected using conventional techniques for detecting protein (e.g., ELISA, Western blotting, flow cytometry, immunofluorescence, immunohistochemistry, etc.).

A "vector" as used herein is a nucleic acid molecule that can be used as a vehicle to transfer genetic material into a cell. A vector can be a plasmid, a virus or bacteriophage, a cosmid or an artificial chromosome such as, e.g., yeast artificial chromosomes (YACs), bacterial artificial chromosomes (BAC) or other sequences which are able to replicate or be replicated in vitro or in a host cell, or to convey a desired nucleic acid segment to a desired location within a host cell. In embodiments a vector refers to a DNA molecule harboring at least one origin of replication, a multiple cloning site (MCS) and one or more selection markers. A vector is typically composed of a backbone region and at least one insert or transgene region or a region designed for insertion of a DNA fragment or transgene such as an MCS. The backbone region often contains an origin of replication for propagation in at least one host and one or more selection markers. A vector can have one or more restriction endonuclease recognition sites (e.g., two, three, four, five, seven, ten, etc.) at which the sequences can be cut in a determinable fashion without loss of an essential biological function of the vector, and into which a nucleic acid fragment can be spliced in order to bring about its replication and cloning. Vectors can further provide primer sites (e.g., for PCR), transcriptional and/or translational initiation and/or regulation sites, recombinational signals, replicons, selectable markers, etc. Clearly, methods of inserting a desired nucleic acid fragment which do not require the use of recombination, transpositions or restriction enzymes (such as, but not limited to, uracil N glycosylase (UDG) cloning of PCR fragments (U.S. Pat. Nos. 5,334,575 and 5,888,795, both of which are entirely incorporated herein by reference), T:A cloning, and the like) can also be applied to clone a fragment into a cloning vector to be used according to the present technology. In embodiments, a vector contains additional features. Such additional features may include natural or synthetic promoters, genetic markers, antibiotic resistance cassettes or selection markers (e.g., toxins such as ccdB or tse2), epitopes or tags for detection, manipulation or purification (e.g., V5 epitope, c-myc, hemagglutinin (HA), FLAG™ polyhistidine (His), glutathione-S-transferase (GST), maltose binding protein (MBP)), scaffold attachment regions (SARs) or reporter genes (e.g., green fluorescent protein (GFP), red fluorescence protein (RFP), luciferase, β-galactosidase etc.). In embodiments, vectors are used to isolate, multiply or express inserted DNA fragments in a target host. A vector can for example be a cloning vector, an expression vector, a functional vector, a capture vector, a co-expression vector (for expression of more than one open reading frame), a viral vector or an episome (i.e., a nucleic acid capable of extrachromosomal replication) etc.

A "cloning vector" as used herein includes any vector that can be used to delete, insert, replace or assemble one or more nucleic acid molecules. In embodiments a cloning vector may contain a counter selectable marker gene (such as, e.g., ccdB or tse2) that can be removed or replaced by another transgene or DNA fragment. In embodiments a cloning vector may be referred to as donor vector, entry vector, shuttle vector, destination vector, target vector, functional vector or capture vector. Cloning vectors typically contain a series of unique restriction enzyme cleavage sites (e.g., type II or type IIS) for removal, insertion or replacement of DNA fragments. Alternatively, DNA fragments can be replaced or inserted by TOPO® Cloning or recombination as, e.g., employed in the GATEWAY® Cloning System offered by Invitrogen/Life Technologies (Carlsbad, CA). A cloning vector that can be used for expression of a transgene in a target host may also be referred to as expression vector. In embodiments a cloning vector is engineered to obtain the modular polypeptides as described herein.

An "expression vector" is designed for expression of a transgene and generally harbors at least one promoter sequence that drives expression of the transgene. Expression as used herein refers to transcription of a transgene or transcription and translation of an open reading frame and can occur in a cell-free environment such as a cell-free expression system or in a host cell. In embodiments expression of an open reading frame or a gene results in the production of a polypeptide or protein. An expression vector is typically designed to contain one or more regulatory sequences such as enhancer, promoter and terminator regions that control expression of the inserted transgene. Suitable expression vectors include, without limitation, plasmids and viral vectors. Vectors and expression systems for various applications are available from commercial suppliers such as Novagen (Madison, WI), Clontech (Palo Alto, CA), Stratagene (La Jolla, CA), and Life Technologies Corp. (Carlsbad, CA). In embodiments an expression vector is engineered for expression of one or more modular proteins as described herein.

A "viral vector" generally relates to a genetically-engineered noninfectious virus containing modified viral nucleic acid sequences. In embodiments, a viral vector contains at least one viral promoter and is designed for insertion of one or more transgenes or DNA fragments. In embodiments a viral vector is delivered to a target host together with a helper virus providing packaging or other functions. In embodiments viral vectors are used to stably integrate transgenes into the genome of a host cell. A viral vector may be used for delivery and/or expression of transgenes.

Viral vectors may be derived from bacteriophage, baculoviruses, tobacco mosaic virus, vaccinia virus, retrovirus (avian leukosis-sarcoma, mammalian C-type, B-type viruses, D type viruses, HTLV-BLV group, lentivirus, spumavirus), adenovirus, parvovirus (e.g., adenoassociated viruses), coronavirus, negative strand RNA viruses such as orthomyxovirus (e.g., influenza virus) or sendai virus, rhabdovirus (e.g., rabies and vesicular stomatitis virus), paramyxovirus (e.g., measles and Sendai), positive strand RNA viruses such as picornavirus and alphavirus (such as Semliki Forest virus), and double-stranded DNA viruses including adenovirus, herpes virus (e.g., Herpes Simplex virus types 1 and 2, Epstein-Barr virus, cytomegalovirus), and poxvirus (e.g., vaccinia, fowlpox and canarypox). Other viruses include without limitation Norwalk virus, togavirus, flavivirus, reoviruses, papovavirus, hepadnavirus, and hepatitis virus. For example common viral vectors used for gene delivery are lentiviral vectors based on their relatively large packaging capacity, reduced immunogenicity and their ability to stably transduce with high efficiency a large range of different cell types. Such lentiviral vectors can be "integrative" (i.e., able to integrate into the genome of a target cell) or "non-integrative" (i.e., not integrated into a target cell genome). Expression vectors containing regulatory elements from eukaryotic viruses are often used in eukaryotic expression vectors, e.g., SV40 vectors, papilloma virus vectors, and vectors derived from Epstein-Barr virus. Other exemplary eukaryotic vectors include pMSG, pAV009/A+, pMTO10/A+, pMAMneo-5, baculovirus pDSVE, and any other vector allowing expression of proteins under the direction of the SV40 early promoter, SV40 late promoter, metallothionein promoter, murine mammary tumor virus promoter, Rous sarcoma virus promoter, polyhedrin promoter, or other promoters shown effective for expression in eukaryotic cells.

A "promoter" as used herein is a transcription regulatory sequence which is capable of directing transcription of a nucleic acid segment (e.g., a transgene comprising, for example, an open reading frame) when operably connected thereto. A promoter is a nucleotide sequence which is positioned upstream of the transcription start site (generally near the initiation site for RNA polymerase II). A promoter typically comprises at least a core, or basal motif, and may include or cooperate with at least one or more control elements such as upstream elements (e.g., upstream activation regions (UARs)) or other regulatory sequences or synthetic elements. A basal motif constitutes the minimal sequence necessary for assembly of a transcription complex required for transcription initiation. In embodiments, such minimal sequence includes a "TATA box" element that may be located between about 15 and about 35 nucleotides upstream from the site of transcription initiation. Basal promoters also may include a "CCAAT box" element (typically the sequence CCAAT) and/or a GGGCG sequence, which can be located between about 40 and about 200 nucleotides, typically about 60 to about 120 nucleotides, upstream from the transcription start site. The transcription of an adjacent nucleic acid segment is initiated at the promoter region. A repressible promoter's rate of transcription decreases in response to a repressing agent. An inducible promoter's rate of transcription increases in response to an inducing agent. A constitutive promoter's rate of transcription is not specifically regulated, though it can vary under the influence of general metabolic conditions.

The choice of a promoter to be included in an expression vector depends upon several factors, including without limitation efficiency, selectability, inducibility, desired expression level, and cell or tissue specificity. For example, tissue-, organ- and cell-specific promoters that confer transcription only or predominantly in a particular tissue, organ, and cell type, respectively, can be used. In embodiments, promoters that are essentially specific to seeds ("seed-preferential promoters") can be useful. In embodiments, constitutive promoters are used that can promote transcription in most or all tissues of a specific species. Other classes of promoters include, but are not limited to, inducible promoters, such as promoters that confer transcription in response to external stimuli such as chemical agents, developmental stimuli, or environmental stimuli. Inducible promoters may be induced by pathogens or stress like cold, heat, UV light, or high ionic concentrations or may be induced by chemicals. Examples of inducible promoters are the eukaryotic metallothionein promoter, which is induced by increased levels of heavy metals; the prokaryotic lacL promoter, which is induced in response to isopropyl-β-D-thiogalacto-pyranoside (IPTG); and eukaryotic heat shock promoters, which are induced by raised temperature. Numerous additional bacterial and eukaryotic promoters suitable for use with the technology described herein are known in the art and described in, e.g., in Sambrook et al., Molecular Cloning, A Laboratory Manual (2nd ed. 1989; 3rd ed., 2001); Kriegler, Gene Transfer and Expression: A Laboratory Manual (1990); and Ausubel et al., Current Protocols in Molecular Biology. Bacterial expression systems for expressing the ZFP are available in, e.g., *E. coli, Bacillus* sp., and *Salmonella* (Palva et al., *Secretion of interferon* by *Bacillus subtilis*. Gene 22:229-235 (1983)). Kits for such expression systems are commercially available. Eukaryotic expression systems for mammalian cells, yeast, and insect cells are well known by those of skill in the art and are also commercially available.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

In one aspect, the present disclosure provides a recombinant nuclease comprising a nucleic acid binding domain and a cleavage domain, wherein the cleavage domain comprises an amino acid sequence having at least 70%, 75%, 80%, 85%, 90%, 91%, 92%, 93%, 94%, 95%, 96%, 97%, 98%, 99%, or 100% sequence identity with the amino acid sequence of any one of SEQ ID NOs: 3 to 259, 282, and 296-299, or a functional fragment thereof. In some embodiments, the cleavage domain comprises an amino acid sequence having at least 80% sequence identity with the amino acid sequence of any one of SEQ ID NOs: 3 to 259, 282, and 296-299, or a functional fragment thereof. In some embodiments, the cleavage domain comprises an amino acid sequence having at least 90% sequence identity with the amino acid sequence of any one of SEQ ID NOs: 3 to 259, 282, and 296-299, or a functional fragment thereof. In some embodiments, the cleavage domain comprises an amino acid sequence having at least 95% sequence identity with the amino acid sequence of any one of SEQ ID NOs: 3 to 259, 282, and 296-299, or a functional fragment thereof. In some embodiments, the cleavage domain comprises an amino acid sequence having at least 96% sequence identity with the amino acid sequence of any one of SEQ ID NOs: 3 to 259, 282, and 296-299, or a functional fragment thereof. In some embodiments, the cleavage domain comprises an amino acid sequence having at least 97% sequence identity with the amino acid sequence of any one of SEQ ID NOs: 3 to 259, 282, and 296-299, or a functional fragment thereof. In some embodiments, the cleavage domain comprises an amino acid sequence having at least 98% sequence identity with the amino acid sequence of any one of SEQ ID NOs: 3 to 259, 282, and 296-299, or a functional fragment thereof. In some embodiments, the cleavage domain comprises an amino acid sequence having at least 99% sequence identity with the amino acid sequence of any one of SEQ ID NOs: 3 to 259, 282, and 296-299, or a functional fragment thereof. In some embodiments, the cleavage domain comprises an amino acid sequence of any one of SEQ ID NOs: 3 to 259, 282, and 296-299, or a functional fragment thereof.

In some embodiments, the cleavage domain comprises an amino acid sequence having at least 70%, 75%, 80%, 85%, 90%, 91%, 92%, 93%, 94%, 95%, 96%, 97%, 98%, 99%, or 100% sequence identity with the amino acid sequence of any one of SEQ ID NOs: 200, 282, and 296-299, or a functional fragment thereof. In some embodiments, the cleavage domain comprises an amino acid sequence having at least 80% sequence identity with the amino acid sequence of any one of SEQ ID NOs: 200, 282, and 296-299, or a functional fragment thereof. In some embodiments, the cleavage domain comprises an amino acid sequence having at least 90% sequence identity with the amino acid sequence of any one of SEQ ID NOs: 200, 282 and 296-299, or a functional fragment thereof. In some embodiments, the cleavage domain comprises an amino acid sequence having at least 95% sequence identity with the amino acid sequence of any one of SEQ ID NOs: 200, 282, and 296-299, or a functional fragment thereof. In some embodiments, the cleavage domain comprises an amino acid sequence having at least 96% sequence identity with the amino acid sequence of any one of SEQ ID NOs: 200, 282, and 296-299, or a functional fragment thereof. In some embodiments, the cleavage domain comprises an amino acid sequence having at least 97% sequence identity with the amino acid sequence of any one of SEQ ID NOs: 200, 282, and 296-299, or a functional fragment thereof. In some embodiments, the cleavage domain comprises an amino acid sequence having at least 98% sequence identity with the amino acid sequence of any one of SEQ ID NOs: 200, 282, and 296-299, or a functional fragment thereof. In some embodiments, the cleavage domain comprises an amino acid sequence having at least 99% sequence identity with the amino acid sequence of any one of SEQ ID NOs: 200, 282 and 296-299, or a functional fragment thereof. In some embodiments, the cleavage domain comprises an amino acid sequence of any one of SEQ ID NOs: 200, 282, and 296-299, or a functional fragment thereof.

In some embodiments, the cleavage domain comprises an amino acid sequence having at least 70%, 75%, 80%, 85%, 90%, 91%, 92%, 93%, 94%, 95%, 96%, 97%, 98%, 99%, or 100% sequence identity with the amino acid sequence of any one of AN18 (SEQ ID NO: 19), AN21 (SEQ ID NO: 22), AN26 (SEQ ID NO: 27), AN32 (SEQ ID NO: 33), AN33 (SEQ ID NO: 34), AN35 (SEQ ID NO: 36), and AN46 (SEQ ID NO: 47), or functional fragments thereof. In some embodiments, the cleavage domain comprises an amino acid sequence having at least 80% sequence identity with the amino acid sequence of any one of SEQ ID NOs: 19, 22, 27, 33, 34, 36, and 47 (AN18, 21, 26, 32, 33, 35, and 46, respectively), or functional fragments thereof. In some embodiments, the cleavage domain comprises an amino acid sequence having at least 90% sequence identity with the amino acid sequence of any one of SEQ ID NOs: 19, 22, 27, 33, 34, 36, and 47 (AN18, 21, 26, 32, 33, 35, and 46, respectively), or functional fragments thereof. In some embodiments, the cleavage domain comprises an amino acid sequence having at least 95% sequence identity with the amino acid sequence of any one of SEQ ID NOs: 19, 22, 27, 33, 34, 36, and 47 (AN18, 21, 26, 32, 33, 35, and 46, respectively), or functional fragments thereof. In some embodiments, the cleavage domain comprises an amino acid sequence of any one of SEQ ID NOs: 19, 22, 27, 33, 34, 36, and 47 (AN18, 21, 26, 32, 33, 35, and 46, respectively), or functional fragments thereof.

In some embodiments, the cleavage domain comprises an amino acid sequence having at least 70%, 75%, 80%, 85%, 90%, 91%, 92%, 93%, 94%, 95%, 96%, 97%, 98%, 99%, or 100% sequence identity with the amino acid sequence of any one of AN6 (SEQ ID NO: 7), AN67 (SEQ ID NO: 70), AN70 (SEQ ID NO: 73), AN77 (SEQ ID NO: 80), AN90 (SEQ ID NO: 93), AN111 (SEQ ID NO: 114), AN131 (SEQ ID NO: 134), AN140 (SEQ ID NO: 143), AN159 (SEQ ID NO: 162), AN162 (SEQ ID NO:165), and AN197 (SEQ ID NO:200), or functional fragments thereof. In some embodiments, the cleavage domain comprises an amino acid sequence having at least 80% sequence identity with the amino acid sequence of any one of SEQ ID NOs: 7, 70, 73, 80, 93, 114, 134, 143, 162, 165, and 200 (AN6, 67, 70, 77, 90, 111, 131, 140, 159, 162, and 197, respectively), or functional fragments thereof. In some embodiments, the cleavage domain comprises an amino acid sequence having at least 90% sequence identity with the amino acid sequence of any one of SEQ ID NOs: 7, 70, 73, 80, 93, 114, 134, 143, 162, 165, and 200 (AN6, 67, 70, 77, 90, 111, 131, 140, 159, 162, and 197, respectively), or functional fragments thereof. In some embodiments, the cleavage domain comprises an amino acid sequence having at least 95% sequence identity with the amino acid sequence of any one of SEQ ID NOs: 7, 70, 73, 80, 93, 114, 134, 143, 162, 165, and 200 (AN6, 67, 70, 77, 90, 111, 131, 140, 159, 162, and 197, respectively), or functional fragments thereof. In some embodiments, the cleavage domain comprises an amino acid sequence of any one of SEQ ID NOs: 7, 70, 73, 80, 93, 114, 134, 143, 162, 165, and 200 (AN6, 67, 70, 77, 90, 111, 131, 140, 159, 162, and 197, respectively), or functional fragments thereof.

In some embodiments, the cleavage domain comprises an amino acid sequence having at least 70%, 75%, 80%, 85%, 90%, 91%, 92%, 93%, 94%, 95%, 96%, 97%, 98%, 99%, or 100% sequence identity with the amino acid sequence of any one of AN3 (SEQ ID NO: 4), AN12 (SEQ ID NO: 13), AN30 (SEQ ID NO: 31), AN36 (SEQ ID NO: 37), AN45 (SEQ ID NO: 46), AN65 (SEQ ID NO: 68), AN68 (SEQ ID NO: 71), AN80 (SEQ ID NO: 83), AN106 (SEQ ID NO: 109), AN108 (SEQ ID NO: 111) and AN155 (SEQ ID NO:158), or functional fragments thereof. In some embodiments, the cleavage domain comprises an amino acid sequence having at least 80% sequence identity with the amino acid sequence of any one of SEQ ID NOs: 4, 13, 31, 37, 46, 68, 71, 83, 109, 111, and 158 (AN3, 12, 30, 36, 45, 65, 68, 80, 106, 108, and 155, respectively), or functional fragments thereof. In some embodiments, the cleavage domain comprises an amino acid sequence having at least 90% sequence identity with the amino acid sequence of any one of SEQ ID NOs: 4, 13, 31, 37, 46, 68, 71, 83, 109, 111, and 158 (AN3, 12, 30, 36, 45, 65, 68, 80, 106, 108, and 155, respectively), or functional fragments thereof. In some embodiments, the cleavage domain comprises an amino acid sequence having at least 95% sequence identity with the amino acid sequence of any one of SEQ ID NOs: 4, 13, 31, 37, 46, 68, 71, 83, 109, 111, and 158 (AN3, 12, 30, 36, 45, 65, 68, 80, 106, 108, and 155, respectively), or functional fragments thereof. In some embodiments, the cleavage domain comprises an amino acid sequence of any one of SEQ ID NOs: 4, 13, 31, 37, 46, 68, 71, 83, 109, 111, and 158 (AN3, 12, 30, 36, 45, 65, 68, 80, 106, 108, and 155, respectively), or functional fragments thereof.

The recombinant nuclease described herein can be operatively linked (e.g., covalently or non-covalently linked) to a nucleic acid binding domain. In some embodiments, the recombinant nucleases are fusion proteins, that include a cleavage domain as described herein, and a DNA binding domain. In some embodiments, fusion proteins provided herein include a linker, e.g., 1, 2, 3, 4, 5, 6, 7, 8, 9, 10, or more, amino acids, between the nuclease domain and the nucleic acid binding domain.

In some embodiments, the recombinant nucleases provided herein include a nucleic acid binding domain operatively linked to the N-terminus of nuclease domain. In some embodiments, the recombinant nucleases provided herein include a nucleic acid binding domain operatively linked to the C-terminus of the nuclease domain.

In addition to fusion proteins, which provide a covalent linkage of two domains (e.g., a recombinant nuclease provided herein and a nucleic acid binding domain) via peptide bonds between amino acids, other means for covalently linking, e.g., a nucleic acid binding domain to the amino- or carboxy-terminus of a nuclease provided herein include, but are not limited to "click chemistry" (see, e.g., U.S. Pat. Nos. 7,375,234 and 7,070,941, and US Patent Publication No. 2013/0046084, the entire disclosures of which are incorporated herein by reference). A number of click reactions can be used to link polypeptide segments (e.g., Cu-azide-alkyne, strain-promoted-azide-alkyne, staudinger ligation, tetrazine ligation, photo-induced tetrazole-alkene, thiol-ene, NHS esters, epoxides, isocyanates, and aldehyde—aminooxy). Ligation of polypeptide molecules using a click chemistry reaction is advantageous because click chemistry reactions are fast, modular, efficient, often do not produce toxic waste products, can be done with water as a solvent, and can be set up to be stereospecific.

Other means to operatively link the recombinant nucleases provided herein to nucleic acid binding domains include the use of polyethylene glycol cross-linkers. Further, cross-linkers may be cleavable or non-cleavable.

One category of cross-linker that may be used to connect recombinant nucleases provided herein to a nucleic acid binding domain is amine-to-sulfhydryl heterobifunctional protein cross-linkers. These may be used to conjugate two polypeptides between primary amine (lysine) and sulfhydryl (cysteine) groups. Further, cross-linkers of this type are available with different lengths and types of spacer arms, such as NHS-haloacetyl, NHS-maleimide, and NHS-pyridyldithiol cross-linkers.

Exemplary cross-linkers that are useful in operatively linking the recombinant cleavage domains and nucleic acid binding domains provided herein are set out herein are shown in Table 1.

TABLE 1

Exemplary Cross-Linkers

| Cross-Linker Type | Chemical Structure | Spacer Arm Length (Angstroms) | Thermo Fisher Scientific, cat. no |
|---|---|---|---|
| NHS-Haloacetyl | 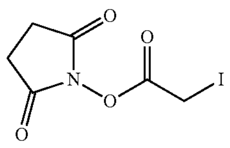 [SMILES: O=C(CI)ON1C(=O)CCC1=O] | 1.5 | 22349 |
| | 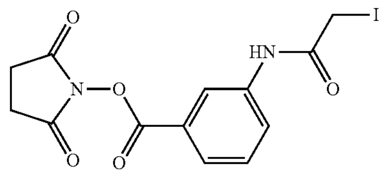 [SMILES: O=C(CI)Nc1cccc(C(=O)ON2C(=O)CCC2=O)c1] | 10.6 | 22327 |

TABLE 1-continued

| Exemplary Cross-Linkers | | | |
|---|---|---|---|
| Cross-Linker Type | Chemical Structure | Spacer Arm Length (Angstroms) | Thermo Fisher Scientific, cat. no |
| NHS-Maleimide | 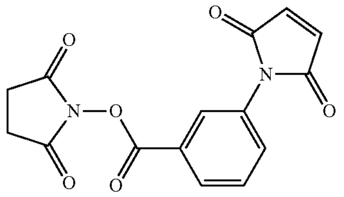 [SMILES: O=C(ON1C(=O)CCC1=O)c1cccc(N2C(=O)C=CC2=O)c1] | 7.3 | 22312 |
| NHS-Pyridyldithiol | 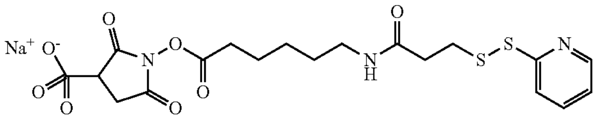 | 15.6 | 21650 |

Alternatively, the recombinant nucleases provided herein can be operatively linked to a nucleic acid binding domain via a non-covalent association. In some embodiments, each of the nuclease domain and the nucleic acid binding domain can include a "linkage domain," that wherein the linkage domain of the nuclease and the linkage domain of the nucleic acid binding domain together form a "binding pair" capable of non-covalent binding with each other. Several "binding pairs" can be used to operatively link the recombinant nucleases and nucleic acid binding domains provided herein, including but not limited to a leucine zipper (e.g., Fos/Jun), streptavidin/strep-tag, nanobody/peptide, an affinity clamp, or the like. The binding pair may also be designed heterodimer domains (DHDs), such as DHD65a/b and DHD154a/b. A number of DHDs are set out in Chen et al., "*Programmable design of orthological protein heterodimers", Nature* 163:106-110 (2019).

In some embodiments, the recombinant nucleases or the recombinant nucleases operatively linked to a nucleic acid binding domain are modified by one or more polyethylene glycan moieties. In some embodiments, pegylation of the isolated recombinant nuclease proteins or recombinant nuclease-nucleic acid binding domain proteins improves stability during delivery of the proteins to a cell. In some embodiments, pegylation of the isolated recombinant nuclease proteins or recombinant nuclease-nucleic acid binding domain proteins increases genome editing after delivery of the proteins to a cell.

In some embodiments, the pegylation is at the N-terminus of the recombinant nuclease protein or of the recombinant nuclease-nucleic acid binding domain proteins. In other embodiments, pegylation is at the C-terminus of the recombinant nuclease protein or of the recombinant nuclease-nucleic acid binding domain proteins. In some embodiments, one or more PEG moieties is attached between the N- and C-termini of the recombinant nuclease protein. In some embodiments, one or more PEG moieties is attached between the N- and C-termini of the nucleic acid binding domain protein. In other embodiments, pegylation is within or at the ends of the linker between the recombinant nuclease and the nucleic acid binding domain. In some embodiments, pegylation is at the N-terminus and/or the C-terminus of the recombinant protein containing an alternative nuclease sequence provided herein. In other embodiments, one or more PEG moieties is attached between the N- and C-termini of the recombinant protein containing an alternative nuclease sequence provided herein.

Exemplary pegylation reagents include, without limitation, NHS ester-(PEG)n, thiol-(PEG)n, and methoxy-(PEG)n compounds. In some embodiments, the recombinant proteins provided herein may be pegylated using, without limitation, mPEG12-NHS, mPEG8-NHS, mPEG4-NHS, mPEG-5K-NHS, mPEG12-SH, mPEG-2K-SH, mPEG-5K-SH, mPEG10K-SH, mPEG-20K-SH, mPEG-40K-SH, and mPEG-B40K-SH.

In some embodiments, the nucleic acid binding domain described herein is transcription activator-like effector (TALE) deoxyribonucleic acid binding domain (DBD). In some embodiments, the TALE DBD is a T-less TALE DBD. In some embodiments, the TALE is derived from *Xanthomonas, Ralstonia*, or *Burkholderia*. In some embodiments, the TALE is derived from *Ralstonia solanacearum*. In some embodiments, the TALE is derived from *Burkholderia rhizoxinica*. In some embodiments, the TALE is derived from a marine organism (e.g., MOrTL1 or MOrTL2). See, e.g., de Lange et al., *Nucleic Acids Research,* 43(20): 10065-10080 (2015), which is incorporated herein by reference in its entirety. In some embodiments, the nucleotide sequence encoding the TALE shares at least about 90% sequence identity with a nucleotide sequence encoding a naturally-occurring TALE. In some embodiments, the TALE shares at least about 90% sequence identity with a naturally-occurring TALE polypeptide sequence.

In other embodiments, the nucleic acid binding domain can include, for example, the DNA binding domain of a zinc finger protein. Zinc finger binding domains useful in the embodiments provided herein are well-known in the art and include, but are not limited to, those described in U.S. Pat. Nos. 5,198,346, 8,106,255, 10,808,020, U.S. Patent Application Publication No. 2011/0281306, and the like. In some embodiments, the nucleic acid binding domain can be a dCas9 ("dead" Cas9), e.g., as described in European Patent No. EP3241092.

In some embodiments, the nucleic acid binding domain binds to a target nucleic acid sequence in a nucleic acid molecule. In some embodiments, the cleavage domain cleaves the nucleic acid molecule when the nucleic acid binding domain is bound to the target nucleic acid sequence.

In some embodiments, the nucleic acid binding domain comprises one or more repeat units. In some embodiments, each of the one or more repeat units is 30 amino acids to 45 amino acids in length, and wherein each repeat unit recognizes a nucleotide base. In some embodiments, each of the one or more repeat units is 32 amino acids to 40 amino acids in length. In some embodiments, at least one repeat unit is a non-naturally occurring repeat unit.

In some embodiments, the nucleic acid binding domain binds to a DNA target sequence. In some embodiments, the nucleic acid binding domain binds to a DNA target sequence and the cleavage domain cleaves DNA.

In another aspect, the present disclosure provides a nucleic acid encoding the recombinant protein described herein.

In another aspect, the present disclosure provides a vector comprising the nucleic acid described herein.

In another aspect, the present disclosure provides a cell comprising the recombinant protein, the nucleic acid, or the vector described herein.

In some embodiments, the cell is a prokaryotic cell. In some embodiments, the cell is a eukaryotic cell. In some embodiments, the cell is a plant cell, a yeast cell, an insect cell, or a mammalian cell. Preferably, the cell can be a mammalian cell such as an immune cell (e.g., a T-cell, a B-cell, an NK cell, a macrophage, a dendritic cell, or the like), or a pluripotent cell (e.g., an embryonic stem cell, an adult stem cell, a mesenchymal stem cell, a placental stem cell, a stem cell derived from Wharton's Jelly, an induced pluripotent stem cell (iPSC), or the like), or other type of mammalian. Other cells useful in the embodiments provided herein include, but are not limited to, CHO cells, HEK-293 cells.

In some embodiments, the cell further comprises a donor nucleic acid, such as a donor DNA and/or a donor RNA.

In some embodiments, the cell is genetically modified.

In another aspect, the present disclosure provides a method of modifying a genome comprising contacting a cell with the recombinant protein described herein.

In another aspect, the present disclosure provides a method of genetically altering a cell, comprising contacting the cell with a recombinant protein described herein under conditions such that the recombinant protein binds a target DNA sequence in the cell.

In another aspect, the present disclosure provides a method of modifying a genome comprising contacting a cell with the nucleic acid or the vector described herein. In some embodiments, this disclosure relates to a vector comprising a promoter operably linked to the nucleic acid. In some embodiments, this disclosure related to a cell comprising one or more recombinant proteins, nucleic acids, and/or vectors as described herein. In some embodiments, this disclosure relates to a cell line comprising a plurality of cells as described herein. In some embodiments, the cell is a bacterial cell, a plant cell, a yeast cell, an insect cell, or a mammalian cell.

In another aspect, the present disclosure provides a method of genetically altering a cell, comprising contacting the cell with the nucleic acid or the vector described herein under conditions such that the recombinant protein is expressed and binds a target DNA sequence in the cell. In some embodiments, the cell is a bacterial cell, a plant cell, a yeast cell, an insect cell, or a mammalian cell.

In some embodiments, the nucleic acid or vector comprises RNA. In some embodiments, the nucleic acid or vector comprises DNA.

In another aspect, the present disclosure provides a method for modifying the genome of a cell, the method comprising: introducing into the cell a recombinant protein described herein, or a nucleic acid encoding a recombinant protein described herein, where the recombinant protein binds to an intracellular nucleic acid binding site, and wherein binding of the recombinant protein with the intracellular nucleic acid binding site results in cleavage of the intracellular nucleic acid binding site and modification of the genome of the cell.

In some embodiments, contacting the cell with the recombinant protein comprises transfecting the cell with a nucleic acid encoding the recombinant protein. In some embodiments, this disclosure relates to a genetically modified cell that was modified by a method as described herein.

In some embodiments, the method further comprises introducing into the cell a donor DNA, such that at least a portion of the donor DNA is inserted into the genome of the cell at the intracellular nucleic acid binding site.

In some embodiments, two or more recombinant proteins or two or more nucleic acids encoding a recombinant protein are introduced into the cell, wherein each recombinant protein binds to and cleaves an intracellular nucleic acid binding site.

In some embodiments, modification the genome of a cell comprises double stranded cleavage of an intracellular nucleic locus.

In some embodiments, the intracellular nucleic locus is a chromosomal locus.

In some embodiments, the genetic modification comprises a knock-in. In some embodiments, the genetic modification comprises a knock-out. In some embodiments, the genetic modification comprises a mutation.

In some embodiments, the genetic modification is achieved via homologous recombination.

In another aspect, the present disclosure provides a kit comprising a first recombinant protein described herein or a first nucleic acid described herein, and at least one reagent for making or using the recombinant protein.

In some embodiments, the kit comprises a vector comprising the nucleic acid described herein.

In some embodiments, the kit further comprises a second recombinant protein or a second nucleic acid, as described herein.

In some embodiments, the at least one additional reagent is selected from a transfection reagent, a DNA cloning reagent, primers to the first and/or second nucleic acid, a control nucleic acid, a third nucleic acid encoding a reporter, and/or a vector.

In another aspect, the present disclosure provides a method of treating a disease or disorder treatable by genetic modification, the method comprising contacting a cell with a recombinant protein described herein, or a nucleic acid encoding a recombinant protein described herein, under conditions such that the recombinant protein is expressed and binds to and cleaves a target DNA sequence in the cell, thereby genetically modifying the cell.

In some embodiments, the method further comprises introducing into the cell a donor DNA, such that at least a portion of the donor DNA is inserted into the genome of the cell at the intracellular nucleic acid binding site.

In some embodiments, modification the genome of a cell comprises double stranded cleavage of an intracellular nucleic locus.

In some embodiments, the intracellular nucleic locus is a chromosomal locus.

In some embodiments, the genetic modification comprises a knock-in. In some embodiments, the genetic modification comprises a knock-out. In some embodiments, the genetic modification comprises a mutation.

In some embodiments, the method further comprises administering the genetically modified cell to a patient. Accordingly, in some embodiments, the genetic modification of the cell is performed ex vivo or in vitro.

In some embodiments, the recombinant protein or nucleic acid is administered to a patient. Accordingly, in some embodiments, the genetic modification of the cell is performed in vivo.

In some embodiments, the disease or disorder described herein is cancer, beta-thalassemia, sickle cell disease, hemophilia, blindness, Leber congenital amaurosis, human immune deficiency syndrome (HIV), cystic fibrosis, Duchenne's muscular dystrophy, Huntington's disease, familial hypercholesterolemia, Alzheimer's disease, retinitis pigmentosa, retinal dystrophy, diabetes, autism spectrum disorder, hypertrophic cardiomyopathy, or Tay-Sachs disease.

In certain embodiments, the disease or disorder described herein is a blood cancer. In some embodiments, the disease or disorder described herein is a leukemia, lymphoma, myeloma, or myelodysplasia, including without limitation B-cell leukemias, B-cell acute lymphoblastic leukemia, B-cell lymphomas, B-cell non-Hodgkin's lymphoma, follicular lymphoma, mantle cell lymphoma, T-cell lymphomas, Hodgkin's lymphoma and multiple myeloma. In certain embodiments, the disease or disorder described herein is a solid tumor cancer such as, without limitation, lung cancer, ovarian cancer, cervical cancer, liver cancer, glioma, glioblastoma, prostate cancer, renal cancer pancreatic cancer, gastric cancer, breast cancer, colorectal cancer, melanomas or sarcomas.

In some embodiments, the recombinant protein described herein, when treated to a group of cells (e.g., immune cells, such as T cells), is capable of maintaining or increasing the amount of CD8+ cells in the group of cells. In some embodiments, the recombinant protein described herein, when treated to a group of cells (e.g., immune cells, such as T cells), is capable of maintaining or increasing the ratio of CD8+ vs. CD4+ cells in the group of cells. In some embodiments, the recombinant protein described herein, when treated to a group of cells (e.g., immune cells, such as T cells), is capable of increasing the amount of CD8+ cells in the group of cells to at least 110%, 120%, 130%, 140%, 150%, 160%, 170%, 180%, 190%, 200%, 250%, 300%, 350%, 400%, 450%, 500%, or more than the amount of CD8+ cells in the group of cells treated with, e.g., a CRISPR editing tool targeting the same locus In another aspect, the present disclosure provides a composition comprising the recombinant protein described herein for treating a group of cells or a subject to maintain or increase the amount of CD8+ cells and/or the ratio of CD8+ cells vs. CD4+ cells in the group of cells or the subject.

In another aspect, the present disclosure provides a method of maintaining or increasing the amount of CD8+ cells and/or the ratio of CD8+ cells vs. CD4+ cells in a group of cells or a subject, the method comprising treating the group of cells or the subject a composition comprising the recombinant protein described herein.

TABLE 2

| AN# | Organism | % Fok1 | % Clo51 | % AN3 | % An14 | Accession No. | SEQ ID NO. | Sequence |
|---|---|---|---|---|---|---|---|---|
| Fok1 | *Flavobacterium okeanokoites* | N/A | 49 | 70 | 56 | AHX83890.1; BAO05317.1 | 1 | QLVKSELEEKKSELRHKLKYVPHEYIELIE-IARN STQDRILEMKVMEF-FMKVYGYRGKHLGGSRKPDG AIYTVGSPIDYGVIVDTKAYSGGYNLPIGQA-DEM QRYVEENQTRNKHINP-NEWWKVYPSSVTEFKFLF VSGHFKGNYKAQLTRLNHITNCNGAVLS-VEELLI GGEMIKAGTLTLEEVRRKFNNGEINF |
| Clo51 | *Clostridium* | 49 | N/A | 51 | 54 | WP_ 008676092.1 | 2 | GEGIKSNISLLKDELRGQISHISHEYLSLID-LAF DSKQNRLFEMKVLELL-VNEYGFKGRHLGGSRKPD GIVYSTTLEDNFGIIVDTKAYSEGYS-LPISQADE MERYVRENSNRDEEVNPNKWWENF-SEEVKKYYFV FISGSFKGKFEEQLRRLSMTTGVNG-SAVNVVNLL LGAEKIRSGEMTIEELERAMFNNSEFILKY |
| AN2 | *Anaerosporobacter mobilis* | 50 | 52 | 49 | 46 | WP_ 073286867.1 | 3 | PTARLEGKSEVETIKEQMRGELTHLSHEY-LGLLD LAYDSKQNRLFELKTMQLL-TEECGFEGLHLGGSR KPDGIVYTKDENEQVGKENYGIIIDTKAYSG-GYS LPISQADEMERYIGENQTRDIRINPNEWW-KNFGD |

TABLE 2-continued

| AN# | Organism | % Fok1 | % Clo51 | % AN3 | % An14 | Accession No. | SEQ ID NO. | Sequence |
|---|---|---|---|---|---|---|---|---|
| | | | | | | | | GVTEYYYLFVAGHFKGKYQEQID-RINCNKNIKGA AVSIQQLLRIVNDYKAGKLTHEDMKLKIFHY |
| AN3 | *Bacillus alkalitelluris* | 70 | 51 | N/A | 56 | WP_ 088077300.1 | 4 | GVTERLVKGEMEKKKAELRHKLKHVPHEYIE-LIE IAQDSKQNRLLEFKVVEFFKEV-YGYHGKHLGGSR KPDGALYTKGLGADHGIILDTKAYKDGYS-LPISQ ADEMQRYVDENNKRDAIINPNEWWKVYPS-SISDF KFLFVSGYFKGDTKKQLTRVSNLTKRK-GAVLSVE QLLLGGEKIKDGSITLEDVAAKFNNDEIVF |
| AN4 | *Bacillus acanthi* | 69 | 51 | 89 | 56 | WP_ 108671537.1 | 5 | GVTEPLVKGEMEKKKSDLRHKLKHVPHEYIE-LIE IAQDSKQNRLFEFKVVEFLKEGYDYN-GKHLGGSR KPDGALYTNGLKTDYGIILDTKAYKDGYS-LPISQ ADEMQRYVDENNNRNAIINPNEWWKVYPN-SILDF KFLFVSGFFKGDYKKQLARVSNLTKRK-GAVLSVE QLLLGGEKIKDGSLTLEDVGDKFNNDEIIF |

TABLE 3

| AN# | Organism | % Fok1 | % Clo51 | % an197 | Accession No. | SEQ ID NO. | Sequence |
|---|---|---|---|---|---|---|---|
| AI1 | *Mesobacillus subterraneus* | 25.19 | <20 | 49.46 | WP_125479403.1 | 210 | ITGFSNQQVEAVLQGFRPDTLSIFETSYLNMAISGTELAREFELATNHIFELLGFHSRHIGTSPLHPDVFAASTTYNFSGIIDAKAYRTYSLTNDHRNRMINNYIPDWSNRFGNLSFFMYVADGFGANIDNQIQQVSNASGKNGCVISARDLLYLLQKHLASPVDHSRLNNIFQYNRRLTVVDIESL |
| AI2 | *Bacillus* | 25.53 | <20 | 50.27 | WP_041508067.1 | 211 | ATGYTTNEVARALDGFRPDTFSLFEATYMNMAVSGRELATEFELATQNVFEELGFNAQHVGAKPLHPDIYVESPLNYSGIIDTKAYRRYSITNDHRNRMVRNYIPTYRDDDFTFFMYVADGFGSNISSQIQSIAEETNINGTVITASNIMRLLQRNQVATIDHASLRNLFTSNEWSISDINSL |
| AI3 | *thermophilic bacterium* 3443-3Ac | 26.71 | 26.81 | 36.65 | QSZ27619.1 | 212 | QTGIDEKLVEEVLLRLYPHGAIGSFMTEYFEMSFKGRDEATEFENVTAELFKIVFGFDAKHIGSIGLTPDVLLLSDVEGYAGIIDNKAYSKYTISNDHHNRMVHNYIRNIKNYYSGSYPLAFFSYIAGGFGRNINTQIRNIAKETSVHGSAMSVSNMIKLVEFHSRTPFSHKHLRDIFSVDRLILISDLE |
| AI4 | *Bacillus wiedmannii* | 24.43 | 24.39 | 48.3 | WP_098819946.1 | 213 | SLGYTELQVESALEGFPDTFSVFEAGYLNMAISGTELAKEFEIATQNIFQQLGFISEHVGNNPLHPDVFVESSSGYSGIIDNKAYRAYSINNDHRNRMINNYIPLYKDKHDNLEFFMYIADGFGSNIDNQLLQISQRTQVNGCVITARNLIRLLQKHLVNPIEQSVLRDVFKCNSSITIHDIDAI |

TABLE 3-continued

| AN# | Organism | % Fok1 | % Clo51 | % an197 | Accession No. | SEQ ID NO. | Sequence |
|---|---|---|---|---|---|---|---|
| AI5 | *Falsibacillus pallidus* | 25.86 | 23.97 | 46.52 | WP_114746436.1 | 214 | STGYSNHQVEDALANFRPDTFSHFEASYLNMALSGTELAADFEIATGGIFEELGFDSEHVGNQPLHPDVFVRSPLNFSGIIDTKAYRQYTISNDHRNRMINNYIPTYQNGNNLEFFMYVADGFGTNIDTQVQDIATRTNVNGSVITAQNMIRLLQRHSSNPLDHNRLRMLFTQNSIIRLSDINSL |
| AI6 | *Anoxybacillus pushchinoensis* | 28.81 | <20 | 46.24 | WP_167357425.1 | 215 | LTGYTVREVEDALDGFRPDTFSQFEASYLNMAISGTELATEFETATQAIFEQLGFRAEHVGNHALHPDVFVESPLNYSGIIDTKAYVRYVINNDHRNRMVNNYIPTYQNQHGNLEFFMYVAHGFGSNIDSQVQSIADRTNVNGSVITARNVIRLLQRNYANPIDHNTLKTLFTKNSRITMADIDSL |
| AI7 | *Psychrobacillus* sp. AK 1817 | 26.39 | 23.13 | 44.92 | WP_151112108.1 | 216 | STGYSIREVEDALDGFRPDTFSQFEASYLNMAISGTELATEFEIATRGIFEQLGFHAEHVGNHALHPDIFVESPQNYSGIIDTKAYRTYTINNDHRNRMVNNYIPTYQNQYGNVEFFMYVADGFGSNIASQVQNIADRTNVNGSVITARNVIRLLQRYQATPIDHNSLRILFANNSVITMSEIDSL |
| AI8 | *Bacillus licheniformis* | 30.83 | 24.68 | 47.57 | WP_063906785.1 | 217 | ATGYNVKEVEESLDGFRPDTFSQFEASYLNMAISGTELATEFEIATGEVFKQLGFCTEHVGSRSLHPDLFVESPKKYSGIIDTKAYRRYTISNDHRNRMTNNYIPNYKNISGNLEFFMYVADGFGNNINSQLQNIADHANTNGSVITARNVIRLLQANQATPIDHDRLKMLFTSNSEITTADIDSCRRR |
| AI9 | *Lentisphaerae bacterium* | <20 | 24.85 | 37.95 | NLG15198.1 | 218 | RTGINSLTVGAVLQKLYPHGAIGSFMNEYFEMAFRGREDATDFERATQTIFQDTFGFEATHIGAAGLTPDVLVLSDSAGYQAIIDNKAYSKYSISNDHRNRMIHNYINGLASYSKSALPLAFFSYIAGGFSPSIDDQLKSIADESGVPGSAMPVSNMIKLINLHSENKFSHEQLKRIFSIGRRIELKDLIH |
| AI10 | *Bacillus* sp. EB01 | 25.17 | 25 | 45.7 | WP_043934191.1 | 219 | VSGYSEKQVEHALENFHPDTYSLFEVTYLKMASSSRELDTEFEKATIDIFTQLGFSAQHVGNKNLHPDGFVESPLNFSGIFDTKAYARYSITNDHHNRMTINYIPTYQQSNPNLSFFLYVAYGFKNTIDGQIQKIKRVNGVNGSAITAKDLLYLLRRHKTKAIDHADLKKLFESNKRITMQEINRLP |
| AI11 | *Bacillus* sp. AFS040349 | 24.68 | 24.57 | 45.9 | WP_098799384.1 | 220 | STGITHSIIEEELANFANGALDSFEASYFDMALKGREQCREFEIATVELFDKAFGFDTSHVGDKGKHPDILAVSEQFSGIIDSKAYASYTISNDHKNRMTHNYIPPYRKQYPNLDFFMYIAGGFGRNFDKQVLSVAQESNLNGCGITANNIIKLARNYKINNWTHDNLQQLFTLNKEIKRTDFT |
| AI12 | *Anaerostipes butyraticus* | 25.76 | 28.68 | 40.53 | WP_201311746.1 | 221 | VTGINGKTVENVLIETYPNGSVGAFMTRYFEMAFKGRDEATEFEKATVELFQDVFGYKAKHVGPIGLTPDVLLLSDSDGYQAIIDNKAYHKYSISNDHYNRMVHNYIENLANYSDSSDRLAFFSYIAGGFGKNIDKQIQSVANATGVNGSAISVTNMIKMVEQHNKVPYSHKKLCEIFSVNRQVLMQDLILREE |
| AI13 | *Desulfallas gibsoniae* | <20 | 27.01 | 36.02 | WP_006520228.1 | 222 | QTGIEVSIVEETLLKLYPYGAIGSFMTEYFEMAFKGRDEATEFEKATVELFKSVFEFEAQHVGPIGLTPDVYILSHESRYVGIIDNKAYSKYTISNDHRNRMVHNYIKTYSAECYPLAFFSYIAGGFGKN |

TABLE 3-continued

| AN# | Organism | % Fok1 | % Clo51 | % an197 | Accession No. | SEQ ID NO. | Sequence |
|---|---|---|---|---|---|---|---|
| | | | | | | | ITSQIKDIVDETLIHGSAMSVSNMIK MVENHQYKKYSHDEIRNIFSVDRQIL LSDL |
| AI14 | *Lachnospiraceae bacterium* | 25 | 29.77 | 39.47 | MBQ4529330.1 | 223 | VTGIDGKTVEDVLIETYPNGSVGAFM TKYFEMAFKGRDEATEFEKATVELFH DVFGYKTKHVGPIGLTPDVLLLSDSD GYQAILDNKAYHKYTISNDHYNRMVH NYIENLENYSDAENRLAFFSYIAGGF GKNIDKQIQSIVDATGVNGSAISVTN MIKLVEQHNKVPYSHRRLCDIFSVNR QVLMQDLI |
| AI15 | *Lachnospiraceae* | 24.06 | 26.25 | 38.42 | WP_065548241.1 | 224 | RTGIDGKTVEDILIETYPNGSVGAFM TKYFEMAFKGRDEATEFEKATVELFQ DVFGFEAKHVGPIGLTPDVLLLSDES GFQAILDNKAYHKYTINNDHYNRMVH NYIGNIGNYSKSDEPLAFFSYIAGGF GSNIDKQLKNIVDATDVNGSAISVSN VIKMVEQHREKPYTHQRIKDIFSVNR QVLMKDIV |
| AI16 | *Anaerobium acetethylicum* | 25.5 | 26.9 | 39.68 | WP_091235627.1 | 225 | QTGIDGKLVEEVLVEQYPTGSVGAFM TKYFEMAFKGREEAVDFEKATVELFH DVFGFESKHVGPIGLTPDVLLISDLD GYQAIIDNKAYSKYTISNDHYNRMVH NYIENLANYSESNNNLAFFSYIAGGF GSNIDGQIRNIVNTTGINGSAISVSN VIRMVDIHNSNPFNHQKIKDVFSMNR QVLLKDLT |
| AI17 | *Roseburia inulinivorans* | 22.81 | 28.47 | 38.95 | WP_118583687.1 | 226 | RTGIDGKTVEDILIETYPHGSVGAFM TKYFEMAFKGRDEATEFEKATVELFQ DVFGFEAKHVGPIGLTPDVLLVSDSE GYQAILDNKAYHKYTINNDHHNRMVH NYIGNIHNYSKSDKPLAFFSYIAGGF GSNIDKQLNNIVEATGVNGSAMSVSN MIKMVEQHECTPYSHQKIRDIFSLNR QVLINDIL |
| AI18 | *Candidatus Stercoripulliclostridium merdipullorum* | | 26.47 | 39.15 | HIV00709.1 | 227 | KTGIDGKFVEETLLKFYPRGAIGSFM TEYFEMAFRGRDEATEFERATTCLFK DVFNFETHHVGPIGLTPDVLLISDQE GYCGIIDNKAYSKYSISNDHHNRMVH NYIEGFSRYCQSQNPLAFFSYIAGGF GNNINGQIQSIVHEAGVHGCAFAVTN VIQLVEKHQVMPYSHLDLKDIFTLDR QVLLSDL |
| AI19 | *Hungatella hathewayi* | 24.24 | 25.87 | 38.42 | WP_006781688.1 | 228 | QTGIDDKTVENILIETYPNGSIGGFM TKYFEMAFKGRDEATEFEKATAELFQ DVFGFETKHVGPIGLTPDVLLISDCA GYQAIIDNKAYHKYTINNDHYNRMVH NYIGNMNKYSSSNNALAFFSYIAGGF GSHIDSQIKSIADATGVNGSAMSVTN VIKMVEQHNKQPYSHEKI KDIFSVNRQVLMNDII |
| AI20 | *Flavonifractor* sp. An91 | 26.85 | 26.16 | 36.84 | WP_087267198.1 | 229 | QTGFDDKLVEETLLRLYPRGSVGAFM TEYFEMAFKGRDEATPFEKATVELFQ DVFGFEAKHVGPIGLTPDVLLVSDVE GYQAIIDNKAYSKYTISNDHHNRMVH NYIENLGRYSSSAAPLAFFSYIAGGF GKNFDSQVRAIVDETGVNGSGFSVST MIKLVECYSDKGYTHKTLRDLFSLNR QVLMTDF |
| AI21 | *Firmicutes bacterium* AM59-13 | 24.67 | 25.51 | 37.77 | RHP89592.1 | 230 | ATGIDGKTVEEVLIETYPRGSIGSFM TKYFEMAFKGRDEATEFEKATVELFR DVFGYQTKHVGPMGLTPDVLLVSPEC SYQAIIDNKAYSNYSINNDHRNRMVH NYLTNISRYSDREYPMAFFTYIAGGF GTAIDKQIESIYEESGVRGSAVSVTN IIKMVEKHQESAYTHQDLRNLFGVNR QILMRDL |

TABLE 3-continued

| AN# | Organism | % Fok1 | % Clo51 | % an197 | Accession No. | SEQ ID NO. | Sequence |
|---|---|---|---|---|---|---|---|
| AI22 | *Lachnospiraceae bacterium* | 20.65 | 28.99 | 37.23 | HBI61615.1 | 231 | VTGIDGKTVENVLVETYPNGSVGAFM TKYFEMAFKGRDEATEFEKATVELFQ DVFGFEARHVGSIGLTPDVLVLSDED GYQAILDNKAYHKYTISNDHFNRMVH NYIGNISSYGDGDKSLAFFSYIAGGF GTNIDKQLKNIVDATGVSGSAVSVSN MIKLVEQHNQTPYSHKRIKEIFSVNR QVLLSDLA |
| AI23 | *Clostridiales bacterium* | <20 | 28.57 | 40.64 | NLJ41069.1 | 232 | QTGIEAKIVEDTLQKNYSRGAIGSFM VEYFEMAFKGRDEATEFELATAELFK SAFGLTTEHIGSKSLMPDVLVLSDQF KYIGIIDNKAYSSYSITNDHKNRMMY NYIPAYKKEQKYPLAFFSYIAGGFGT NIDSQIKEIVDSTNINGSAISVSNVI NLVTNYQSKGYNHTKIKNIFSIDRQV LISDL |
| AI24 | *Clostridium tetani* | 24.24 | 26.95 | 40.64 | WP_035109238.1 | 233 | QTGIDARFVEETLLKYYPHGAIGSFM TEYFEMAFRGRDDATEFELATVELFK SAFGFETEHVGPIGLTPDVLILSNQD NYIGIIDNKAYSKYTISNDHKNRMIH NYIKTYKQEQKYPLAFFSYIAGGFGK NINSQIKEIVDESKINGSAISVTNLI KLVEYYGTKNYDHGKIRDIFSVNRQV LMSDL |
| AI25 | *Firmicutes bacterium* | 24.56 | 26.49 | 38.42 | MBQ3660513.1 | 234 | RTGIDPRVVEEILIEKYPHGSPSAFM SEYFSMAFKGREEAADFEKATVELFQ NVFGYEASHVGPIGRSPDVLLESKSA HYQAILDNKAYSRYTVSNDHHNRMVD NYIRDKAHYSTSPYPLAFFSYIAGGF GSNIDPQIQSIVHDGGVNGSCITVSN VIQMVENSETKPYTHEKLRQIFGLNR QVLISDLQQ |
| AI26 | *Oscillospiraceae bacterium* | 24.46 | 26.6 | 38.1 | MBQ8171046.1 | 235 | KTGCNAKVVEEKLCKLYPNGAVGSFM TEYFNMAFKGTEQAADFEKATVELFR DVFGYETEHVGSIGLTPDVLLVSDSD GYQAIFDNKAYSSYSISNDHRNRMIH NYIENLGKYSKHSHPLAFFSYIAGGF GNKIDSQIQSVVQETGISGSAISVSN VISLVEKHQSNPYSHKQLKDLFSLER QILLSDL |
| AI27 | *Candidatus Scatousia excrementigallinarum* | 25.29 | 28.67 | 38.42 | HIS36845.1 | 236 | QTGIDGRLVEENLQRLYPHGAIGAFM TQYFDMATKGRDEATEFEKATVTIFN EVFGFNSKHVGPIGLTPDVLLLSDSD KYSAIIDNKAYSRYSISNDHHNRMIH NYIEGFKNYCDSPYPLAFFSYIAGGF GSNIDAQLMKIVNETGVNGSAVTVSS VIQMVEKQQAEPYSHAKIRELFSLNR QLVLSDL |
| AI28 | *Gilliamella bombi* | 24.18 | 28.48 | 39.15 | WP_085165852.1; WP_198222622.1 | 237 | KTGFLPDLVEDCLQELYPQGAIGAFL SEYFEMAFKGREQATDFELATVDLFQ NVFGFTARHVGPKGLTPDVLLLSDDE GYSAILDNKAYSKYSITNDHHNRMVY NYIGQLNNYYNGTYPLSFFSYIAGGF GSNINIQLNRVVNETGINGSAINIST MINLVYEHTSNPYTQQRIRDIFSLNR RVLQADL |
| AI29 | *Trichococcus shcherbakoviae* | 26.32 | 28.48 | 41.36 | SYZ78703.1; WP_200831741.1 | 238 | VSGFEYRVVEQILLRKYPHGAIGSFM SNYFEMAFRGRDEAIEFETATVEIFE NVFGMKANHVGPIGLTPDILVISDDA GYLGIIDNKAYSRYSITNDHKNRMIY NYIPSYQRDEYPLAFFTYIAGGFGNN INRQLNDISSATNVHGSAINVSNMIQ LVQNFSEYSYDHFTLKDIFSLDRQIT QSDI |
| AI30 | *Victivallales bacterium* | <20 | 28.04 | 37.04 | MBR4222081.1 | 239 | DTGIAGNTVEEVLQKNYPHGAIGSFM TEYFEMAFKGRDEATEFEVATRTIFE ETFGFKARHVGPIGLTPDVLLLSDNA GYQAIIDNKAYSKYSISNDHRNRMVH NYINGLANYSQSSLPLAFFSYIAGGF |

TABLE 3-continued

| AN# | Organism | % Fok1 | % Clo51 | % an197 | Accession No. | SEQ ID NO. | Sequence |
|---|---|---|---|---|---|---|---|
| | | | | | | | SPSIDAQLKSITEETGIKGSAMPVSNMIRLINQHSETPFTHEQLRGIFSLNRKIELKDLIHS |
| AI31 | *Rothia* sp. HMSC064F07 | 22.67 | 25.62 | 35.93 | OHQ12456.1 | 240 | EQILSKKYPYGFGDLFLQKYIELSRGGRKRATEFEKATSSIFADMFGVCAEHIGQKGSVPDIVVGSRDGKWAGILDTKAYNKKYSISNDHKNRMIGYIERYSEYGFEFANLSFFAYVVSDYGKNINSQIRYISNKSGVLGSAVTARDIIRMVERHQKKPYTHDEIREIFSVNRAITLKDID |
| AI32 | *Lentisphaeria bacterium* | <20 | 25.37 | 37.77 | MBR1965818.1 | 241 | LTGIDSKLVEDTLLRWYPHGAIGSFMTEYQEMAFKGREDATDFEKATVAIFRDSFGFAAEHVGPIGLTPDVLLLSDAAGYQAIIDNKAYSRYSISNDHRNRMVHNYICQLSSYSKSAHPLAFFSYIAGGFGNNISTQIKSIADETGIAGSAVSVFNIIKLAEENQRNPYSHESIRDIFSKNRLIELKDL |
| AI33 | *Dorea longicatena* | <20 | 26.2 | 38.83 | WP_055195530.1 | 242 | STGLKESFVWEILQKRFPRGSIGAFMTQYYEMAFKGREEATEFEKATAELFHDVFKFKTKHVGPIGLTPDVLIESEDVGFVGIIDNKAYSKYSISNDHHNRMVHNYINGLGNYYKGKKNLAFFSYIAGGFGINIDSQIKSIVDETEICGSCINVHNMIELVKRNEKRAYSHEDLKKIFSVNREILLSDLC |
| AI34 | *Eubacterium* sp. | 24.32 | 28.07 | 38.74 | HAJ49432.1 | 243 | ITGADGKLVENTLLETYPNGAISGFMTEYFEMAFKGTEEAVNFEIATTELFKEVFGFETKHLGQTGSKSAPDVLLVSNNEGYQAIIDNKAYSKYSISGDHHNRMVHNYIENISKYSEYSHPIGFFTYIAGGFGNQIDRQIQSIVAECGVHGSGMTVSNMIKLVEKQNETPLSHRDIKNIFSVDRQIVLSDIEVI |
| AI35 | *Clostridium massiliodielmoense* | 24.12 | 25.58 | 37.37 | WP_085829289.1 | 244 | QTGFEDKLVEETLLKLYPRGSVGAFMTEYFEMAFKGRDEATDFEKATVELFQSVFGFQAKHVGPIGLTPDVLILSDAEGYQAILDNKAYSKYTISNDHHNRMVHNYIKNLKRYSNADVSLAFFSYIAGGFGNNINSQINDIVNVTGVAGSGISVSNMIKLVELYEPKNYTHKNIRDIFSVNRQILLSDL |
| AI36 | *Lachnospiraceae bacterium* | <20 | 25.3 | 39.47 | MBR6896690.1 | 245 | VTGVDGKLVENVLVETYPKGALGGFMTEYFEMAFKGTEEAIEFEKATTNLFQDVFGFNAIHLGQTGSKSAPDILLLSDSEGYQAIIDNKAYHKYSISGDHRNRMIHNYIESISNYSSFTQPIGFFSYVAGGFGNQIDKQIQDIADATGVHGSGITVSNMIELVKQQDIKPMNHAQIRTLFGVDRQIRIADF |
| AI37 | *Rothia mucilaginosa* | 22.67 | 25.62 | 34.74 | MBF1672104.1 | 246 | KSGVPFGNTEQILSKKYPYGFGDLFLQKYIELSRGGRKRATEFEKATSSIFADMFGVCAEHIGQKGSVPDIVVGSRDGKWAGILDTKAYNKKYSISNDHKNRMIGYIERYSEYGFEFANLSFFAYVVSDYGKNINSQIRYISNKSGVLGSAVTARDIIRMVERHQKKPYTHDEIREIFSVNRAITLKDID |
| AI38 | *Ruminococcus* sp. | 24.84 | 26.74 | 36.9 | MBS1397219.1 | 247 | TTGIDERFVEETLLKFYPKGSIGAFMTEYFEMAFKGRDEATEFEKATVNIFQDVFGFSAKHVGPIGLTPDVLVLSDVDGYSAIIDNKAYSKYTINNDHHNRMVHNYIGNLSNYYDGTYSLAFFSYIAGGFGTNINKQLQSITNETGIKGSAMNVSNMIELIKRYDTCNYNHSTIREIFSVGRQILHSDFK |
| AI39 | *Eubacterium* sp. | 25.77 | 27.88 | 34.39 | MBR1530827.1 | 248 | KTGLAFSQVEELLLKLYPHGAVGAFMNEYFEMAFKGRDEATDFEKATVELFR |

TABLE 3-continued

| AN# | Organism | % Fok1 | % Clo51 | % an197 | Accession No. | SEQ ID NO. | Sequence |
|---|---|---|---|---|---|---|---|
| | | | | | | | DVFGFDAKHVGPIGLTPDVLLLSDSA<br>GYCGIIDNKAYSKYTISNDHHNRMVH<br>NYIGGFSNYCDSENELAFFSYIAGGF<br>GSNIDKQLLKIIDETGVHGSAVTVSN<br>IIKMVENQQKQPYSHIQIRDIFSLDR<br>QIALSDI |
| AI40 | *Planctomycetes bacterium* | <20 | 26.99 | 37.57 | MBP7021766.1 | 249 | KSGINEKIVEEILLKFYPRGSVGAFM<br>TEYFEMAFRGRDNATDFEKSTVQIFS<br>DLFNYETIHVGSIGLTPDILILSDED<br>GYQAILDNKAYHSYSISNDHHNRMVH<br>NYIAGLNKYSNSRLPLAFFSYISGGF<br>GANINSQINKIYNETNIKGSAMTVSN<br>MIYLIENYSEKSKSHRSLRKIFSVNR<br>QILKSDIDIGL |
| AI41 | *Rothia* sp. HMSC062F03 | 23.7 | 22.78 | 34.74 | OHP73990.1;<br>WP_084824410.1 | 250 | KSGVPFKDTERILSGKYPHGFKDRFL<br>QEYIELSRSGRDKATEFEKATSSIFA<br>DVFGLRAEHIGQKGIVPDIVVASRGE<br>KWAGILDTKSYKKKYSISNDHKNRML<br>EYIERYSEYGLEFANLSFFAYVVSDY<br>GKNINSQLENISNRSGLLGSVITARY<br>LARMVERHQKNPYSHEEIRKIFSVNR<br>AITLKDID |
| AI42 | *Clostridium moniliforme* | 26.19 | 26.42 | 37.37 | MBP1889103.1;<br>WP_209795806.1 | 251 | QTGFNDKLVEEVLLKLYPSGSIGGFM<br>TAYFEMAFKGRDKATDFEKATVELFK<br>NVFGFETKHVGPIGLTPDVLILSNSD<br>GYQAIIDNKAYSKYTVSNDHRNRMIY<br>NYIKNLKNYSNFSVPLSFFSYIAGGF<br>GNNINSQIMDIVNATNIAGSAMSVSN<br>MIKLVELYESKNYTHKNIKDIFSVNR<br>QILLSDL |
| AI43 | *Clostridium intestinale* | 24.71 | 28.35 | 35.26 | WP_021802266.1 | 252 | QTGFGDKLVEETLLKLYPRGSIGAFM<br>TEYFEMAFKGRDEAIDFEKATVELFQ<br>NVFGFESKHVGPIGLTPDVLILSDED<br>GYQAIIDNKAYSKYTISNDHHNRMVH<br>NYIKNLERYSNSDVPLAFFSYVAGGF<br>GKNINTQINDIVNVTGVSGSAMSVSN<br>MIKLVELYESKNYTHKSIREIFSVNR<br>QILLSDL |
| AI44 | *Tissierella creatinini* | 24.12 | 28.66 | 37.89 | WP_136713134.1 | 253 | KTGFEDKLIEETLLKLYPRGSVGAFM<br>TEYFEMAFKGRDEASDFEKATVELFQ<br>NVFGFEAKHVGPIGLTPDVLILSDTD<br>GYQAIIDNKAYSKYTISNDHHNRMVH<br>NYIKDLNRYSSYTVPLAFFSYIAGGF<br>GKNINSQVMDIVNVTKVSGSAISVSN<br>MIKLVELYEQKNYTNKKIRDVFSVNR<br>QILLSDL |
| AI45 | *Eubacterium* sp. | <20 | 25.3 | 38.42 | MBQ8950757.1 | 254 | VTGVDGKLVENILVETYPKGALGGFM<br>TEYFEMAFKGTEEAVEFEKATTNLFQ<br>DVFGFNAIHLGQTGSKSAPDILLLSD<br>SEGYQAIIDNKAYSKYSITGDHKNRM<br>IHNYIEHISNFSSFTQPIGFFSYVAG<br>GFGNQIDKQIQDITSETGIHGSGITV<br>SNMIELVKQQDIKPMNHAQIRTLFGV<br>DRQIRMADF |
| AI46 | *Pseudobutyrivibrio* sp. | 37.5 | 25.75 | 38.42 | MBR5636726.1 | 255 | ITGTDRKLVEETLLSSYPHGLVGGFL<br>ANYYEMAFKGTEEAVEFEKATTEIFN<br>SVFGYKAIHLGQTGSKSAPDILLLSD<br>DEGYQAIIDNKAYSKYSITGDHHNRM<br>VHNYIGKIGNYSESHYPLAFFSYIAG<br>GFISTIDKQIASEVYESNVHGSGITV<br>GTFIKMVEKHNATPYSHKELRNIFSV<br>DREVKLADI |
| AI47 | *Rothia* sp. HMSC062F03 | 21.14 | 24.85 | 34.94 | WP_070824649.1 | 256 | ETGVSAVETERILSAKYPNGLVDSFL<br>SEYVQMAFESRDRATEFEKATTSIFA<br>DIFGLYAEHIGQKGIVPDVVVASREE<br>GWSGILDSKAYAKGYSIGHDHRNRMV<br>EYIERYPKYGPEFATLAFFSYVVSDY |

TABLE 3-continued

| AN# | Organism | % Fok1 | % Clo51 | % an197 | Accession No. | SEQ ID NO. | Sequence |
|---|---|---|---|---|---|---|---|
| | | | | | | | KNSVTPQIRTISEKSGVPGSVITARD IVRMVERHQKKPYTHSEIREIFSLNR AITFEDIE |
| AI48 | *Clostridium akagii* | 24.83 | 25.3 | 34.92 | WP_026881459.1 | 257 | QTGLDGKIVEETLLKLYPKGSVGAFM TEYFEMAFKGRDEATGFEKATVELFK NVFGYEAKHVGAIGLTPDVLILSDTD GYQAIIDNKAYSKYTISNDHHNRMVH NYIKGLNLYSTSSAPLAFFSYIAGGF GKNINSQIKGIVSETTIHGSAMSVSN MIRLVENYTDKGYKHSKIKEIFSLDR QILMSDI |
| AI49 | *Solobacterium* sp. | 25.49 | 27.84 | 36.26 | MBF1072067.1 | 258 | NEVTVEKYLQKNYPNGSIGAFMTSYF EMAFKGKDEAIDFEKATTEIFTSVFK YKAQHLGQTGSTSAPDILLISDEDGY QSIIDNKAYSEYSINGDHHNRMVHNY IRNIKNYSSCEYPIGYFSYIAGGFIK SIDKQIQAVASESGVNGSGITVGNFI KLIERNQIKPFSHKELRKIFGLNKQI LLEDI |
| AI50 | *Candidatus Saccharibacteria bacterium* | 24.83 | 25.58 | 36.79 | MBR3122411.1 | 259 | RTGIDDRTVESYLIQNHRHGSLSEFF MAYRELAHSGRAGATDFELATCEIFQ RLFHMRAKHVGPDGNTPDVFIESSEC GYCGIIDNKAYHDKYSITAGHKRAML VDYIPKYRGYGETDLPLAFYTYIAGS FGTNINNQLAAITKETGINGSAMPVD ILIDFAQDYAERGCDHEYIKNLFSVN REIRLQDIATTK |

EXAMPLES

One skilled in the art would understand that descriptions of making and using the particles described herein is for the sole purpose of illustration, and that the present disclosure is not limited by this illustration.

Example 1. Methods and Materials

Designing/Ordering the AN

The Alternative Nucleases (ANs) candidate sequences were identified using a BLAST sequence comparison algorithm, available at the NCBI web site at ncbi.nlm.nih.gov/BLAST, to search proteins having certain sequence homology to Fokl or Clo51. Default algorithm parameters were adjusted to increase Max Target Sequences to 1000 to list identified homologs.

Sequences with a percent identity of 60% or less to cleavage domain of Fokl or Clo51 were analyzed further. Table 2 provides the AN number, source organism, percent identity to Fokl and Clo51, percent identity to AN3 and AN14, Accession number, SEQ ID NO, and amino acid sequence for some of the candidate sequence. Other such candidate AN sequences are provided in Table 3, FIG. 10A and SEQ ID NOs: 3-259, 282, and 296-299. Table 3 provides the AN number, source organism, percent identity to Fokl and Clo51, percent identity to AN197, Accession number, SEQ ID NO, and amino acid sequence for candidate nuclease sequences.

The putative N-terminus of each nuclease was determined by using the Multiple Alignment tool with the Blast algorithm, available at ncbi.nlm.nih.gov/tools/cobalt/cobalt.cgi?LINK LOC=BlastHomeLink, by aligning multiple sequences together based on similarity. Since there is no existing structure model for most of the AN, new AN sequences were then aligned against Fokl and Clo51 amino acid sequences (SEQ ID NOs: 1 and 2, respectively) to predict its N-terminal sequence.

AN sequences were reverse-translated into the corresponding encoding DNA sequences. An adaptor for GOLDENGATE™ cloning containing an AarI restriction enzyme recognition site was added to the N-terminus of the encoding DNA sequences (see SEQ ID NO: 262). A C-terminal nuclear localization signal (NLS), stop codon, and priming site for adding a polyA tail was added to the C-terminus of the encoding DNA sequences (see SEQ ID NO: 263). The sequences were then optimized to contain human codons using the Thermo Fisher Scientific GENEART™ tool. The new human codon optimized DNA sequence was copied for reference, and all constructs were ordered as sequence confirmed plasmids from GeneArt.

Assembling the TALENs

Plasmids containing the optimized AN sequences were engineered to include a TALEN nucleic acid binding domain using standard molecular biology techniques.

An AAVS1 (Adeno-Associated Virus Integration Site 1) sequence was chosen as the target for screening the AN due to previously demonstrated high efficiency in editing by Fokl. Therefore, a separate fragment spanning either the forward or reverse direction of a TALEN (Transcription Activator-Like Effector Nucleases) AAVS1 RVD sequence was generated by a PCR (Polymerase Chain Reaction) using sequence verified Fokl TALEN plasmids engineered to recognize the AAVS1 target site (Forward and Reverse) (see SEQ ID NOs: 264-281).

PCR Enrichment/polyA Tail Addition

The PCR products of the cloning reactions described above were further processed by performing another amplification reaction with primers that add a polyA tail to the PCR products. The PCR reaction products for each AN sequence were verified using gel electrophoresis.

mRNA Generation/Purification

IVT reactions were set up using the MMESSAGE MMACHINE® T7 Ultra kit (Thermo Fisher Scientific, Cat. AMB13455) according to the manufacturer's protocol. IVT reaction proudcts were purified using the KINGFISHER™ Flex instrument and a DYNABEADS™ MYONE™ Carboxylic Acid bead (Thermo Fisher Scientific, Cat. 65012) cleanup protocol. Samples were eluted in 30 μL of Ultrapure water. Concentration was determined using a QUANT-IT™ RNA Assay BR kit (Thermo Fisher Scientific Cat. Q10213) on a spectrophotometer, with samples measured in duplicate. mRNA samples were also run on a 1.2% GP gel.

Transfection 100 ng of mRNA for each the nuclease (e.g., AN recombinant protein or Fokl TALEN) arms, e.g., a forward and a reverse AN recombinant protein or Fokl nuclease respectively each an RVD that specifically binds to a target half site within the target site (200 ng of mRNA in total for each transfection) were used for transfection. All transfections were done in duplicate for each nuclease pair tested. Approximately fifty thousand HEK293FT cells were used for each transfection. The cells were maintained at 37° C. in culture medium. Each transfection utilized 10 μL NEON™ Transfection System kit (Thermo Fisher Scientific cat. MPK1025) and NEON™ Transfection System (Thermo Fisher Scientific, MPK5000). The cells were recovered in DMEM growth media in 96-well flat bottom plates at 37° C. Transfected cells were allowed to recover for 48-72 hours before checking for editing.

Genomic Cleavage Detection (GCD) Assay

Editing was tested using a genomic cleavage detection assay. The media was first carefully drained from the plates and 20 μL of lysis buffer (with 0.4 μL of Proteinase K) was added to each well. The cells and lysis buffer were allowed to rest at 37° C. for 2-3 minutes before being gently removed into a 96-well microamp half-skirt plate. The plate was sealed and loaded onto a PCR machine to lyse using the protocol: incubating at 68° C. for 15 min, at 95° C. for 10 min and then holding at 4° C.

After lysing, PCR reaction products were set up using GCD AAVS1 primer pair provided in the GCD kit. The PCR reaction mixtures consisted of: 25 μL of AMPLITAQ™ Gold 360 Master Mix (Thermo Fisher Scientific, Cat. 4398790), 23 μL of Ultrapure Water, 1 μL of GCD AAVS1 F/R primer mix, and 1 μL of cell lysate. The PCR protocol included: incubating the PCR reaction mixture at 95° C. for 10 min, followed by 40 cycles of incubations, each cycle including incubating the reaction mixture at 95° C. for 30 s, at 55° C. for 30 s, and then at 72° C. for 30 s. After the 40 cycles, the reaction mixture was further incubated at 72° C. for 7 min, at 95° C. for 5 min, at 85° C. for 5 s, at 25° C. for 5 s, and then held at 4° C.

Once finished, the PCR reaction mixtures were kept on ice. A 48-well 2% Ex-gel (Thermo Fisher Scientific, Cat. G800802) was used to analyze the PCR samples to confirm that the PCR products have the correct size (400 bp). An enzymatic digest was performed for each PCR reaction using: 6 μL of Ultrapure water, 1 μL of GCD enzyme buffer, 1 μL of GCD T7 endonuclease enzyme mix, and 2 μL of PCR reaction.

The reaction was at 37° C. for 1 hour. After the reaction the total mixture volume of 10 μL was loaded onto a 48 well 2% EX-gel for analysis. If the sample was edited, two bands (150 bp and 250 bp) would appear beneath the larger, uncut sample band (400 bp). The brighter the lower bands, the more population of the sample were edited. The editing efficiency was analyzed by the ALPHAIMAGER® HP software.

Cloning the AN into pCMV

Each of the top performing AN sequences was further cloned (both the forward and reverse chains of the constructs) into a modified pCMV vector. Starting from template DNA including the AN197 nuclease domain operatively linked to TAL binding domains that specifically bind to the AAVS1 locus, used in the addition of the AAVS1 binding sites to the AN197 cleavage domains, PCR was used to replace the TALEN domains specific for the AAVS1 locus with TALEN domains specific for the TAC48 locus.

The PCR product was run on a 2% EX gel to check for laddering and having the correct size (3.5 kb), then digested with 1 μL of Dpn1 at 37° C. for 2 hours. The product was then purified using a PURELINK™ Quick PCR Purification kit. The modified pCMV vector was linearized as follows: 5 μl of modified pCMV plasmid, 3 μL of Buffer G, 2 μL of BsaI restriction enzyme, and 20 μL of water.

A 2% EX-GEL™ agarose gel (Thermo Fisher Scientific, cat. G401002) was used to check the digested fragments have the correct sizes, which should be 3292 bp and 500 bp. and the linearized plasmid was purified using a PURELINK™ Quick PCR Purification kit (Thermo Fisher Scientific, cat. K310001). The purified pCMV linear vector was then diluted to 50 ng/μL.

A Seamless Cloning reaction (Thermo Fisher Scientific, cat. A13288) was set up to include: 8 μL UltraPure Water, 1 μL of linear pCMV vector, 5 μL of PCR-purified AAVS1-AN construct (forward or reverse), 4 μL of 5× Enzyme Buffer, and 2 μL of 10× Enzyme mix.

The reaction mixture was incubated at room temperature for 30 min. Fifty microliters of DH10b (Thermo Fisher Scientific, cat. 12331013) cells were then mixed with 5 μL of Seamless reaction (50 μL cells per Seamless reaction; multiple tubes would be used for multiple Seamless reactions). The reaction mixture was then recovered in SOC medium at 37° C. for 1 hour. One hundred microliters of the reaction mixture were then plated onto LB-AMP agar plates and let sit at 37° C. for 14-20 hours. Each of resulting colonies was picked into 5 mL of LB-AMP media for grow overnight under shaking at 37° C. for 14-20 hours. Once finished, the DNA components were extracted by miniprep using the PURELINK™ Quick Plasmid Miniprep Kit (Thermo Fisher Scientific, cat. K210011), and then sequenced using standard BIGDYE™ sequencing kit, according to manufacturer's protocol (Thermo Fisher Scientific, Cat. 4337455) and the sequencing primers in the Supplementary Materials. Plasmids were verified using the Geneious Prime software.

Testing at the TRAC locus

Top performing AN sequences were tested at the TRAC locus to determine if they contained any target-specific bias. To generate the TRAC RVD (F and R) PCR fragments used a sequence confirmed TRAC48 plasmid and the primers TD1F2 and TD8 RVD R (See SEQ ID NOs: 284-295). The PCR reaction setup and PCR cycling were the same as making the AAVS1 RVD fragments.

The AN fragments (containing the TALEN-derived nucleic acid binding C-term domain and N-term cleavage domain (AN)) were created by using a sequence verified AAVS1-AN plasmid and the primers TD8F3 and TD8R2. The reactions were: 25 μL of 2× Phusion Flash PCR Master Mix (F-548), 22.5 μL of UltraPure Water, 1 μL of each primer at 10 μM, and 0.5 μL of AN AAVS1 plasmid. The PCR protocol was: incubating the PCR reaction mixture at 98° C. for 1 min, followed by 25 cycles of incubations, each cycle including incubating the reaction mixture at 98° C. for 1 s, 64.7° C. for 5 s, and at 72° C. for 15 s. After the 25 cycles, the reaction mixture was further incubated at 72° C. for 2 min, and then held at 4° C.

PCR product was run on a 2% gel to check for correct size (1.1 kb), then digested using 1 μL Dpn1 for 2 hours at 37° C., followed by purification using a PURELINK™ Quick PCR Purification kit.

The GOLDENTGATE™ cloning reaction mixture was set up using BsaI as follows: 50 ng of AN plasmid, 50 ng of purified TALEN RVD for the TRAC target (forward or reverse), 2 μL of Buffer G, 2 μL of BsaI restriction enzyme, 3 μL of ATP, 1 μL of T4 ligase, and water to make a total volume of 20 μL.

The PCR protocol was: incubating the PCR reaction mixture at 37° C. for 10 min, followed by 15 cycles of incubations, each cycle including incubating the reaction mixture at 37° C. for 1 min, and at 16° C. for 1 min. After the 15 cycles, the reaction mixture was further incubated at 37° C. for 5 min, at 65° C. for 10 min, and then held at 4° C.

After the GOLDENGATE™ cloning reaction was complete, the reaction products encoding the recombinant proteins with nucleic acid binding sites specific for the TRAC locus were used in transfection reactions as described elsewhere herein. Transfected cells were assayed using the genomic cleavage detection (GCD) assay as described elsewhere herein, using the GCD TRAC F and GCD TRAC R primers.

Cells (for T Cell Experiment)

The Leukopak from healthy donors were purchased from AllCells Inc. The peripheral blood mononuclear cells were isolated by density gradient centrifugation. Cells were activated with the Dynabeads (1:1 beads: cell) A Human T-Activator CD3/CD28 (Thermo Fisher Scientific) in CTS OpTimizer medium (Thermo Fisher Scientific, Catalog #A3705001) supplemented with 2% human serum (Valley biomedical) with 200 U ml-1 IL-2 (Thermo Fisher Scientific, Catalog #PHC0021) at a density of $10^6$ cells per ml. The medium was changed every 2 days, and cells were re-plated at $10^6$ cells per ml. NALM6-Fluc-GFP cell line was purchased from the Imanis Life Sciences.

Flow Cytometry.

T cell basal and post-activation phenotypes were characterized by flow cytometry staining with PE conjugated TCR alpha/beta antibody (Thermo Fisher Scientific, Catalog #MA1-10455), and analyzed with an Attune NxT flow cytometer (Thermo Fisher Scientific). All data were analyzed with the Flow Jo_V10 software (Tree Star Inc.).

The following mAbs against human proteins were from Thermo Fisher Scientific: V5—PE (Catalog #12-6796-42), CD25 AF-700 (Catalog #56-0259-42), CD69 eFluor450 (Catalog #48-0699-42), CD62L APC (Catalog #17-0629-42), CD95 eFluor450 (Catalog #48-0959-42), LAG-3 eFluor506 (Catalog #69-2239-42), PD-1 SB702 (Catalog #67-2799-42), TIM3 APC (Catalog #61-3109-42), TCR α/β SB436 (Catalog #62-9986-42), CD4 APC-780 (Catalog #47-0049-42), CD8 eFluor450 (Catalog #48-0088-42). SYTOX™ Red Dead Cell Stain was used as a viability marker (Thermo Fisher Scientific, Catalog #S34859). Samples were analyzed with an Attune NxT flow cytometer (Thermo Fisher Scientific). All data were analyzed with the Flow Jo_V10 software (Tree Star Inc.).

Electroporation of Activated T Cells

The Activated T cells were pelleted and resuspended at $4\times10^7$ cells/ml in R buffer (Neon Transfection System Kit, Thermo Fisher Scientific). Two hundred nanograms of the TALEN alternative nucleases mRNA were added to 10 μL ($2\times10^5$) on ice. Single arm TALEN mRNA (i.e., mRNA only encoding one monomer of the dimeric pair) was used as a control in some experiments. This mixture was electroporated with the Neon Transfection system (Thermo Fisher Scientific) using program 16 (two pulses of 1400 V and 20 ms pulse width). T cells were recovered in warm CTS OpTimizer medium containing 200 U/mL IL-2.

Gene Cleavage Detection (for T Cell Experiment)

Gene editing was evaluated by the genome cleavage detection (GCD) assay using GeneArt® Genomic Cleavage Detection Kit (Thermo Fisher Scientific, USA), a method that detects locus-specific double-stranded break (DSB) formation by direct polymerase chain reaction (PCR) amplification and endonuclease activity that cuts specifically at hetero-duplex mismatches.

Genomic Cleavage Detection (GCD) Assay

T cells from two different donors (donor A and donor B) were electroporated with TALEN alternative nuclease 197 or FokI TALEN mRNA targeting human AAVS1 locus using Neon Transfection system. A negative control sample for gene modification was also prepared by transfecting with TALEN single arm mRNA. The above samples were PCR amplified using the same set of primers flanking the region of interest. After re-annealing, samples were treated with Detection Enzyme and run on a 2% E-Gel® EX Gel.

TCR α/β Knockout Test by Flow Cytometry

The Activated T cells were electroporated with TALEN alternative nucleases 197, 6, 159 and TALEN Fok 1 mRNA targeting human TRAC locus. After 4 days, the TCR α/β knockout frequency was tested by flow cytometry. The TCR α/β knockout efficiency with FokI TALEN, TALEN alternative nuclease 197, and a CRISPR/Cas9 (Clustered Regularly Interspaced Short Palindromic Repeats/CRISPR Associated Protein 9) in 2 different T cell donors were measured and compared. Each group had two independent electroporation. The TALEN alternative nuclease 197, FokI TALEN and CRISPR/Cas9—targeted CAR gene integration into the TRAC locus was also tested. Knock-in efficiency was proportional to the AAV6-CAR dosage. These results demonstrate the high efficiency and precision of gene targeting offered by TALEN alternative nuclease 197.

T-Cell Phenotypic Analysis by Flow Cytometer.

A FACS (Fluorescence-Activated Cell Sorting) analysis of activation, memory and exhaustion markers in T cells (day 5 after transfection) were performed. All the TALEN alternative nuclease 197, FokI TALEN and CRISPR/Cas9 generated CAR-T (Chimeric Antigen Receptor) cells maintained a phenotype analogous to untransduced T cells, mainly composed of naïve and central memory cells (CD62L+ cells), a phenotype associated with greater in vivo anti-tumor activity.

In Vitro Killing Assay

Figure 16:
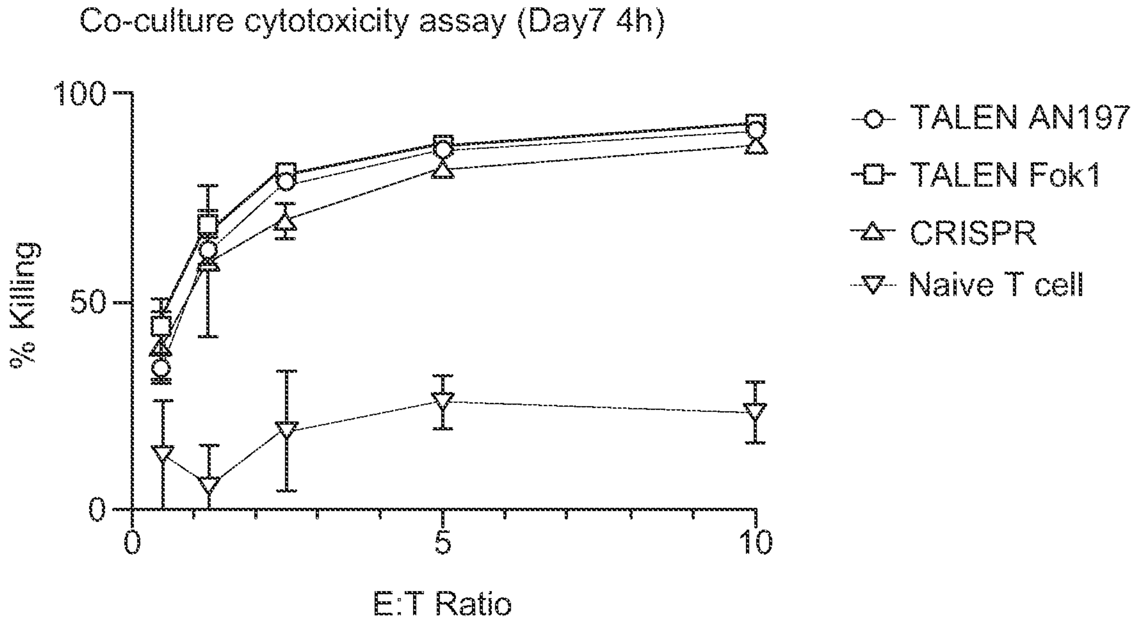
FIG. 16 is a graph showing the performance of CAR-T cells (or negative control (naïve T cells)), generated using a recombinant AN197 TALEN nuclease, a Fokl TALEN, or CRISPR. Cytotoxicity of CAR-T cells was measured by the in vitro eradication of CD19-positive NALM6 cells. A flow cytometry-based assay to quantify the number of viable, CD19+ cells. NALM6 (CD19+) cells were almost completely eliminated after 4 hr of co-culture at effector (E): target (T) ratios 10:1 and 5:1. Percentage of killed cells relative to naïve T cells are shown in the graph (mean of 3 experiments±SEM).
Figure 17A:
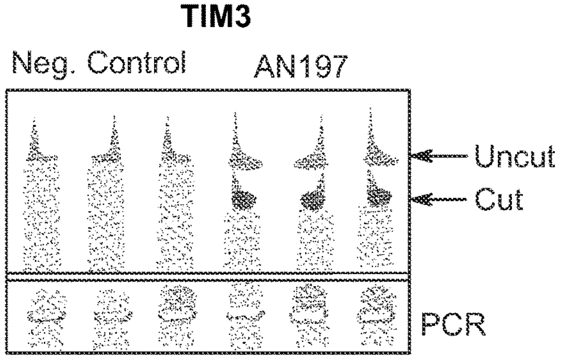
FIGS. 17A-17F depict TALEN AN197 editing efficiency at different targets in primary T cells.
Figure 17B:
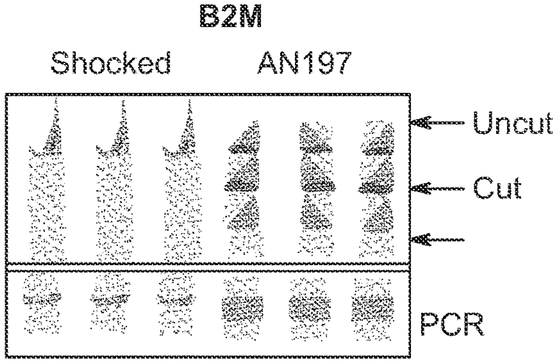
Figure 17C:
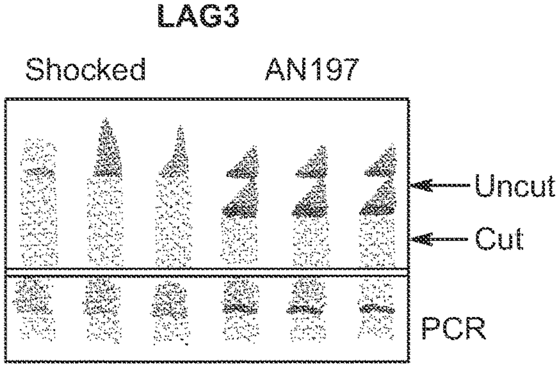
Figure 17D:
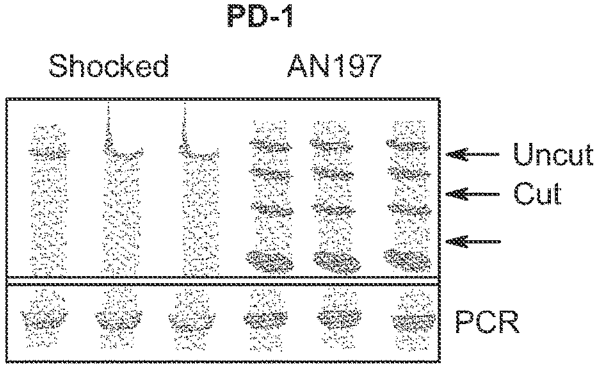
Figure 17E:
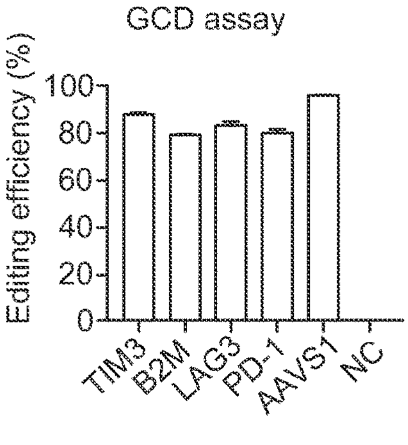
Figure 17F:
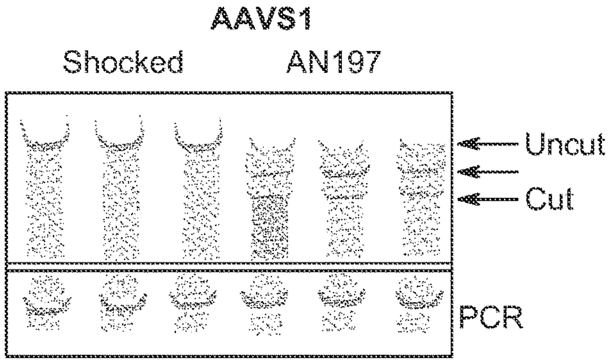
Figure 18A:
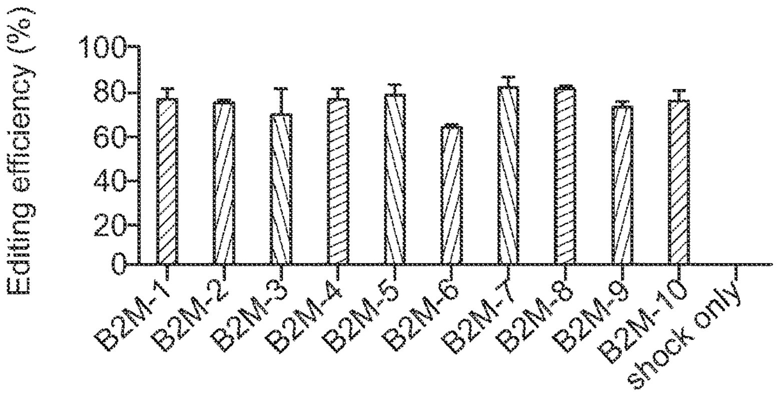
FIGS. 18A-18D are graphs depicting GCD editing efficiency results of TALEN AN197 target screening for B2M (FIG. 18A), TIM3 (FIG. 18B), LAG3 (FIG. 18C) and C2TA (FIG. 18D) in HEK 293 cells.
Figure 18B:
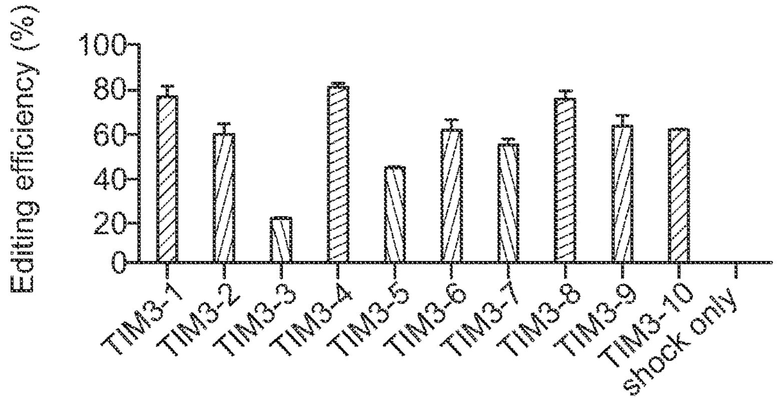
Figure 18C:
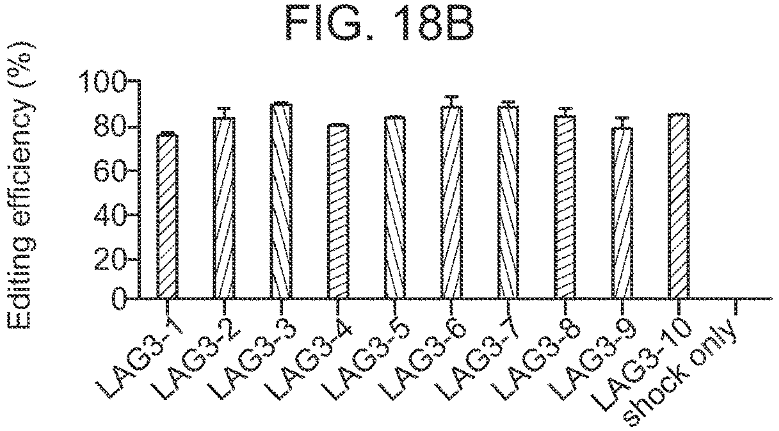
Figure 18D:
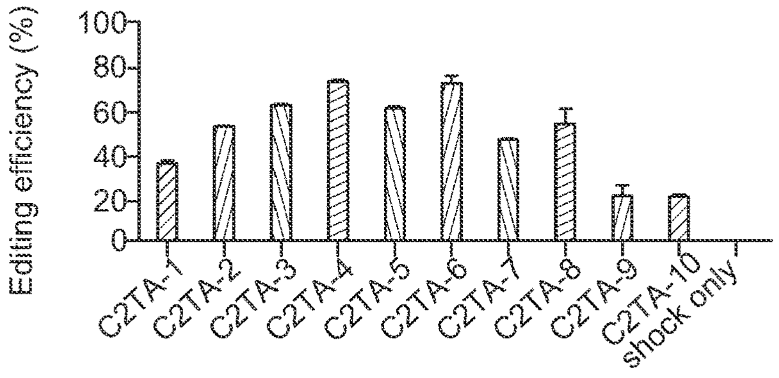

The Cytotoxicity of CAR-T cells was measured by the in vitro eradication of the CD19-positive NALM6 cell line. For this purpose, a flow cytometry-based assay was used to quantify the number of viable, CD19+ cells. NALM6 (CD19+) cells were almost completely eliminated after 4 hr of co-culturing at effector (E): target (T) ratios of 10:1 and 5:1. Percentage of cell killing, relative to naïve T cells, is shown in FIG. 16 (mean of 3 experiments±SEM).

Example 2. Identification of Alternative Nuclease (AN) by Screening

New alternative nucleases (ANs) were identified by screening the NCBI database for sequences having certain homology to the restriction endonuclease FokI or Clo51. As a result, 206 Alternative Nucleases (ANs) were identified and named as AN1-AN206, including three batches: AN14 (including AN1-AN14), AN50 (including AN15-AN64), and AN142 (including AN65-AN206). All these ANs were cloned and further screened for editing activity at AAVS1 target site, a target at which FokI TALENs achieve 100% editing efficiency (by Sanger sequencing).

Figure 2:
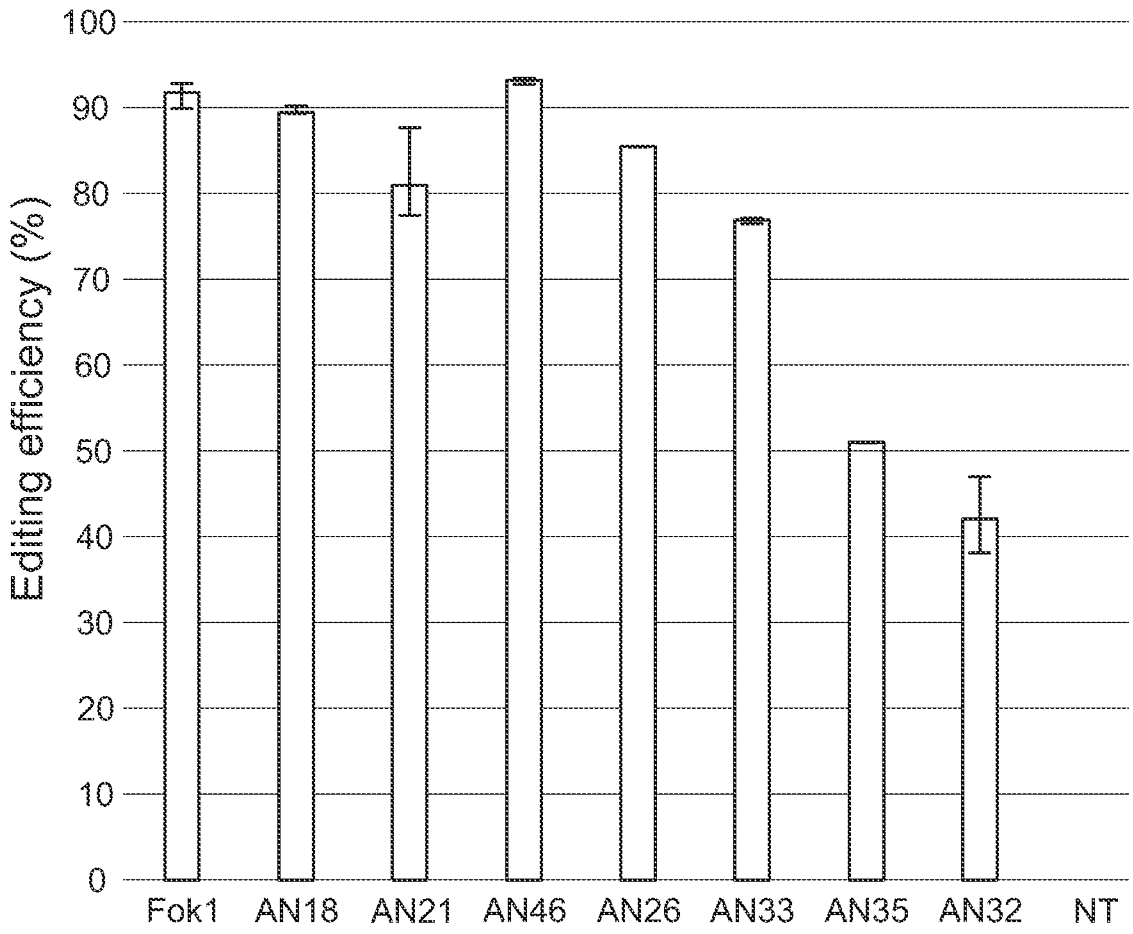
FIG. 2 is a bar graph showing gene editing efficiency (determined by GCD) for the top six alternative nucleases from the set of alternative nucleases depicted in FIG. 1. The alternative nucleases were tested again for repeatability in HEK293FT cells at the AAVS1 target. 100 ng of each mRNA (encoding a first and a second recombinant protein) as described herein (200 ng per recombinant protein pair) was used and transfected into cells using the Neon electroporator. Transfections were performed in duplicate and the editing efficiency was averaged. Percent identity of each alternative nuclease to FokI or Clo51 is displayed under the graph. The alternative nucleases exhibiting the highest editing efficiencies were designated with circles at the end of the bars.
Figure 3:
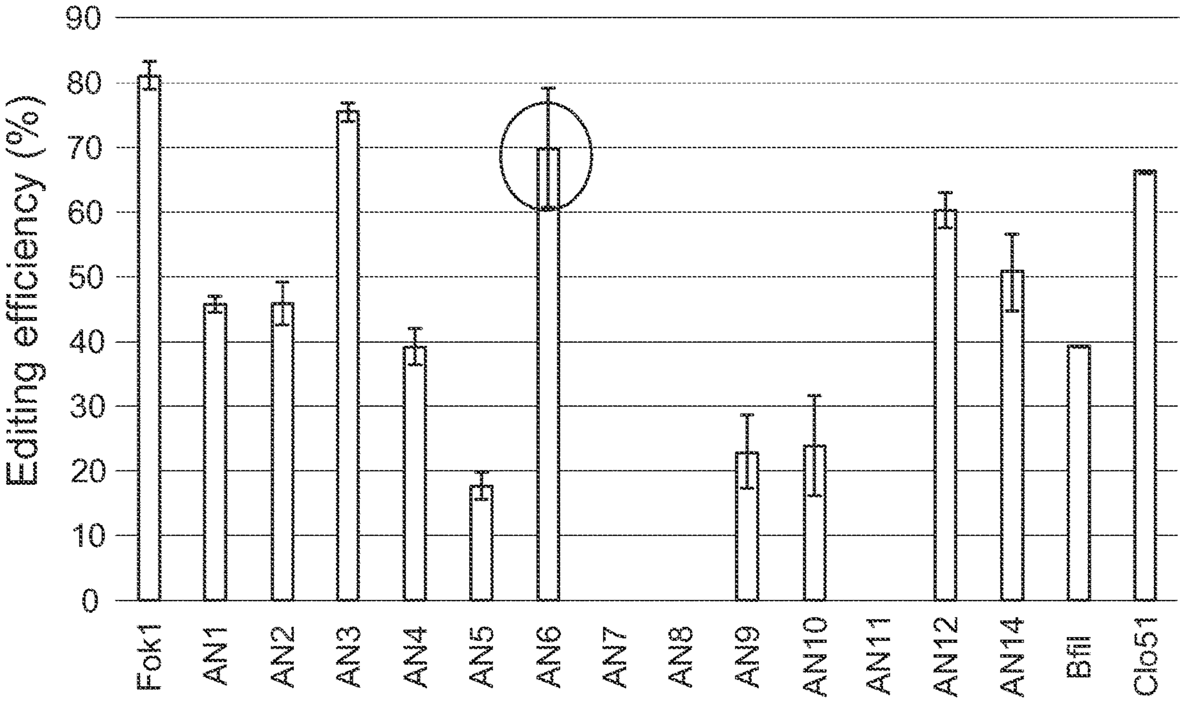
FIG. 3 is a bar graph showing gene editing efficiency (determined by GCD) for 14 alternative nucleases screened at the AAVS1 locus in HEK293FT cells as described in Examples 1 and 2. 100 ng of each mRNA (encoding a first and a second recombinant protein) as described herein (200 ng per recombinant protein pair) was used and transfected into cells using the Neon electroporator. Transfections were performed in duplicate and the editing efficiency was averaged. Percent identity of each alternative nuclease to Fokl or Clo51 is displayed under the bar graph. The alternative nucleases exhibiting the highest editing efficiencies were designated with circles at the end of the bars.

FIG. 1 shows an exemplary result of screening of 50 ANs ("the AN50 batch"), using the Genomic Cleavage Detection Kit, to assess cleavage efficiency of the AAVS1 (Adeno-Associated Virus Integration Site 1) target site. Top performing ANs, (e.g., the circled candidates, such as AN18, AN21, AN26, AN33, AN35, and AN46), which showed high editing efficiency, were re-tested to confirm the data repeatability (FIG. 2) and cloned into pCMV plasmid for sequence verification of the constructs.

Figure 4:
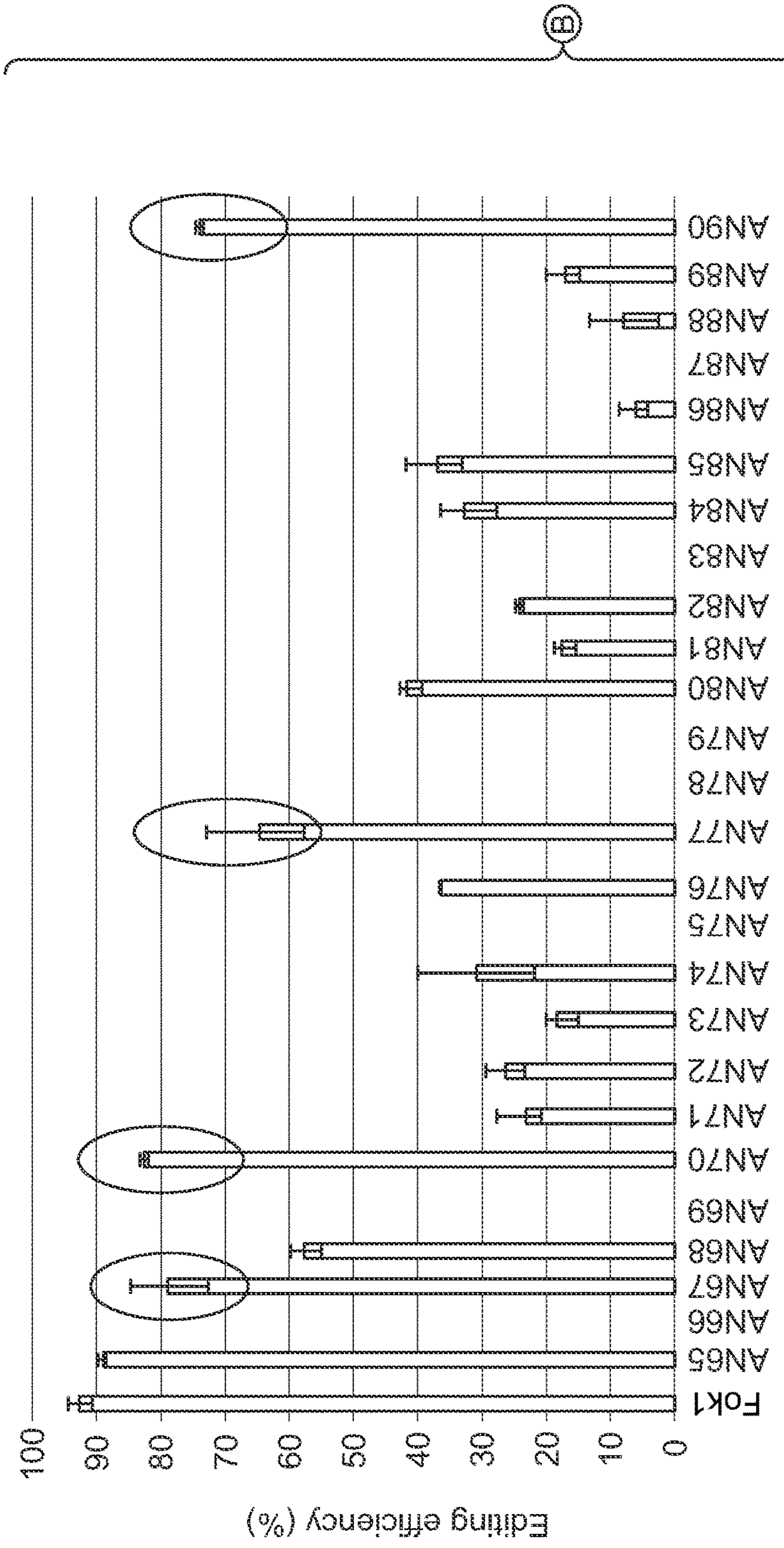
FIG. 4 is a bar graph showing gene editing efficiency (determined by GCD) for alternative nucleases screened at the AAVS1 locus in HEK293FT cells as described in Examples 1 and 2. 100 ng of each mRNA (encoding a first and a second recombinant protein) as described herein (200 ng per recombinant protein pair) was used and transfected into cells using the Neon electroporator. Transfections were performed in duplicate and the editing efficiency was averaged. Percent identity of each alternative nuclease to Fokl or Clo51 is displayed under the bar graph. The alternative nucleases exhibiting the highest editing efficiencies were designated with circles at the end of the bars.
Figure 4:
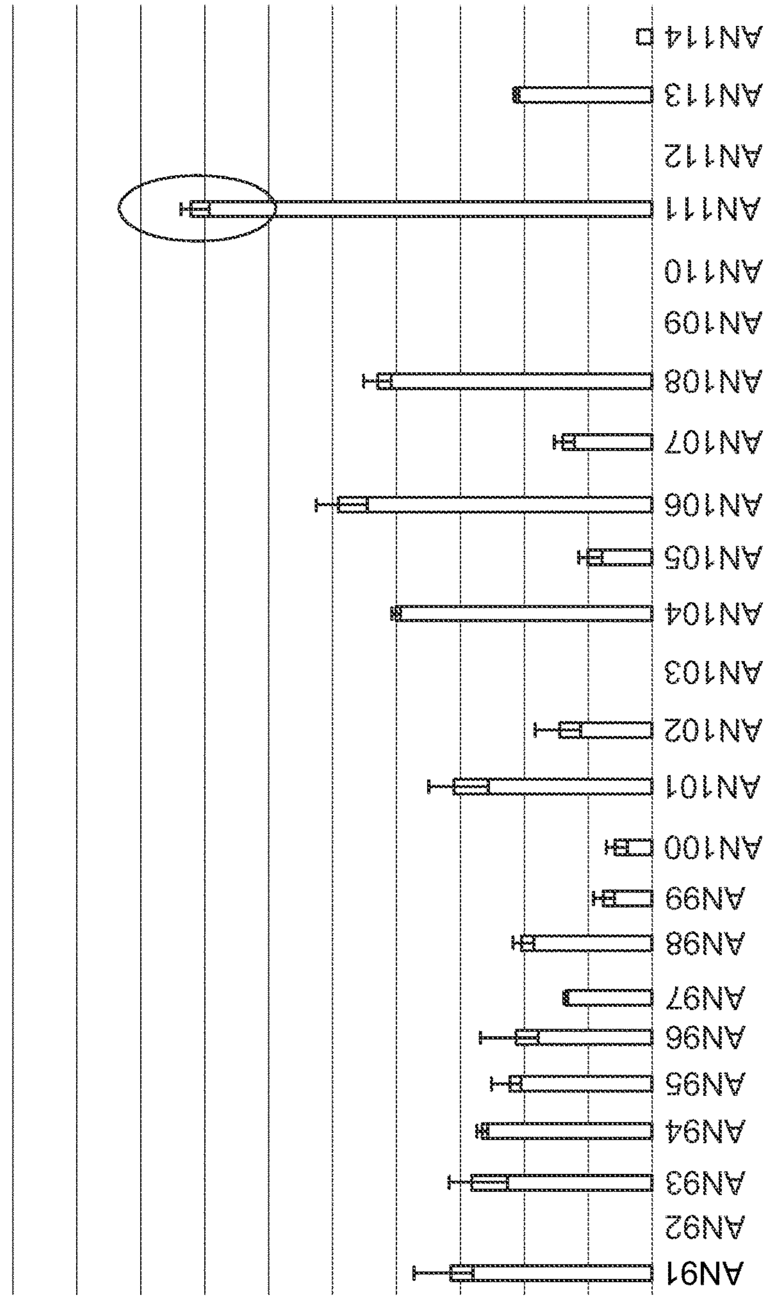
Figure 5:
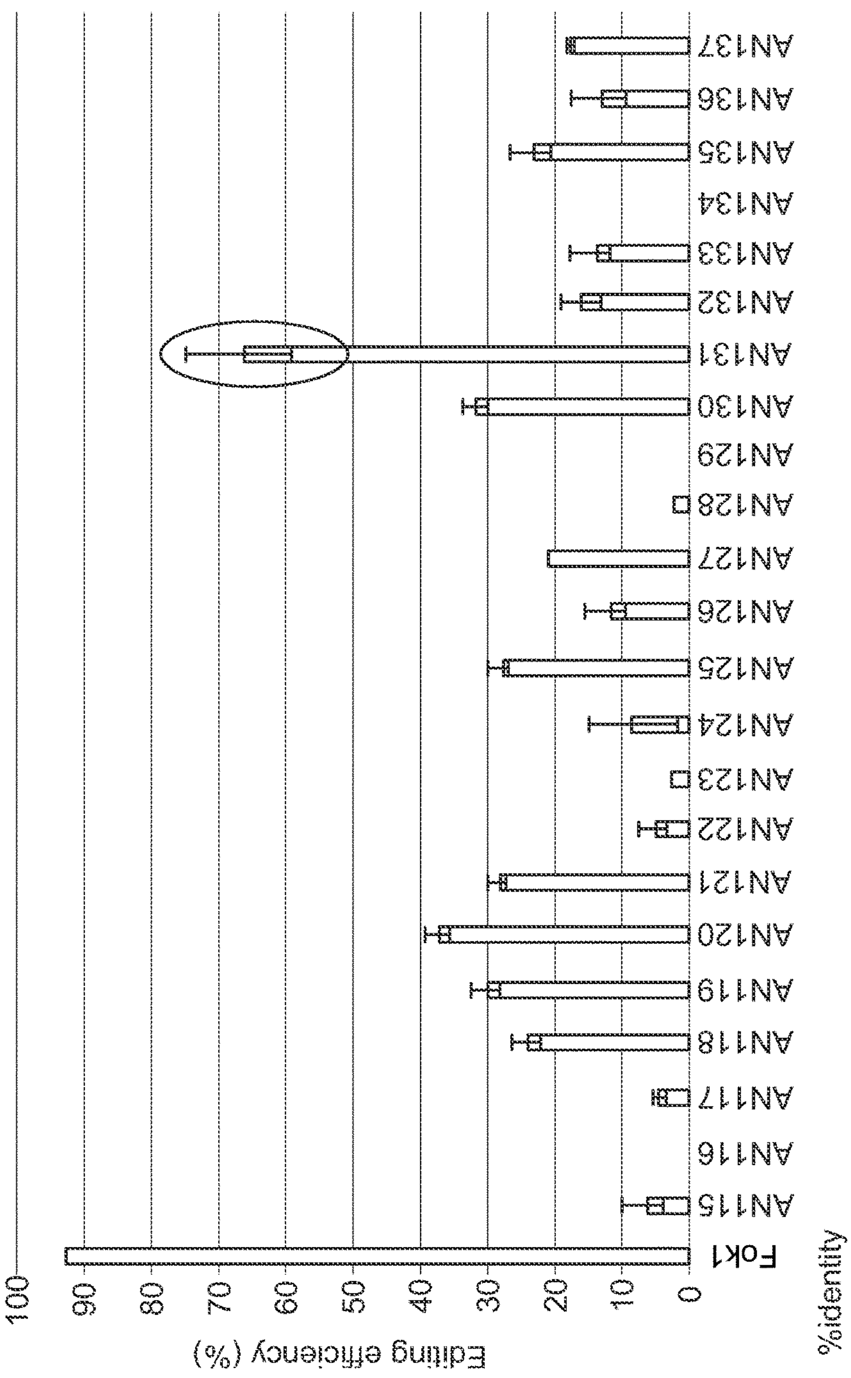
FIG. 5 is a bar graph showing gene editing efficiency (determined by GCD) for alternative nucleases screened at the AAVS1 locus in HEK293FT cells as described in Examples 1 and 2. 100 ng of each mRNA (encoding a first and a second recombinant protein) as described herein (200 ng per recombinant protein pair) was used and transfected into cells using the Neon electroporator. Transfections were performed in duplicate and the editing efficiency was averaged. Percent identity of each alternative nuclease to Fokl or Clo51 is displayed under the bar graph. The alternative nucleases exhibiting the highest editing efficiencies were designated with circles at the end of the bars.
Figure 5:
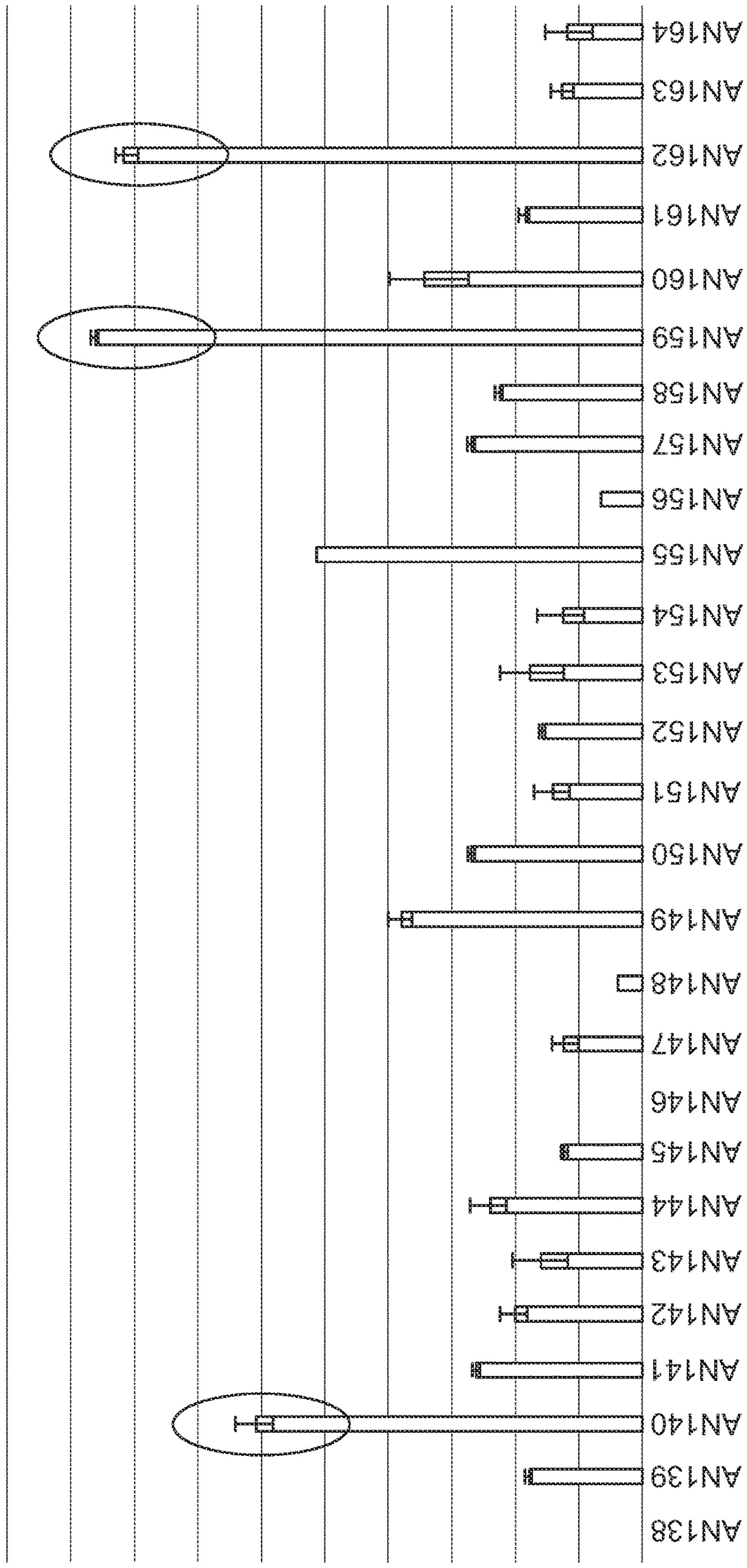
Figure 6:
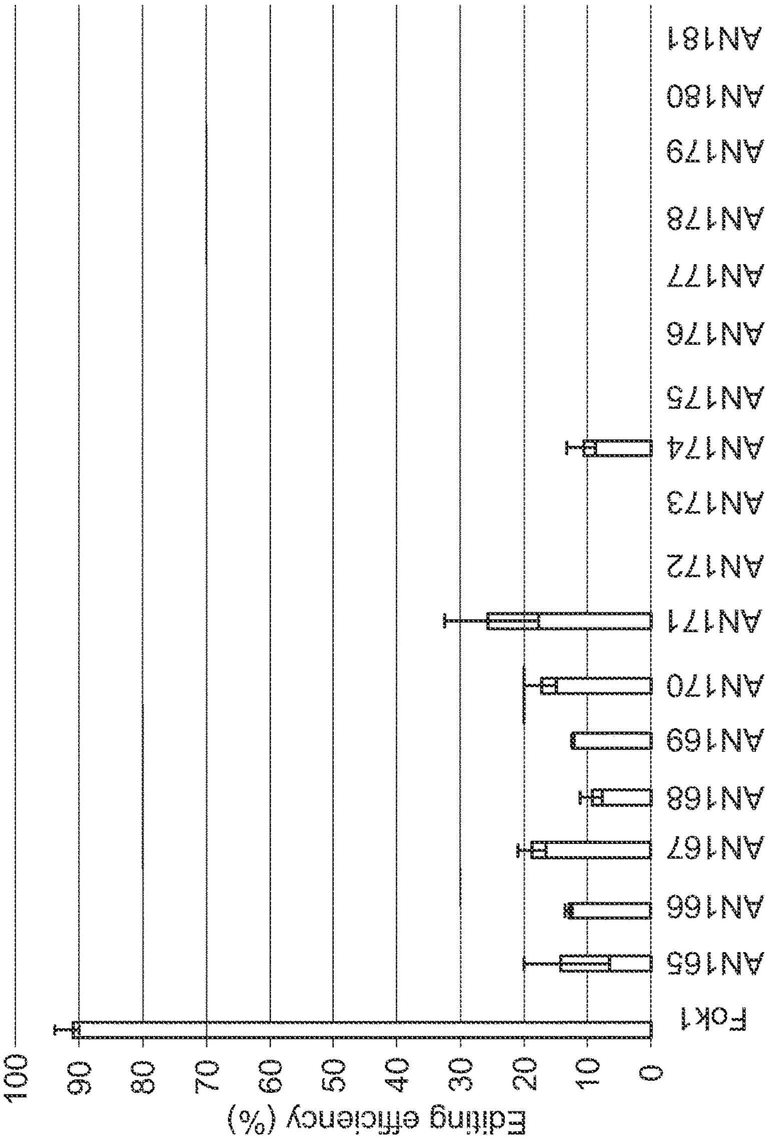
FIG. 6 is a bar graph showing gene editing efficiency (determined by GCD) for alternative nucleases screened at the AAVS1 locus in HEK293FT cells as described in Examples 1 and 2. 100 ng of each mRNA (encoding a first and a second recombinant protein) as described herein (200 ng per recombinant protein pair) was used and transfected into cells using the Neon electroporator. Transfections were performed in duplicate and the editing efficiency was averaged. Percent identity of each alternative nuclease to Fokl or Clo51 is displayed under the bar graph. The alternative nuclease exhibiting the highest editing efficiency was designated with a circle at the end of the bar.
Figure 6:
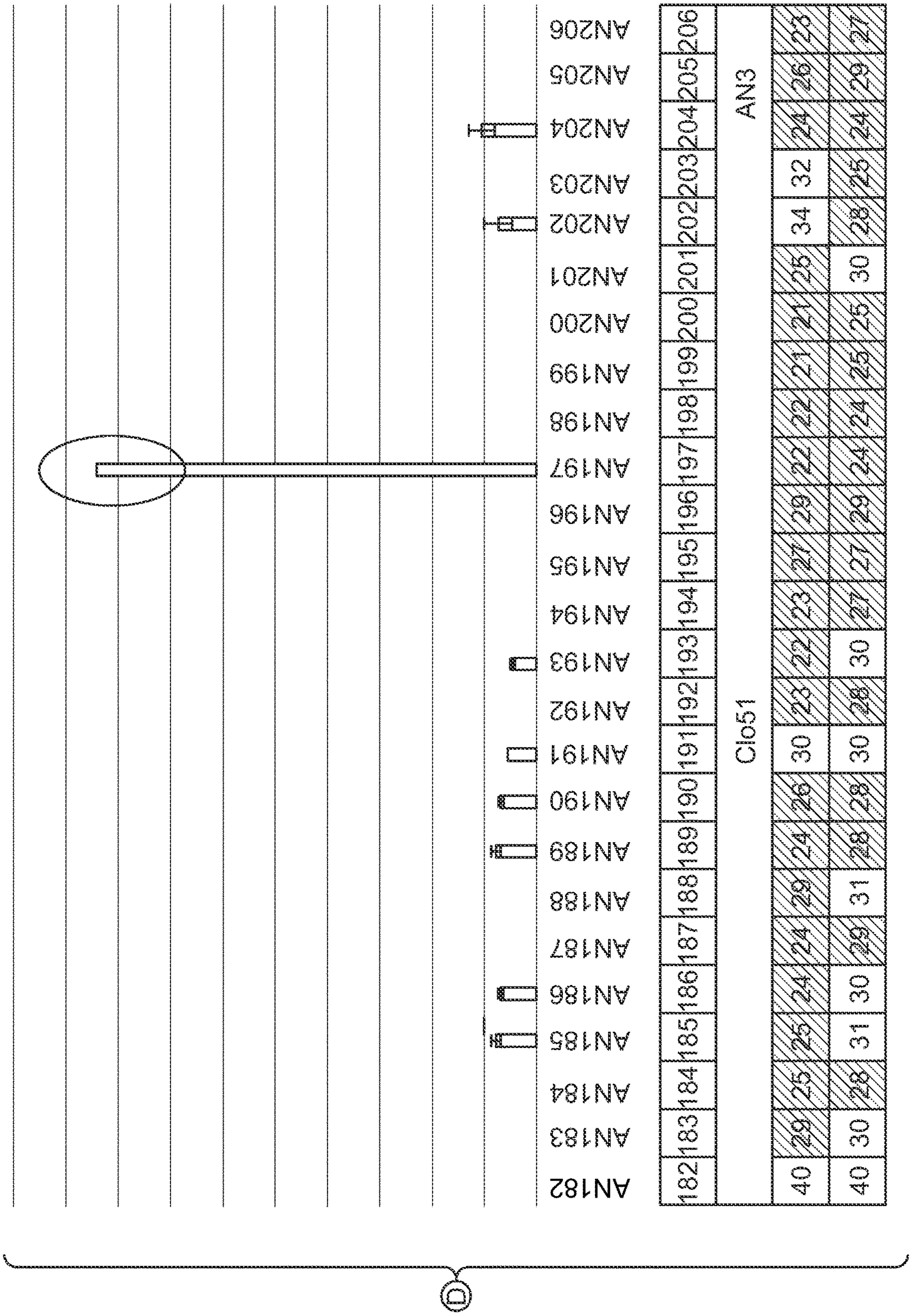
Figure 7:
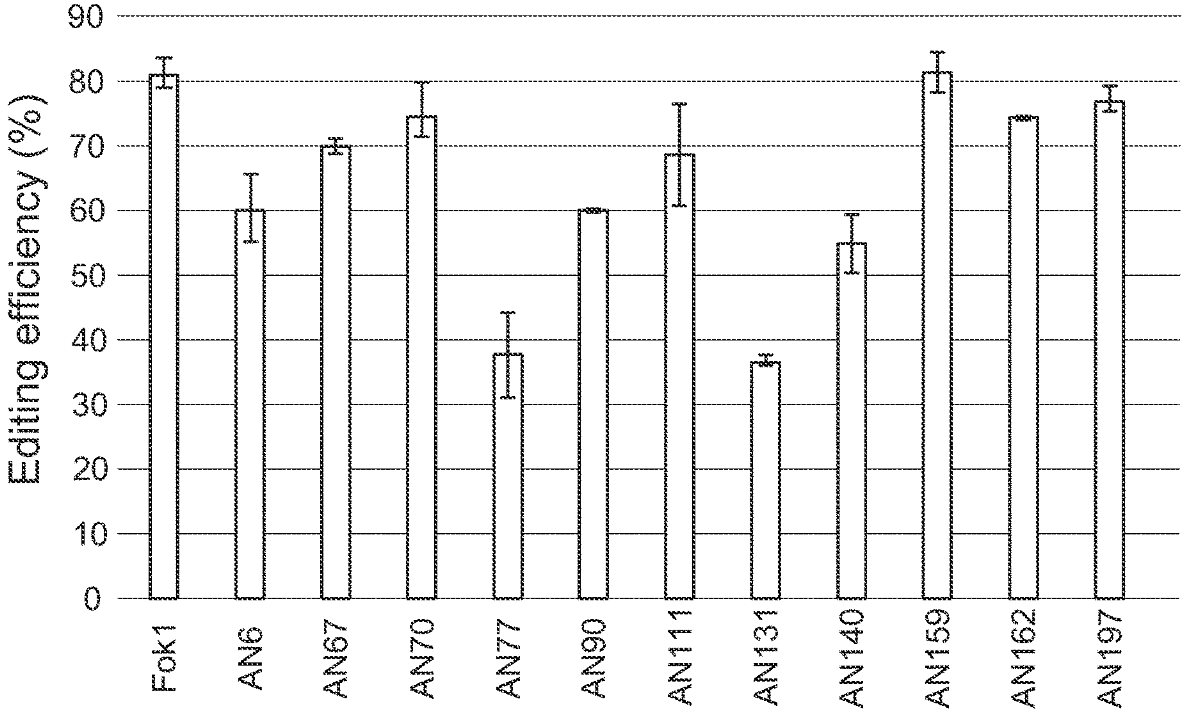
FIG. 7 is a bar graph showing gene editing efficiency (determined by GCD) for the top performing alternative nucleases shown in FIGS. 3-6. The alternative nucleases were tested again for repeatability in HEK293FT cells at the AAVS1 target. 100 ng of each mRNA (encoding a first and a second recombinant protein) as described herein (200 ng per recombinant protein pair) was used and transfected into cells using the Neon electroporator. Transfections were performed in duplicate and the editing efficiency was averaged. Percent identity of each alternative nuclease to Fokl or Clo51 is displayed under the graph.

Similarly, AN6 was identified as a top performing AN (FIG. 3), while AN67, AN70, AN77, AN90, AN111, AN131, AN140, AN159, AN162, and AN197 in the AN142 batch were identified as top performing ANs (FIGS. 4-6). FIG. 7 shows the retest result of these top performing ANs. The tables below the bar graphs in FIGS. 1-7 provide the percent identity of each of the AN sequence in the graph to FokI and Clo51.

Figure 8:
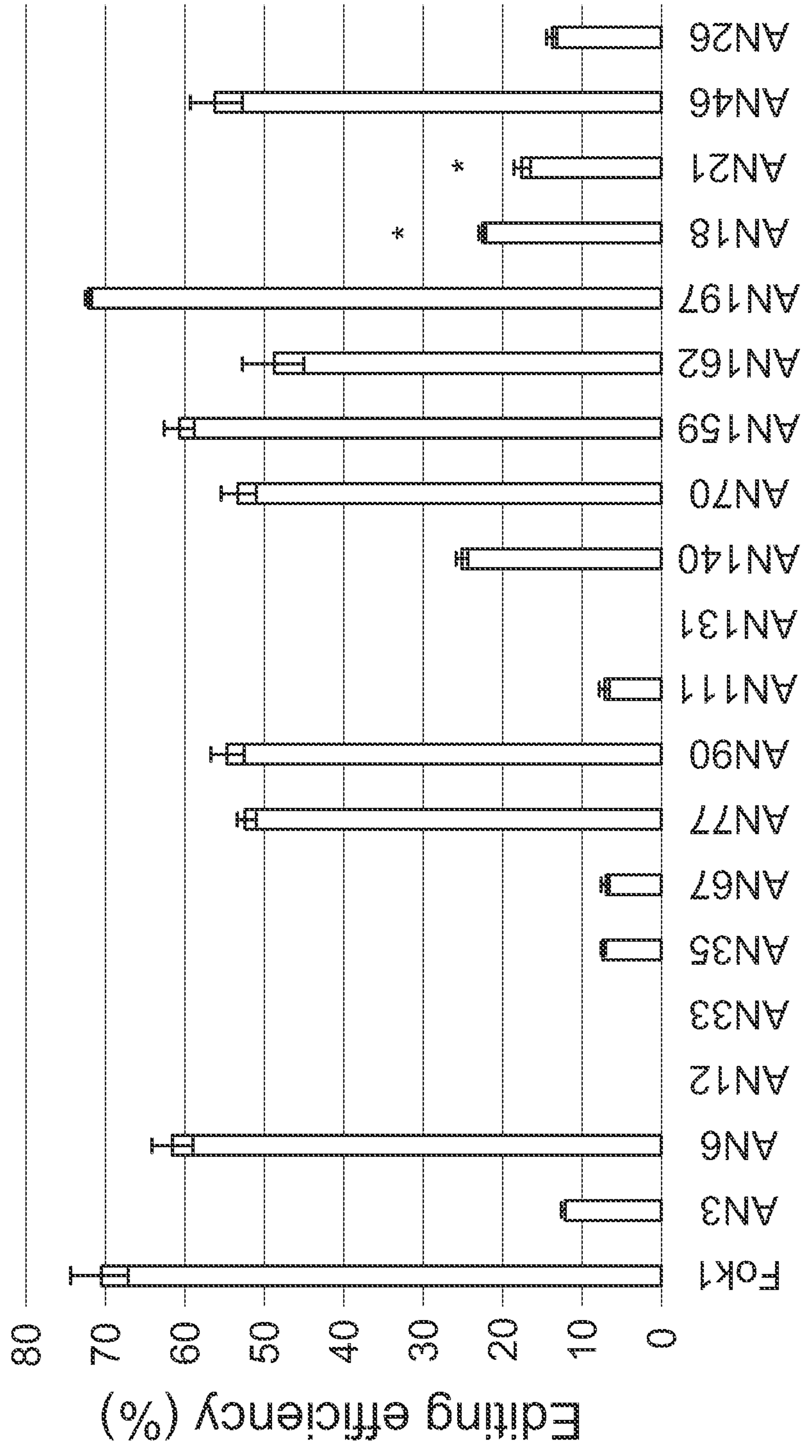
FIG. 8 is a bar graph showing gene editing efficiency (determined by GCD) for the top performing alternative nucleases showing in FIG. 7, tested at the TRAC48 locus. 100 ng of each mRNA (encoding a first and a second recombinant protein) as described herein (200 ng per recombinant protein pair) was used and transfected into cells using the Neon electroporator. Transfections were performed in duplicate and the editing efficiency was averaged. * indicates extreme toxicity shown post-transfection
Figure 9:
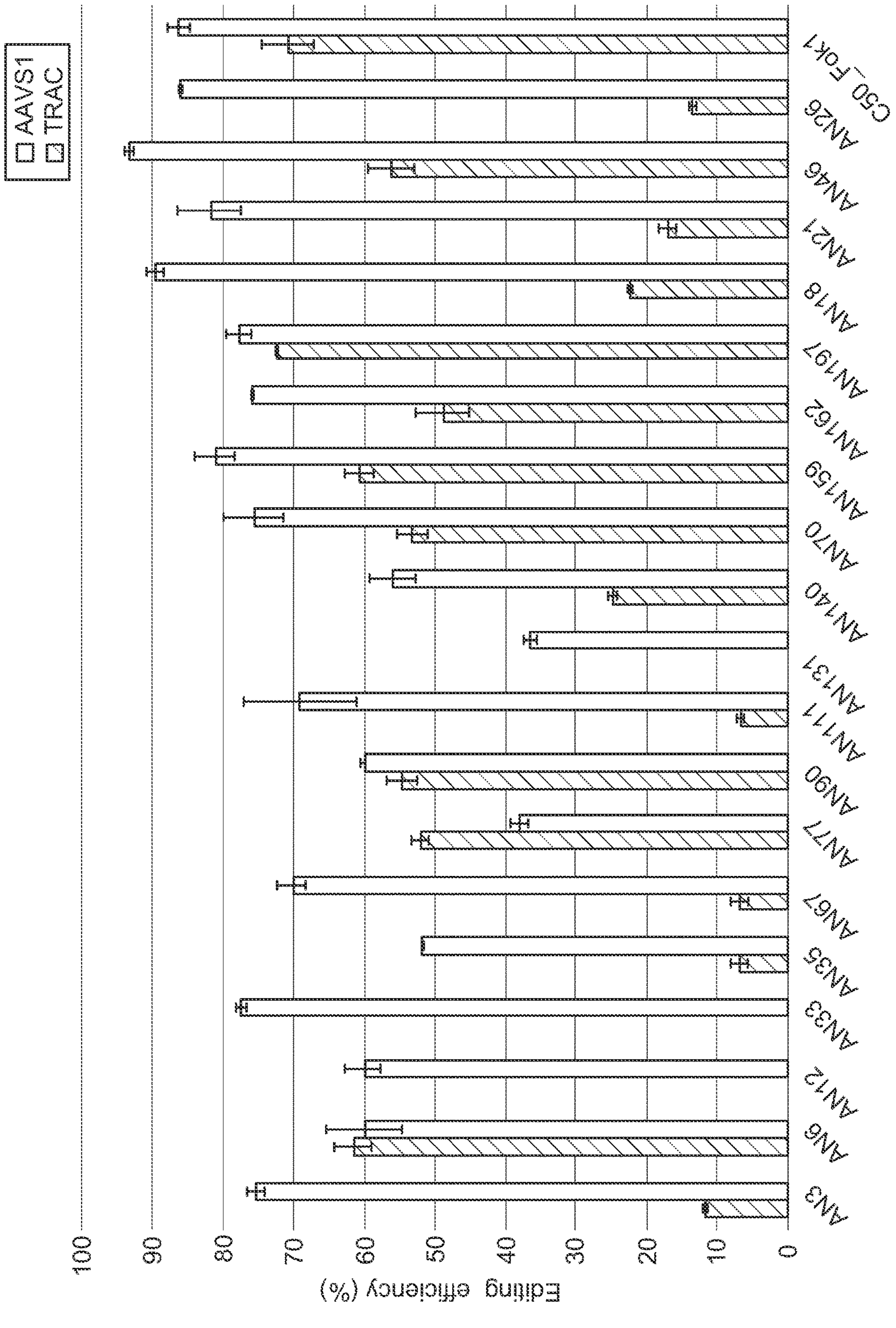
FIG. 9 is a bar graph showing the gene editing efficiency (determined by GCD) at AAVS1 versus TRAC48 for each indicated alternative nuclease.

These top performing ANs at the AAVS1 target site were then screened for their activity to the TRAC site, a target of relevance to the CAR-T therapy field (using TRAC48 TALENs). As shown in FIGS. 8-9, ANs acted differently at different targets. AN197 (SEQ ID NO:200) was shown to work well at both AAVS1 and TRAC48 sites (FIG. 9).

Figure 10A:
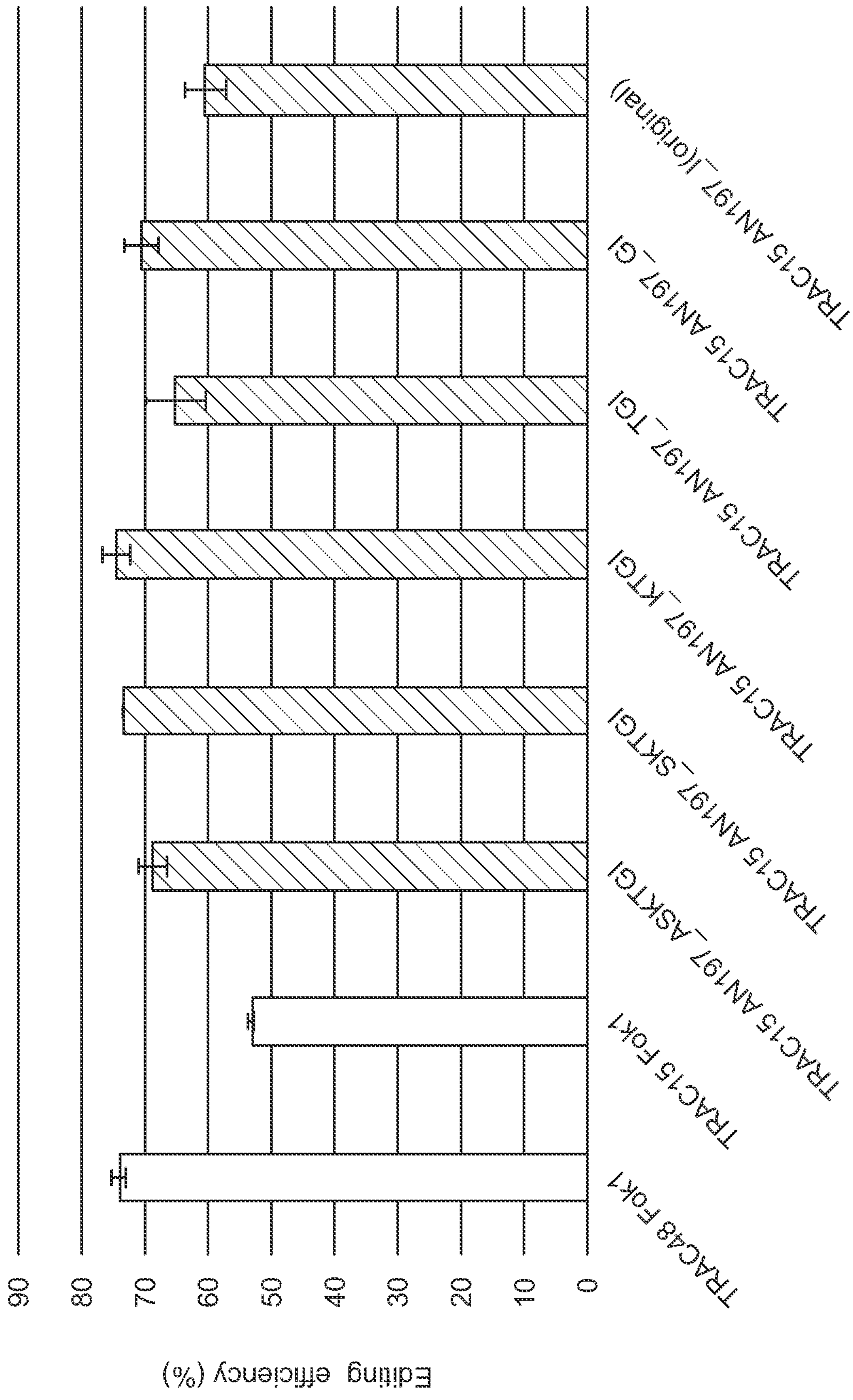
FIG. 10A is a bar graph showing gene editing efficiency of various versions of the AN197 TALEN recombinant protein, with different versions including successive amino acid additions at the N-terminus, as indicated, compared to a Fokl TALEN nuclease. The recombinant AN197 TALEN proteins were tested for gene editing efficiency (determined by GCD) at the TRAC48 and TRAC15 loci in HEK293 cells, as described in Examples 1 and 2.
Figure 10B:
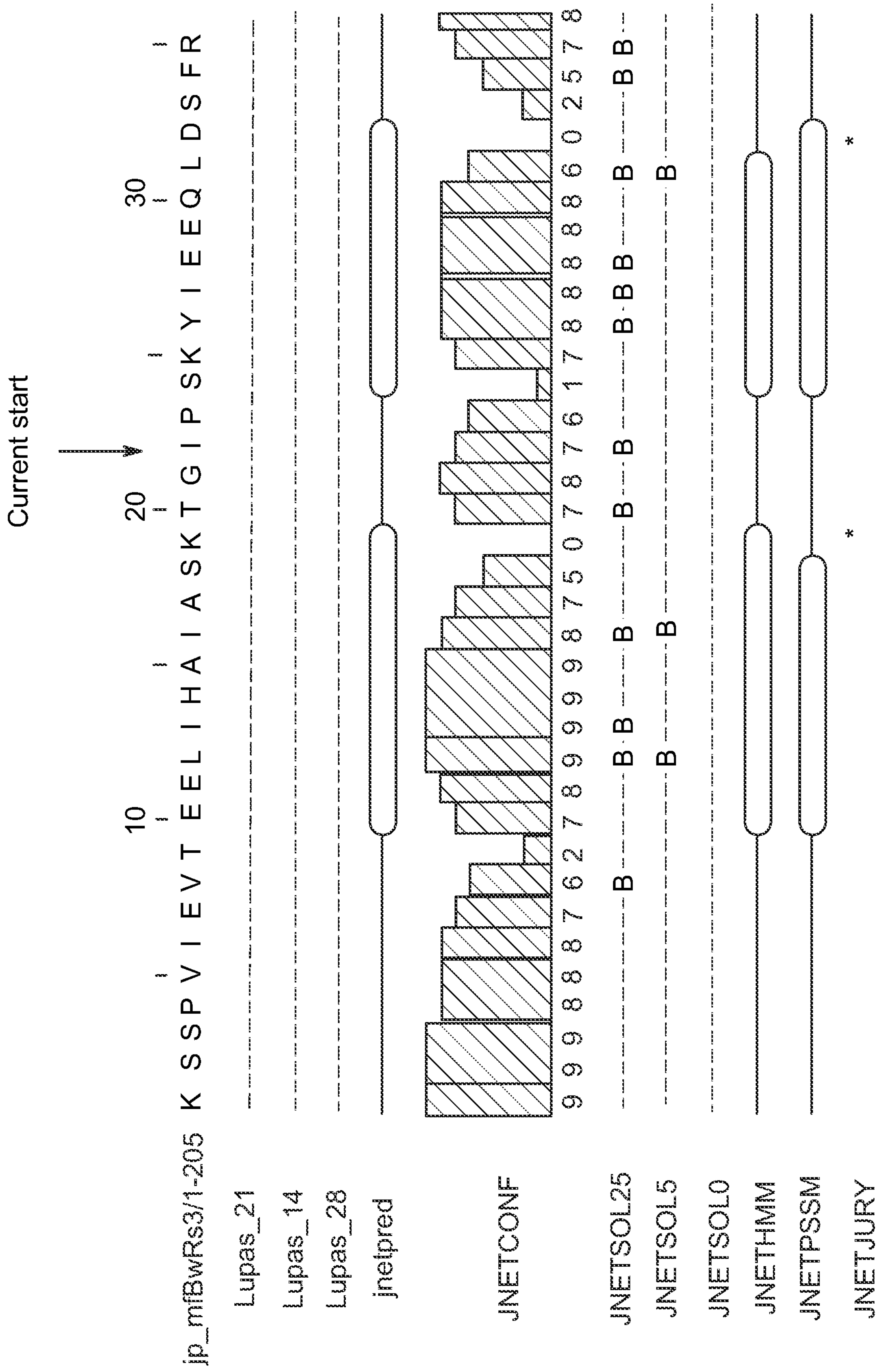
FIG. 10B is a screenshot from JPRED4 of the predicted secondary structure of the N-terminus of AN197 nuclease. The original construct used in the GCD assays shown in FIG. 6, FIG. 7 and FIG. 8 assays starts at the isoleucine indicated by the arrow. The constructs showing in FIG. 10A increase the N-terminus in succession up to the alanine in position 17.
Figure 11A:
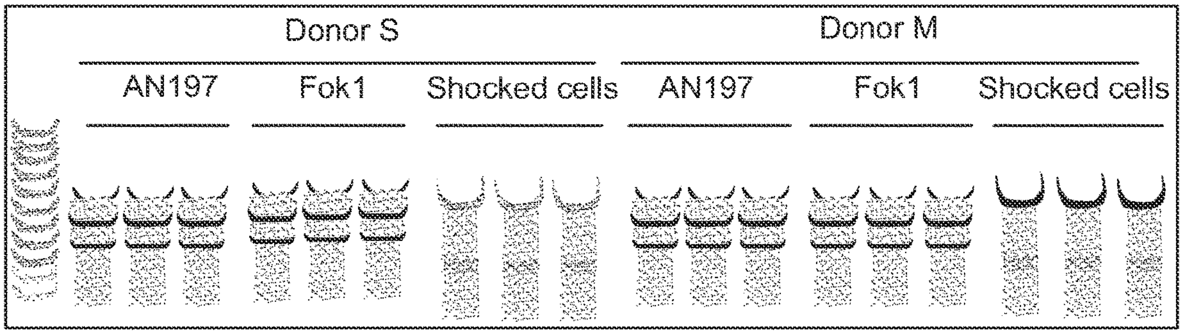
FIG. 11A shows an agarose gel depicting a genomic cleavage detection assay in primary T cells from two different donors (Donor S and Donor M). Primary T cells were electroporated with mRNA encoding an AN197 recombinant protein as described herein, an mRNA encoding Fokl TALEN, or negative control (shocked cells). The AN197 TALEN and Fokl TALEN nucleases were designed to target the human AAVS1 locus, as described in Examples 1 and 2.
Figure 11B:
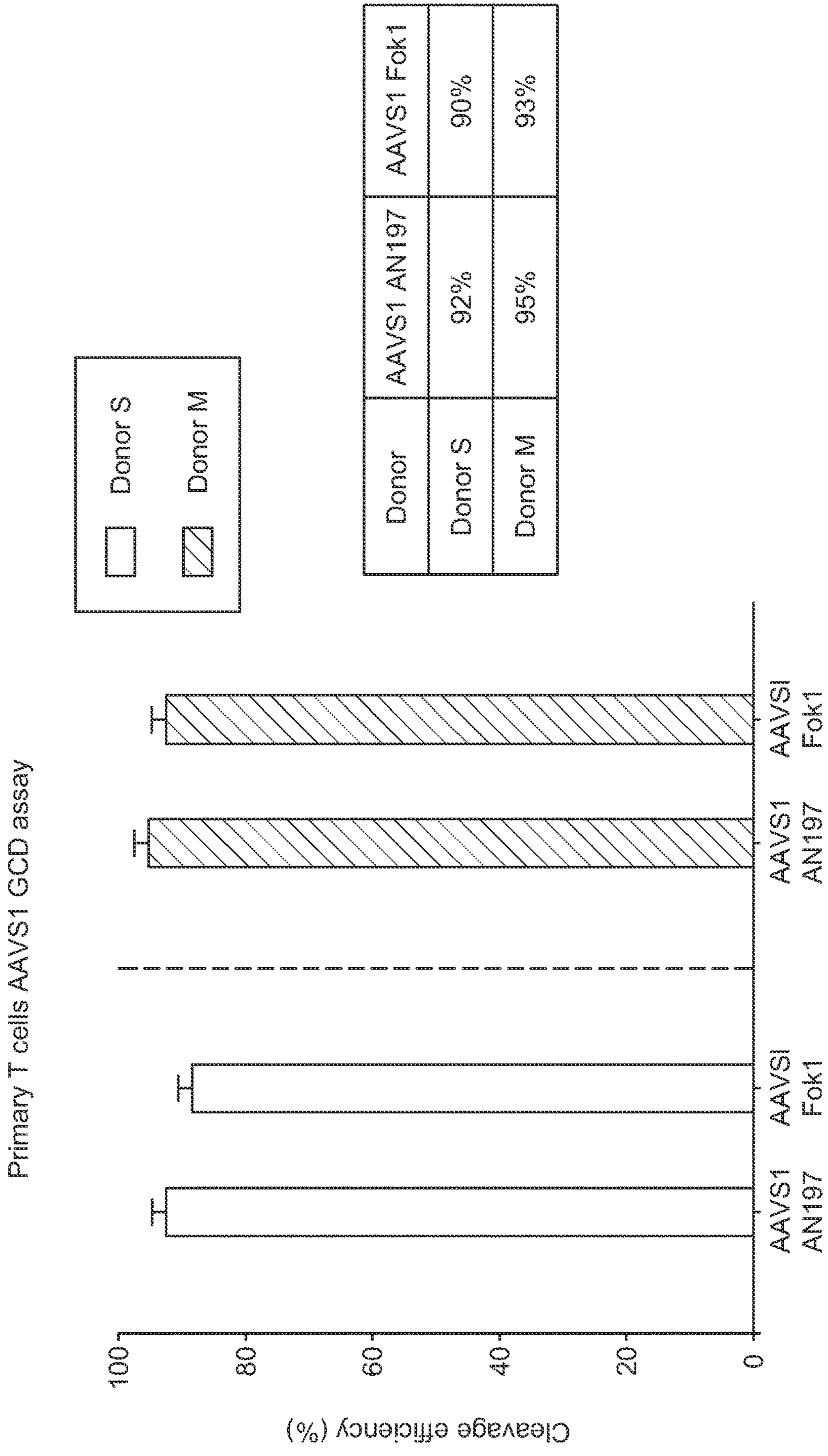
FIG. 11B is a bar graph and Table showing the percent cleavage efficiency data from FIG. 11A, as determined using ALPHAMIMAGER® Software. AN197 TALEN shows similar cleavage efficiency compared to Fokl TALEN at the AAVS1 locus.
Figures 12A, 12B, 12C, 12D, 12E, 12F:
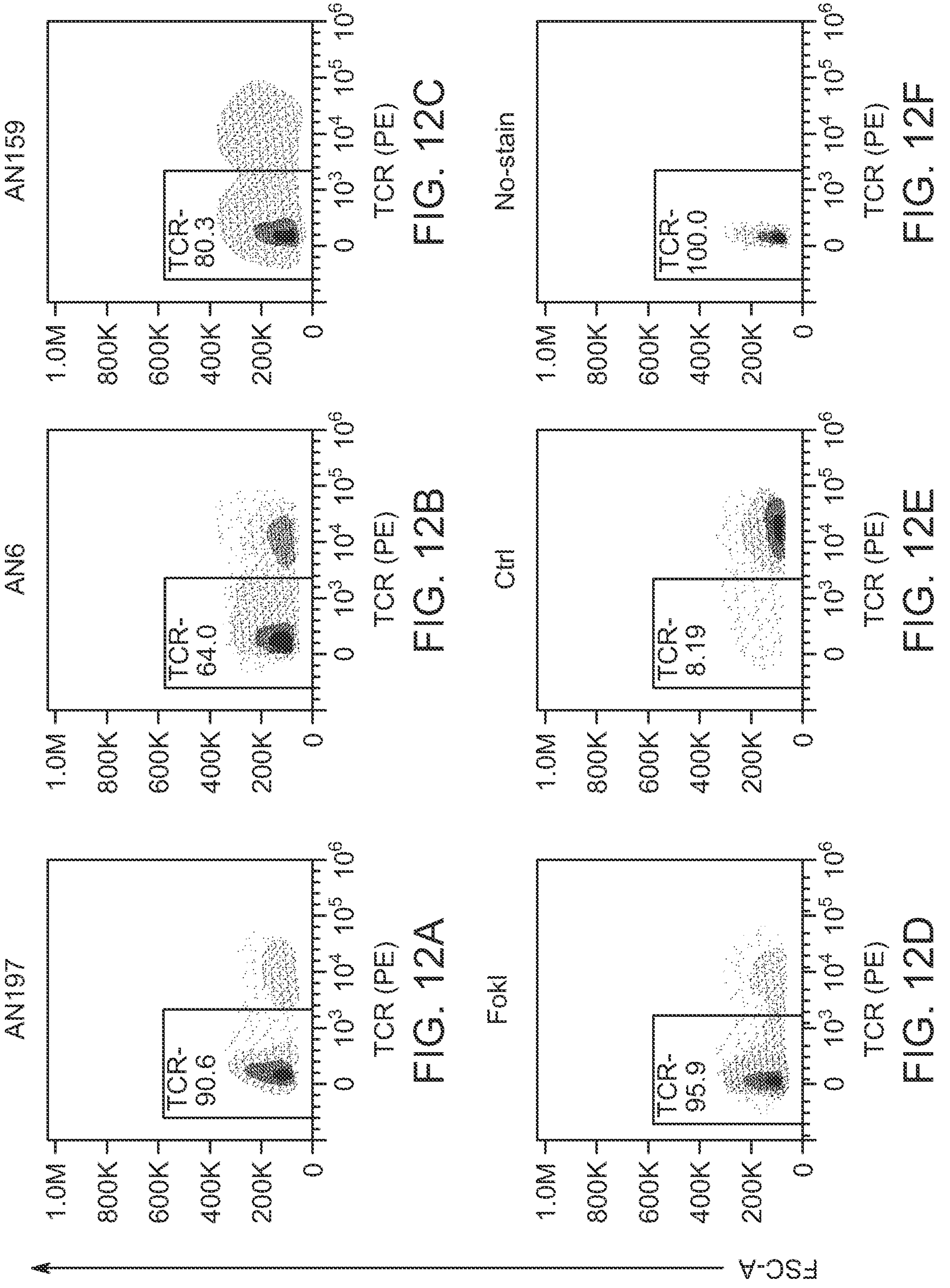
FIGS. 12A-12G are density plots depicting TCR knock-outs in activated T cells electroporated with mRNA encoding an AN197 recombinant protein operatively linked to a TALEN binding domain (FIG. 12A), mRNA encoding an AN6 recombinant protein operatively linked to a TALEN binding domain (FIG. 12B), mRNA encoding an AN159 recombinant protein operatively linked to a TALEN binding domain (FIG. 12C), mRNA encoding a Fokl TALEN (FIG. 12D) recombinant protein, or a negative control (FIG. 12E).
Figure 12G:
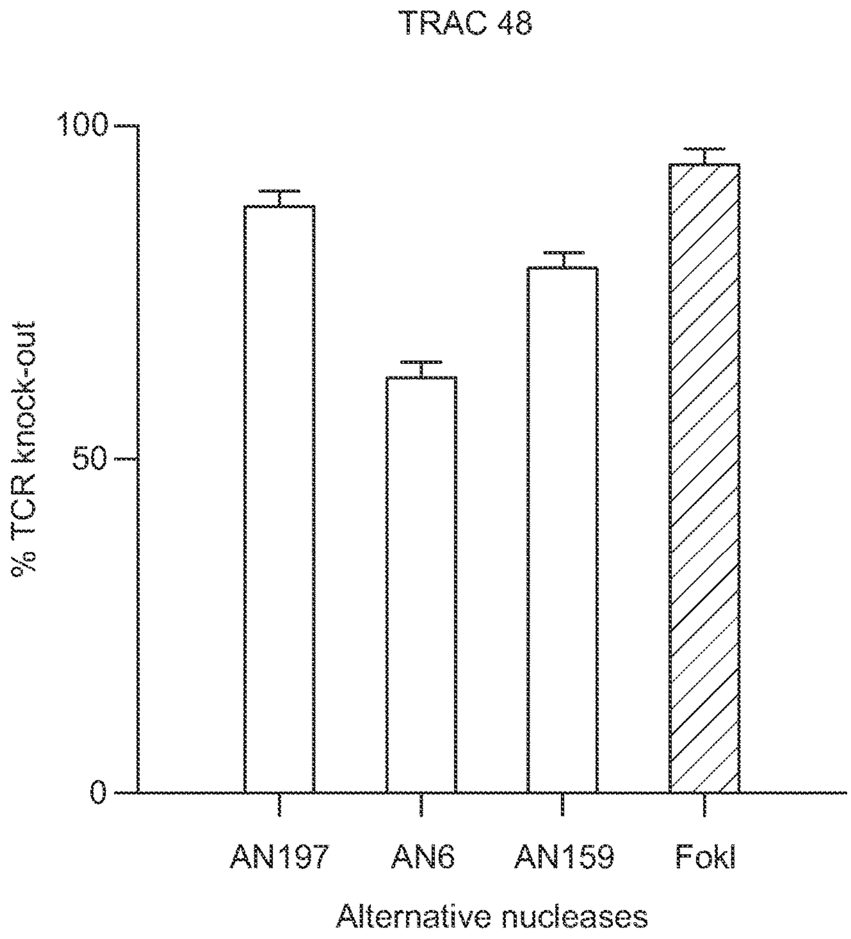
Figure 13:
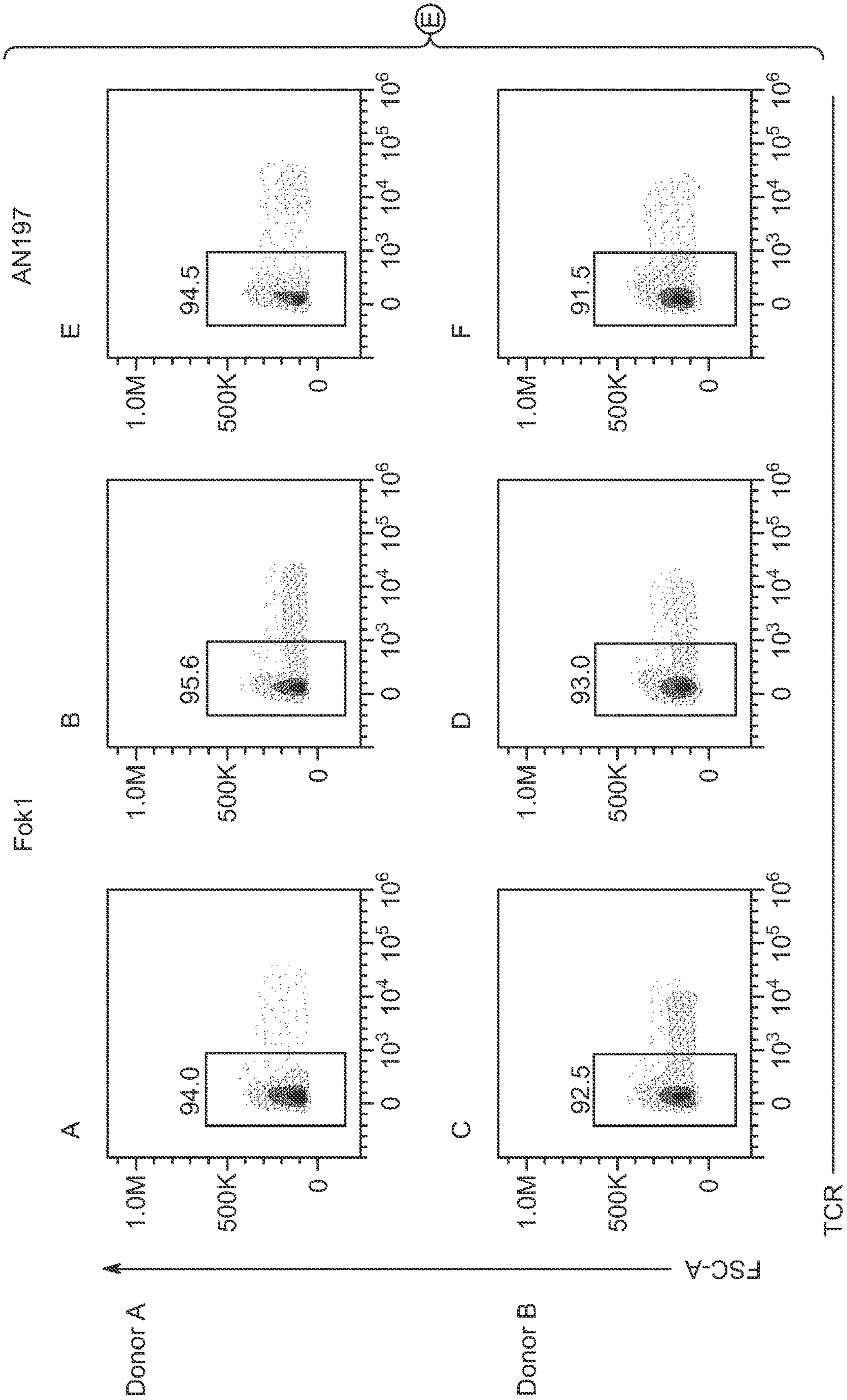
FIG. 13 depicts panels of density plots of TCR knock out results in primary T cells from two different donors. Panels A-D are density plots depicting TCR knock out in primary T cells from two different donors (Donor A, panels A-B) (Donor B, panels C-D) electroporated with mRNA encoding a Fokl TALEN nuclease targeting the TRAC48 locus. Panels E-H are density plots depicting TCR knock out in primary T cells from two different donors (Donor A, panels E, G)(Donor B, panels F, H) electroporated with mRNA encoding AN197 operatively linked to a TALEN binding domain targeting the TRAC48 locus. Panels I-L are density plots depicting TCR knock out in primary T cells from two different donors (Donor A, panels I, K)(Donor B, panels J, L) electroporated with a CRISPR Cas9/sgRNA targeting the TRAC48 locus. Panels M-N are density plots depicting a negative control (shock only) for TCR knock out in primary T cells from two different donors (Donor A, panel M)(Donor B, panel N). Panels O-P are density plots depicting a negative control (no stain) for TCR knock out in primary T cells from two different donors (Donor A, panel 0) (Donor B, panel P). The table shows the TCR knock out efficiency data from panels A-P.
Figure 13:
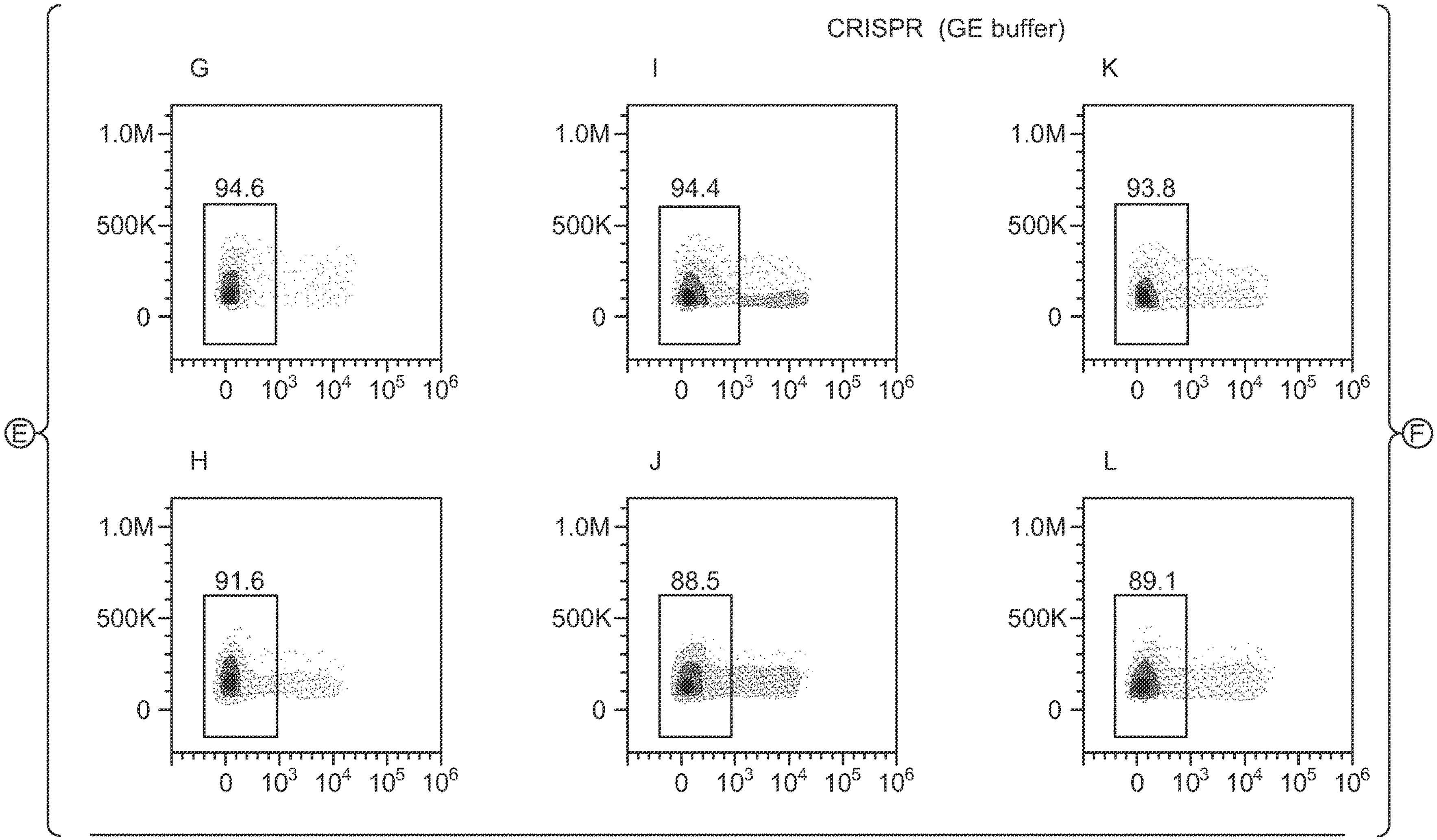
Figure 13:
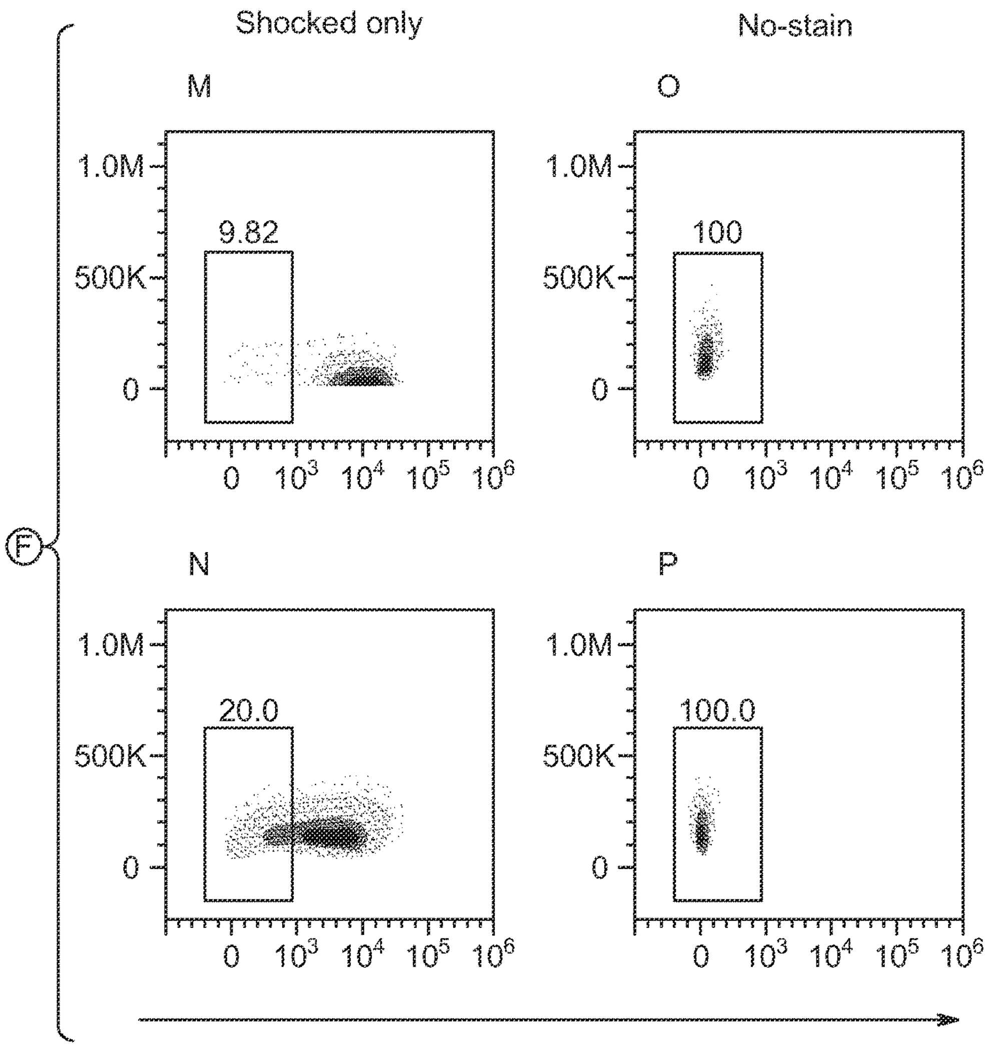
Figure 14:
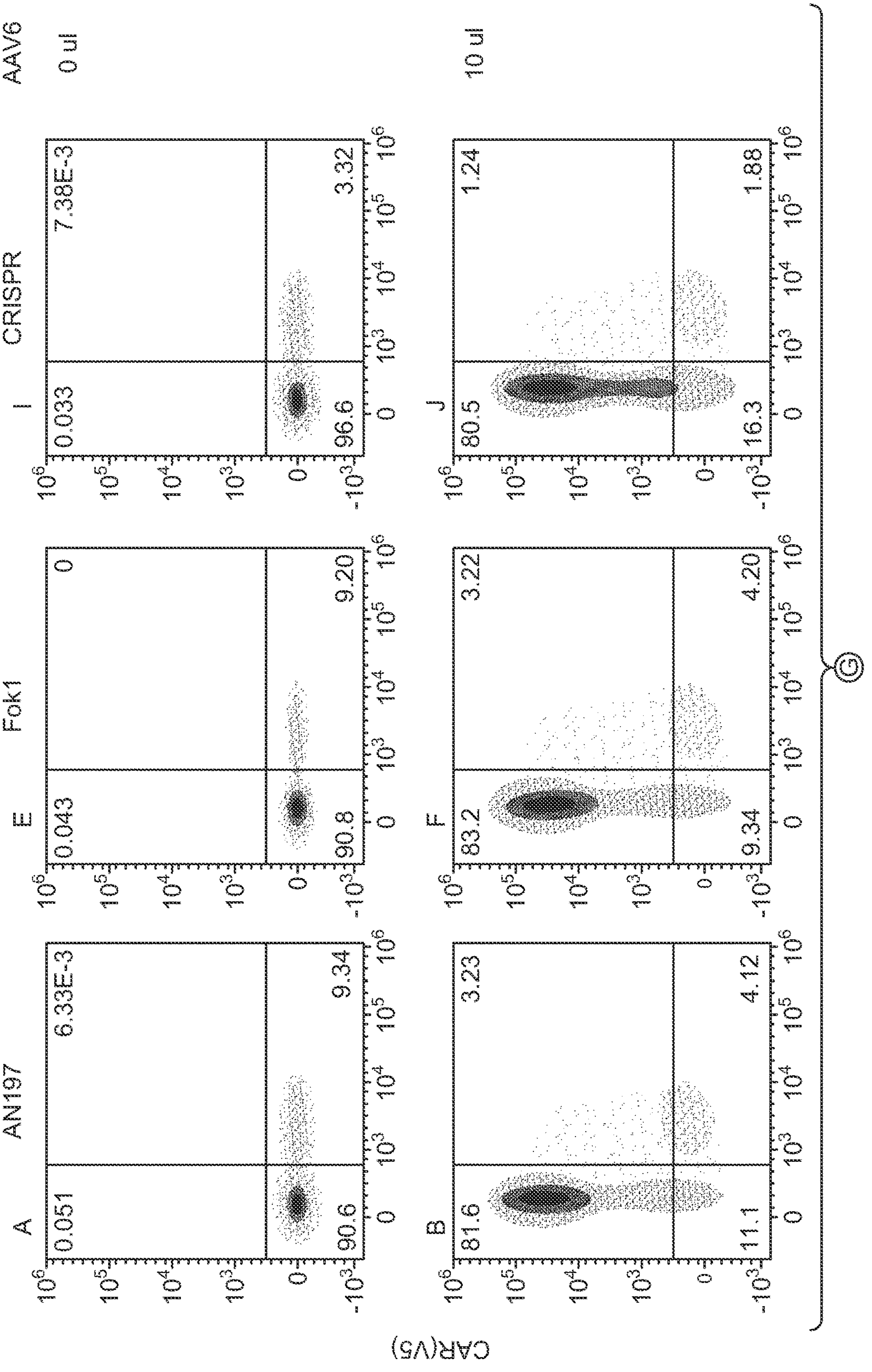
FIG. 14 depicts panels of density plots depicting TCR knock out (panels A, E, I) and CAR knock in, using increasing concentration of viral particles harboring donor DNA (10 μl: panels B, F, J) (20 μl: panels C, G, K) (30 μl: panels D, H, L)) in cells transfected with AN197 operatively linked to a TALEN binding domain (panels A-D), Fokl TALEN (panels E-H), or CRISPR (panels I-L).
Figure 14:
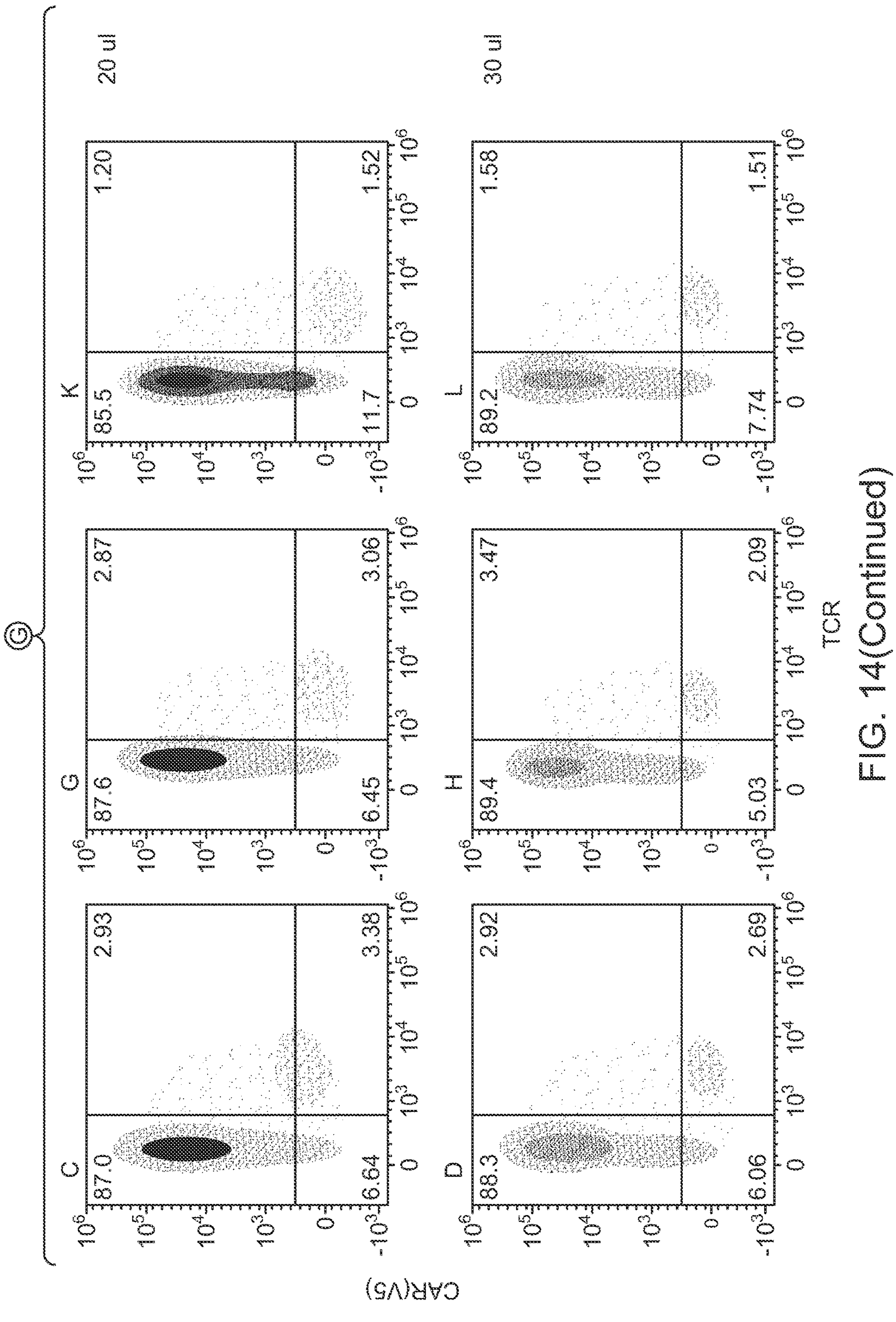

The AN197 recombinant protein used in the experiments depicted in FIGS. 6-9 was further optimized by changing its N-terminus sequence. As shown in FIGS. 10A and 10B, the optimization extends the N-terminus of original AN197 ("AN197_I" in FIG. 10A, SEQ ID NO: 200) up to 5 amino acids longer. As shown in FIG. 10A, AN197_ASKTGI extends the N-terminus by 5 amino acids (SEQ ID NO: 299), AN197 SKTGI extends the N-terminus by 4 amino acids (SEQ ID NO: 298), AN197_KTGI extends the N-terminus by 3 amino acids (SEQ ID NO: 297), AN197_TGI extends the N-terminus by 2 amino acids (SEQ ID NO: 282), and AN197_GI extends the N-terminus by 1 amino acid (SEQ ID NO: 296). The optimized AN197 recombinant proteins were tested for their editing efficiency at TRAC15, a target hard to edit for FokI. It was shown that the original and optimized AN197 recombinant proteins had better editing efficiency than FokI at the TRAC15 site (FIG. 10A). One exemplary AN197 amino acid sequence is shown in SEQ ID NO: 282. Other exemplary AN197 amino acid sequences are shown in SEQ ID NOS: 296-299. The optimized AN197-based nucleases displayed similar editing efficiencies.

Several top performing ANs were further tested in human primary T cells for their editing efficiency (e.g., at the AAVS1 or TRAC48 site). A GCD assay as described elsewhere herein was used to determine the editing efficiency on the AAVS1 site, while flow cytometry was used for testing the editing on the TRAC48 site.

Figure 15:
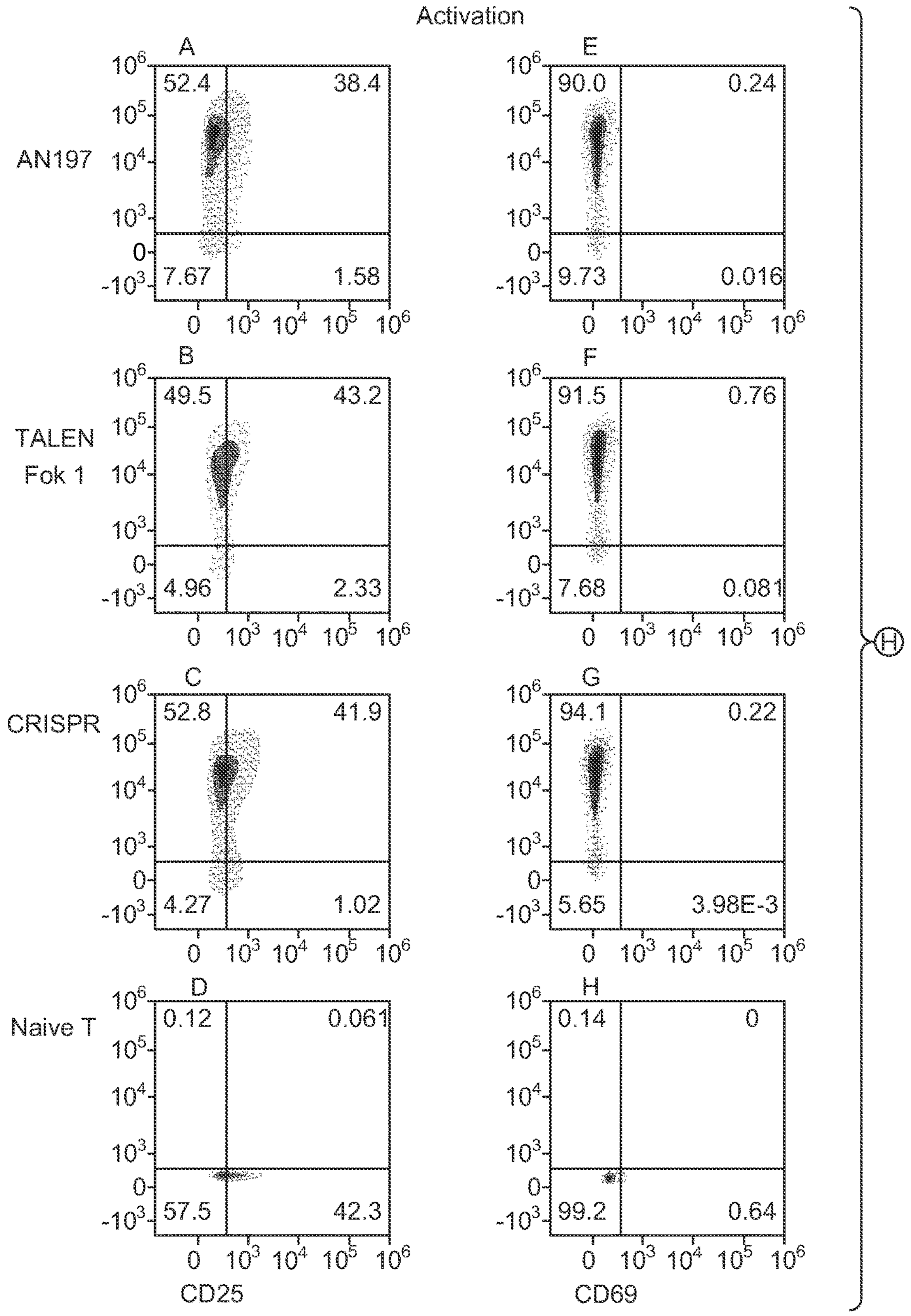
FIG. 15 depicts panels of density plots depicting cells stained for markers indicative of T cell activation (CD26: panels A-D)(CD49: panels E-H), Memory T cells (CD95: panels I-L)(CD42L: panels M-P), T cell exhaustion (LAG-3: panels Q-T)(PD-1: panels U-X)(TM3: panels Y-AB); TCR (panels AC-AF); and CD4/CD8 (panels AG-AJ) in T cells transfected with AN197 operatively linked to a TALEN binding domain mRNA (panels A, E, I, M, Q, U, Y, AC, AG), Fokl TALEN mRNA (panels B, F, J, N, R, V, Z, AD, AH) or CRISPR (panels C, G, K, O, S, W, AA, AE, AI). Panels D, H, L, P, T, X, AB, AF, and AJ are naïve T cells.
Figure 15:
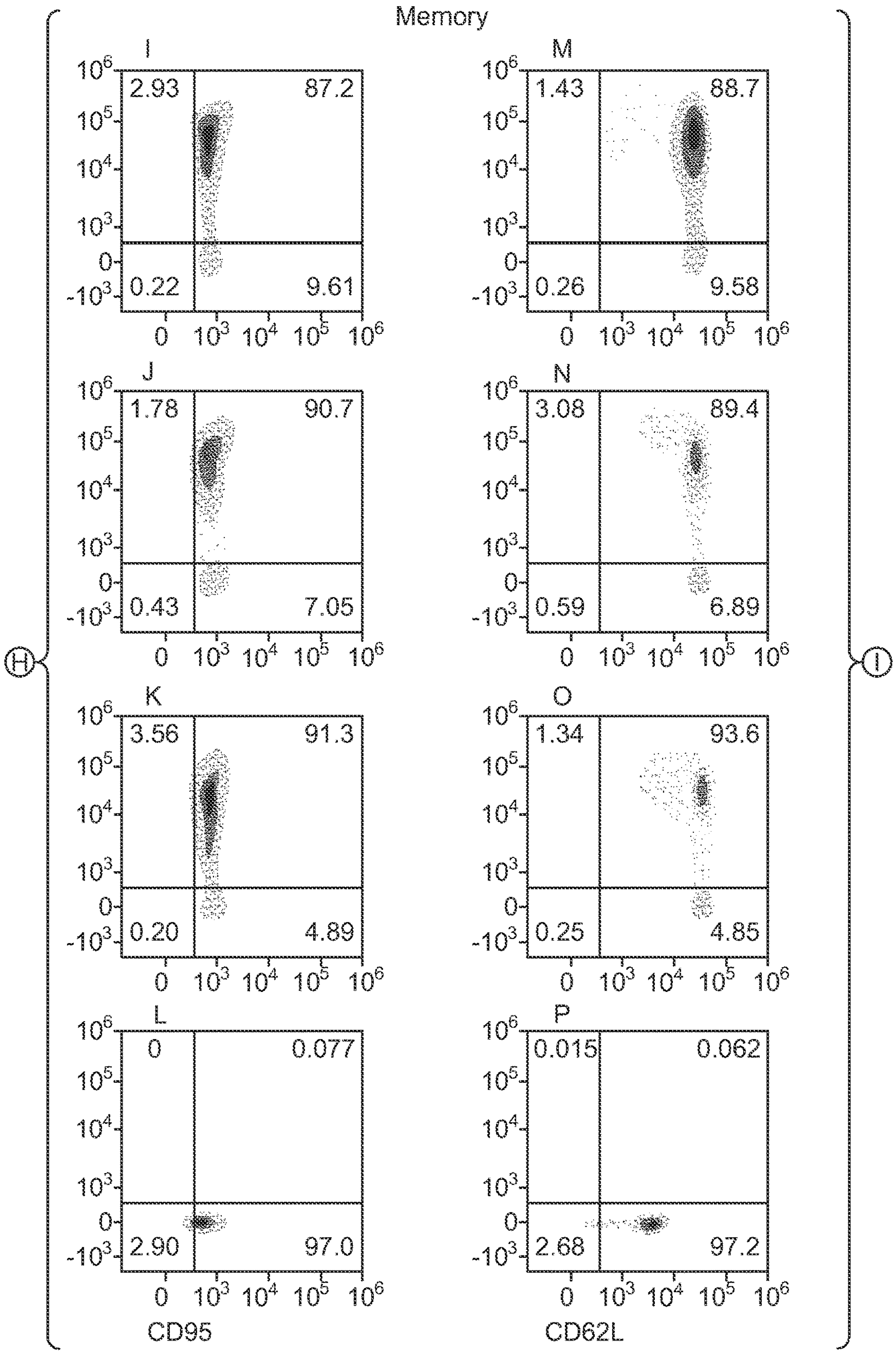
Figure 15:
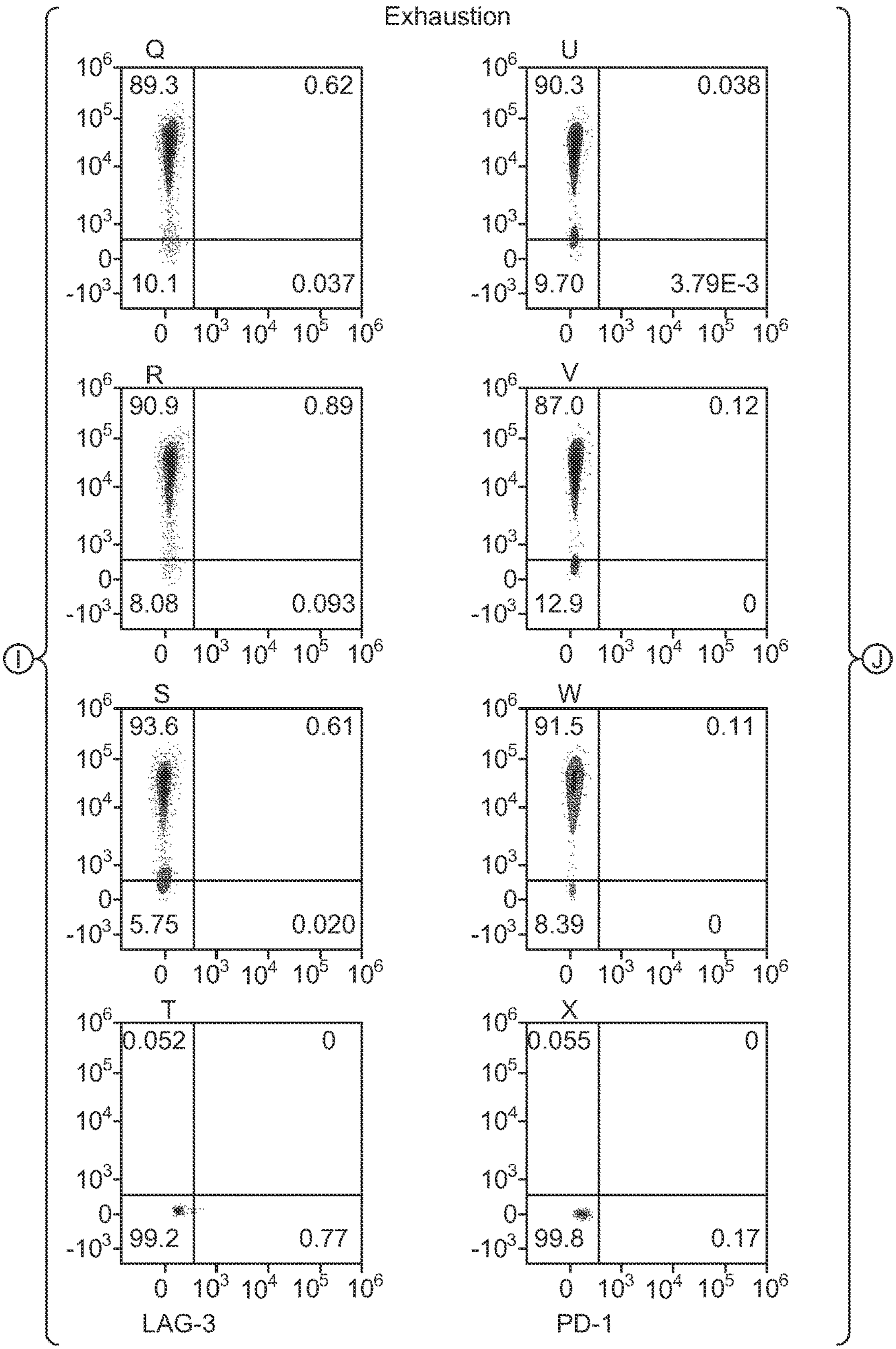
Figure 15:
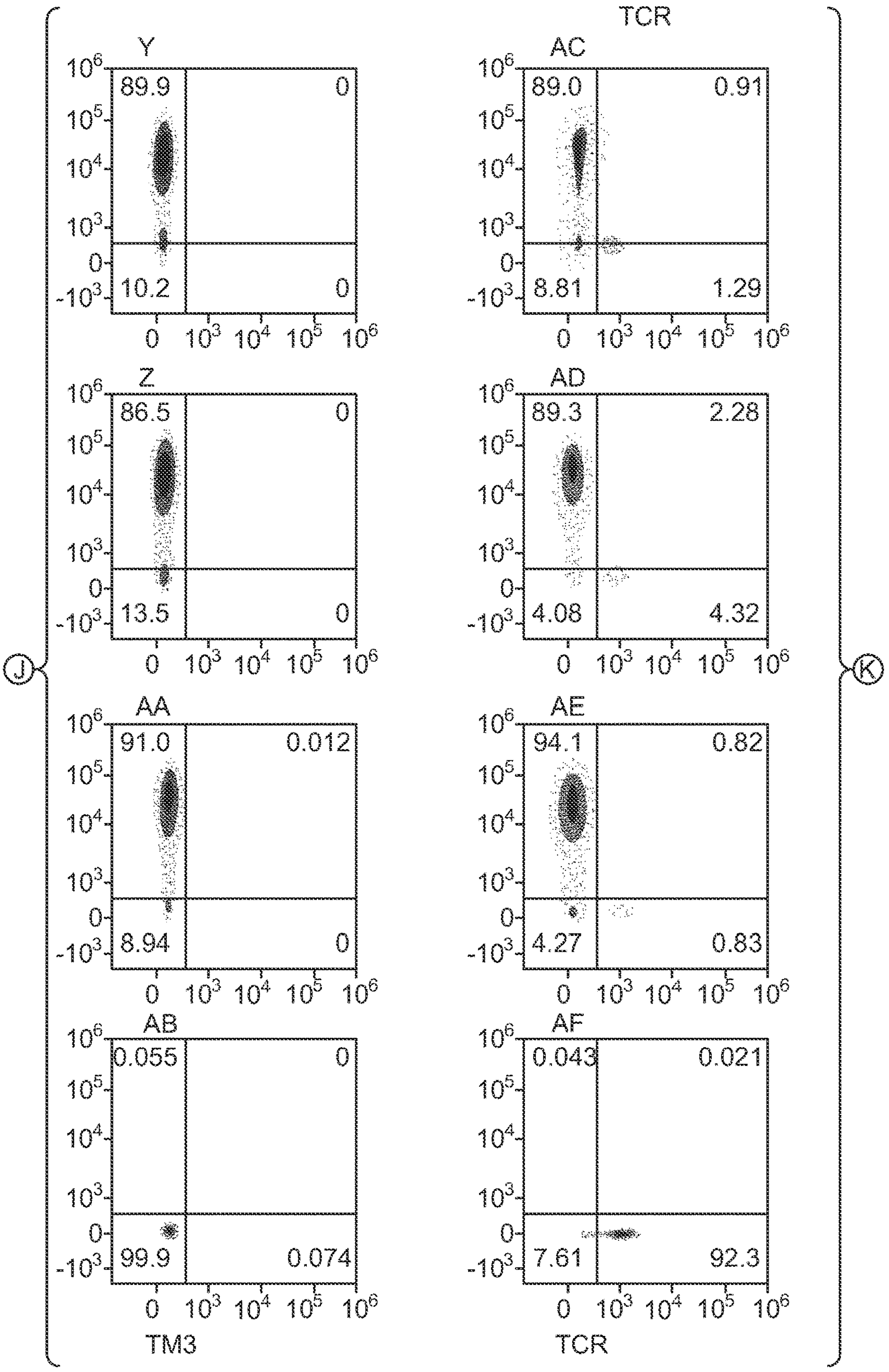
Figure 15:
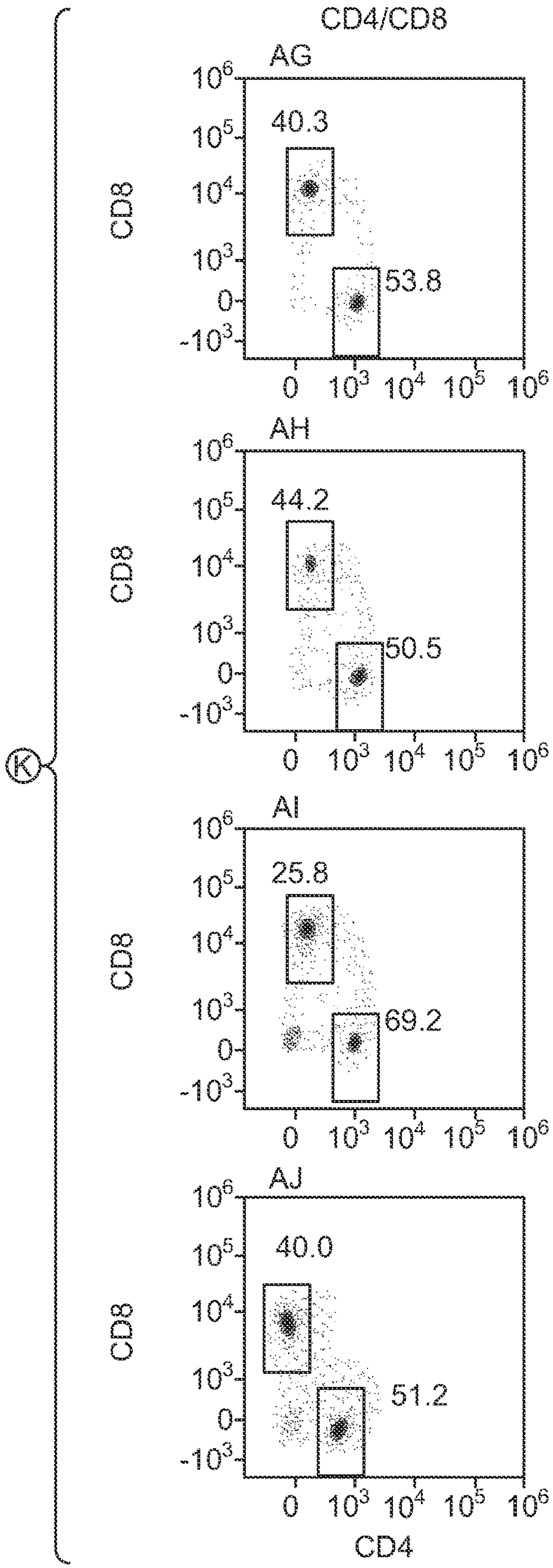

Surprisingly, as shown in FIGS. 11A, 11B, 12A-12G, 13 and 14, AN197 worked as well (as measured by gene editing efficiency) as FokI TALEN and CRISPR for TRAC knock out and CAR knock-in in human primary T cells at both the AAVS1 and TRAC48 loci. Furthermore, AN197 CAR-T cells had similar phenotype (read by activation, memory and exhaustion markers) as FokI TALEN and CRISPR CAR-T (FIG. 15). Interestingly, cells transfected with nucleic acids encoding either FokI TALEN or an AN197 recombinant protein resulted in a higher number of CD8+ cells than the editing with CRISPR (FIG. 15).

AN197 CAR-T cells had comparable cytotoxicity to target cells as FokI TALEN CAR-T cells in the killing assay (FIG. 16). Surprisingly, the TALEN-edited cells performed better than the CRISPR-edited cells in this killing assay, probably contributed by the higher amount of CD8+ cells resulted from the former editing. Given the extremely low homology of AN197 to known nucleases such as FokI and Clo51, it is surprising and unexpected that AN197 not only functioned as well as FokI TALEN and CRISPR, but further that AN197 showed beneficial properties compared to CRISPR.

Example 3. Editing with Alternative Nuclease

TALEN alternative nuclease 197 (TALEN AN197) editing efficiency was tested in several targets (TIM3, B2M, LAG3, PD-1 and AAVS1) in human primary T cells and HEK 293 cells. The selected target pairs were identified from a previous screen to have good editing efficiency. The same protocols as described elsewhere herein were used for the mRNA generation, transfection and GCD assay. Exemplary editing efficiency results for the various targets are shown in FIGS. 17A-17F. All targets showed higher than 80% editing efficiency detected by GCD.

Figure 19A:
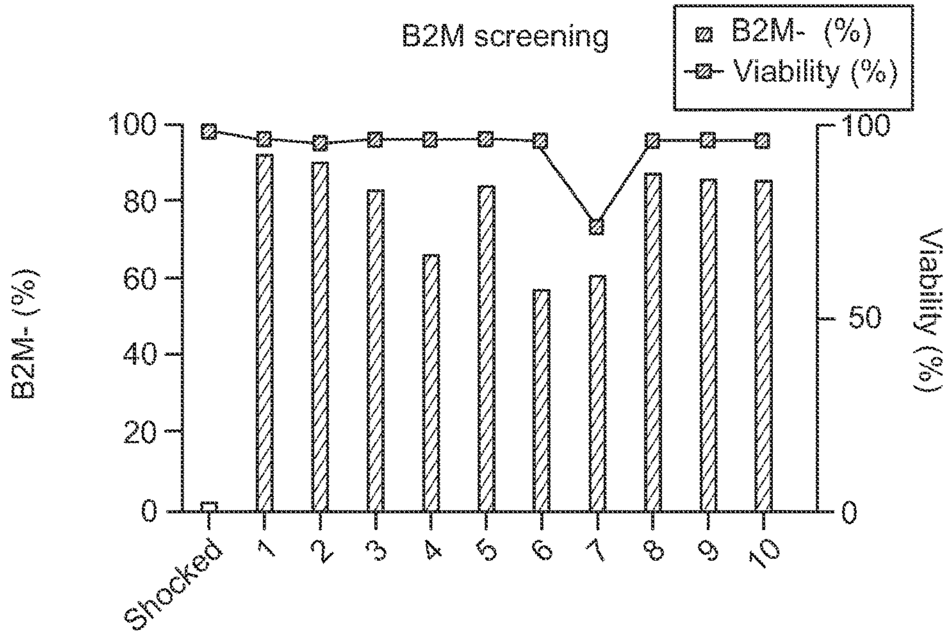
FIGS. 19A-19C are graphs depicting the results of TALEN AN197 target screening in primary T cells for TIM3 (FIG. 19B) and LAG3 (FIG. 19C) with GCD and B2M knock out (FIG. 19A).
Figure 19B:
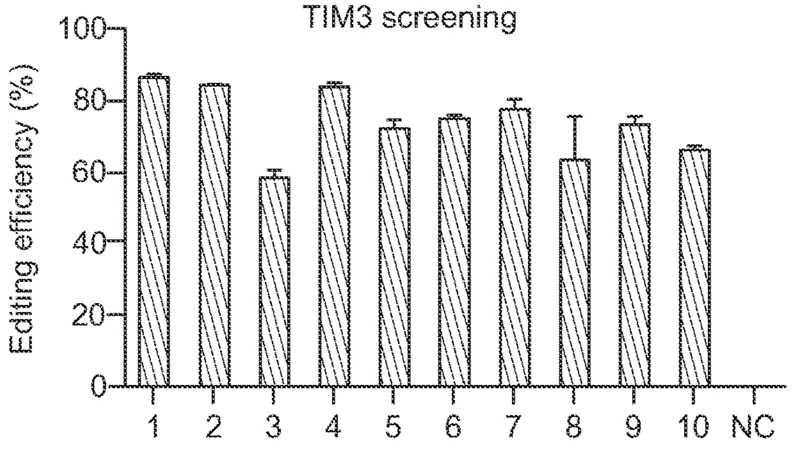
Figure 19C:
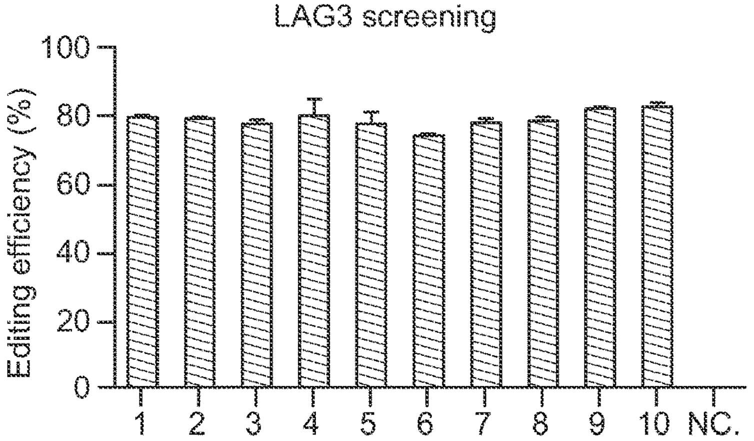

Ten consecutive TALEN AN197 mRNA pairs targeting either B2M, TIM-3, LAG3 or C2TA were electroporated into HEK293 cells or primary human T cells to determine the best editing TALEN AN197 pair for each target. The cells were harvested 2-3 days after electroporation and editing efficiency was determined by the GCD assay. For T cell B2M screening, B2M KO was determined by flow cytometry as described herein. Exemplary results of editing efficiency for the targets in HEK 293 cells is shown in FIGS. 18A-18D. Exemplary results of editing efficiency for the LAG3 and TIM3 targets and B2M KO in primary T cells is shown in FIGS. 19A-19C.

Fifty consecutive TALEN AN197 pairs (each AN197 pair was moved 1 bp to the right along the sequence) targeting near the exon1 region of TRAC. Each pair was transfected into human primary T cells and tested for editing efficiency by both GCD and flow cytometry. Target cleavage by the TALEN AN197 pairs was observed at all fifty sites.

Figure 20:
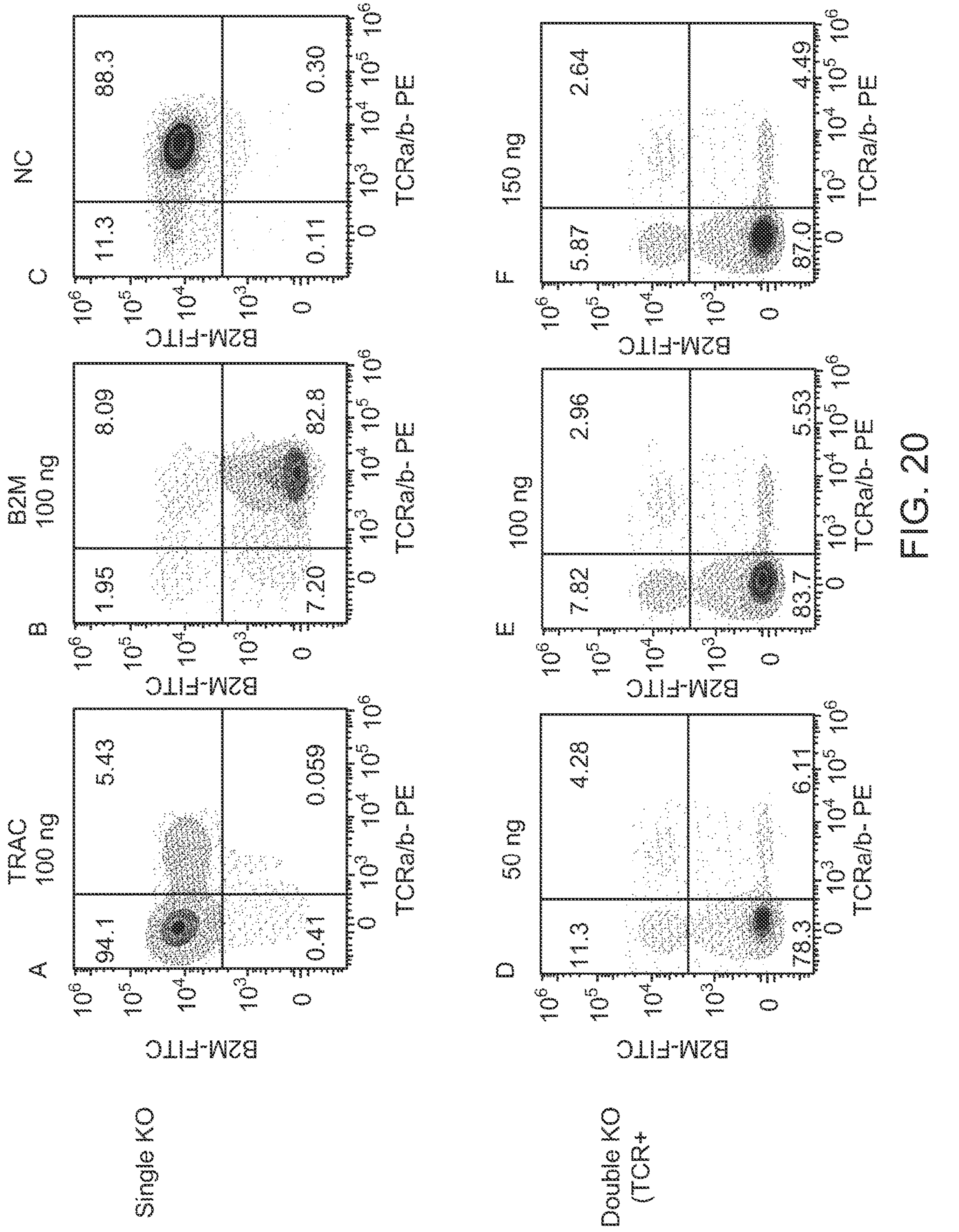
FIG. 20 depicts panels of density plots depicting single TRAC knock out (panel A) or single B2M knock out (panel B) or double TRAC+B2M knock out (panels D-F) with TALEN AN197 at the same time. Panel C depicts a density plot depicting a knock out negative control.
Figure 21A:
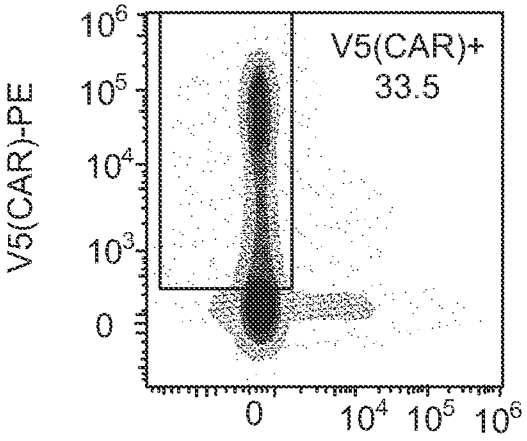
FIGS. 21A-21D are density plots depicting TALEN AN197 CAR knock-in with non-viral double-stranded DNA donor in T cells from two different donors (Donor A, FIG. 21A; Donor B, FIG. 21C) and density plots for the non-edited T cells (Donor A, FIG. 21B; Donor B, FIG. 21D).
Figure 21B:
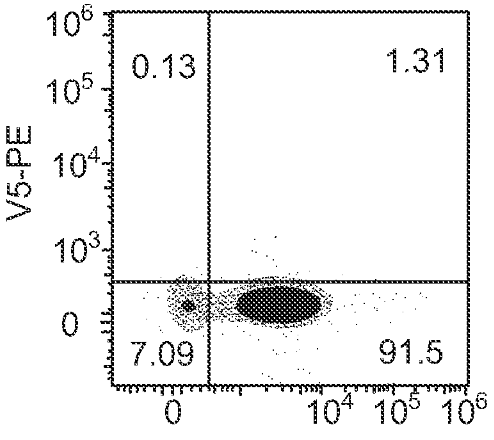
Figure 21C:
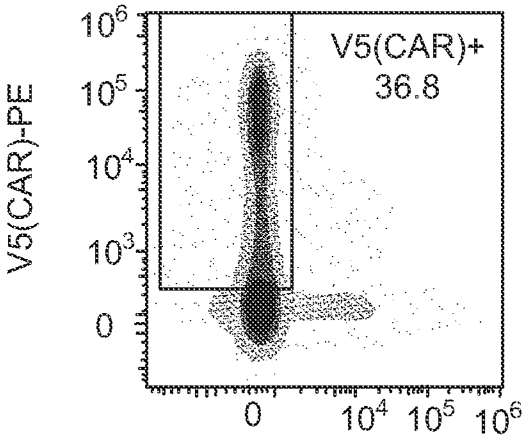
Figure 21D:
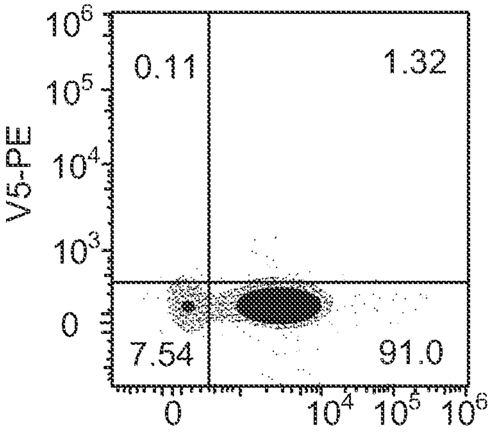
Figure 22A:
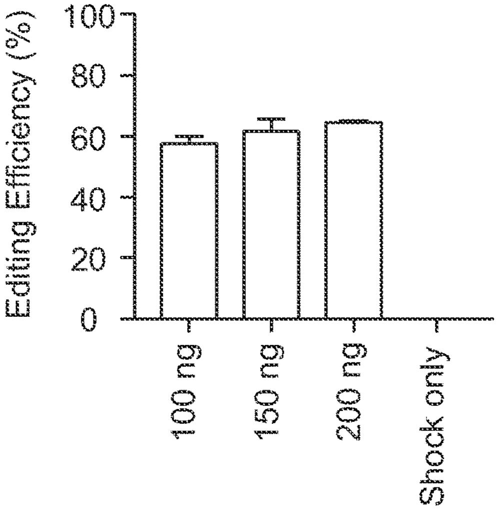
FIGS. 22A-22D depicts editing results in primary human NK cells with TALEN AN197 and CRISPR/Cas9. The graph of FIG. 22A and agarose gel of FIG. 22B depict GCD assay results for varying amounts of TALEN AN197 mRNA. The graph of FIG. 22C and agarose gel of FIG. 22D depict GCD assay results for varying amounts of CRISPR/Cas9 RNP payload.
Figure 22B:
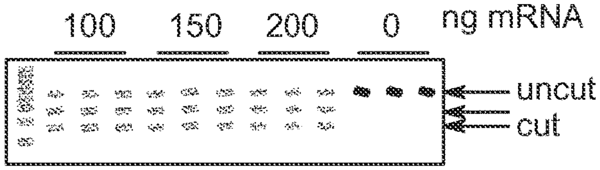
Figure 22C:
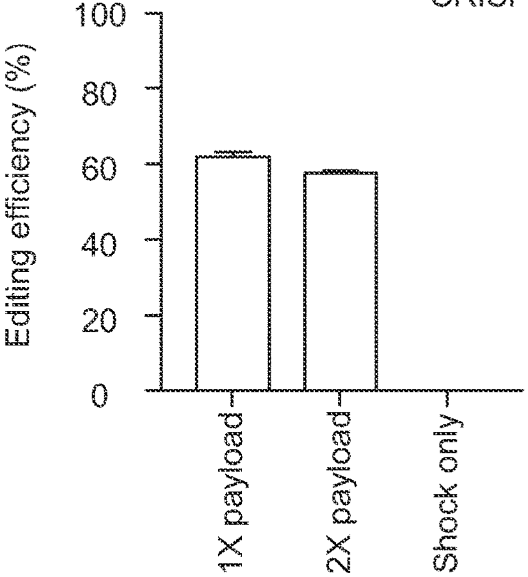
Figure 22D:
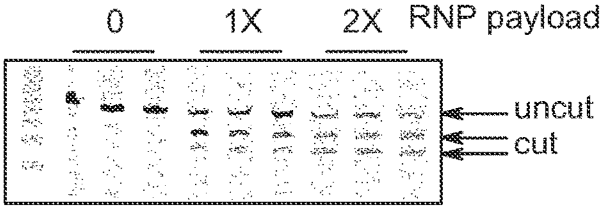

To determine whether multiple genes can be edited at the same time with TALEN AN197, we transfected different concentrations (50 ng, 100 ng, 150 ng of forward and reverse each) of AN197 mRNA targeting TRAC and AN197 mRNA targeting B2M at the same time. TRAC or B2M targeting AN197 mRNA were also electroporated separately to compare the editing efficiency to the multiplex reaction (100 ng of each AN197 forward and reverse). TRAC or B2M knock out efficiencies were determined by flow cytometry, as previously described (B2M-FITC, Thermo Fisher Scientific, Catalog #A15737). As shown in FIG. 20, double knock-outs of TRAC and B2M were readily achieved with the multiplex reaction.

Multiplex editing was also tested by transfecting HEK293T cells with TALEN AN197 pairs targeting different targets at the same time (1 pair, 2 pairs, 3 pairs or 4 pairs). The editing efficiency and cell viability of each combination of transfection was examined. All samples showed similar editing efficiencies, whether they were editing 1, 2, 3 or 4 targets at the same time. The viable cell count decreased slightly with 4 targets combined, possibly because of the increased amount of mRNA used. As shown in FIGS. 26A-26B and 27A-27B, the results demonstrate that TALEN AN197 can edit multiple targets at the same time. This may be particular use for clinical applications where multiple edits are needed.

The TRAC knock out and CAR knock-in efficiencies in human primary T cells was tested with CAR double-strand DNA (dsDNA) donors using the AN197 mRNA or CRISPR/Cas9 RNP systems. To prepare the dsDNA donors, long double-strand HDR templates encoding an anti-CD19 CAR with 500 bp homology arms were synthesized and cloned into a pAAV plasmid, which then served as a template for generating a dsDNA donor. Specific PCR primers targeting the left and right homology arms were synthesized without chemical modifications. Amplicons were generated with Phusion Flash PCR Master Mix (Thermo Fisher Scientific), purified by PureLink™ Pro 96 PCR Purification Kit (Thermo Fisher Scientific), and resuspended in water to 1-3 µg/µl measured by light absorbance on a NanoDrop spectrophotometer (Thermo Fisher Scientific).

HDR templates were mixed and incubated with AN197 mRNA or CRISPR/Cas9 RNPs for at least 5 min prior to mixing with and electroporating into cells. This mixture was electroporated with the Neon Transfection system (Thermo Fisher Scientific) using program 16 (two pulses of 1400 V and 20 ms pulse width). T cells were recovered in warm CTS OpTimizer medium containing 200 U/mL IL-2. At 3 days after electroporation, cells were collected for staining and flow cytometry analysis. In brief, cells were stained TCR α/b, V5 and live—dead dye, then analyzed on an Attune NxT flow cytometer with an automated 96-well sampler (Thermo Fisher Scientific) sampling a defined volume (50-150 µL per well) to obtain quantitative cell counts. Cytometry data were processed and analyzed using FlowJo software (BD Bioscience).

Primary human T cells were transfected TALEN AN197 or CRISPR with both systems targeting TRAC. For AN197, 300 ng of dsDNA donor was used and for CRISPR, 800 ng dsDNA donor was used. We observed 33-36% TCR knock out and CAR knock-in efficiencies with AN197, while the CRISPR efficiency was around 27% in the two donors tested. FIG. 21 shows exemplary results of AN197CAR knock-in with non-viral ds-DNA donor. In other transfection reactions, the AN197 system achieved up to 41.5% CAR knock-in efficiency with non-viral ds-DNA donor.

Example 4. Editing of NK Cells

Primary human NK cells were obtained from healthy donor leukopaks from AllCells Inc. The peripheral blood mononuclear cells were isolated by density gradient centrifugation. NK cells were subsequently obtained by depletion of non-NK cells using the Miltenyi NK cell separation kit (Miltenyi Biotech, Bergisch Gladbach, Germany), according to the manufacturer's instruction. Freshly isolated NK cells were cultured with Gibco™ CTS™ NK-Xpander™ Medium (A50190, Thermo Fisher Scientific) in the presence of 500 U/ml recombinant human IL-2 (PHC0023, Thermo Fisher Scientific). Every 4-6 days NK cells were expanded until the right exponential growth phase was reached to perform gene editing. After day 5, fresh CTS™ NK-Xpander™ complete medium with fresh IL-2 (500U/mL) was added every 1-2 days as necessary.

The expanded NK cells were pelleted and resuspended at $4\times10^7$ cells/ml in R buffer (Neon Transfection System Kit, Thermo Fisher System). Two hundred nanograms of the TALEN alternative nucleases mRNA or and a CRISPR/Cas9 (Clustered Regularly Interspaced Short Palindromic Repeats/CRISPR Associated Protein 9) was added to 10 µL ($2\times10^5$) on ice. Shocked only was used as a control for all experiments. This mixture was electroporated with the Neon Transfection system (Thermo Fisher Scientific) using program 5 (one pulses of 1700 V and 20 ms pulse width). NK cells were recovered in warm Gibco™ CTS™ NK-Xpander™ Medium containing 500 U/mL IL-2. After 3 days, cells were collected for GCD assay.

Human primary NK cells were Neon electroporated with TALEN AN197 mRNA or CRISPR/Cas9 targeting AAVS1. Cells were collected 3 days after transfection to determine the editing efficiency using the GCD assay. Different amounts of mRNA (100-200 ng) or RNP (1× to 2× payload) were used. A 1×RNP payload was 1.2 micrograms Cas9, 7.5 pmole gRNA. Both systems showed similar editing efficiencies of around 60%. Exemplary results are shown in FIGS. 22A-22D.

TALEN alternative nuclease CAR knock-in with viral donor was performed in NK cells. The expanded NK cells were pelleted and resuspended in R buffer (Neon Transfection System Kit, Thermo Fisher Scientific) electroporated with TALEN AN mRNA or and a CRISPR/Cas9 as described above. The electroporated NK cells were recovered in warm Gibco™ CTS™ NK-Xpander™ Medium containing 500 U/mL IL-2. AAV6-CAR was added in the cell suspension with different multiplicity of infection (MOI). The expansion started immediately after the electroporation with Gibco™ CTS™ NK-Xpander™ Medium (A50190, Thermo Fisher Scientific) in the presence of 500 U/ml recombinant human IL-2 (PHC0023, Thermo Fisher Scientific). The CAR knock-in efficiencies (detected by Flow Cytometry with a V5-PE antibody) were monitored over the course of time (up to Day 28).

Figure 23:
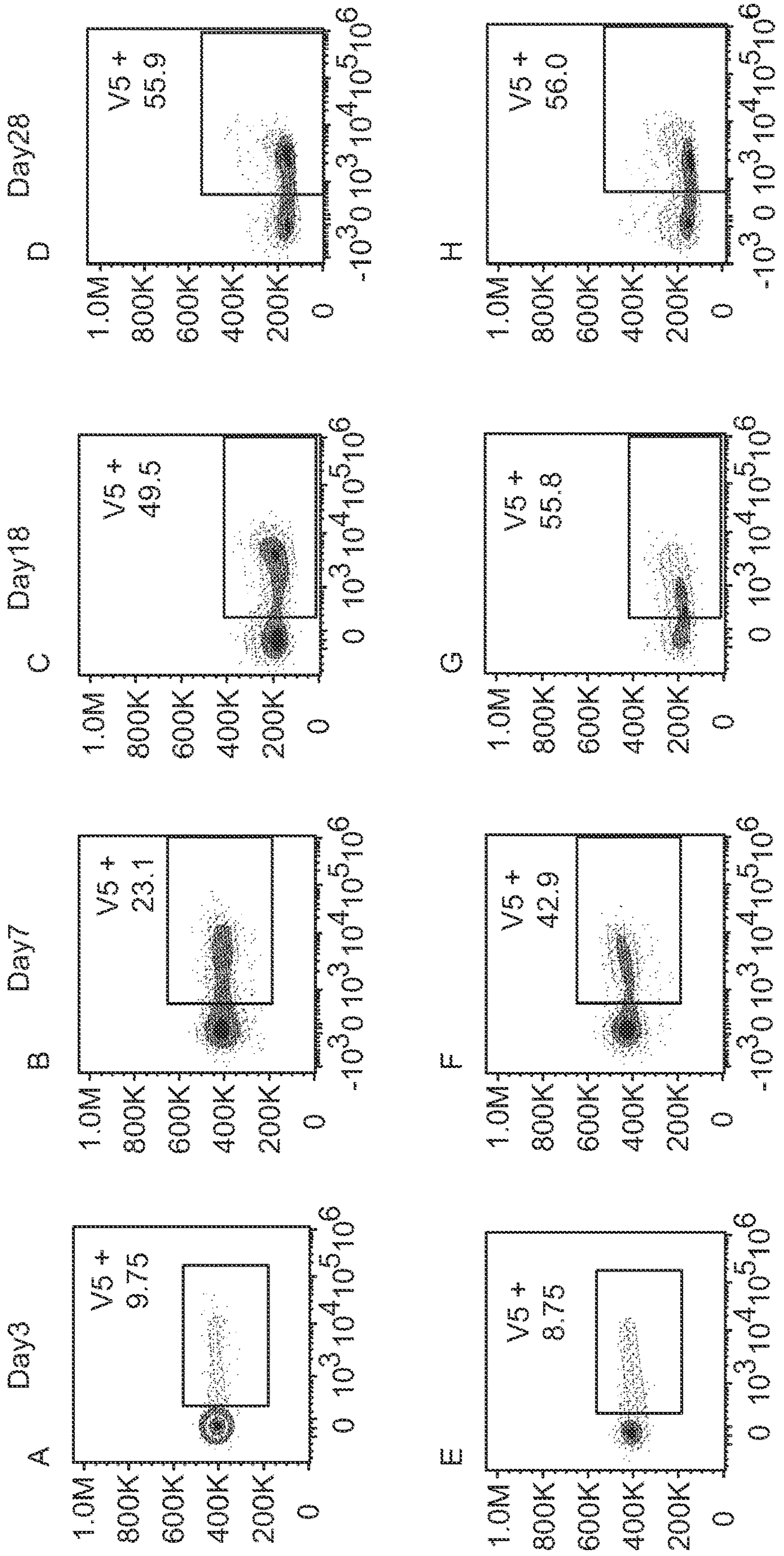
FIG. 23 depicts panels of density plots depicting AN197 CAR knock-in in expanded primary NK cells with AAV delivery. AN197 mRNA targeting AAVS1 was transfected into NK cells followed by the addition of AAV6-CAR at different MOI. An MOI of 7500 was used with the cells in the top row of plots (panels A-D) and an MOI of 30,000 AAV was used with the cells in the bottom row of plots (panels E-H).
Figure 24A:
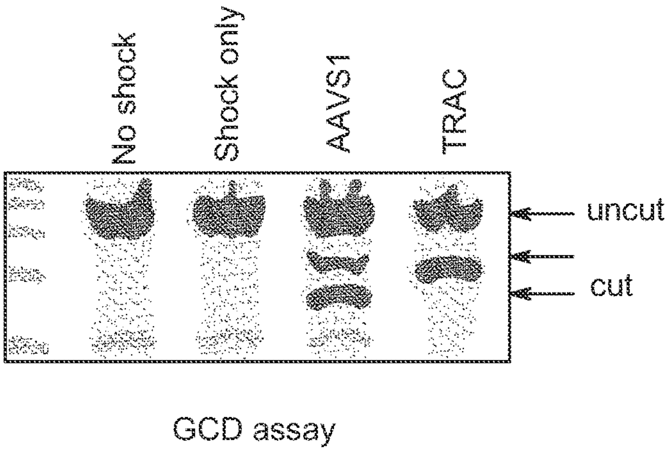
FIGS. 24A-24D depicts exemplary results from iPSC's transfected with TALEN AN197 mRNA targeting either AAVS1 or TRAC. The agarose gel of FIG. 24A and graph of FIG. 24B depict GCD assay results in iPSCs for AAVS1 and TRAC targeted AN197 TALEN mRNA.
Figure 24B:
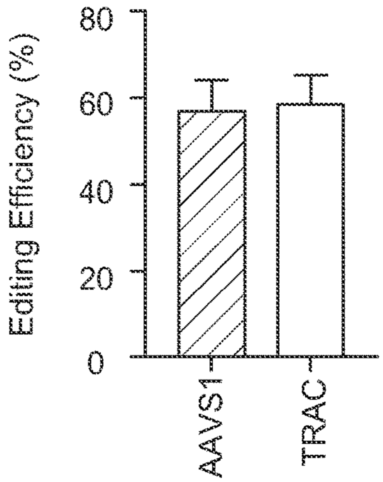
Figure 24C:
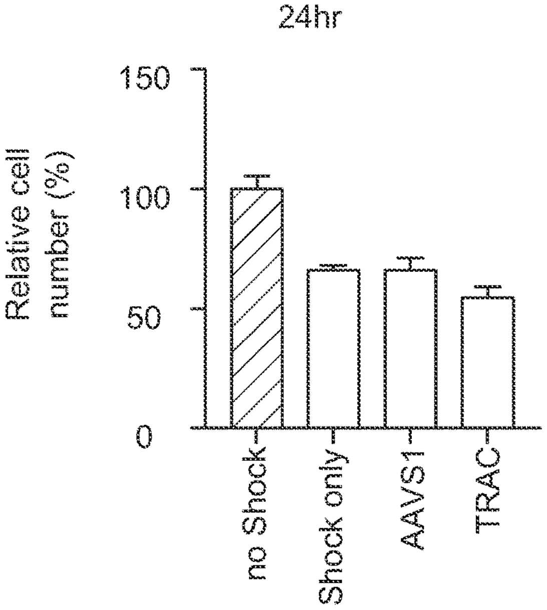
Figure 24D:
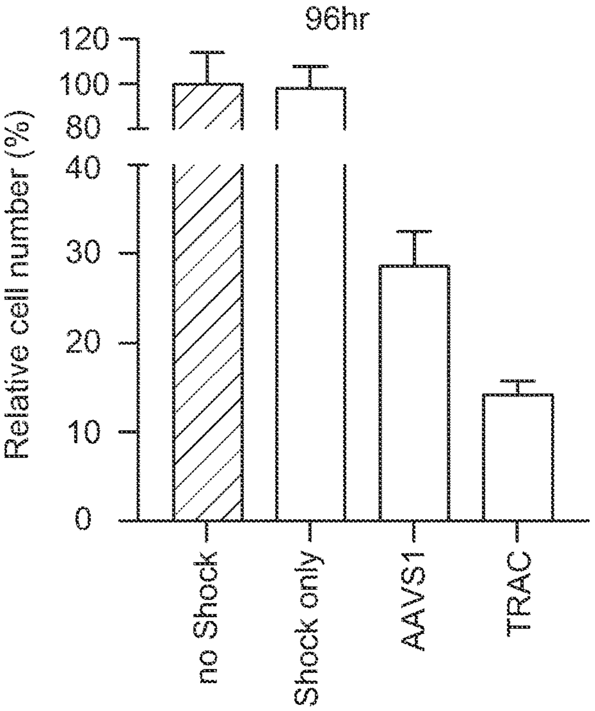

AN197 mRNA targeting AAVS1 was transfected into NK cells followed by the addition of AAV6-CAR at different MOI. An increase in CAR+ population was observed with longer culture times. CAR knock-in efficiency was higher in higher AAV6 MOI cells, however over time the knock-in efficiency became similar to the lower AAV6 MOI samples. Exemplary results of AN197 CAR knock-in with viral delivery in NK cells are shown in FIG. 23.

Example 5. Editing of iPSCs iPSC's were transfected with TALEN AN197 mRNA targeting either AAVS1 or TRAC with the Neon electroporator. Cells were harvested 7 days after electroporation for GCD assay analysis.

iPSC's were cultured in StemFlex Medium (Thermo Fisher Scientific) in rhLaminin-521 coated plates at 37° C., 5% CO2. 100 ng of each mRNA pair targeting either TRAC or AAVS1 were transfected into 40,000-200,000 cells using the neon electroporator (program 2). Immediately after transfection, the cells were transferred to StemFlex Medium containing 1× RevitaCell™ Supplement (Thermo Fisher Scientific). 24 hours later, the media was changed to StemFlex Medium without RevitaCell™ Supplement. Seven days after transfection, the cells were harvested for GCD assay. Exemplary results are shown in FIGS. 24A-24D. For both AAVS1 and TRAC targets, about 60% editing efficiency was observed.

Example 6. Protein Expression and Cleavage Assays

TALEN AN197 proteins were produced in *E. coli* BL21 (DE3) cells transformed with a pET28a plasmid containing the AN197 sequence (AAVS1 TALF or TALR). A single colony was grown overnight (12-14 hours) in 100 mL BRM supplemented with 50 m/ml kanamycin at 37° C. with shaking. The following day, 20 ml of the overnight culture was added to each 1 Liter BRM supplemented with 50m/mlkanamycin and incubated at 37° C. with shaking until the optical density at 600 nm (OD600) reached 0.4-0.6. The culture was then incubated at 22° C. to an OD600 of 0.8. AN197 protein was induced by the addition of isopropyl β-d-1-thiogalactopyranoside (IPTG) to a final concentration of 0.5 mM for 16 ~18 hours at 22° C. with shaking.

The cells were harvested by centrifugation at 5,000 rpm for 30 minutes at 4° C. and the pellet was resuspended in 3 volumes lysis buffer (25 mM Tris-HCl, pH 8.0, 300 mM NaCl, lx Protease Inhibitor Cocktail (Pierce), 1 mM TCEP, 0.5% Triton-X100,10% glycerol). Cells were lysed 3 times using a microfluidizer at 20,000 psi. After the cell debris was removed by centrifugation at 24,200 RCF for 1 hour at 4° C., AN197 protein in the soluble fraction was first purified using the AKTA pure chromatography system (Cytiva) with a 10 ml POROS™ 50 HE column. The cleared lysate was loaded onto the column, washed with Buffer A (25 mM Tris-HCl pH 8.0, 300 mM NaCl, 1 mM TCEP, 10% glycerol), and eluted with linear salt gradient up to 1 M NaCl. The peak fractions with major AN197 proteins were pooled and further purified with a 5 ml HisPur™ Ni-NTA column. After loading, the column was first washed with Buffer C (25 mM Tris-HCl pH 8.0, 1M NaCl, 1 mM TCEP, 10% glycerol) and subsequently with buffer D (40 mM imidazole, 25 mM Tris-HCl pH 8.0, 500 mM NaCl, 1 mM TCEP, 10% glycerol), and eluted with linear gradient up to 0.5M imidazole. Protein fractions were subsequently concentrated and buffer exchanged to 25 mM Tris-HCl, pH 8.0, 1 mM TCEP, 250 mM NaCl, and 50% glycerol, using an Amicon Ultra15 Centrifugal Filter Unit (EMD Millipore). Protein samples were filtered through a 0.22 μM low-protein binding filter (EMD Millipore), aliquoted, and stored at −80° C. Protein purities were assessed by SDS-PAGE and concentration were measured by Bradford assay.

Figure 25A:
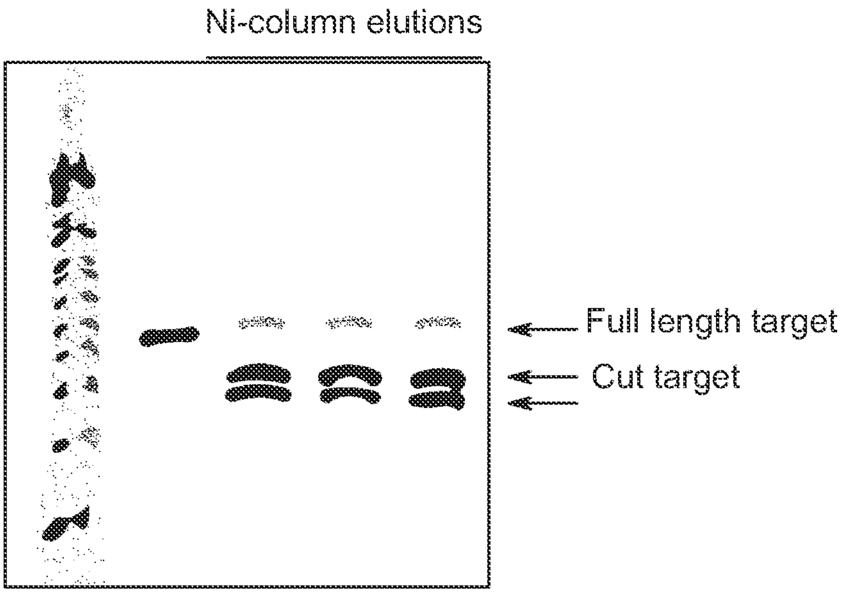
FIGS. 25A-25B depict exemplary results of TALEN AN197 protein purification (FIG. 25B) and in vitro functional activity (FIG. 25A).
Figure 25B:
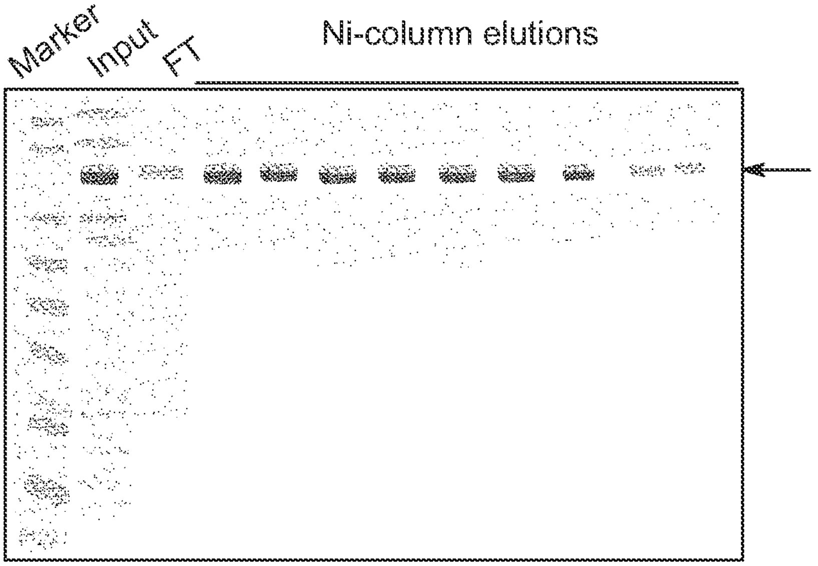
Figure 26A:
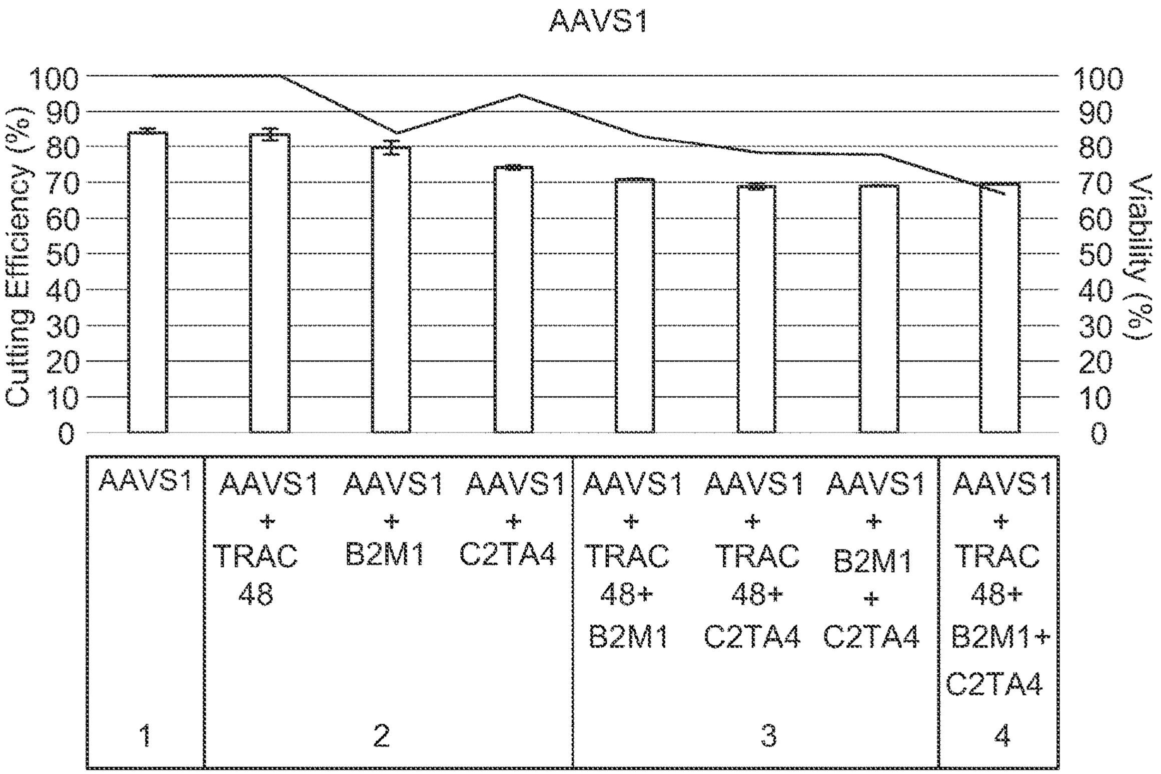
FIGS. 26A-26B depicts exemplary multiplex target editing in HEK 293 cells with 1, 2, 3, or 4 TALEN AN197 pairs targeting the indicated targets.
Figure 26B:
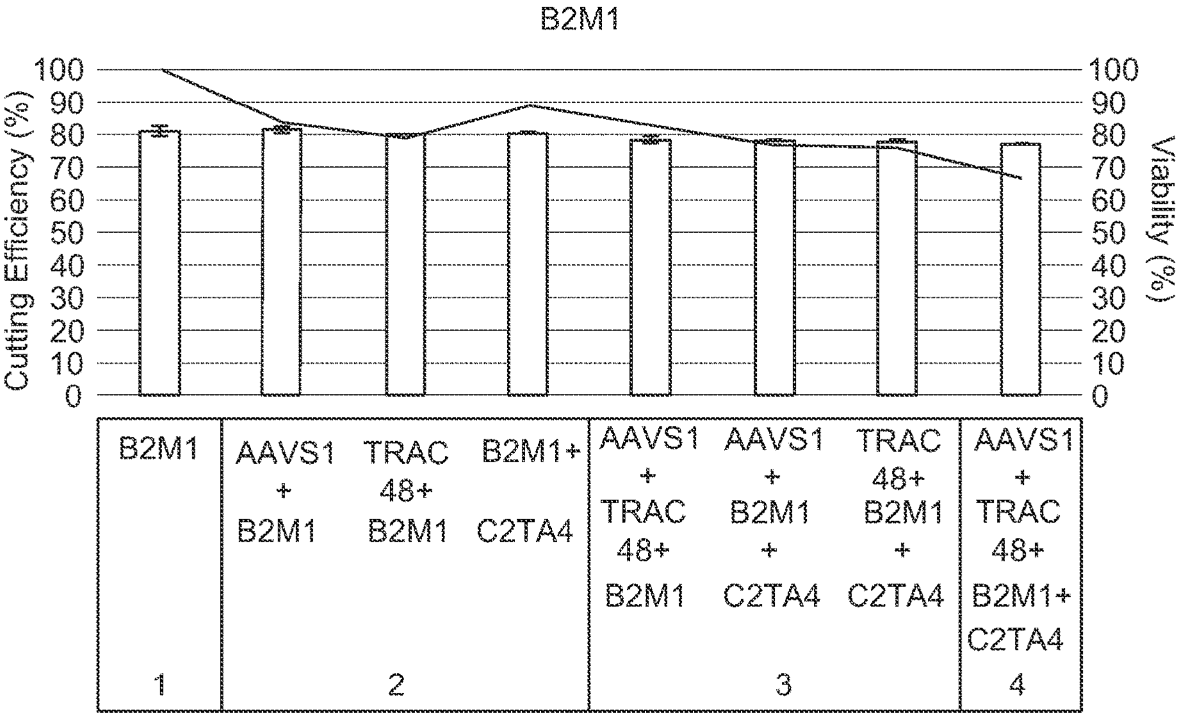
Figure 27A:
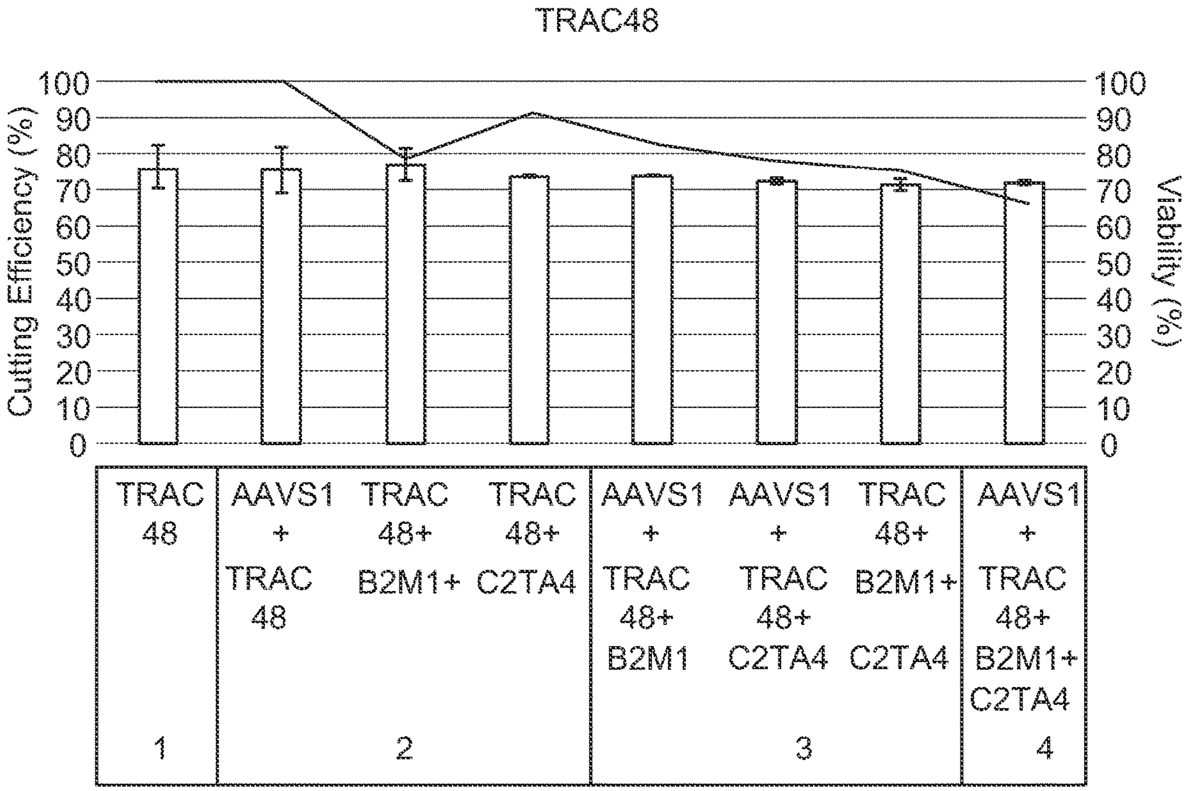
FIGS. 27A-27B depicts exemplary multiplex target editing in HEK 293 cells with 1, 2, 3, or 4 TALEN AN197 pairs targeting the indicated targets.
Figure 27B:
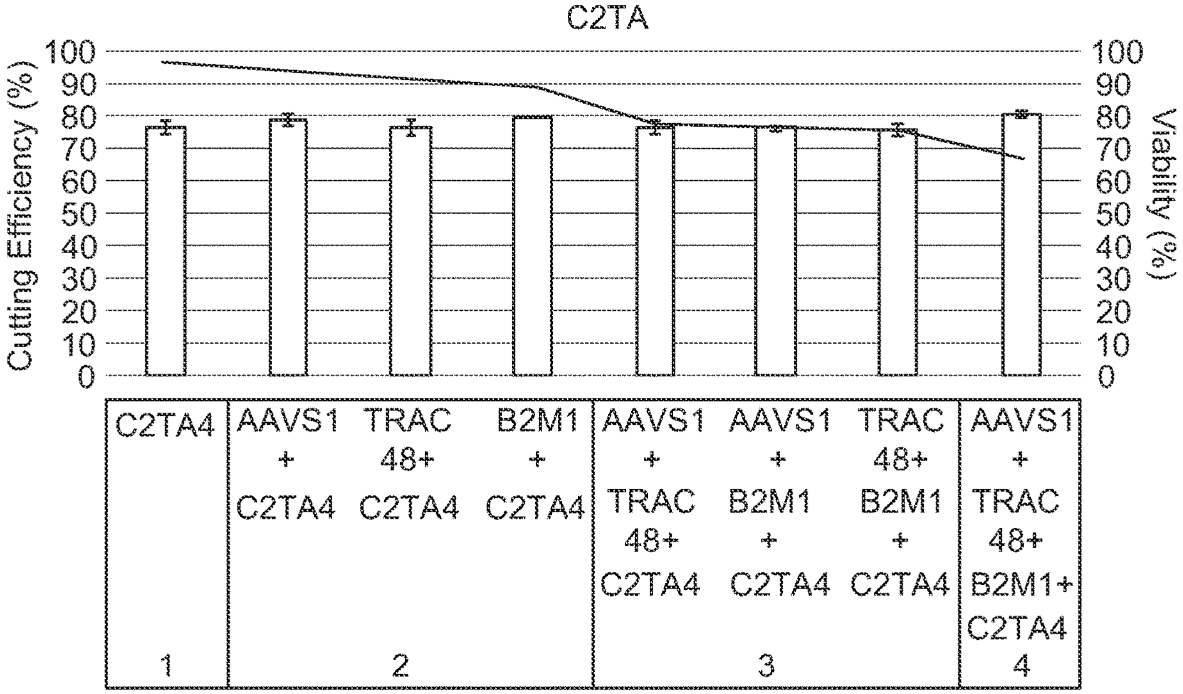

With first the Heparin column followed by a Ni-NTA purification column in the AKTA pure chromatography system, a pure TALEN AN197 protein preparation was obtained (see FIG. 25B).

To test whether the TALEN AN197 protein was functional, an in vitro functional assay was performed. Purified AN197 protein was mixed with a substrate that contained the same two AN197 binding sites (palindromic) with 16 bp spacing. The in vitro cleavage assay was performed by mixing 100 ng of PCR amplified target DNA substrate, 50 mM potassium acetate, 20 mM Tris-acetate, 10 mM magnesium acetate, 100 m/ml BSA, 1 mM DTT at pH 7.9 and purified AN197 proteins in 10 μl total reaction volume each. Cleavage reactions were incubated at 25° C. for 1 hour or 37° C. for 15 to 60 minutes. Cleavage products were separated by E-Gel™ EX 2% Agarose Gels (Invitrogen). The gel image was captured and processed with iBright imaging system (Invitrogen). The substrate fragment contains two target sites in palindrome with 16 bp spacing in between. As shown in FIG. 25A, purified TALEN AN197 protein efficiently cuts the target substrate, confirming its functional activity. The cutting pattern and resulting fragment termini from the AN197 nuclease is similar to that of Fokl.

To test the activity of the isolated TALEN AN197 protein in cells, purified TALEN AN197 protein was introduced into cells using the Neon™ Transfection System (Thermo Fisher Scientific). Electroporation of HEK293FT cells with the purified TALEN AN197 protein resulted in about 35-40% editing as detected by GCD assays. While the purified protein was soluble in high salt buffer, the protein was somewhat less stable in the Neon electroporation buffer (R buffer) leading to some precipitation of the protein. To improve the stability of purified TALEN AN197 under these conditions, the protein was PEGylated using pegylating reagents such as PEG-SH and PEG-NHS reagents. When AAVS1 targeting TALEN AN197 protein was pegylated with mPEG-5K-SH, we obtained up to 75% editing of the target site in HEK293FT cells. Delivering PEGylated TALEN AN197 protein to cells resulted in up to 60% cell editing in primary human T cells and up to 48% cell editing in iPSCs. This demonstrates that the PEGylated TALEN AN197 protein is functional in multiple cell types.

SEQUENCE LISTING

```
Sequence total quantity: 299
SEQ ID NO: 1            moltype = AA  length = 196
FEATURE                 Location/Qualifiers
REGION                  1..196
                        note = Synthetic Construct
source                  1..196
                        mol_type = protein
                        organism = synthetic construct
SEQUENCE: 1
QLVKSELEEK KSELRHKLKY VPHEYIELIE IARNSTQDRI LEMKVMEFFM KVYGYRGKHL  60
GGSRKPDGAI YTVGSPIDYG VIVDTKAYSG GYNLPIGQAD EMQRYVEENQ TRNKHINPNE  120
WWKVYPSSVT EFKFLFVSGH FKGNYKAQLT RLNHITNCNG AVLSVEELLI GGEMIKAGTL  180
TLEEVRRKFN NGEINF                                                  196

SEQ ID NO: 2            moltype = AA  length = 200
FEATURE                 Location/Qualifiers
REGION                  1..200
                        note = Synthetic Construct
source                  1..200
                        mol_type = protein
                        organism = synthetic construct
SEQUENCE: 2
GEGIKSNISL LKDELRGQIS HISHEYLSLI DLAFDSKQNR LFEMKVLELL VNEYGFKGRH  60
LGGSRKPDGI VYSTTLEDNF GIIVDTKAYS EGYSLPISQA DEMERYVREN SNRDEEVNPN  120
KWWENFSEEV KKYYFVFISG SFKGKFEEQL RRLSMTTGVN GSAVNVVNLL LGAEKIRSGE  180
MTIEELERAM FNNSEFILKY                                              200
```

-continued

```
SEQ ID NO: 3           moltype = AA  length = 201
FEATURE                Location/Qualifiers
REGION                 1..201
                       note = Synthetic Construct
source                 1..201
                       mol_type = protein
                       organism = synthetic construct
SEQUENCE: 3
PTARLEGKSE VETIKEQMRG ELTHLSHEYL GLLDLAYDSK QNRLFELKTM QLLTEECGFE  60
GLHLGGSRKP DGIVYTKDEN EQVGKENYGI IIDTKAYSGG YSLPISQADE MERYIGENQT  120
RDIRINPNEW WKNFGDGVTE YYYLFVAGHF KGKYQEQIDR INCNKNIKGA AVSIQQLLRI  180
VNDYKAGKLT HEDMKLKIFH Y                                           201

SEQ ID NO: 4           moltype = AA  length = 200
FEATURE                Location/Qualifiers
REGION                 1..200
                       note = Synthetic Construct
source                 1..200
                       mol_type = protein
                       organism = synthetic construct
SEQUENCE: 4
GVTERLVKGE MEKKKAELRH KLKHVPHEYI ELIEIAQDSK QNRLLEFKVV EFFKEVYGYH  60
GKHLGGSRKP DGALYTKGLG ADHGIILDTK AYKDGYSLPI SQADEMQRYV DENNKRDAII  120
NPNEWWKVYP SSISDFKFLF VSGYFKGDTK KQLTRVSNLT KRKGAVLSVE QLLLGGEKIK  180
DGSITLEDVA AKFNNDEIVF                                             200

SEQ ID NO: 5           moltype = AA  length = 200
FEATURE                Location/Qualifiers
REGION                 1..200
                       note = Synthetic Construct
source                 1..200
                       mol_type = protein
                       organism = synthetic construct
SEQUENCE: 5
GVTEPLVKGE MEKKKSDLRH KLKHVPHEYI ELIEIAQDSK QNRLFEFKVV EFLKEGYDYN  60
GKHLGGSRKP DGALYTNGLK TDYGIILDTK AYKDGYSLPI SQADEMQRYV DENNNRNAII  120
NPNEWWKVYP NSILDFKFLF VSGFFKGDYK KQLARVSNLT KRKGAVLSVE QLLLGGEKIK  180
DGSLTLEDVG DKFNNDEIIF                                             200

SEQ ID NO: 6           moltype = AA  length = 214
FEATURE                Location/Qualifiers
REGION                 1..214
                       note = Synthetic Construct
source                 1..214
                       mol_type = protein
                       organism = synthetic construct
SEQUENCE: 6
GLLFPEAQSF LPVKSQVSIL KDYLRSCLSH VDHKYLILLD LGFDGTSDRD YEIQTAQLLT  60
AELSFLGGRL GDTRKPDVCI YYEDNGLIID NKAYGKGYSL PIKQADEMYR YIEENKERSE  120
LLNPNCWWNI FDEGVKTFRF AFLSGEFTGG FKDRLNHISM RSGIKGAAVN SANLLIIAEQ  180
LKSGTMSYEE FFQLFDQNDE ITVPHLSLQG GLIL                             214

SEQ ID NO: 7           moltype = AA  length = 201
FEATURE                Location/Qualifiers
REGION                 1..201
                       note = Synthetic Construct
source                 1..201
                       mol_type = protein
                       organism = synthetic construct
SEQUENCE: 7
MSQSFTKSDF EETKEQIRGK LLHLPHEYLS LIDLAYDSKQ NRLFEMKTLG LLTEECGYQG  60
LHLGGSRKPD GIIYTSSEKY NYGVIIDTKA YSRGYNLPIS QADEMERYIG ENQTRDAKIN  120
PNKWWKHFPE EVNEFYFMFV SGHFIGNFKA QIMRISRNKA INGTAIAVAN LLLCVEAYKA  180
GQLTHEVIKT KVFNNGEFEL L                                           201

SEQ ID NO: 8           moltype = AA  length = 204
FEATURE                Location/Qualifiers
REGION                 1..204
                       note = Synthetic Construct
source                 1..204
                       mol_type = protein
                       organism = synthetic construct
SEQUENCE: 8
VPKKLAKSSQ SETKEKLREK LRNLPHEYLS LVDLAYDSKQ NRLFEMKVIE LLTEECGFQG  60
LHLGGSRRPD GVLYTAGLTD NYGIILDTKA YSSGYSLPIA QADEMERYVR ENQTRDELVN  120
PNQWWENFEN GLGTFYFLFV AGHFNGNVQA QLERISRNTG VLGAAASISQ LLLLADAIRG  180
GRMDRERLRH LMFQNEEFLL EQEL                                        204
```

-continued

```
SEQ ID NO: 9            moltype = AA  length = 201
FEATURE                 Location/Qualifiers
REGION                  1..201
                        note = Synthetic Construct
source                  1..201
                        mol_type = protein
                        organism = synthetic construct
SEQUENCE: 9
VIEHEQTIKS SIEELKSELR TQLNVISHDY LQLVDISQDS QQNRLFEMKV MDLFINEFGY  60
NGSHLGGSRK PDGILYTEGL SKDYGIIVDT KAYKDGYNLP IAQADEMERY IRENIDRNEV  120
VNPNRWWEVF PSKINDYKFL FVSAYFKGNF KEQLERISIN TGILGGAISV EHLLLGAEYF  180
KRGILSLEDV RDKFCNTEIE F                                            201

SEQ ID NO: 10           moltype = AA  length = 201
FEATURE                 Location/Qualifiers
REGION                  1..201
                        note = Synthetic Construct
source                  1..201
                        mol_type = protein
                        organism = synthetic construct
SEQUENCE: 10
LQITQTLVDI EKERKKAYFL KETSLSPRYI ELLEIAFDPK RNRDFEVITA ELLKAGYGLK  60
AKVLGGGRRP DGIAYTKDYG LIVDTKAYSN GYGKNIGQAD EMIRYIEDNQ KRDNKRNPIE  120
WWREFEVQIP ANSYYYLWVS GRFTGRFDEQ LVYTSSQTNT RGGALEVEQL LWGADAVMKG  180
KLNVSDLPKY MNNSIIKLTK K                                            201

SEQ ID NO: 11           moltype = AA  length = 206
FEATURE                 Location/Qualifiers
REGION                  1..206
                        note = Synthetic Construct
source                  1..206
                        mol_type = protein
                        organism = synthetic construct
SEQUENCE: 11
KLRFYEENIT KETTDAIVVK DRARVRLHNI NHKYLTLIDY AFSGKNNCTE FEIYTIDLLV  60
NELAFNGIHL GGTRKPDGIF DYNQQGIIID NKAYSKGFTI TRSMADEMVR YVQENNDRNP  120
ERNKTQWWLN FGDNVNHFNF VFISSMFKSE VKHMLNNIKQ STGVDGCVLT AENLLYFADA  180
IKGGTVKRTD FINLFGKNDE LVYPYN                                       206

SEQ ID NO: 12           moltype = AA  length = 201
FEATURE                 Location/Qualifiers
REGION                  1..201
                        note = Synthetic Construct
source                  1..201
                        mol_type = protein
                        organism = synthetic construct
SEQUENCE: 12
LEITQELKDE QAEKRKAKFL KETNLPMKYI ELLDIAYDGK RNRDFEIVTM ELFRNVYRLH  60
SKLLGGGRKP DGLLYQDRFG VIVDTKAYGK GYSKSINQAD EMIRYIEDNK RRDENRNPIK  120
WWEAFPDTIP QEEFYFMWVS SKFIGKFQEQ LDYTSNETQI KGAALNVEQL LLGADLVLKG  180
QLHISDLPSY FQNKEIEFVK A                                            201

SEQ ID NO: 13           moltype = AA  length = 216
FEATURE                 Location/Qualifiers
REGION                  1..216
                        note = Synthetic Construct
source                  1..216
                        mol_type = protein
                        organism = synthetic construct
SEQUENCE: 13
PRTKISKTNV LELKDKVRDK LKYVDHRYLA LIDLAYDGTA NRDFEIQTID LLINELKFKG  60
VRLGESRKPD GIISYNINGV IIDNKAYSTG YNLPINQADE MIRYIEENQT RDEKINSNKW  120
WESFDDEVKD FNYLFVSSFF KGNFKNNLKH IANRTGVNGG AINVENLLYF AEELKAGRLS  180
YVDSFTMYDN DEIYVGNIID YSNLKIAADE EGLYSI                             216

SEQ ID NO: 14           moltype = AA  length = 175
FEATURE                 Location/Qualifiers
REGION                  1..175
                        note = Synthetic Construct
source                  1..175
                        mol_type = protein
                        organism = synthetic construct
SEQUENCE: 14
MKYIELLDIA YDGKRNRDFE IVTMELFRNV YRLHSKLLGG GRKPDGLLYQ DRFGVIVDTK  60
AYGKGYSKSI NQADEMIRYI EDNKRRDENR NPIKWWEAFP DTIPQEEFYF MWVSSKFIGK  120
FQEQLDYTSN ETQIKGAALN VEQLLLGADL VLKGQLHISD LPSYFQNKEI EFVKA        175

SEQ ID NO: 15           moltype = AA  length = 197
FEATURE                 Location/Qualifiers
```

-continued

```
REGION                  1..197
                        note = Synthetic Construct
source                  1..197
                        mol_type = protein
                        organism = synthetic construct
SEQUENCE: 15
VTDLNQIVKS SIEMSKANMR DNLQMLPHDY IELIEISQDP YQNRIFEMKV MDLFINEYGF  60
SGSHLGGSRK PDGAMYAHGF GVIVDTKAYK DGYNLPISQA DEMERYVREN IDRNEHVNSN  120
RWWNIFPEDT NEYKFLFVSG FFKGNFEKQL ERISIDTGVQ GGALSVEHLL LGAEYIKRGI  180
LTLYDFKNSF LNKEIQF                                                197

SEQ ID NO: 16           moltype = AA  length = 196
FEATURE                 Location/Qualifiers
REGION                  1..196
                        note = Synthetic Construct
source                  1..196
                        mol_type = protein
                        organism = synthetic construct
SEQUENCE: 16
EASRSSVEEL KSELRPQLRV LSHDYLQLVE IAQEPDQNRL FEMKVMELFV NELGFQGCHL  60
GGSRRPDGIL YTTDLEKNYG VIVDTKAYRE GYSLPIGQAD EMERYIRENI DRNPSVNPNK  120
WWEAFPDDIE NFTFLFVSGF FKGNFKDQLE RISLNTGAAG GAISVEHLLL GADYYKRGVL  180
TLEDFENHFC NGEIQF                                                 196

SEQ ID NO: 17           moltype = AA  length = 192
FEATURE                 Location/Qualifiers
REGION                  1..192
                        note = Synthetic Construct
source                  1..192
                        mol_type = protein
                        organism = synthetic construct
SEQUENCE: 17
EVKKSSTEEL KAQLRTQLTN ISLDYLQLVD ISTDSKQNRL FEMKVMDLFI NELDFKGSHL  60
GGGRKPDGAV YTTNYGIIVD TKAYKDGYNL PISQADEMER YVRENIDRNK GINPNEWWTI  120
FPSSINDFTF LFVSGYFKGN FEGQLQRISM STGIKGGAIG VEHLLLCAEY YKRGILSHQD  180
IRDSFKNAEI EF                                                     192

SEQ ID NO: 18           moltype = AA  length = 198
FEATURE                 Location/Qualifiers
REGION                  1..198
                        note = Synthetic Construct
source                  1..198
                        mol_type = protein
                        organism = synthetic construct
SEQUENCE: 18
SLAKSDFVET KERIRDKLLH LPHEYLSLID LAYDSKQNRL FEMKTLGLLT EECGYHGLHL  60
GGSRKPDGII YTDTERYNYG VIIDTKAYSR GYNLPISQAD EMERYIGENQ TRDVKINPNK  120
WWEYFPADVE EFYFMFVSGH FIGNFRSQIE RISRNKAING TAIAVANLLL CVEAYKAGEL  180
THEAIKTKVF NNGEFELS                                               198

SEQ ID NO: 19           moltype = AA  length = 193
FEATURE                 Location/Qualifiers
REGION                  1..193
                        note = Synthetic Construct
source                  1..193
                        mol_type = protein
                        organism = synthetic construct
SEQUENCE: 19
PTARLEGRSE LEYKKEEVRH QLTHLSHEYL GLLDLAYDSK QNRLFELKTM QLLTEECDFE  60
GLHLGGSRKP DGIAYSESYG IIIDTKAYSG GYSLPISQAD EMERYIGENQ TRDPKVNPNE  120
WWKNFSDTTQ EFYFMFVAGH FKGKYQDQIE RISCNKSVKG AAVSIEQLLL TVNAYKAGKL  180
DHEGIKKALF ESV                                                    193

SEQ ID NO: 20           moltype = AA  length = 198
FEATURE                 Location/Qualifiers
REGION                  1..198
                        note = Synthetic Construct
source                  1..198
                        mol_type = protein
                        organism = synthetic construct
SEQUENCE: 20
NLAKSSLAEI KDEIRPQMTH LSHEYLSLID LAYDSVQNRL FEMKTLELLT EECKFTGLHL  60
GGSRKPDGII YTNDLTENYG VIVDTKAYSK GYNLPISQAD EMERYIRENQ TRDKKINSNE  120
WWLNFNTNIE TYYFMFVAGH FIGNFVNQLE RISMSTGVYG TALSVKNMLI CANAIKSGDM  180
CHEDMKNNMF HNSEYQII                                               198

SEQ ID NO: 21           moltype = AA  length = 190
FEATURE                 Location/Qualifiers
REGION                  1..190
```

```
                          note = Synthetic Construct
source                    1..190
                          mol_type = protein
                          organism = synthetic construct
SEQUENCE: 21
SLQKSSLSGM KDQIRARLTA LPHEYLSLID LAYDSEQNRL FEMKIIELFT EECGFSGRHL  60
GGSNKPDGVI SAADLSYGII VDTKAYSKGY GLPLSQADEM ERYVRENLTR DSRINPNEWW  120
LAFDGAVPRF AFLFVSGHFT GTYGQRIERI IRSTGVPGAA LAISKLLLYA DTLKSGRISQ  180
QDFYRLVFPS                                                         190

SEQ ID NO: 22             moltype = AA  length = 200
FEATURE                   Location/Qualifiers
REGION                    1..200
                          note = Synthetic Construct
source                    1..200
                          mol_type = protein
                          organism = synthetic construct
SEQUENCE: 22
PTARLEGKSE VEIIKEQMRG ELTHLSHEYL GLLDLAYDSK QNRLFELKTM QLLTEECGFE  60
GLHLGGSRKP DGIVYTKDES EQVDKENYGI IIDTKAYSGG YSLPISQADE MERYIGENQT  120
RDIRINPNEW WKNFGDGVTE YYYLFVAGHF KGKYQEQIER INCNKSIKGA AVSIQQLLRI  180
VNDYKAGKLT HEDMKLKLFY                                              200

SEQ ID NO: 23             moltype = AA  length = 200
FEATURE                   Location/Qualifiers
REGION                    1..200
                          note = Synthetic Construct
source                    1..200
                          mol_type = protein
                          organism = synthetic construct
SEQUENCE: 23
DLTRTDLLDV KEELREKLTH LSHEYLALID LAYDSRQHRL FEMKTMELLI EECGYQGDHL  60
GGSRRPDGIC YTHNLYENYG IIIDTKAYKD GYNLPITQAD EMERYIGDNA IRDTQRNPNK  120
WWEHFSQDIR LFYFMFISGH FKGQYQDKIN LLELNTGVCG AAIDIKKLLL TVNYYKAGII  180
SHEDIASDFF QTTNDEADNS                                              200

SEQ ID NO: 24             moltype = AA  length = 194
FEATURE                   Location/Qualifiers
REGION                    1..194
                          note = Synthetic Construct
source                    1..194
                          mol_type = protein
                          organism = synthetic construct
SEQUENCE: 24
KAEKSEFLIE KDKLREKLDT LPHDYLSMVD LAYDSKQNRL FEMKTIELLI NECNYKGLHL  60
GGTRKPDGIV YTNNEVENYG IIIDTKAYSK GYNLPISQVD EMTRYVEENN KREKKRNPNE  120
WWNNFDSDVK KFYFSFISGK FVGNIEEKLQ RITLFTEIYG NAITVTTLLY IANEIKANRM  180
KKSDIMEYFN DKVY                                                    194

SEQ ID NO: 25             moltype = AA  length = 213
FEATURE                   Location/Qualifiers
REGION                    1..213
                          note = Synthetic Construct
source                    1..213
                          mol_type = protein
                          organism = synthetic construct
SEQUENCE: 25
KISKTNILEL KDKVRDKLKY VDHRYLALID LAYDGTANRD FEIQTIDLLI NELKFKGVRL  60
GESRKPDGII SYNINGVIID NKAYSTGYNL PINQADEMIR YIEENQTRDE KINSNKWWES  120
FDEKVKDFNY LFVSSFFKGN FKNNLKHIAN RTGVNGGAIN VENLLYFAEE LKAGRISYLD  180
SFKMYNNDEI YLGDISDYSY VKFAAEEEGE YLT                                213

SEQ ID NO: 26             moltype = AA  length = 201
FEATURE                   Location/Qualifiers
REGION                    1..201
                          note = Synthetic Construct
source                    1..201
                          mol_type = protein
                          organism = synthetic construct
SEQUENCE: 26
PLEDSDIKNV KNRLMNKLPN LDPADFGLVD LAFAKAGTQS ENTKMANEFE ARTVEFMKQY  60
FKLSGVHLGG GNRPDGALYD NDKYGIILDT KAYSQGYKPD TKQVREMSDY IQNVWYDSGR  120
KEARAWWKNF PANLDKTSIH FIWVAGTFKS GMNDMIVAAK GHTAMTGGAI TVEKLLTIAD  180
NVVAHNYNYD VLSDKFMDAV I                                            201

SEQ ID NO: 27             moltype = AA  length = 206
FEATURE                   Location/Qualifiers
REGION                    1..206
                          note = Synthetic Construct
```

-continued

```
source                  1..206
                        mol_type = protein
                        organism = synthetic construct
SEQUENCE: 27
SLQKSSLSGM KDQIRARLTA LPHEYLSLID LAYDSEQNRL FEMKIIELFT EECGFSGRHL  60
GGSNKPDGVI SAADLSYGII VDTKAYSKGY GLPISQADEM ERYVRENLTR DSRINPNEWW  120
LAFDGAVPRF AFLFVSGHFT GTYGQRIERI IRSTGVPGAA LEISKLLLYA DALKSGRISQ  180
RDFYRLVFPP QPESEGLRRC PKPRKL                                       206

SEQ ID NO: 28           moltype = AA  length = 192
FEATURE                 Location/Qualifiers
REGION                  1..192
                        note = Synthetic Construct
source                  1..192
                        mol_type = protein
                        organism = synthetic construct
SEQUENCE: 28
EVVRSDIEET KAMLRENLKV LPHEYIELVE IAQDPDQNRV FEMKVIELFI KEYGFNGSHL  60
GGSRRPDGAI FTDTFGVIVD TKAYKDGYNL PISQADEMER YVRENKERNE VANPNKWWSI  120
FPETVKEYMF LFVSSFFKGN FRNHLERISL NTGVRGGVIS VEHLLLGADY IKRGVLTLDD  180
FRNKFNNDEI EF                                                      192

SEQ ID NO: 29           moltype = AA  length = 193
FEATURE                 Location/Qualifiers
REGION                  1..193
                        note = Synthetic Construct
source                  1..193
                        mol_type = protein
                        organism = synthetic construct
SEQUENCE: 29
KVSKTNILEL KDNTREKLVY LDHRYLSLFD LAYDDKASRD FEIQTIDLLI NELQFKGLRL  60
GERRKPDGII SYGVNGVIID NKAYSKGYNL PIRQADEMIR YIQENQSRDE KLNPNKWWEN  120
FEEETSKFNY LFISSKFISG FKKNLQYIAD RTGVNGGAIN VENLLCFAEM LKSGKLEYND  180
FFNQYNNDEI IMR                                                     193

SEQ ID NO: 30           moltype = AA  length = 196
FEATURE                 Location/Qualifiers
REGION                  1..196
                        note = Synthetic Construct
source                  1..196
                        mol_type = protein
                        organism = synthetic construct
SEQUENCE: 30
QLIKGEMENK KAELRQKLKH VPHEYIELIE IAQDSKQNRL LEFKVVEFFK KIYGYDGRHL  60
GGSRKPDGAL YTGSLKSNYG IILDTKAYKD GYSLPISQAD EMQRYVDENN SRNQVINPNK  120
WWEVYPISIV DFKFLFVSGF FKGEYKKQLE RVSHLTKRKG AVLSIEQLLL GGEKIKDGSL  180
TLVEVSDKFK NDAINF                                                  196

SEQ ID NO: 31           moltype = AA  length = 196
FEATURE                 Location/Qualifiers
REGION                  1..196
                        note = Synthetic Construct
source                  1..196
                        mol_type = protein
                        organism = synthetic construct
SEQUENCE: 31
FLVKGAMEIK KSELRHKLRH VPHEYIELIE IAQDSKQNRL LEFKVVEFFK KIYGYRGKHL  60
GGSRKPDGAL FTDGLVLNHG IILDTKAYKD GYRLPISQAD EMQRYVDENN KRSQVINPNE  120
WWEIYPTSIT DFKFLFVSGF FQGDYRKQLE RVSHLTKCQG AVMSVEQLLL GGEKIKEGSL  180
TLEEVGKKFK NDEIVF                                                  196

SEQ ID NO: 32           moltype = AA  length = 198
FEATURE                 Location/Qualifiers
REGION                  1..198
                        note = Synthetic Construct
source                  1..198
                        mol_type = protein
                        organism = synthetic construct
SEQUENCE: 32
LPVKSEVSVF KDYLRTHLAH VDHRYLILVD LGFDGSSDRD YEMKTAELLT TELGFKGARL  60
GDTRKPDVCV YHGNNGLIID NKAYGKGYSL PIKQADEINR YIEENKERNE LLNPNRWWNI  120
FDHTVTHFRF AFISGSFTGG FKDRLNLISM RSGICGAAIN SVNLLLMAEE LKAGRLGYEE  180
WFEAFDCNDE ISFPLDLI                                                198

SEQ ID NO: 33           moltype = AA  length = 144
FEATURE                 Location/Qualifiers
REGION                  1..144
                        note = Synthetic Construct
source                  1..144
```

-continued

```
                        mol_type = protein
                        organism = synthetic construct
SEQUENCE: 33
PVLKDAALQK TKNTLLNELT EIDPADIEVI EMSWKKATTR SQNTLEATLF EVKVVEIFKK  60
YFELNGEHLG GQNRPDGAVY YNSTYGIILD TKAYSNGYNI PVDQQREMVD YITDVIDKNQ  120
NVTPNRWWEA FPATLLKIIY IIYG                                        144

SEQ ID NO: 34           moltype = AA  length = 196
FEATURE                 Location/Qualifiers
REGION                  1..196
                        note = Synthetic Construct
source                  1..196
                        mol_type = protein
                        organism = synthetic construct
SEQUENCE: 34
VPVKSEVSLL KDYLRTHLLH VDHRYLILLD LGFDGTSDRD YEIQTAQLLT GELNFKGARL  60
GDTRKPDVCV YYGEDGLIID NKAYGKGYSL PIKQADEMYR YIEENKERNE KLNPNKWWEI  120
FNNDVIHYHF AFISGAFTGG FKERLDNIRM RSGIYGAAVN SMNLLLMAEE LKSGRLGYKE  180
CFKLFDCNDE IVLQRS                                                 196

SEQ ID NO: 35           moltype = AA  length = 190
FEATURE                 Location/Qualifiers
REGION                  1..190
                        note = Synthetic Construct
source                  1..190
                        mol_type = protein
                        organism = synthetic construct
SEQUENCE: 35
PEADVERMLA KSFQHGALGM FIHEFAQMAT ESRKRATEFE QATASIFADV FGFQARHIGQ  60
AGAVERPDVV LASTSEHYGA ILDSKAYASG YSARAGHRNT MRNYIERFAD YALTEDPVAF  120
FAYIVSDAKK TLNGQIKAIA DQNGVPGSAI TARDIIRMVE RHQSGRPYTH QEIRDLLSNN  180
RTLDYQDLNL                                                        190

SEQ ID NO: 36           moltype = AA  length = 196
FEATURE                 Location/Qualifiers
REGION                  1..196
                        note = Synthetic Construct
source                  1..196
                        mol_type = protein
                        organism = synthetic construct
SEQUENCE: 36
VPVKSEVSLC KDYLRSYLTH VDHKYLILLD LGFDGTSDRD YEIQTAQLLT AELDFKGARL  60
GDTRKPDVCV YYGEDGLIID NKAYGKGYSL PIKQADEIYR YIEENKKRDE KLNPNKWWEI  120
FDKGVVRYHF AFVSGAFTGG FKERLDNIRM RSGICGAAIN SMNLLLMAEE LKSGRLGYEE  180
CFALFDCNDE ITFQSS                                                 196

SEQ ID NO: 37           moltype = AA  length = 193
FEATURE                 Location/Qualifiers
REGION                  1..193
                        note = Synthetic Construct
source                  1..193
                        mol_type = protein
                        organism = synthetic construct
SEQUENCE: 37
GATKSDLSLL KDDIRKKLNH INHKYLVLID LGFDGTADRD YELQTADLLT SELAFKGARL  60
GDSRKPDVCV YHDKNGLIID NKAYGSGYSL PIKQADEMLR YIEENQKRDK ALNPNEWWTI  120
FDDAVSKFNF AFVSGEFTGG FKDRLENISR RSYTNGAAIN SVNLLLLAEE IKSGRISYGD  180
AFTKFECNDE III                                                    193

SEQ ID NO: 38           moltype = AA  length = 213
FEATURE                 Location/Qualifiers
REGION                  1..213
                        note = Synthetic Construct
source                  1..213
                        mol_type = protein
                        organism = synthetic construct
SEQUENCE: 38
KISKTNVLEL KDKVRDRLKY VDHRYLALID LAYDGTANRD FEIQTIDLLI NELKFKGVRL  60
GESRKPDGII SYNINGVIID NKAYSTGYNL PINQADEMIR YIEENQTRDE KINSNKWWES  120
FDEKVKDFNY LFVSSFFKGN FKNNLKHIAN RTGVNGGAIN VENLLYFAEE LKAGRLSYID  180
SFTMYDNDEI YVGNFSDYSY VKFAAEDQSD YRV                              213

SEQ ID NO: 39           moltype = AA  length = 222
FEATURE                 Location/Qualifiers
REGION                  1..222
                        note = Synthetic Construct
source                  1..222
                        mol_type = protein
                        organism = synthetic construct
```

-continued

```
SEQUENCE: 39
NIAKSDFSII KDNIRRKLQY VNHKYLLLID LGFDSDSNRD YEIQTAELLT TELAFKGARL  60
GDTRKPDVCV YYGENGLIID NKAYSKGYSL PMSQADEMVR YIEENKARQS SINPNQWWKI  120
FEDTVCNFNY AFVSGEFTGG FKDRLNNICE RTRVSGGAIN TINLLLLAEE LKSGRMSYPK  180
CFSYFDTNDE VHIPTYRDDD YEIHRSMAAE KSVEYGSQHG VN                    222

SEQ ID NO: 40          moltype = AA  length = 204
FEATURE                Location/Qualifiers
REGION                 1..204
                       note = Synthetic Construct
source                 1..204
                       mol_type = protein
                       organism = synthetic construct
SEQUENCE: 40
VLVKSEVSIL KDYLRTHMIH VDHKYLILLD LGFDGTSDRD YEMQTAELLT KELAFQGARL  60
GDTRKPDVCV YYGENGLIID NKAYGKGYSL PMKQADEMYR YIEENKERSE RFNKNKWWQI  120
FDDQVKQFRF VFLSGSFTGG FKDRLNHISM RSGLNGAAIS SVNLLLLAEE LKSGRMRYED  180
CFKLFDGNDE VRLPGSFKRG GLMK                                        204

SEQ ID NO: 41          moltype = AA  length = 193
FEATURE                Location/Qualifiers
REGION                 1..193
                       note = Synthetic Construct
source                 1..193
                       mol_type = protein
                       organism = synthetic construct
SEQUENCE: 41
VPVKSEVSIC KDYLRSHLTH VDHKYLVLLD LGYDGNSDRD YEIQTAQLLT SELDFQGARL  60
GDTRKPDVCV YYGKDGLIID NKAYGKGYSL PIKQADEIYR YIEENKERNE MLNPNKWWEV  120
FEESVTRYHF AFISGTFTGG FKDRLNNISM RSGICGAVIN SMNLLLMAEA LKSGRLSYEE  180
CFSLFDCNDE IIF                                                    193

SEQ ID NO: 42          moltype = AA  length = 199
FEATURE                Location/Qualifiers
REGION                 1..199
                       note = Synthetic Construct
source                 1..199
                       mol_type = protein
                       organism = synthetic construct
SEQUENCE: 42
KEIKNNINYV IDNTKNLDQN LIEKIIEQSF SGQKYCKEFE DSIFELYNKV IGFEGIKLGG  60
VGNREPDSLM WYRASIDDDS YGLIVDAKAY SKGFRINTNS SRQMNDYIYT FANKLQDEYK  120
INRSYYHWVS SKYVGNRDIE NFAENVRNMY SFESKGSIVS ISNALLLADR FQIHRDFKKL  180
ESLIAIQREI LQKDIEILF                                              199

SEQ ID NO: 43          moltype = AA  length = 201
FEATURE                Location/Qualifiers
REGION                 1..201
                       note = Synthetic Construct
source                 1..201
                       mol_type = protein
                       organism = synthetic construct
SEQUENCE: 43
IPVKSEVSVY KDYLRSRLTR IDHRYLILVD LGFDGNSDRD YEIQTAELLT KELSFQGARL  60
GDTRKPDVCV FYGDKGLIID NKAYGKGYSL PIKQADEMNR YLEENRERSD LLNPNRWWEI  120
FDESVTHFRF AFLSGAFIGG FRDRLNLISV RNGLKGAAVS SVTLLLLAEE LKSGRLKYED  180
FFLLFDCNDE ISCPGLPEGL F                                           201

SEQ ID NO: 44          moltype = AA  length = 198
FEATURE                Location/Qualifiers
REGION                 1..198
                       note = Synthetic Construct
source                 1..198
                       mol_type = protein
                       organism = synthetic construct
SEQUENCE: 44
ISVKSDMAVV KDSVRERLAH VSHEYLLLID LGFDGTSDRD YEIQTAELLT RELDFLGGRL  60
GDTRKPDVCI YYGKDGMIID NKAYGKGYSL PIKQADEMYR YLEENKERNE KINPNRWWKV  120
FDEGVTDYRF AFVSGSFTGG FKDRLENIHM RSGLCGGAID SVTLLLLAEE LKAGRMEYSE  180
FFRLFDCNDE VTFQSIVI                                               198

SEQ ID NO: 45          moltype = AA  length = 193
FEATURE                Location/Qualifiers
REGION                 1..193
                       note = Synthetic Construct
source                 1..193
                       mol_type = protein
                       organism = synthetic construct
SEQUENCE: 45
```

-continued

```
APVKSEVSVC KDYLRSRLTH VDHKYLLLLD LGYDGTSDRD YEIQTAGLLT DELDFKGARL  60
GDTRKPDVCV YYGEDGLILD NKAYGKGYSL PIKQADEMYR YIEENKERNE MLNPNKWWEI  120
FDRRVVRYHF AFVSGAFTGG FKERLNNIRM RSGICGAAVN SMNLLLMAEE LKSGRLGYKE  180
CFALFDCNDE IVL                                                     193

SEQ ID NO: 46          moltype = AA  length = 192
FEATURE                Location/Qualifiers
REGION                 1..192
                       note = Synthetic Construct
source                 1..192
                       mol_type = protein
                       organism = synthetic construct
SEQUENCE: 46
PEEKSEVLLV KERVRSKLRA LDPTYLRLVD LAYDGTADRE FEISTIDLFT NELDFEGKHL  60
GGSRKPDGII YRDCNGLLID NKAYSKGYSL PRAQVDEMGR YVRENKNRNA AINPLKWWEN  120
FPNSVTEFNF AFISSFFTGQ YAERLSEIYH EYGVKGGVID VENLLYIAEG LKSGDLSYSE  180
FFELFDNSQI LF                                                      192

SEQ ID NO: 47          moltype = AA  length = 201
FEATURE                Location/Qualifiers
REGION                 1..201
                       note = Synthetic Construct
source                 1..201
                       mol_type = protein
                       organism = synthetic construct
SEQUENCE: 47
EELRDKVIEE QKAIFLQKTK LPLSYIELLE IARDGKRSRD FELITMELFK NIYKINAIVL  60
GGARKPDGVL YMPEFGVIVD TKAYADGYSK SIAQADEMIR YIEDNKRRDP SRNSTKWWEH  120
FPTSIPANNF YFLWVSSVFV NKFHEQLSYT AQETQTVGAA LSVEQLLLGA DSVLKGNLTT  180
KKFIDSFKNQ EIVFAPSILH S                                            201

SEQ ID NO: 48          moltype = AA  length = 197
FEATURE                Location/Qualifiers
REGION                 1..197
                       note = Synthetic Construct
source                 1..197
                       mol_type = protein
                       organism = synthetic construct
SEQUENCE: 48
NLTQELKDAA LEEKKLKYQQ LTKLPIKYIE LLEIAYDGRR NRDFEILVAD IFKNLYKFHS  60
ILLGGGRKPD GLIFTDKFGV IIDTKAYGEG YGKLITQEDE MVRYIEDNQQ RDKNRNSITW  120
WEKFNDAIPA NSYYFMWVSS NFTGNFQEQL NSTSNRTGVK GAALNVEQLL LGAANAQQGI  180
LDISTFPSYM NNKEIIW                                                 197

SEQ ID NO: 49          moltype = AA  length = 197
FEATURE                Location/Qualifiers
REGION                 1..197
                       note = Synthetic Construct
source                 1..197
                       mol_type = protein
                       organism = synthetic construct
SEQUENCE: 49
KELKDEQSEK RKAYFLKETN LPLKYIELLD IAYDGKRNRD FEIVTMELFR NVYRLQSKLL  60
GGVRKPDGLL YKHRFGIIVD TKAYGEGYSK SISQADEMIR YIEDNKRRDE NRNSTKWWEH  120
FPDCIPKQSF YFMWVSSKFV GKFQEQLDYT ANETKTNGAA LNVEQLLWGA DLVAKGKLDI  180
SQLPSYFQNK EIEFVKA                                                 197

SEQ ID NO: 50          moltype = AA  length = 201
FEATURE                Location/Qualifiers
REGION                 1..201
                       note = Synthetic Construct
source                 1..201
                       mol_type = protein
                       organism = synthetic construct
SEQUENCE: 50
TELRDELIEQ QKAIFLQKTK LPIEYIELLE IARDGNRSRD FEIITMGLFR DIYKINSTVL  60
GGSRKPDGLL HMSDFGVIVD TKAYADGYSK NIAQADEMIR YIEDNKRRDS NRNPTKWWEI  120
FPQTIPENKF YFLWISSSFV NKFPEQLNYT AQETQTVGAA LNVEQLLLGA DAILKNKLTI  180
RKVVDSFKNQ EIYFVPSILN N                                            201

SEQ ID NO: 51          moltype = AA  length = 197
FEATURE                Location/Qualifiers
REGION                 1..197
                       note = Synthetic Construct
source                 1..197
                       mol_type = protein
                       organism = synthetic construct
SEQUENCE: 51
KELKNEQSEK LRSKFLKLTN LPMKYLELLD IAFDGKRNRD FEIVTMDLFR NVYKLNAKLL  60
```

-continued

```
GGGRKPDGLI YTDGFGVIVD TKAYGEGYSK NINQADEMIR YIEDNKRRDL NRNPIEWWKD  120
YPDSIPVDSF YFMWVSSKFV GKFQEQLEYT ANETQTLGGA LNVEQLLLGA DLVAKGQFDA  180
KELHSMFNNK EIVFDKV                                                 197

SEQ ID NO: 52          moltype = AA  length = 200
FEATURE                Location/Qualifiers
REGION                 1..200
                       note = Synthetic Construct
source                 1..200
                       mol_type = protein
                       organism = synthetic construct
SEQUENCE: 52
QLVPSYITQT KLRLSTLINY IDHSYFDLID LGFDGRQNRL YELRIVELLN LISSLRALHL  60
SGGNRPEIIA YSPDVNPING VIMDSKSYRN GFNIPNSERD KMVRYIHEYN QKNPNLNSNK  120
WWENFRVPNY PRSPIKYTFV SGNFISQFLS QIQYILTQTG INGGVITSEK LIKKVDTVLN  180
PNISYTINDF FHELGCNGLV                                              200

SEQ ID NO: 53          moltype = AA  length = 198
FEATURE                Location/Qualifiers
REGION                 1..198
                       note = Synthetic Construct
source                 1..198
                       mol_type = protein
                       organism = synthetic construct
SEQUENCE: 53
SPVKSEVSVF KDYLRTHLTH VDHRYLILVD LGFDGSSDRD YEMKTAELFT AELGFMGARL  60
GDTRKPDVCV YHGAHGLIID NKAYGKGYSL PIKQADEIYR YIEENKERAV RLNPNQWWKV  120
FDESVAHFRF AFISGSFTGG FKDRIELISM RSGICGAAVN SVNLLLMAEE LKSGRLNYEE  180
WFQYFDCNDE ISLPMSLT                                                198

SEQ ID NO: 54          moltype = AA  length = 202
FEATURE                Location/Qualifiers
REGION                 1..202
                       note = Synthetic Construct
source                 1..202
                       mol_type = protein
                       organism = synthetic construct
SEQUENCE: 54
DEFKSSEADK IKTFLRPVLK HIDHHYLQAV DIAFKKNTSN QENTQFEILS TDLFTKEMGF  60
HGRHLGGANK PDGFVYDQTD GWIIDSKAYS QGFAFTAHNT DAMSRYIRQY RTRNDKSTWW  120
KDLPDNLPNT QFIYISSYFT GKYRQQLADY EHSNQMRGSL MEIAKLLMLA EKVKAGILNY  180
NDFKKYALDK NTDFEFYSFI LK                                           202

SEQ ID NO: 55          moltype = AA  length = 200
FEATURE                Location/Qualifiers
REGION                 1..200
                       note = Synthetic Construct
source                 1..200
                       mol_type = protein
                       organism = synthetic construct
SEQUENCE: 55
RISPSNLEQT KQQLREELIN LDHQYLDILD FSIAGNVGAR QFEVRIVELL NEIIIAKHLS  60
GGNRPEIIGF NPKENPEDCI IMDSKAYKEG FNIPANERDK MIRYVEEYNA KDNTLNNNEW  120
WKNFESPNYP TNQVKFSFVS SSFIGQFTNQ LTYINNRTNV NGSAITAETL LRKVENVMNV  180
NTEYNLNNFF EELGSNTLVA                                              200

SEQ ID NO: 56          moltype = AA  length = 197
FEATURE                Location/Qualifiers
REGION                 1..197
                       note = Synthetic Construct
source                 1..197
                       mol_type = protein
                       organism = synthetic construct
SEQUENCE: 56
KELKDEQSEK RKAKFLKETK LPMKYIELLD IAYDGKRNRD FEIVTMELFR EVYRLNSKLL  60
GGGRKPDGLI YTDDFGVIVD TKAYGEGYSK SINQADEMIR YIEDNKRRDE KRNPIKWWES  120
FPSSISQNNF YFLWVSSKFV GKFQEQLAYT ANETQTKGGA INVEQILIGA DLIMQKMLDI  180
NAIPSFFENQ EIIFKKV                                                 197

SEQ ID NO: 57          moltype = AA  length = 195
FEATURE                Location/Qualifiers
REGION                 1..195
                       note = Synthetic Construct
source                 1..195
                       mol_type = protein
                       organism = synthetic construct
SEQUENCE: 57
DILVDKEREM RKAKFLKETV LDSKFISLLD LAADATKSRD FEIVTAELFK EAYNLNSVLL  60
GGSNKPDGLV FTDDFGILLD TKAYKNGFSI YAKDRDQMIR YVDDNNKRDK IRNPNEWWKS  120
```

-continued

```
FSPLIPNDKF YYLWVSNFFK GQFKNQIEYV NRETNTYGAV LNVEQLLYGA DAVIKGIINP  180
NKLHEYFSND EIKFK                                                   195

SEQ ID NO: 58          moltype = AA  length = 197
FEATURE                Location/Qualifiers
REGION                 1..197
                       note = Synthetic Construct
source                 1..197
                       mol_type = protein
                       organism = synthetic construct
SEQUENCE: 58
KELKNEQSEK RKAKFLKETD LPMKYIELLD IAYDGKRNRD FEIVTMELFR KVYKLHSKLL  60
GGGRKPDGLI YKDDFGIIVD TKAYGEGYSK SIHQADEMIR YIEDNKRRDE NRNPVKWWEH  120
FPSIIPQDKF YFMWVSSKFV GKFQEQLDYT ANETNTKGAA LNVEQLLLGA DLVSKGKLNA  180
TTLPSYFKNA EIEFIKA                                                 197

SEQ ID NO: 59          moltype = AA  length = 194
FEATURE                Location/Qualifiers
REGION                 1..194
                       note = Synthetic Construct
source                 1..194
                       mol_type = protein
                       organism = synthetic construct
SEQUENCE: 59
KELKDAALEH KKVQFQQLTQ LPMKYIELLE IAYDGKRNRD FEILTADLFK YVYGFESILL  60
GGGRKPDGLI FTDKFGVIID TKAYSQGYGK SINQEDEMVR YIEDNQQRDE TRNSVTWWDN  120
FDDSIPDDSF YFLWVSSKFN GNFQEQLTST HNRTGINGGA INVEQLLIGA AKVSKGQLDI  180
STLPSYMDNK EIIW                                                    194

SEQ ID NO: 60          moltype = AA  length = 197
FEATURE                Location/Qualifiers
REGION                 1..197
                       note = Synthetic Construct
source                 1..197
                       mol_type = protein
                       organism = synthetic construct
SEQUENCE: 60
KELKDKASEQ RKAEFMNKTD LPAKYIELLE IAFDGNRNRD FEIITAEIFK KVYGLKSVLL  60
GGGRKPDCLV FNANFGMIID TKAYSTGYSK SISQEDEMVR YIEDNQYRDT TRNPIEWWNN  120
FPSSIKKEKY YFMWVSSKFI GRFQEQIEST YNRTNTKGAA LNVEQLLLGA NAVLRGELDA  180
NRISDYIDNK EILWVNN                                                 197

SEQ ID NO: 61          moltype = AA  length = 203
FEATURE                Location/Qualifiers
REGION                 1..203
                       note = Synthetic Construct
source                 1..203
                       mol_type = protein
                       organism = synthetic construct
SEQUENCE: 61
SCVKDEVNDI VDRVRVKLKN IDHKYLILIS LAYSNETERT KKNSDARDFE IQTAELFTKE  60
LGFNGIRLGE SNKPDVLISF GANGTIIDNK SYKDGFNIPR ATSDQMIRYI NENNQRTTQL  120
NPNEWWKNFD SSVSNYTFLF VTSFLKGSFK NQIEYISNAT NGTRGAAINV ENLLYISEDI  180
KSGIIKQSDF YSKFKNDEIV YPI                                          203

SEQ ID NO: 62          moltype = AA  length = 195
FEATURE                Location/Qualifiers
REGION                 1..195
                       note = Synthetic Construct
source                 1..195
                       mol_type = protein
                       organism = synthetic construct
SEQUENCE: 62
KVQKSNILDV IEKCREKINN IPHEYLALIP MSFDENESTM FEIKTIELLT EHCKFDGLHC  60
GGASKPDGLI YSEDYGVIID TKSYKDGFNI QTPERDKMKR YIEENQNRNP QHNKTRWWDE  120
FPHNISNFLF LFVSGKFGGN FKEQLRILSE QTNNTLGGAL SSYVLLNIAE QIAINKIDHC  180
DFKTRISCLD EVAFD                                                   195

SEQ ID NO: 63          moltype = AA  length = 202
FEATURE                Location/Qualifiers
REGION                 1..202
                       note = Synthetic Construct
source                 1..202
                       mol_type = protein
                       organism = synthetic construct
SEQUENCE: 63
AIRKEHITEL KDKIRKKLHH ISHSYLLLVD LAYSDADTKA KKNLEAKEFE IQTAKLFTKE  60
LDFSGSRLGD SNRPDVILSY GTQGTIIDNK SYKDGFNLDA GCRDEMSRYI EENQQRIPGV  120
PSNEWWKSFD PSVTDFTFLF VTSYLKGNFK KGLSYISTMR KIQGACVNVE NLLYLAENIK  180
```

-continued

```
SGKTSYTEFF SLFNNEEIVI GS                                          202

SEQ ID NO: 64          moltype = AA  length = 197
FEATURE                Location/Qualifiers
REGION                 1..197
                       note = Synthetic Construct
source                 1..197
                       mol_type = protein
                       organism = synthetic construct
SEQUENCE: 64
AEADVTSEKI KNHFRRVTEL PERYLELLDI AFDHKRNRDF EMVTAGLFKD VYGLESVHLG  60
GANKPDGVVY NDNFGIILDT KAYENGYGKH ISQIDEMVRY IDDNRLRDTT RNPNKWWENF  120
DADIPSDQFY YLWVSGKFLP NFAEQLKQTN YRSHANGGGL EVQQLLLGAD AVKRRKLDVN  180
TIPNYMKNEV ITLVPEA                                                197

SEQ ID NO: 65          moltype = AA  length = 211
FEATURE                Location/Qualifiers
REGION                 1..211
                       note = Synthetic Construct
source                 1..211
                       mol_type = protein
                       organism = synthetic construct
SEQUENCE: 65
LPQKDQVQQQ QDELRPMLKN VDHRYLQLVE LALDSDQNSE YSQFEQLTME LVLKHLDFDG  60
KPLGGSNKPD GIAWDNDGNF IIFDTKAYNK GYSLAGNTDK VKRYIDDVRD RDTSRTSTWW  120
QLVPKSIDVH NLLRFVYVSG NFTGNYMKLL DSLRSWSNAQ GGLASVEKLL LTSELYLRNM  180
YSHQELIDSW TDNNVKHDEY FLKIEKQLTI K                                211

SEQ ID NO: 66          moltype = AA  length = 170
FEATURE                Location/Qualifiers
REGION                 1..170
                       note = Synthetic Construct
source                 1..170
                       mol_type = protein
                       organism = synthetic construct
SEQUENCE: 66
MNFFSLHPNV YATGRPKGLI GMLENVWVSN HTPGEGTLYL ISGFSNYNGG VRFYETFTEH  60
INQGGRVIAI LGGSTSQRLS SRQVVEELLN RGVEVHIINR KRILHAKLYG TSNNLGESLV  120
VSSGNFTGPG MSQNIEASLL LDNNTTQSMG FSWNDMISEM LNQNWHIHNM             170

SEQ ID NO: 67          moltype = AA  length = 194
FEATURE                Location/Qualifiers
REGION                 1..194
                       note = Synthetic Construct
source                 1..194
                       mol_type = protein
                       organism = synthetic construct
SEQUENCE: 67
ISVKSDMAVI KDSVRERLAH VSHEYLLLID LGFDGTSDRD YEIQTAELLT RELDFLGGRL  60
GDTRKPDVCI YYGKDGMIID NKAYGKGYSL PIKQADEMYR YLEENKERNE KINPNRWWKV  120
FDEGVTDYRF AFVSGSFTGG FKDRLENIHM RSGLCGGAMD SVTLLLLAEE LKAGRMEYSE  180
FFRLFDCNDE VTFR                                                   194

SEQ ID NO: 68          moltype = AA  length = 196
FEATURE                Location/Qualifiers
REGION                 1..196
                       note = Synthetic Construct
source                 1..196
                       mol_type = protein
                       organism = synthetic construct
SEQUENCE: 68
PLVKGEMEKK KSDLRHKLKH VPHEYIELIE IAQDSKQNRL FEFKVVEFLK EVYDYNGKHL  60
GGSRKPDGAL YTNGLKTDYG IILDTKAYKD GYSLPISQAD EMQRYVDENN NRNAIINPNE  120
WWKVYPNSIL DFKFLFVSGF FKGDYKKQLA RVSNLTKRKG AVLSVEQLLL GGEKIKDGSL  180
TLEDVGDKFN NDEIIF                                                 196

SEQ ID NO: 69          moltype = AA  length = 136
FEATURE                Location/Qualifiers
REGION                 1..136
                       note = Synthetic Construct
source                 1..136
                       mol_type = protein
                       organism = synthetic construct
SEQUENCE: 69
PLVKGEMEKK KSDLRHKLKH VPHEYIELIE IAQDSKQNRL FEFKVVEFLK QVYDYNGKHL  60
GGSRKPDGAL YTNGLKTDYG IILDTKAYKD GYSLPISQAD EMQRYVDENN NRNAIINPNE  120
WWKVYPNSIL DFKFLF                                                 136

SEQ ID NO: 70          moltype = AA  length = 197
```

-continued

```
FEATURE                Location/Qualifiers
REGION                 1..197
                       note = Synthetic Construct
source                 1..197
                       mol_type = protein
                       organism = synthetic construct
SEQUENCE: 70
SLAKSDLAES KEAVRAKLLN LSHEYLSLID LAYDSKQNRL FEMKTLDLLI EECDYQGLHL  60
GGSRKPDGII YTITDKCKYG VIIDTKAYSK GYNLPISQAD EMERYIGENQ VRDEKVNPNM  120
WWRNFDDEIN EFYFMFVSGH FVGNYKAQIE RISRTKGICG TALAVINLLL CAEAYKSGRL  180
THEDIKKEVF NNGEFVL                                                197

SEQ ID NO: 71          moltype = AA  length = 199
FEATURE                Location/Qualifiers
REGION                 1..199
                       note = Synthetic Construct
source                 1..199
                       mol_type = protein
                       organism = synthetic construct
SEQUENCE: 71
DNVKSNISLL KDELRGQINH ISHEYLSLVD LAFDSKQNRL FEMKVLELLV NEYGFKGKHL  60
GGSRKPDGVV YSTTLEDNFG IIVDTKAYSG GYNLPISQAD EMERYIRENT NRDEEVNPNK  120
WWENFSEEVE KYYFVFISGS FKGKFEEQLK RLSMTTGVTG SAVNVVNLLL GAEKLKSGEF  180
TIEELEKAMF NNSEFIVKY                                              199

SEQ ID NO: 72          moltype = AA  length = 201
FEATURE                Location/Qualifiers
REGION                 1..201
                       note = Synthetic Construct
source                 1..201
                       mol_type = protein
                       organism = synthetic construct
SEQUENCE: 72
KLAKSSQSET KEKLREKLRN LPHEYLSLVD LAYDSKQNRL FEMKVIELLT EECGFQGLHL  60
GGSRRPDGVL YTAGLTDNYG IILDTKAYSS GYSLPIAQAD EMERYVRENQ TRDELVNPNQ  120
WWENFENGLG TFYFLFVAGH FNGNVQAQLE RISRNTGVLG AAASISQLLL LADAIRGGRM  180
DRERLRHLMF QNEEFLLNQE L                                           201

SEQ ID NO: 73          moltype = AA  length = 190
FEATURE                Location/Qualifiers
REGION                 1..190
                       note = Synthetic Construct
source                 1..190
                       mol_type = protein
                       organism = synthetic construct
SEQUENCE: 73
SLQKSSLSGM KDQIRARLTA LPHEYLSLID LAYDSEQNRL FEMKIIELFT EECGFSGRHL  60
GGSNKPDGVI SAADLSYGVI VDTKAYSKGY GLPLSQADEM ERYVRENLTR DSRINPNEWW  120
LAFDGAVPRF AFLFVSGHFT GTYGQRIERI IRSTGVPGAA LAISKLLLYA DELKSGRISQ  180
QDFYRLVFPS                                                        190

SEQ ID NO: 74          moltype = AA  length = 201
FEATURE                Location/Qualifiers
REGION                 1..201
                       note = Synthetic Construct
source                 1..201
                       mol_type = protein
                       organism = synthetic construct
SEQUENCE: 74
PHYKDLSEKS ELSAEKEIVR AQLKNISHEY LSLMDIAFDS QQSRLFEMKF MELFLRECNF  60
LGDHLGGASK PDGALYTDVY EGNYGIIVDT KAYSKGYDLP VNQRDEMLRY IRENHLRDKK  120
QNPNEWWKIF PDNLNKFYFM FVSGKFKGGI AGKLEKIAAV HNVSGTAMPI STALLVAEKI  180
KGGKMSMIEF ANGIRNTEYE I                                           201

SEQ ID NO: 75          moltype = AA  length = 198
FEATURE                Location/Qualifiers
REGION                 1..198
                       note = Synthetic Construct
source                 1..198
                       mol_type = protein
                       organism = synthetic construct
SEQUENCE: 75
KISKTNVLEL KDKVRDKLKY VDNRYLALID LAYDGTANRD FEIQTIDLLI NELKFKGVRL  60
GESRKPDGII SYDINGVIID NKAYSSGYNL PINQADEMIR YIEENQTRDK KINPNKWWES  120
FDDKVKDFNY LFVSSFFKGN FKNNLKHIAN RTGVNGGVIN VENLLYFAEE LKSGRLSYVD  180
LFKMYDNDEI NIGNYCRL                                               198

SEQ ID NO: 76          moltype = AA  length = 213
FEATURE                Location/Qualifiers
```

-continued

```
REGION                 1..213
                       note = Synthetic Construct
source                 1..213
                       mol_type = protein
                       organism = synthetic construct
SEQUENCE: 76
KISKTNVLEL KDKVRDKLKY VDHRYLALID LAYDGTANRD FEIQTIDLLI NELKFKGVRL  60
GESRKPDGII SYDINGVIID NKAYSTGYNL PINQADEMIR YIEENQTRDK KINSNKWWES  120
FDDKVKNFNY LFVSSFFKGN FKNNLKHIAN RTGVNGGAIN VENLLYFAEE LKAGRLSYVD  180
SFTMYDNDEI YVGNIIDYSN VKIAAEEESH YSI                              213

SEQ ID NO: 77          moltype = AA  length = 196
FEATURE                Location/Qualifiers
REGION                 1..196
                       note = Synthetic Construct
source                 1..196
                       mol_type = protein
                       organism = synthetic construct
SEQUENCE: 77
LTEKSELSAE KEILRAQLKN ISHEYLSLMD IAFDSQQNRL FEMKFMELFL HECNFKGRHL  60
GGASKPDGAL YTDVYEGNYG IIVDTKAYSK GYDLPVSQRD EMLRYIRENS LRDKKQNPNE  120
WWKIFPEELN KFYFMFVSGK FKGDIKGKLE KIAAVHNVNG TAMPIVTALL VAEKIRGGKM  180
SMIEFARGIR NTEYEI                                                  196

SEQ ID NO: 78          moltype = AA  length = 213
FEATURE                Location/Qualifiers
REGION                 1..213
                       note = Synthetic Construct
source                 1..213
                       mol_type = protein
                       organism = synthetic construct
SEQUENCE: 78
KISKTNVLEL KDKVRDKLKY VDHRYLALID LAYDGTANRD FEIQTIDLLI NELKFKGVRL  60
GESRKPDGII SYNINGVIID NKAYSTGYNL PINQADEMIR YIEENQTRDE KINSNKWWES  120
FDDKVKDFNY LFVSSFFKGN FKNNLKHIAN RTGVSGGAIN VENLLYFAEE LKAGRLSYVD  180
SFKMYDNDEI YVGDFSDYSY VKFAAEEEGE YLT                              213

SEQ ID NO: 79          moltype = AA  length = 213
FEATURE                Location/Qualifiers
REGION                 1..213
                       note = Synthetic Construct
source                 1..213
                       mol_type = protein
                       organism = synthetic construct
SEQUENCE: 79
KISKTNVLEL KDKVRNKLKY VDHRYLALID LAYDGTANRD FEIQTIDLLI NELKFKGVRL  60
GESRKPDGII SYDINGVIID NKSYSTGYNL PINQADEMIR YIEENQTRDE KINSNKWWES  120
FDEKVKDFNY LFVSSFFKGN FKNNLKHIAN RTGVNGGAIN VENLLYFAEE LKSGRLSYVD  180
SFTMYDNDEI YVGSFTDYSN VKIAAEEESH YSI                              213

SEQ ID NO: 80          moltype = AA  length = 193
FEATURE                Location/Qualifiers
REGION                 1..193
                       note = Synthetic Construct
source                 1..193
                       mol_type = protein
                       organism = synthetic construct
SEQUENCE: 80
GAAKSDLSML KDDIRKKLNH VNHKYLVLID LGFDGTADRD YELQTADLLT SELAFKGARL  60
GDSRKPDVCV YHDKNGLIID NKAYGSGYSL PIKQADEMLR YIEENQKRDK ALNPNEWWSI  120
FDDAVSKFNF AFVSGEFTGG FKDRLENISR RSHTNGAAIN SVNLLLLAEE IKSGRLTYGD  180
ALAKFECNDE ILL                                                     193

SEQ ID NO: 81          moltype = AA  length = 197
FEATURE                Location/Qualifiers
REGION                 1..197
                       note = Synthetic Construct
source                 1..197
                       mol_type = protein
                       organism = synthetic construct
SEQUENCE: 81
KELKDEQSEK RKAKFLKETN LPMKYIELLD IAYDGKRNRD FEIVTMELFR KVYKLHSKLL  60
GGGRKPDGLL YQDDFGVIVD TKAYGEGYSK SINQADEMIR YIEDNKRRDK NRNPIKWWEH  120
FPSDIPQDKF YFMWVSSKFV GKFQEQLDYT ANETNTKGAA LNVEQLLLGA DLVSKGELNT  180
DTLPSYFKNT EIEFIKA                                                 197

SEQ ID NO: 82          moltype = AA  length = 194
FEATURE                Location/Qualifiers
REGION                 1..194
```

-continued

```
                      note = Synthetic Construct
source                1..194
                      mol_type = protein
                      organism = synthetic construct
SEQUENCE: 82
SLRRKSLFLK YTLLPPEYIE LLDIAYDGKR SRDFEIMTME LFKKIYGMNT VLLGGGRKPD  60
GICFRSTFGI IVDTKAYSEG YSKNISQEDE MVRYITDNKL RDKARNPTQW WTAFPASIEN  120
YYFLWVSSRF IGKFAEQLTS TARETKTNGG ALNVEQLLLG ADMILKKELP PDSIANHFNN  180
KEIFFADSII DKHQ                                                    194

SEQ ID NO: 83         moltype = AA  length = 191
FEATURE               Location/Qualifiers
REGION                1..191
                      note = Synthetic Construct
source                1..191
                      mol_type = protein
                      organism = synthetic construct
SEQUENCE: 83
SVFKDYLRTH LTHVDHRYLI LVDLGFDGSS DRDYEMKTAE LFTAELGFMG ARLGDTRKPD  60
VCVYHGANGL IIDNKAYGKG YSLPIKQADE IYRYIEENKE RDARLNPNQW WKVFDESVTH  120
FRFAFISGSF TGGFKDRIEL ISMRSGICGA AVNSVNLLLM AEELKSGRLD YEEWFQYFDC  180
NDEISFPVSL T                                                       191

SEQ ID NO: 84         moltype = AA  length = 197
FEATURE               Location/Qualifiers
REGION                1..197
                      note = Synthetic Construct
source                1..197
                      mol_type = protein
                      organism = synthetic construct
SEQUENCE: 84
KELRNEKFEQ RRAKFLKITN LPMKYIELLE IAFDGARNRD FEILTMDLFR NIYKLPSKLL  60
GGGRKPDGLV YTDKFGIIID TKAYGEGYSK SINQADEMIR YIEDNKRRDV NRNPIEWWKE  120
YPSSISNDSF YFLWISSQFV GKFQEQLDYT ANETQTTGGA LNVEQLLIGA DLVAKGEFSS  180
NELYSLFKNE EIIFKEV                                                 197

SEQ ID NO: 85         moltype = AA  length = 201
FEATURE               Location/Qualifiers
REGION                1..201
                      note = Synthetic Construct
source                1..201
                      mol_type = protein
                      organism = synthetic construct
SEQUENCE: 85
TELRDELIEQ QKAIFLQKTK LPIEYIELLE IARDGNRSRD FEIVTMGLFR DIYKINSTVL  60
GGSRKPDGLL HMSDFGVIVD TKAYADGYSK NIAQADEMIR YIEDNKRRDS NRNPTKWWEI  120
FPQTIPENKF YFLWISSSFV NKFPEQLNYT AQETQTVGAA LNVEQLLLGA DAILKNKLTI  180
RKVVDSFKNQ EIYFVPSILN N                                            201

SEQ ID NO: 86         moltype = AA  length = 197
FEATURE               Location/Qualifiers
REGION                1..197
                      note = Synthetic Construct
source                1..197
                      mol_type = protein
                      organism = synthetic construct
SEQUENCE: 86
QELKDEQAEK RKAKFLKETN LPMKYIELLD IAYDGKRNRD FEIVTMELFR NVYRLHSKLL  60
GGGRKPDGLL YQDCFGVIVD TKAYGKGYSK SINQADEMIR YIEDNKRRDE NRNPIKWWEA  120
FPDKIPQEEF YFMWVSSKFI GKFQEQLDYT SNETQIKGAA LNVEQLLLGA DLVLKGQLHI  180
SDLPSYFQNK EIEFVKA                                                 197

SEQ ID NO: 87         moltype = AA  length = 201
FEATURE               Location/Qualifiers
REGION                1..201
                      note = Synthetic Construct
source                1..201
                      mol_type = protein
                      organism = synthetic construct
SEQUENCE: 87
EELRDKVIEE QKAIFLQKTK LPLSYIELLE IARDGKRSRD FELITMELFR DIYKIKAIVL  60
GGARKPDGVL YMPEFGVIVD TKAYADGYSK SIAQADEMIR YIEDNKRRDP SRNSTKWWEH  120
FPTSIPANNF YFLWVSSVFV NKFHEQLSYT AQETQTVGAA LSVEQLLLGA DSVLKGNLTT  180
EKFIDSFKNQ EIVFAPSILH S                                            201

SEQ ID NO: 88         moltype = AA  length = 194
FEATURE               Location/Qualifiers
REGION                1..194
                      note = Synthetic Construct
```

```
source                  1..194
                        mol_type = protein
                        organism = synthetic construct
SEQUENCE: 88
AELKDKAADA VKAKFLKLTG LSMKYIELLD IAYDSSRNRD FEILTADLFK NVYGLDAMHL  60
GGGRKPDAIA QTSHFGIIID TKAYSNGYSK SISQEDEMVR YIEDNQQRSI TRNSVEWWKN  120
FNSSIPSTAF YFLWVSSKFV GKFDDQLLST YNRTNTCGGA LNVEQLLIGA YKVKAGLLGI  180
GQIPSYFKNK EIAW                                                   194

SEQ ID NO: 89           moltype = AA  length = 194
FEATURE                 Location/Qualifiers
REGION                  1..194
                        note = Synthetic Construct
source                  1..194
                        mol_type = protein
                        organism = synthetic construct
SEQUENCE: 89
AELKDKAADA VKAKFLKLTG LSMKYIELLD IAYDSSRNRD FEILTADLFK NVYGLDAMHL  60
GGGRKPDAIA QTSHFGIIID TKAYGNGYSK SISQEDEMVR YIEDNQQRSI TRNSVEWWKN  120
FNSSIPSTAF YFLWVSSKFV GKFDDQLLAT YNRTNTCGGA LNVEQLLIGA YKVKAGLLGI  180
GQIPSYFKNK EIAW                                                   194

SEQ ID NO: 90           moltype = AA  length = 197
FEATURE                 Location/Qualifiers
REGION                  1..197
                        note = Synthetic Construct
source                  1..197
                        mol_type = protein
                        organism = synthetic construct
SEQUENCE: 90
QELKDEKAEQ RKAKFLKETN LSMKYIELLD IAYDGKRDRD FEIVTMELFR KVYKLKSKLL  60
GGGRKPDGLV YSDEFGIIVD TKAYGNGYPK SISQADEMIR YIEDNKRRDE KRNSTKWWEY  120
FSSVIPDDSF YFMWISSKFI GKFQEQLIYT ANETEINGAA LNVEQLLIGA DKILKGELSV  180
NKLPNYFINQ EIIFEKT                                                197

SEQ ID NO: 91           moltype = AA  length = 199
FEATURE                 Location/Qualifiers
REGION                  1..199
                        note = Synthetic Construct
source                  1..199
                        mol_type = protein
                        organism = synthetic construct
SEQUENCE: 91
NELRNAALDK QKVNFINKTG LPMKYIELLE IAFDGSRNRD FEMVTADLFK NVYGFNSILL  60
GGGRKPDGLI FTDRFGVIID TKAYGNGYSK SIGQEDEMVR YIEDNQLRDS NRNSVEWWKN  120
FDEKIESENF YFMWISSKFI GQFSDQLQST SDRTNTKGAA LNVEQLLLGA AAARDGKLDI  180
NSLPIYMNNK EILWSGDFS                                              199

SEQ ID NO: 92           moltype = AA  length = 196
FEATURE                 Location/Qualifiers
REGION                  1..196
                        note = Synthetic Construct
source                  1..196
                        mol_type = protein
                        organism = synthetic construct
SEQUENCE: 92
KELRNEVAEE RRAYFLKNTN LPTKYIELLD IAYDGKRNRD FEILTMDLFR NVYKLNSKLL  60
GGGRKPDGLV YSNQFGIIVD TKAYSEGYSK SIQQADEMIR YIEDNKRRDI NRNPIEWWKD  120
FPNSIKDDSY YFLWVSSKFV GKFPEQLTYT ANQTETIGGA LNVEQLLLGA DKVKKGEIQS  180
DKLNTYFENK EIIFQS                                                 196

SEQ ID NO: 93           moltype = AA  length = 201
FEATURE                 Location/Qualifiers
REGION                  1..201
                        note = Synthetic Construct
source                  1..201
                        mol_type = protein
                        organism = synthetic construct
SEQUENCE: 93
EELRDKVIEE QKAIFLQKTK LPLSYIELLE IARDGKRSRD FELITMELFK NIYKINAIVL  60
GGARKPDGVL YMPEFGVIVD TKAYADGYSK SIAQADEMIR YIEDNKRRDP SRNSTKWWEH  120
FPTSIPANNF YFLWVSSVFV NKFHEQLSYT AQETQTVGAA LSVEQLLLGA DSVLKGNLTT  180
EKFIDSFKNQ EIVFAPSILH S                                           201

SEQ ID NO: 94           moltype = AA  length = 201
FEATURE                 Location/Qualifiers
REGION                  1..201
                        note = Synthetic Construct
source                  1..201
```

```
                         mol_type = protein
                         organism = synthetic construct
SEQUENCE: 94
EELRDKVIEE QKAIFLQKTK LPLSYIELLE IARDGKRSRD FELITMELFK NIYKINASIL  60
GGARKPDGVL YMPEFGVIVD TKAYADGYSK SIAQADEMIR YIEDNKRRDP SRNSTKWWEH  120
FPTSIPANNF YFLWVSSVFV NKFHEQLSYT AQETQTVGAA LSVEQLLLGA DSVLKGNLTT  180
EKFIDSFKNQ EIVFAPSILH S                                            201

SEQ ID NO: 95            moltype = AA  length = 194
FEATURE                  Location/Qualifiers
REGION                   1..194
                         note = Synthetic Construct
source                   1..194
                         mol_type = protein
                         organism = synthetic construct
SEQUENCE: 95
QELKDAALEE KKLKYQQLTK LPIKYIELLE IAYDGRRNRD FEILVADIFK NIYKFHSILL  60
GGGRKPDGLI FTDKFGVIID TKAYGEGYGK LITQEDEMVR YIEDNQQRDK NRNSITWWEK  120
FNDAIPANSY YFMWVSSNFT GNFQEQLNST SNRTGVKGAA LNVEQLLLGA ANAQQGILDI  180
STFPSYMNNK EIIW                                                    194

SEQ ID NO: 96            moltype = AA  length = 201
FEATURE                  Location/Qualifiers
REGION                   1..201
                         note = Synthetic Construct
source                   1..201
                         mol_type = protein
                         organism = synthetic construct
SEQUENCE: 96
EELRDKVIEE QKAIFLQKTK LPLSYIELLE IARDGKRSRD FEFITMELFK NIYKINARIL  60
GGARKPDGVL YMPEFGVIVD TKAYADGYSK SIAQADEMIR YIEDNKRRDP SRNSTKWWEH  120
FPTSIPANNF YFLWVSSVFV NKFHEQLSYT AQETQTVGAA LSVEQLLLGA DSVLKGNLTT  180
EKFIDSFKNQ EIVFAPSILH S                                            201

SEQ ID NO: 97            moltype = AA  length = 211
FEATURE                  Location/Qualifiers
REGION                   1..211
                         note = Synthetic Construct
source                   1..211
                         mol_type = protein
                         organism = synthetic construct
SEQUENCE: 97
DSINDFDIPN LQITQTLVDI EKERKKAYFL KETSLSPRYI ELLEIAFDPK RNRDFEVITA  60
ELLKAGYGLK AKVLGGGRRP DGIAYTKDYG LIVDTKAYSN GYGKNIGQAD EMIRYIEDNQ  120
KRDNKRNPIE WWREFEVQIP ANSYYYLWVS GRFTGRFDEQ LVYTSSQTNT RGGALEVEQL  180
LWGADAVMKG KLNVSDLPKY MNNSIIKLTK K                                 211

SEQ ID NO: 98            moltype = AA  length = 201
FEATURE                  Location/Qualifiers
REGION                   1..201
                         note = Synthetic Construct
source                   1..201
                         mol_type = protein
                         organism = synthetic construct
SEQUENCE: 98
EELRDKVIEE QKAIFLQKTK LPLSYIELLE IARDGKRSRD FELITMELFK NIYKINASIL  60
GGARKPDGVL YMPEFGVIVD TKSYADGYSK SIAQADEMIR YIEDNKRRDP SRNSTKWWEH  120
FPTSIPANNF YFLWVSSVFV NKFHEQLSYT AQETQTVGAA LSVEQLLLGA DSVLKGNLTT  180
EKFIDSFKNQ EIVFAPSILH S                                            201

SEQ ID NO: 99            moltype = AA  length = 198
FEATURE                  Location/Qualifiers
REGION                   1..198
                         note = Synthetic Construct
source                   1..198
                         mol_type = protein
                         organism = synthetic construct
SEQUENCE: 99
ISVKSDMAVV KDSVRERLAH VSHEYLILID LGFDGTSDRD YEIQTAELFT RELDFLGGRL  60
GDTRKPDVCI YYGKDGMIID NKAYGKGYSL PIKQADEMYR YLEENKERNE KINPNRWWKV  120
FDEGVTDYRF AFVSGSFTGG FKDRLENIHM RSGLCGGAID SVTLLLLAEE LKAGRMEYSE  180
FFRLFDCNDE VTFQSIVI                                                198

SEQ ID NO: 100           moltype = AA  length = 197
FEATURE                  Location/Qualifiers
REGION                   1..197
                         note = Synthetic Construct
source                   1..197
                         mol_type = protein
```

```
                         organism = synthetic construct
SEQUENCE: 100
KELKDKASEQ RKAEFMNKTD LPAKYIELLE IAFDGNRNRD FEIITAEIFK KVYGLKSVLL  60
GGGRKPDCLV FNANFGMIID TKAYSTGYSK SISQEDEMVR YIEDNQYRDT TRNPIEWWNN  120
FPSSIKKEKY YFMWVSSKFI GRFQEQIEST YNRTNTKGAA LNVEQLLLGA NAVLRGELDA  180
NRISDYIDNK EILWFNN                                                 197

SEQ ID NO: 101           moltype = AA  length = 198
FEATURE                  Location/Qualifiers
REGION                   1..198
                         note = Synthetic Construct
source                   1..198
                         mol_type = protein
                         organism = synthetic construct
SEQUENCE: 101
TQTLVDIEKE RKKAYFLKET SLSPRYIELL EIAFDPKRNR DFEVITAELL KAGYGLKAKV  60
LGGGRRPDGI AYTKDYGLIV DTKAYSNGYG KNIGQADEMI RYIEDNQKRD SKRNPIEWWR  120
EFEVQIPANS YYYLWVSGRF TGRFDEQLVY TSSQTNTRGG ALEVEQLLWG ADAVMKGKLN  180
VSDLPKYMNN SIIKLTKK                                                198

SEQ ID NO: 102           moltype = AA  length = 198
FEATURE                  Location/Qualifiers
REGION                   1..198
                         note = Synthetic Construct
source                   1..198
                         mol_type = protein
                         organism = synthetic construct
SEQUENCE: 102
NLDKVERDSR KAEFLAKTSL PPRFIELLSI AYESKSNRDF EMITAEFFKD VYGLGAVHLG  60
NARKPDALAF TDNFGIVIDT KAYSNGYSKN INQEDEMVRY IEDNQIRSPE RNKNEWWLSF  120
PPSIPENNFH FLWVSSYFTG YFEEQLQETS DRAGGMTGGA LDIEQLLIGG SLVQEGKLAP  180
HDIPEYMQNR VIHFGDLN                                                198

SEQ ID NO: 103           moltype = AA  length = 198
FEATURE                  Location/Qualifiers
REGION                   1..198
                         note = Synthetic Construct
source                   1..198
                         mol_type = protein
                         organism = synthetic construct
SEQUENCE: 103
NLDNVERDNR KAEFLAKTSL PPRFIELLSI AYESKSNRDF EMITAELFKD VYGLGAVHLG  60
NAKKPDALAF NDDFGIIIDT KAYSNGYSKN INQEDEMVRY IEDNQIRSPD RNNNEWWLSF  120
PPSIPENDFH FLWVSSYFTG RFEEQLQETS ARTGGTTGGA LDVEQLLIGG SLIQEGSLAP  180
HEVPAYMQNR VIHFGDLN                                                198

SEQ ID NO: 104           moltype = AA  length = 194
FEATURE                  Location/Qualifiers
REGION                   1..194
                         note = Synthetic Construct
source                   1..194
                         mol_type = protein
                         organism = synthetic construct
SEQUENCE: 104
ISVKSDMAVV KDSVRERLAH VSHEYLLLID LGFDGTSDRD YEIQTAELLT RELDFLGGRL  60
GDTRKPDVCI YYGKDGMIID NKAYGKGYSL PIKQADEMYR YLEENKERNE KINPNRWWKV  120
FDEGVTDYRF AFVSGSFTGG FKDRLENIHM RSGLCGGAID SVTLLLLAEE LKAGRMEYSE  180
FFRLFDCNDE VIFR                                                    194

SEQ ID NO: 105           moltype = AA  length = 194
FEATURE                  Location/Qualifiers
REGION                   1..194
                         note = Synthetic Construct
source                   1..194
                         mol_type = protein
                         organism = synthetic construct
SEQUENCE: 105
ISVKSDMAVV KDSVRERLAH VSHEYLLLID LGFDGTSDRD YEIQTAELLT RELDFLGGRL  60
GDTRKPDVCI YYGKDGMIID NKAYGKGYSL PIKQADEMYR YLEENKERNE KINPNRWWKV  120
FDEGVTDYRF AFVSGSFTGG FKDRLENIHM RSGLCGGAID SVTLLLLAEE LKAGRMEYSE  180
FFRLFDCNDE VTFR                                                    194

SEQ ID NO: 106           moltype = AA  length = 198
FEATURE                  Location/Qualifiers
REGION                   1..198
                         note = Synthetic Construct
source                   1..198
                         mol_type = protein
                         organism = synthetic construct
```

-continued

```
SEQUENCE: 106
TQTLVDIEKE RKKAYFLKET SLSPRYIELL EIAFDPKRNR DFEVITAELL KAGYGLKAKV  60
LGGGRRPDGI AYTKDYGLIV DTKAYSNGYG KNIGQADKMI RYIEDNQKRD SKRNPIEWWR  120
EFEVQIPANS YYYLWVSGRF TGRFDEQLVY TSSQTNTRGG ALEVEQLLWG ADAVMKGKLN  180
VSDLPKYMNN SIIKLTKK                                                198

SEQ ID NO: 107         moltype = AA  length = 194
FEATURE                Location/Qualifiers
REGION                 1..194
                       note = Synthetic Construct
source                 1..194
                       mol_type = protein
                       organism = synthetic construct
SEQUENCE: 107
ISVKSDMAVI KDSVRGRLAH VSHEYLLLID LGFDGTSDRD YEIQTAELLT RELDFLGGRL  60
GDTRKPDVCI YYGKDGMIID NKAYGKGYSL PIKQADEMYR YLEENKERNE KINPNRWWKV  120
FDEGVTDYRF AFVSGSFTGG FKDRLENIHM RSGLCGGAMD SVTLLLLAEE LKAGRMEYSE  180
FFRLFDCNDE VTFR                                                    194

SEQ ID NO: 108         moltype = AA  length = 194
FEATURE                Location/Qualifiers
REGION                 1..194
                       note = Synthetic Construct
source                 1..194
                       mol_type = protein
                       organism = synthetic construct
SEQUENCE: 108
QELKDKYSDA LKAKYIKLTG LPMKYIELLD IAFDGKRNRD FEIITADLFK NIYGLESVLL  60
GGGRKPDGII FTDKFGVIVD TKAYGNGYSK EIKQEDEMVR YIEDNQLRDK ERNPVEWWNN  120
FNPSIPSNSF YFMWISSKFI GKFTEQLEST YNRTGVHGGA LNVEQLLLGA HKVQIGELDV  180
HHLPDYIQNK EIFW                                                    194

SEQ ID NO: 109         moltype = AA  length = 199
FEATURE                Location/Qualifiers
REGION                 1..199
                       note = Synthetic Construct
source                 1..199
                       mol_type = protein
                       organism = synthetic construct
SEQUENCE: 109
KITKSDLTVV KDQIRKQLVH IDHKYLVLID LGFDGRANRD YEIQTAELLT GELEFKGTRL  60
GDTRKPDVCV YYGKDGLIID NKAYGKGYSL PISQADEMVR YLEENKTRQT AVNPNEWWNI  120
FEDSVKDFHF AFVSGEFVGG FQDKLQNIYE RTGVRGAAMN TANLLLFAEE LKAGRLEYSD  180
CFSYFDGNEE IRDFYIWNQ                                               199

SEQ ID NO: 110         moltype = AA  length = 200
FEATURE                Location/Qualifiers
REGION                 1..200
                       note = Synthetic Construct
source                 1..200
                       mol_type = protein
                       organism = synthetic construct
SEQUENCE: 110
QLTQSQGDKA REQLKAKFLA KTNLLPRYVE LLDIAYDSKR NRDFEMVTAE LFNFAYLLPA  60
VHLGGVRKPD ALVATKKFGI IVDTKAYANG YSRNANQADE MARYITENQK RDPKTNPNRW  120
WDNFDARIPP NAYYFLWVSS FFTGQFDDQL SYTAHRTNTH GGALNVEQLL IGANMIQTGQ  180
LDRNKLPEYM QDKEITFGTI                                              200

SEQ ID NO: 111         moltype = AA  length = 204
FEATURE                Location/Qualifiers
REGION                 1..204
                       note = Synthetic Construct
source                 1..204
                       mol_type = protein
                       organism = synthetic construct
SEQUENCE: 111
LPVKSQVSIL KDYLRSYLSH VDHKYLILLD LGFDGTSDRD YEIWTAQLLT AELSFLGGRL  60
GDTRKPDVCI YYEDNGLIID NKAYGKGYSL PIKQADEMYR YIEENKERSE LLNPNCWWNI  120
FGEGVKTFRF AFLSGEFTGG FKDRLNHISM RSGIKGAAVN SANLLIMAEQ LKSGTMSYEE  180
FFQLFDHNDE IIFPHLSLQG GLIL                                         204

SEQ ID NO: 112         moltype = AA  length = 204
FEATURE                Location/Qualifiers
REGION                 1..204
                       note = Synthetic Construct
source                 1..204
                       mol_type = protein
                       organism = synthetic construct
SEQUENCE: 112
```

-continued

```
LPVKSQVSIL KDYLRSCLSH VDHKYLILLD LGFDGTSDRD YEIQTAQLLT AELSFLGGRL  60
GDTRKPDVCI YYEDNGLIID NKAYGKGYSL PIKQADEMYR YIEENKERSE LLNPNCWWNI  120
FDEGVKTFRF AFLSGEFTGG FKDRLNHISM RSGIKGAAVN SANLLIMAEQ LKSGTMSYEE  180
FFQLFDHNDE IIFPHLSIQG GLIL                                         204

SEQ ID NO: 113         moltype = AA  length = 196
FEATURE                Location/Qualifiers
REGION                 1..196
                       note = Synthetic Construct
source                 1..196
                       mol_type = protein
                       organism = synthetic construct
SEQUENCE: 113
QELKDLETER RKAEFMNKTD LSAKYIELLE IAYDGKRNRD FEIVTAELFK KVYGLQSILL  60
GGGRKPDAIV FTDKFGFIID TKAYGEGYSK SISQADEMIR YIEDNKRRDI NRNPTEWWID  120
FDPIIPQNQF YFMWVSSKFV GRFQEQLDYT ASQTSTNGGA LNVEQLLLGA DAVLKGILDA  180
NTLPLYMKNK EIEFIS                                                  196

SEQ ID NO: 114         moltype = AA  length = 201
FEATURE                Location/Qualifiers
REGION                 1..201
                       note = Synthetic Construct
source                 1..201
                       mol_type = protein
                       organism = synthetic construct
SEQUENCE: 114
QIAKDTTDTV AVKNRARLRL HNIDHKYLTL IDYAFSGKDK CIDFEVYTID LLVNELAFNG  60
VHLGGTRKPD GIFYHNNNGV IIDNKAYSKG FTISRGMADE MTRYVQENND RNPERNPNQW  120
WLNFSDNVNH FNFVFISSLF KGNIELMLNN IKQSTGVEGC ALTVENLLYF ADAIKGGDMH  180
KDAFIDQFGA GKEIVCTIYR T                                            201

SEQ ID NO: 115         moltype = AA  length = 196
FEATURE                Location/Qualifiers
REGION                 1..196
                       note = Synthetic Construct
source                 1..196
                       mol_type = protein
                       organism = synthetic construct
SEQUENCE: 115
LPMKSEVSIL KDYLRSHLTY IDHKYLILVD LGYDGTSDRD YEIQTAQLLT AELSFLGGRL  60
GDTRKPDVCI YYENNGLIID NKAYGKGYSL PIKQADEMYR YIEENKERSE LLNPNCWWNI  120
FGKDVKNFRF AFLSGEFTGG FRDRLNHISM RSGMKGAAVN SANLLIMAEK LKAGIMGYEE  180
FFRLFDTNDE IIFLHE                                                  196

SEQ ID NO: 116         moltype = AA  length = 204
FEATURE                Location/Qualifiers
REGION                 1..204
                       note = Synthetic Construct
source                 1..204
                       mol_type = protein
                       organism = synthetic construct
SEQUENCE: 116
LPVKSQVSIL KDYLRSYLSH VDHKYLILLD LGFDGTSDRD YEIQTAQLLT AELSFVGGRL  60
GDTRKPDVCI YYEDNGLIID NKAYGKGYSL PIKQADEMYR YIEENKERSE LLNPNCWWNI  120
FDEGVKTFHF AFLSGEFTGG FKDRLNHISM RSGIKGAAVN SANLLIMAEQ LKSGTMSYEE  180
FFQLFDHNDE IIFPHLSLQG GLIL                                         204

SEQ ID NO: 117         moltype = AA  length = 195
FEATURE                Location/Qualifiers
REGION                 1..195
                       note = Synthetic Construct
source                 1..195
                       mol_type = protein
                       organism = synthetic construct
SEQUENCE: 117
LTSKEKSNLK LKEFFISETA IPNKFITLFD LAYDGSANRD FEIITSELFR DVYKLNTKHL  60
GGTRKPDILI WNKEYGIIAD TKAYSKGYKK NISEEDKMVR YIDENIKRNK NDNPNEWWKI  120
FDKNISSANY FYLWISSEFV GKFEEQLQGT VTRTNTNGAS LNVYQLLMGA HLVQIEELSV  180
NSIPAYMNNM EIKFV                                                   195

SEQ ID NO: 118         moltype = AA  length = 197
FEATURE                Location/Qualifiers
REGION                 1..197
                       note = Synthetic Construct
source                 1..197
                       mol_type = protein
                       organism = synthetic construct
SEQUENCE: 118
LPVKSEVSIL KDYLRSHLTH IDHKYLILVD LGYDGTSDRD YEIQTAQLLT AELSFLGGRL  60
```

-continued

```
GDTRKPDVCI YYEDNGLIID NKAYGKGYSL PIKQADEMYR YIEENKERSQ LLNPNCWWDI  120
FGKDVKTFHF AFVSGEFTGG FRDRLNHISM RSGLKGAAVN SANLLIMAEK LKAGTMEYGE  180
FFRFFDTNDE ILFLHES                                                 197

SEQ ID NO: 119        moltype = AA  length = 195
FEATURE               Location/Qualifiers
REGION                1..195
                      note = Synthetic Construct
source                1..195
                      mol_type = protein
                      organism = synthetic construct
SEQUENCE: 119
LSNNDKQRLK LKEYFIQNTN LPAKFITLLD IAYDGQANRD FEIITTELFR DVYKLKAQHM  60
GGTRKPDALI WTSQFGVIVD TKAYSKGYKK NISEADKMVR YVNENIERNK KSNPNEWWKS  120
FDSSIPSNQY YYLWISSEFI GRFDEQLKET TSRTRTNGAA LNVYQLLSGA DLVQKNNLDS  180
NNLPSYINNT EIKFV                                                   195

SEQ ID NO: 120        moltype = AA  length = 204
FEATURE               Location/Qualifiers
REGION                1..204
                      note = Synthetic Construct
source                1..204
                      mol_type = protein
                      organism = synthetic construct
SEQUENCE: 120
LPVKSQVSIL KDYLRSYLSH VDHKYLILLD LGFDGTSDRD YEIQTAQLLT AELSFLGGRL  60
GDTRKPDVCI YYEDNGLIID NKAYGKGYSL PIKQADEMYR YIEENKERSE LLNPNCWWNI  120
FDEGVKTFRF AFLSGEFTGG FKDRLNLISM RSGIKGAAVN SANLLIMAEQ LKSGTMSYEE  180
FFQLFDHNDE IIFPHLSLQG GLIL                                         204

SEQ ID NO: 121        moltype = AA  length = 203
FEATURE               Location/Qualifiers
REGION                1..203
                      note = Synthetic Construct
source                1..203
                      mol_type = protein
                      organism = synthetic construct
SEQUENCE: 121
ECVKDNVVDI KDRVRNKLIH LDHKYLALID LAYSDAASRA KKNADAREFE IQTADLFTKE  60
LSFNGQRLGD SRKPDVIISY GLDGTIVDNK SYKDGFNISR TCADEMSRYI NENNLRQKSL  120
NPNEWWKNFD STITAYTFLF ITSYLKGQFE DQLEYVSNAN GGIKGAAIGV ESLLYLSEGI  180
KAGRISHADF YSNFNNKEMI YTA                                          203

SEQ ID NO: 122        moltype = AA  length = 196
FEATURE               Location/Qualifiers
REGION                1..196
                      note = Synthetic Construct
source                1..196
                      mol_type = protein
                      organism = synthetic construct
SEQUENCE: 122
VPVKSEVSLL KDYLRSHLLH VDHRYLVLLD LGFDGTSDRD YEIQTAQLLT GELNFKGARL  60
GDTRKPDVCV YYGEDGLIID NKAYGKGYSL PIKQADEMYR YIEENKERNE KLNPNKWWEI  120
FDNNVIHYHF AFVSGAFTGG FKERLDNIRM RSGIYGAAVN SMNLLLMAEE LKSGRLGYKE  180
CFKLFDCNDE IVLQRS                                                  196

SEQ ID NO: 123        moltype = AA  length = 193
FEATURE               Location/Qualifiers
REGION                1..193
                      note = Synthetic Construct
source                1..193
                      mol_type = protein
                      organism = synthetic construct
SEQUENCE: 123
NEEKDKLKVK EFFISETSIP NKFITLLDLA YDGNANRDFE IITSEFIREV YKLNTKHLGG  60
TRKPDILIWN DEFGIIADTK AYSKGYKKNI SEEDKMVRYI DENAKRSKDD NPNEWWINFG  120
KNIPSSNYFY LWVSSEFIGK FEEQLKETAS RTNTNGASLN VYQLLMGGHL VQTGRFNISN  180
LPAYMNNSEI KFS                                                     193

SEQ ID NO: 124        moltype = AA  length = 197
FEATURE               Location/Qualifiers
REGION                1..197
                      note = Synthetic Construct
source                1..197
                      mol_type = protein
                      organism = synthetic construct
SEQUENCE: 124
NALKDKHLEK IKEKFLENTS LDPRFISLIE ISRDKKQNRA FEIITAELFN TSYKLSATHL  60
GGGRRPDVLV YNDNFGIIVD TKAYKDGYGR NVNQEDEMVR YITENNIRKQ DINKNDWWKY  120
```

-continued

```
FSKSIPSTSY YHLWISSQFV GMFSDQLRET SSRTGENGGA MNVEQLLIGA NQVLNNVLDP  180
NCLPKYMENK EIIFETL                                                197

SEQ ID NO: 125         moltype = AA  length = 196
FEATURE                Location/Qualifiers
REGION                 1..196
                       note = Synthetic Construct
source                 1..196
                       mol_type = protein
                       organism = synthetic construct
SEQUENCE: 125
LPVKSEVSIL KDYLRSHLTN IDHKYLILVD LGYDGTSDRD YEIQTAQLLT AELSFHGGRL  60
GDTRKPDVCI YYEDNGLIID NKAYGKGYSL PIKQADEMYR YIEENKERSE LLNPNCWWNI  120
FGKDVKTYHF AFLSGEFTGG FRDRLNNISM RSGIKGAAVN SANLLILAER LKSGTMRYEE  180
FFRLFDTNDE ILFLHE                                                 196

SEQ ID NO: 126         moltype = AA  length = 196
FEATURE                Location/Qualifiers
REGION                 1..196
                       note = Synthetic Construct
source                 1..196
                       mol_type = protein
                       organism = synthetic construct
SEQUENCE: 126
VPVKSEMSLL KDYLRTHLLH VDHRYLILLD LGFDGASDRD YEIQTAQLLT GELNFKGARL  60
GDTRKPDVCV YYGEDGLIID NKAYGKGYSL PIKQADEMYR YIEENKERNE KLNPNKWWEI  120
FDNDVIHYHF AFVSGAFTGG FKERLDNIRM RSGIYGAAVN SMNLLLMAEE LKSGRLGYKE  180
CFKLFDCNDE IVLQRS                                                 196

SEQ ID NO: 127         moltype = AA  length = 198
FEATURE                Location/Qualifiers
REGION                 1..198
                       note = Synthetic Construct
source                 1..198
                       mol_type = protein
                       organism = synthetic construct
SEQUENCE: 127
NLKLRTEEKE RLELKEYFIS NTDIPSKYIT LLDLAYDGNA NRDFEIVTAE LFKDVFQLKT  60
KHLGGTRKPD ILIWTDKFGV IADTKAYSKG YKKNISEADK MVRYVNENTN RNKNDNSNEW  120
WNSFETKIPA NAYYFLWISS KFIGKFNEQL IETSSRTGRN GAAIDVYQLL RGADLVQKSK  180
FNVHDLPSLM QNKEIQFI                                               198

SEQ ID NO: 128         moltype = AA  length = 196
FEATURE                Location/Qualifiers
REGION                 1..196
                       note = Synthetic Construct
source                 1..196
                       mol_type = protein
                       organism = synthetic construct
SEQUENCE: 128
VPVKSEVSLL KDYLRTHLLH VDHRYLILLD LGFDGTSDRD YEIQTAQLLT GELNFKGARL  60
GDTRKPDVCV YYGEDGLIID NKAYGKGYSL PIKQADEMYR YIEENKERNE KLNPNKWWEI  120
FDNDVIHYHF AFISGAFTGG FKERLDNIRM RSGIYGAAVN SMNLLLMAEE LKSGRLGYKE  180
CFKLFDCNDE IVLQRS                                                 196

SEQ ID NO: 129         moltype = AA  length = 203
FEATURE                Location/Qualifiers
REGION                 1..203
                       note = Synthetic Construct
source                 1..203
                       mol_type = protein
                       organism = synthetic construct
SEQUENCE: 129
SCVKDEVNDI VDRVRVKLKN IDHKYLILIS LAYSDETERT KKNSDARDFE IQTAELFTKE  60
LGFNGIRLGE SNKPDVLISF GANGTIIDNK SYKDGFNIPR VTSDQMIRYI NENNQRTTQL  120
NPNEWWKNFD SSVSNYTFLF VTSFLKGSFK NQIEYISNAT NGTRGAAINV ESLLYISEDI  180
KSGKIKQSDF YSEFKNDEIV YPI                                         203

SEQ ID NO: 130         moltype = AA  length = 196
FEATURE                Location/Qualifiers
REGION                 1..196
                       note = Synthetic Construct
source                 1..196
                       mol_type = protein
                       organism = synthetic construct
SEQUENCE: 130
APVKSEVSLC KDILRSHLTH VDHKYLILLD LGFDGTSDRD YEIQTAQLLT AELDFKGARL  60
GDTRKPDVCV YYGEDGLILD NKAYGKGYSL PIKQADEMYR YIEENKERNE RLNPNKWWEI  120
FDKDVVRYHF AFVSGTFTGG FKERLDNIRM RSGICGAAVN SMNLLLMAEE LKSGRLGYKE  180
```

-continued

```
CFALFDCNDE IAFQCS                                              196

SEQ ID NO: 131          moltype = AA  length = 196
FEATURE                 Location/Qualifiers
REGION                  1..196
                        note = Synthetic Construct
source                  1..196
                        mol_type = protein
                        organism = synthetic construct
SEQUENCE: 131
VPVKSEVSLC KDYLRSHLNH VDHRYLILLD LGFDGTSDRD YEIQTAQLLT GELNFKGARL  60
GDTRKPDVCV YYGEDGLIID NKAYGKGYSL PIKQADEMYR YIEENKERNE KLNPNKWWEI  120
FDKDVIHYHF AFVSGAFTGG FKERLENIRM RSGIYGAAVN SMNLLLMAEE LKSGRLDYKE  180
CFKLFDCNDE IVLQRS                                              196

SEQ ID NO: 132          moltype = AA  length = 195
FEATURE                 Location/Qualifiers
REGION                  1..195
                        note = Synthetic Construct
source                  1..195
                        mol_type = protein
                        organism = synthetic construct
SEQUENCE: 132
LTSKEKNNLE LKEFFVSNTN IPSKFISLLD LAYDGSVSRD FEIVTSELFR EVYKLNTKHL  60
GGTRKPDILI WNEDFGIITD TKAYSKGYKK NISEEDKMVR YIDENIKRSK SDNQNEWWNI  120
FDKNISSTNF FYLWISSEFI GKFEEQLHET ASRTNTNGAS LNVYQLLMGA HLVQTGKIDI  180
SNIPSFMNNE EIKFV                                               195

SEQ ID NO: 133          moltype = AA  length = 203
FEATURE                 Location/Qualifiers
REGION                  1..203
                        note = Synthetic Construct
source                  1..203
                        mol_type = protein
                        organism = synthetic construct
SEQUENCE: 133
SCVKDEVNDI VDRVRVKLKH VDHKYLILIS LAYSNETERT KKNSDARDFE IQTAELFTKE  60
LGFNGIRLGE SNKPDVLISF GANGTIIDNK SYKDGFNIPR ATSDQMIRYI NENNQRTTQL  120
NPNEWWKNFD SSVLNYTFLF VTSFLKGSFK NQIEYISKAT NGTRGAAINV ENLLYISEDI  180
KSGNIKQSDF YSEFKNDEIV YSI                                      203

SEQ ID NO: 134          moltype = AA  length = 196
FEATURE                 Location/Qualifiers
REGION                  1..196
                        note = Synthetic Construct
source                  1..196
                        mol_type = protein
                        organism = synthetic construct
SEQUENCE: 134
VPVKSEVSLC KDYLRSHLNH VDHKYLILLD LGFDGTSDRD YEIQTAQLLT GELNFKGARL  60
GDTRKPDVCV YYGEDGLIID NKAYGKGYSL PIKQADEMYR YIEENKERNE KLNPNKWWEI  120
FDNDVIHYHF AFVSGAFTGG FRERLENIRM RSGIYGAAVN SMNLLLMAEE LKSGRLGYKE  180
CFKLFDCNDE IVLQRS                                              196

SEQ ID NO: 135          moltype = AA  length = 197
FEATURE                 Location/Qualifiers
REGION                  1..197
                        note = Synthetic Construct
source                  1..197
                        mol_type = protein
                        organism = synthetic construct
SEQUENCE: 135
NVLKDKHLEK IKEKFLENTS LDPRFISLIE ISRDKKQNRA FEIITAELFN TSYNLSAIHL  60
GGGRRPDVLV YNDNFGIIVD TKAYKDGYGR NVNQEDEMVR YITENNIRKQ DISKNNWWKY  120
FSKSIPSTSY YHLWISSEFV GMFSDQLRET SSRTGENGGA MNVEQLLIGA NQVLNNVLDP  180
NRLPEYMENK EIIFGTL                                             197

SEQ ID NO: 136          moltype = AA  length = 196
FEATURE                 Location/Qualifiers
REGION                  1..196
                        note = Synthetic Construct
source                  1..196
                        mol_type = protein
                        organism = synthetic construct
SEQUENCE: 136
VPVKSEVSLC KDYLRSHLNH VDHKYLLLLD LGFDGTSDRD YEIQTAQLLT GELNFKGARL  60
GDTRKPDVCV YYGEDGLIID NKAYGKGYSL PIKQADEMYR YIEENKERNE KLNPNKWWEI  120
FDKDVIHYHF AFVSGAFTGG FRERLENIRM RSGIYGAAVN SMNLLLMAEE LKSGRLGYKE  180
CFKIFDCNDE IVLQRS                                              196
```

-continued

```
SEQ ID NO: 137          moltype = AA  length = 197
FEATURE                 Location/Qualifiers
REGION                  1..197
                        note = Synthetic Construct
source                  1..197
                        mol_type = protein
                        organism = synthetic construct
SEQUENCE: 137
NVLKDKHLEK IKEKFLENTS LDPRFISLIE ISRDKKQNRA FEIITAELFN TSYNLSAIHL  60
GGGRRPDVLV YNDNFGIIVD TKAYKDGYGR NVNQEDEMVR YITENNIRKQ DISKNNWWKY  120
FSKSIPSTSY YHLWISSEFV GMFSDQLRET SSRTGENGGA INVEQLLIGA NQVLNNVLDP  180
NRLPEYMKNQ EIIFGTL                                                197

SEQ ID NO: 138          moltype = AA  length = 195
FEATURE                 Location/Qualifiers
REGION                  1..195
                        note = Synthetic Construct
source                  1..195
                        mol_type = protein
                        organism = synthetic construct
SEQUENCE: 138
EAIISERATQ KERLMQSTDL PMRFYELIDI AYDGRRNRDF EMLTMDLLRE GYGFETQLLG  60
GGRKPDVIAY NDDFGIIVDT KAYGKGYHRS QPEEDKMVRY VEDNRERDAS VNNTQWWLGF  120
PETLSYQSVY FLWVSSFFTG QFGSQLTNTA IRSRTNGAAL GVENLLVGAD KFLKGKLNHN  180
QIQLKIRQDS EIIWD                                                  195

SEQ ID NO: 139          moltype = AA  length = 196
FEATURE                 Location/Qualifiers
REGION                  1..196
                        note = Synthetic Construct
source                  1..196
                        mol_type = protein
                        organism = synthetic construct
SEQUENCE: 139
VPVKSEVSLC KDYLRSHLIH VDHRYLILLD LGFDGTSDRD YEIQTAQLLT AELDFKGARL  60
GDTRKPDVCV YYGEDGLIID NKAYGKGYSL PIKQADEMYR YIEENKERNE KLNPNKWWEI  120
FDKGVIRYHF AFVSGAFTGG FRERLENIRM RSGIRGAAVN SMNLLLMAEE LKSKRLDYNE  180
CFKLFDCNDE IGFQRS                                                 196

SEQ ID NO: 140          moltype = AA  length = 194
FEATURE                 Location/Qualifiers
REGION                  1..194
                        note = Synthetic Construct
source                  1..194
                        mol_type = protein
                        organism = synthetic construct
SEQUENCE: 140
TEADLDSERI KNHYRKITNL PEKYIELLDI AFDHHRHQDF EIITAGLFKE CYGLSSIHLG  60
GQNKPDGVVF NSNFGIILDT KAYEKGYGMH INQIDEMCRY IEDNKQRDRI RQPNEWWNNF  120
DDNIPENKFY YLWVSGKFLP KFNEQLKQTH YRTGSNGGGL EVSQLLLGAD AVMKGALNVN  180
NLPTYMHNNV IQLV                                                   194

SEQ ID NO: 141          moltype = AA  length = 193
FEATURE                 Location/Qualifiers
REGION                  1..193
                        note = Synthetic Construct
source                  1..193
                        mol_type = protein
                        organism = synthetic construct
SEQUENCE: 141
NEEKDTLKVK EFFISETSIP NKFITLLDLA YDGNSNRDFE IITSEFIREV YKLNTKHLGG  60
TRKPDILIWN EKFGIIADTK AYSKGYKKNI SEEDKMVRYI DENTKRSKED NPNEWWINFG  120
ENIPSNNYFY LWISSEFIGK FEEQLKETAS RTNTNGASLN VYQLLMGGHL AQIGRFNVNN  180
LPAFMNNSEI KFS                                                    193

SEQ ID NO: 142          moltype = AA  length = 198
FEATURE                 Location/Qualifiers
REGION                  1..198
                        note = Synthetic Construct
source                  1..198
                        mol_type = protein
                        organism = synthetic construct
SEQUENCE: 142
NLNLATDEKE RLELKEYFIS NTNIPSKFIT LLDLAYDGKA NRDFEIVTAE LFEDVFKLKA  60
KHMGGTRKPD ILIWTDKFGI IADTKAYSKG YKKNISEADK MVRYVNENNI RNKKDNGNEW  120
WNSFDSNIPE DKYFYLWISS EFVGKFDEQL TETASRTGRD GAAINVYQLL RGADLAQKSQ  180
FDVHDFPSLM KNNEIKFV                                               198
```

-continued

```
SEQ ID NO: 143         moltype = AA  length = 196
FEATURE                Location/Qualifiers
REGION                 1..196
                       note = Synthetic Construct
source                 1..196
                       mol_type = protein
                       organism = synthetic construct
SEQUENCE: 143
VPVKSEVSLC KDYLRSHLAH VDHKYLILLD LGFDGTSDRD YEIQTAQLLT AELDFKGARL  60
GDTRKPDVCV YYGEDGLIID NKAYGKGYSL PIKQADEIYR YIEENKKRDE KLNPNKWWEI  120
FDKGVVRYHF AFVSGAFTGG FKERLDNIRM RSGICGAAIN SMNLLLMAEE LKSGRLGYEE  180
CFALFDCNDE ITFQSF                                                 196

SEQ ID NO: 144         moltype = AA  length = 198
FEATURE                Location/Qualifiers
REGION                 1..198
                       note = Synthetic Construct
source                 1..198
                       mol_type = protein
                       organism = synthetic construct
SEQUENCE: 144
NLKLTVDEKE RLELKEYFIS NTRIPSKYIT LLDLAYDGNA NRDFEIVTAE LFKDIFKLQS  60
KHMGGTRKPD ILIWTDKFGV IADTKAYSKG YKKNISEADK MVRYVNENTN RNKVDNTNEW  120
WNSFDSRIPK DAYYFLWISS EFVGKFDEQL TETSSRTGRN GASINVYQLL RGADLVQKSK  180
FNIHDLPNLM QNNEIKFI                                               198

SEQ ID NO: 145         moltype = AA  length = 197
FEATURE                Location/Qualifiers
REGION                 1..197
                       note = Synthetic Construct
source                 1..197
                       mol_type = protein
                       organism = synthetic construct
SEQUENCE: 145
NVLKDKHLEK IKEKFLENTS LDPRFISLIE ISRDKKQNRA FEIITAELFN TSYNLSAIHL  60
GGGRRPDVLA YNDNFGIIVD TKAYKNGYGR NVNQEDEMVR YITENKIRKQ DISKNNWWKY  120
FSKSIPSTSY YHLWISSEFV GMFSDQLRET SSRTGENGGA MNVEQLLIGA NQVLNNVLDP  180
NRLPEYMENK EIIFGTL                                                197

SEQ ID NO: 146         moltype = AA  length = 193
FEATURE                Location/Qualifiers
REGION                 1..193
                       note = Synthetic Construct
source                 1..193
                       mol_type = protein
                       organism = synthetic construct
SEQUENCE: 146
NGEKDTLKVK EFFISETSIP NKFITLLDLA YDGNSNRDFE IITSEFIREV YKLNTKHLGG  60
TRKPDILIWN EKFGIIADTK AYSKGYKKNI SEEDKMVRYI DENTKRSKED NPNEWWINFG  120
ENIPSNNYFY LWISSEFIGK FGEQLKETAS RTNTNGASLN VYQLLMGGHL AQIGRFNVNN  180
LPAFMNNSEI KFS                                                    193

SEQ ID NO: 147         moltype = AA  length = 198
FEATURE                Location/Qualifiers
REGION                 1..198
                       note = Synthetic Construct
source                 1..198
                       mol_type = protein
                       organism = synthetic construct
SEQUENCE: 147
NLKLTSREKS RLNLKEYFVS NTNLPNKFIT LLDLAYDGKA NRDFELITSE LFREIYKLNT  60
RHLGGTRKPD ILIWNENFGI IADTKAYSKG YKKNISEEDK MVRYIDENIK RSKDYNPNEW  120
WKVFDNEISS NNYFYLWISS EFIGKFEEQL QETAQRTNVK GASINVYQLL MGAHKVQTKE  180
LNVNSIPKYM NNTEIKFL                                               198

SEQ ID NO: 148         moltype = AA  length = 202
FEATURE                Location/Qualifiers
REGION                 1..202
                       note = Synthetic Construct
source                 1..202
                       mol_type = protein
                       organism = synthetic construct
SEQUENCE: 148
TPAESDISSE KLKNHFRRIT DLPEKYINLL DIAFDKDRNR DFEIITASLF KEGYGLSSIH  60
LGGQNKPDGV IYNDNFGIIL DTKAYGKGYG KYISQIDEMV RYIQDNQERD TFRNPNRWWE  120
NFSEFIPKDS YYYLWVSGKF LPTFTEQLKQ TNHRSHVNGG GLEVQQLLLG ADAVMKGNLD  180
VNDLPKYMKN EVIRFSSSES KI                                          202

SEQ ID NO: 149         moltype = AA  length = 204
```

```
FEATURE                 Location/Qualifiers
REGION                  1..204
                        note = Synthetic Construct
source                  1..204
                        mol_type = protein
                        organism = synthetic construct
SEQUENCE: 149
PVLKDAALQK TKNTLLNELT EIDPADIEVI EMSWKKATTR SQNTLEATLF EVKVVEIFKK  60
YFELNGEHLG GQNRPDGAVY YNSTYGIILD TKAYSNGYNI PVDQQREMVD YITDVIDKNQ  120
NVTPNRWWEA FPATLLKNNI YYLWVAGGFT GKYLDQLTRT HNQTNMDGGA MTTEVLLRLA  180
NKVSSGNLKT TDIPKLMTNK LILS                                         204

SEQ ID NO: 150          moltype = AA  length = 200
FEATURE                 Location/Qualifiers
REGION                  1..200
                        note = Synthetic Construct
source                  1..200
                        mol_type = protein
                        organism = synthetic construct
SEQUENCE: 150
EIQDQRIAAK KAQFLENTNI NPKYLELLDI AYNGSRNRDF EILTADLFNN VFGVDTILLG  60
GGRKPDAIIN DNNFGVIIDT KAYESGYSKN ITEEDKMVRY IEDNQYRDTE RNSTAWWGDF  120
KDTIPTTEFY FMWVSSKFIG EFHTQLEATN KRTQTNGCSI NVEQLLIGAD LVLKNQLHTK  180
NFPEYMQNKE INWRDLGLIH                                              200

SEQ ID NO: 151          moltype = AA  length = 196
FEATURE                 Location/Qualifiers
REGION                  1..196
                        note = Synthetic Construct
source                  1..196
                        mol_type = protein
                        organism = synthetic construct
SEQUENCE: 151
AEADLNSEKI KNHYRKITNL PEKYIELLDI AFDHRRHQDF EIVTAGLFKD CYGLSSIHLG  60
GQNKPDGVVF NNKFGIILDT KAYEKGYGMH IGQIDEMCRY IDDNKKRDKV RQPNEWWKNF  120
GDNIPKDQFY YLWISGKFLP RFNEQLKQTH YRTSINGGGL EVSQLLLGAN AAMKGKLDVN  180
TLPEHMNNQV IKLVHQ                                                  196

SEQ ID NO: 152          moltype = AA  length = 195
FEATURE                 Location/Qualifiers
REGION                  1..195
                        note = Synthetic Construct
source                  1..195
                        mol_type = protein
                        organism = synthetic construct
SEQUENCE: 152
ANADIYLENM KNHYRKITNL PERYLELLDV AFDHNRHQDF EIMTAGIFKD CYGLSSIHLG  60
GQNKPDGVIY NNNFGIILDT KAYEKGYGMH IDQIDEMCRY IYDNKQRDIV RQPNEWWNNF  120
DKNIPKDQFY YLWVSGKFLK NFDKQLKNTH YRTNINGGGL EVSQLLLGAD AVMKGNLDVN  180
TLPNYMKNNV IKLVI                                                   195

SEQ ID NO: 153          moltype = AA  length = 196
FEATURE                 Location/Qualifiers
REGION                  1..196
                        note = Synthetic Construct
source                  1..196
                        mol_type = protein
                        organism = synthetic construct
SEQUENCE: 153
AEADLNSEKI KNHYRKITNL PEKYIELLDI AFDHRRHQDF EIVTAGLFKD CYGLSSIHLG  60
GQNKPDGVVF NNKFGIILDT KAYEKGYGMH IGQIDEMCRY IDDNKKRDIV RQPNEWWKNF  120
GDNIPKDQFY YLWISGKFLP RFNEQLKQTH YRTSINGGGL EVSQLLLGAN AAMKGKLDVN  180
TLPKHMNNQV IKLVHQ                                                  196

SEQ ID NO: 154          moltype = AA  length = 193
FEATURE                 Location/Qualifiers
REGION                  1..193
                        note = Synthetic Construct
source                  1..193
                        mol_type = protein
                        organism = synthetic construct
SEQUENCE: 154
QESKEHEEIK NTFRRKTNLP EKYLELLDIA FDPKRNRDFE IITTDLFRDV YKLEAVHLGG  60
GSKPDGVVYN NNFGIILDTK AYEKGYGKDI KQIDEMVRYI EDNAERDRKR NPNMWWENFG  120
FDIPGNNYYY LWVSGKFLPR FQEQLKMTNY RTEVNGGGLN VRQLLWGADA VQKGELDVNE  180
IPRYMNNTVI EFV                                                     193

SEQ ID NO: 155          moltype = AA  length = 200
FEATURE                 Location/Qualifiers
```

```
REGION                  1..200
                        note = Synthetic Construct
source                  1..200
                        mol_type = protein
                        organism = synthetic construct
SEQUENCE: 155
RISPSNLEQT KQQLREELIY LDHQYLDILD FSIAGNTGAR QFEVRIVELL NEIIIAKHLS  60
GGNRPEIIGF NPRENPEDCI IMDSKAYREG FNIPANERDK MIRYVEEYNA KDNTLNNNKW  120
WKNFESPNYP TNQVKFSFVS SSFIGQFTNQ LTYINNRTNV NGSAITAETL LRKVEKVMNV  180
NAEYNLSNFF EELGNNTLVA                                              200

SEQ ID NO: 156          moltype = AA  length = 200
FEATURE                 Location/Qualifiers
REGION                  1..200
                        note = Synthetic Construct
source                  1..200
                        mol_type = protein
                        organism = synthetic construct
SEQUENCE: 156
RISPSNLEQT KQQLREELIN FDHQYLDILD FSIAGNVGAR QFEVRIVELL NEIIIAKHLS  60
GGNRPEIIGF NPKENPEDCI IMDSKAYKEG FNIPANERDK MIRYVEEYNA KDNTLNNNEW  120
WKNFESPNYP TNQVKFSFVS SSFIGQFTNQ LTYINNRTNV NGSAITAETL LRKVENVMNV  180
NTEYNLNNFF EELGSNTLVA                                              200

SEQ ID NO: 157          moltype = AA  length = 200
FEATURE                 Location/Qualifiers
REGION                  1..200
                        note = Synthetic Construct
source                  1..200
                        mol_type = protein
                        organism = synthetic construct
SEQUENCE: 157
RISPSNLEQT KQQLREELIN LDHQYLDILD FSIAGNVGAR QFEVRIVELL NEIIIAKHLS  60
GGNRPEIIGF NPKENPEDCI IMDSKAYKEG FNIPANERDK MIRYVEEYNA KDNTLNNNKW  120
WKNFESPNYP TNQVKFSFVS SSFIGQFTNQ LTYINNRTNV NGSAITAETL LRKVENVMNV  180
NTEYNLNNFF EELGSNTLVA                                              200

SEQ ID NO: 158          moltype = AA  length = 197
FEATURE                 Location/Qualifiers
REGION                  1..197
                        note = Synthetic Construct
source                  1..197
                        mol_type = protein
                        organism = synthetic construct
SEQUENCE: 158
KQIKDKYLED LKLELYKKTN LPNKYYEMVD IAYDGKRNRE FEIYTSDLMQ EIYGFKTTLL  60
GGTRKPDVVS YSDAHGYIID TKAYANGYRK EIKQEDEMVR YIEDNQLKDV LRNPNKWWEC  120
FDDAEHKKEY YFLWISSKFV GEFSSQLQDT SRRTGIKGGA VNIVQLLLGA HLVYSGEISK  180
DQFAAYMNNT EINFEGA                                                 197

SEQ ID NO: 159          moltype = AA  length = 200
FEATURE                 Location/Qualifiers
REGION                  1..200
                        note = Synthetic Construct
source                  1..200
                        mol_type = protein
                        organism = synthetic construct
SEQUENCE: 159
NLTPSSLEQT KQVLRTELNT LDHKYLDLLD FSISGTSGAR QFEVRIVELL NEIIIAKHLS  60
GGNRPEIIGF NPKENPLDCL IFDSKAYSKG FNIPANERDK MIRYIEEYNV KNETLNSNKW  120
WEEFKSPNYP TNEVKFGFVS SSFNGQYLSQ LAYITNRTNR NGCLMSVETL LKKVYNILNT  180
NNKYDLTSFF AEIGSNQFLN                                              200

SEQ ID NO: 160          moltype = AA  length = 201
FEATURE                 Location/Qualifiers
REGION                  1..201
                        note = Synthetic Construct
source                  1..201
                        mol_type = protein
                        organism = synthetic construct
SEQUENCE: 160
SISKTDITQL KEKIRENLKT VDHKYLVLVD LAYSDASTKG KKNADAREFE IQTAELFTRE  60
LNFSGMRLGD ANRPDVIISY EDFGAIIDNK SYKDGFNIDR KCADEMSRYI NENTRRVPGI  120
PKNEWWKNFD IKVHTFYFLF ITSFLKGNFK SQLDYISKSQ SDIQGGAVSV DNLLYIAEKL  180
KSGVIRYEDF FKLFVNEDII V                                            201

SEQ ID NO: 161          moltype = AA  length = 201
FEATURE                 Location/Qualifiers
REGION                  1..201
```

-continued

```
                            note = Synthetic Construct
source                      1..201
                            mol_type = protein
                            organism = synthetic construct
SEQUENCE: 161
SISKTDITQL KEKIRENLKT VDHKYLVLVD LAYSDASTKG KKNADAREFE IQTAELFTRE   60
LNFSGMRLGD ANRPDVIISY EDFGAIIDNK SYKDGFNIDR KCADEMSRYI NENTRRVPGI  120
PKNEWWKNFD IKVHTFYFLF ITSFLKGNFK SQLDYISKSQ SDIQGGAVSV DNLLYIAEKL  180
KSGVIRYEDF FKLFANEDII V                                            201

SEQ ID NO: 162         moltype = AA   length = 195
FEATURE                Location/Qualifiers
REGION                 1..195
                       note = Synthetic Construct
source                 1..195
                       mol_type = protein
                       organism = synthetic construct
SEQUENCE: 162
EEISDIALQK EKAYFYKNTA LSKRHISILE IAFDGSKNRD LEILSAEVFK DYYQLESIHL   60
GGGLKPDGIA FNQNFGIIVD TKAYKGAYSR SRAEADKMFR YIEDNKKRDP KRNQSLWWRS  120
FNEHIPANNF YFLWISGKFQ RNFDTQINQL NYETGYRGGA LSARQFLIGA DAIQKGKINI  180
NDLPSYFNNS VISFE                                                   195

SEQ ID NO: 163         moltype = AA   length = 209
FEATURE                Location/Qualifiers
REGION                 1..209
                       note = Synthetic Construct
source                 1..209
                       mol_type = protein
                       organism = synthetic construct
SEQUENCE: 163
IPVKENHTFQ TTEADNLKRK LLPVLKHVDH KYLQAIDIAY KKNTSNAENT LLEVLSTDLF   60
VKEMDYKGSH LGGSNKPDAF VYTSKAGWIL DSKAYSDGFH VTAANTDAMG RYIQQYRDHK  120
DKSTWWKKFP NNLPITYFAY ISSFYNGNYQ SQLKDFEDRN KMRGGLIEIP KLILLAEEYQ  180
DKKISQAQIN QQLLDDKIDW KDYSTILLP                                    209

SEQ ID NO: 164         moltype = AA   length = 195
FEATURE                Location/Qualifiers
REGION                 1..195
                       note = Synthetic Construct
source                 1..195
                       mol_type = protein
                       organism = synthetic construct
SEQUENCE: 164
EEISDIALQK EKAYFYKNTA LSKRHISILE IAFDGSKNRD LEILSAEVFK NYYQLESIHL   60
GGGLKPDGIA FNQNFGIIVD TKAYKGAYSR SRAEADKMFR YIEDNKKRDP KRNQSLWWRS  120
FNEHIPANNF YFLWISGKFQ RNFDTQINQL NYDTGYRGGA LSARQFLIGA DAIQKGKINI  180
NDLLSYFNNS VISFE                                                   195

SEQ ID NO: 165         moltype = AA   length = 195
FEATURE                Location/Qualifiers
REGION                 1..195
                       note = Synthetic Construct
source                 1..195
                       mol_type = protein
                       organism = synthetic construct
SEQUENCE: 165
EEISDIALQK EKAYFYKNTA LSKRHISILE IAFDGSKNRD LEILSAEVFK DYYQLESIHL   60
GGGLKPDGIA FNQNFGIIVD TKAYKGVYSR SRAEADKMFR YIEDNKKRDP KRNQSLWWRS  120
FNEHIPANNF YFLWISGKFQ RNFDTQINQL NYETGYRGGA LSARQFLIGA DAIQKGKIDI  180
NDLPSYFNNS VISFE                                                   195

SEQ ID NO: 166         moltype = AA   length = 209
FEATURE                Location/Qualifiers
REGION                 1..209
                       note = Synthetic Construct
source                 1..209
                       mol_type = protein
                       organism = synthetic construct
SEQUENCE: 166
LPKKDNVQRQ QDELRPLLKH VDHRYLQLVE LALDSSQNSE YSMLESMTME LLLTHLDFDG   60
ASLGGASKPD GIAWDKDGNF LIVDTKAYDN GYSLAGNTDK VARYIDDVRA KDPNRASTWW  120
TQVPESLNVD DNLSFMYVSG SFTGNYQRLL KDLRARTNAR GGLTTVEKLL LTSEAYLAKS  180
GYGHTQLLND WTDDNIDHSE YYDKIVNQI                                    209

SEQ ID NO: 167         moltype = AA   length = 195
FEATURE                Location/Qualifiers
REGION                 1..195
                       note = Synthetic Construct
```

-continued

```
source                  1..195
                        mol_type = protein
                        organism = synthetic construct
SEQUENCE: 167
EEISDIALQK EKAYFYKNTA LSKRHISILE IAFDGSKNRD LEILSAEVFK NYYQLESIHL  60
GGGLKPDGIA FNQNFGIIVD TKAYKGAYSR SRAEADKMFR YIEDNKKRDP KRNQSLWWRS  120
FNEHIPANNF YFLWISGKFQ RNCDTQINQL NYDTGYRGGA LSARQFLIGA DAIQKGKINI  180
NDLPSYFNNS VISFE                                                 195

SEQ ID NO: 168          moltype = AA  length = 202
FEATURE                 Location/Qualifiers
REGION                  1..202
                        note = Synthetic Construct
source                  1..202
                        mol_type = protein
                        organism = synthetic construct
SEQUENCE: 168
TFKASEADKI KEKLLPVLHN LDHTYLQAVD IAYKDKTTNQ ENAQLEILST SLFTKEMEFR  60
GLHLGGVNKP DGFAYDDNDG WIIDSKAYHN GFPLTVSHTD AMGRYIRQYR DRNDNSNWWK  120
TLPSNLPNTQ FIYVSSFFIG NYKKQLKDFE TRNKMKGSLM EIPQLILLAE RYKAGKSSHE  180
EFKNYALANK HNFNEYLAEL TK                                         202

SEQ ID NO: 169          moltype = AA  length = 203
FEATURE                 Location/Qualifiers
REGION                  1..203
                        note = Synthetic Construct
source                  1..203
                        mol_type = protein
                        organism = synthetic construct
SEQUENCE: 169
ACVKENINDL KDKIRGKLKT LDHKYLVLID LAYSDASSKT KKNADAREFE IQTADLFTGE  60
LAFSGMRLGD SNKPDVIISH GDKGTIIDNK SYQDGFNISA GCRDEMSRYI KENIMRSPAL  120
NPNKWWENFD PKVTDYTFLF ITSYLKGQFA NQLEYISVAH GGIKGAAISV ENLLYLSEGI  180
KSGKIRHEDF YNSFHNKEMI FTL                                        203

SEQ ID NO: 170          moltype = AA  length = 203
FEATURE                 Location/Qualifiers
REGION                  1..203
                        note = Synthetic Construct
source                  1..203
                        mol_type = protein
                        organism = synthetic construct
SEQUENCE: 170
ACVKENVNDL KDKIRGKLKT LDHKYLVLID LAYSDASSKT KKNADAREFE IQTADLFTGE  60
LSFSGMRLGD SNKPDVIISY GDKGTIIDNK SYQDGFNISA GCRDEMSRYI KENIMRSPTL  120
NPNKWWENFD PKITDYTFLF ITSYLKGQFA NQLEYISVAH GGIKGAAISV ENLLYLSEGI  180
KSGKISHEDF YNSFHNKEMI FTL                                        203

SEQ ID NO: 171          moltype = AA  length = 206
FEATURE                 Location/Qualifiers
REGION                  1..206
                        note = Synthetic Construct
source                  1..206
                        mol_type = protein
                        organism = synthetic construct
SEQUENCE: 171
TLQKSDIEKF KNQLRTELTN IDHSYLKGID IASKKTTTNV ENTEFEAIST KVFTDELGFF  60
GEHLGGSNKP DGLIWDNDCA IILDSKAYSE GFPLTASHTD AMGRYLRQFK ERKEEIKPTW  120
WDIAPDNLAN TYFAYVSGSF SGNYKAQLQK FRQDTNHMGG ALEFVKLLLL ANNYKAHKMS  180
INEVKESILD YNISYEEYAP LLTEIE                                     206

SEQ ID NO: 172          moltype = AA  length = 195
FEATURE                 Location/Qualifiers
REGION                  1..195
                        note = Synthetic Construct
source                  1..195
                        mol_type = protein
                        organism = synthetic construct
SEQUENCE: 172
EEISDIVLQK EKAYFYKNTA LSKRHISILE IAFDGSKNRD LEILSAEVFK DYYQLESIHL  60
GGGLKPDGIA FNQNFDIIVD TKAYKGVYSR SRAEADKMFR YIEDNKKRDP KRNQSLWWRS  120
FNEHIPANNF YFLWISGKFQ RNFDTQINQL NYETGYRGGA LSARQFLIGA DAIQKGKIDI  180
NDLPSYFNNS VISFE                                                 195

SEQ ID NO: 173          moltype = AA  length = 206
FEATURE                 Location/Qualifiers
REGION                  1..206
                        note = Synthetic Construct
source                  1..206
```

-continued

```
                        mol_type = protein
                        organism = synthetic construct
SEQUENCE: 173
VLEKSDIEKF KNQLRTELTN IDHSYLKGID IASKKKTSNV ENTEFEAIST KIFTDELGFS  60
GKHLGGSNKP DGLLWDDDCA IILDSKAYSE GFPLTASHTD AMGRYLRQFT ERKEEIKPTW  120
WDIAPEHLDN TYFAYVSGSF SGNYKEQLQK FRQDTNHLGG ALEFVKLLLL ANNYKTQKMS  180
KKEVKKSILD YNISYEEYAP LLAEIE                                      206

SEQ ID NO: 174          moltype = AA  length = 209
FEATURE                 Location/Qualifiers
REGION                  1..209
                        note = Synthetic Construct
source                  1..209
                        mol_type = protein
                        organism = synthetic construct
SEQUENCE: 174
LPKKDNVQRQ QDELRPLLAH VDHRYLQLVE LALDSSQNSE YSMLESMTME LLLTYLDFDG  60
ASLGGANKPD GIAWDSDGNF LIVDTKAYDN GYSLAGNTDK VARYIDDVRA RDSNRTSTWW  120
TQVPESLNVD DNLSFMYVSG SFTGNYRKLL KDLRARTNAR GGLTTVEKLL LTSEVYLTNN  180
KYGHTQLLRD WTNDAIEHDE YYDQLVANI                                   209

SEQ ID NO: 175          moltype = AA  length = 210
FEATURE                 Location/Qualifiers
REGION                  1..210
                        note = Synthetic Construct
source                  1..210
                        mol_type = protein
                        organism = synthetic construct
SEQUENCE: 175
LPHKDNVIKQ QDELRPMLKH VNHKYLQLVE LAFESSRNSE YSQFETLTME LVLKYLDFSG  60
KSLGGANKPD GIAWDPLGNF LIFDTKAYKH GYTLSNNTDR VARYINDVRD KDIQRISRWW  120
QSIPTYIDVK NKLQFVYISG SFTGHYLRLL NDLRSRTRAK GGLVTVEKLL LTTERYLAEA  180
DYTHKELFDD WMDDNIEHEE YFYSLQDALK                                  210

SEQ ID NO: 176          moltype = AA  length = 206
FEATURE                 Location/Qualifiers
REGION                  1..206
                        note = Synthetic Construct
source                  1..206
                        mol_type = protein
                        organism = synthetic construct
SEQUENCE: 176
TFSPDAAQVA KEKLRPLLQN VSHSYLYAID LAFKDKTTAK ENAELEIIST QAFDYFNYET  60
KHLGGQRRPD GIATSSEENW VIDTKAYHNG FSLTVNHTDA MVRYMRQADG QIQSDDANEL  120
WWRDLTPDVP ARYIYISSKF IGNYEAQNRS LMNVTGHEGS VAPVAKLLLL AELKLRDKLT  180
KEQFIQELLS PTGSFEEYLP TFESML                                      206

SEQ ID NO: 177          moltype = AA  length = 202
FEATURE                 Location/Qualifiers
REGION                  1..202
                        note = Synthetic Construct
source                  1..202
                        mol_type = protein
                        organism = synthetic construct
SEQUENCE: 177
ETFDSTVADN LKNLILPKLK ELDHKYLQAI DIAYKRSNTT NHENTLLEVL SADLFTKEMD  60
YHGKHLGGAN KPDGFVYDEE TGWILDSKAY RDGFAVTAHT TDAMGRYIDQ YRDRDDKSTW  120
WEDFPKDLPQ TYFAYVSGFY IGKYQEQLQD FENRKHMKGG LIEVAKLILL AEKYKENKIT  180
HDQITLQILN DHISQDEYIK DF                                          202

SEQ ID NO: 178          moltype = AA  length = 204
FEATURE                 Location/Qualifiers
REGION                  1..204
                        note = Synthetic Construct
source                  1..204
                        mol_type = protein
                        organism = synthetic construct
SEQUENCE: 178
TRLAADPVKV RDVLRQRFSA GYGGFLMHYT ELAQGSNTAA TKFEQATTEI FSKVFGYRAK  60
HIGAQPLRPD VVLYSETDRY GAILDTKAYA KRYTLSHDQR GVMRNYVVDY PKYKIGDGDL  120
AFFSYVSGRF GPNIDAQLAE VSERADGVPG SAITAHDIVL MCKRHLGAEK YTHAQLREFF  180
SGNKQVQVAG HERSLADLVA AATA                                        204

SEQ ID NO: 179          moltype = AA  length = 191
FEATURE                 Location/Qualifiers
REGION                  1..191
                        note = Synthetic Construct
source                  1..191
                        mol_type = protein
```

```
                         organism = synthetic construct
SEQUENCE: 179
GLERAMVARV AQQVLGRDRT VDQFLSTYAN LVHDESPRAA KLFEESTANI LKAVFRVDAK  60
LVGSQGREPD VVVSGDGWRG IVDTKAYSGE YTLPSGHDRA MREYVENYRA GDSPLRFWAF  120
ICGAVARGAS AKVHFLGKQV GLAGTVVGMV AWLQMIKLAE AGVIGGSDLP RLFSIGRELT  180
LEDLPTLVAG G                                                       191

SEQ ID NO: 180          moltype = AA  length = 199
FEATURE                 Location/Qualifiers
REGION                  1..199
                        note = Synthetic Construct
source                  1..199
                        mol_type = protein
                        organism = synthetic construct
SEQUENCE: 180
GFSHSEVEKA AKKVLGTDRT LDNFLYSYQS LPYSSAKDAP RKFELATAEL FRRVFKLDAE  60
CVGQAGREPD VVVTKPGEWR GIVDTKAYSG DYSLPSSHER AMREYVETYR AAPGAPLRFW  120
VFIAASVSKG ARHRVRQLAD LVDSPGAVIG MLAWTEMIRF AQKGKIDSER MADLFALNSE  180
LTMEDLKKVL SADRDVSLG                                               199

SEQ ID NO: 181          moltype = AA  length = 212
FEATURE                 Location/Qualifiers
REGION                  1..212
                        note = Synthetic Construct
source                  1..212
                        mol_type = protein
                        organism = synthetic construct
SEQUENCE: 181
LLVDGATSDI ISRLVAETGY EYSEVEVAAK KVLGTDRTLD SFLSNYQSLV FSDDKSAPRY  60
FERATAEIFR RIFNLEAECV GQSGREPDVV VTKRDAWRGI VDTKAYSGEY SLPSEHERAM  120
REYVETYRAV PGAPLSFWVF IAGSISKGAK HRVRGLADRV DSPGSVIGML AWTEMIRLAQ  180
DGKIDADRMA ELFKSNSELT LDDVRRLPKA DV                                212

SEQ ID NO: 182          moltype = AA  length = 203
FEATURE                 Location/Qualifiers
REGION                  1..203
                        note = Synthetic Construct
source                  1..203
                        mol_type = protein
                        organism = synthetic construct
SEQUENCE: 182
SGYLDLEEAS RAAFFNDDGI HWFITGDIAE IHSDGTFSII DRKKDIVKLA NGEFISLGKI  60
EATLKSSCYV DNICIVPNAT LNCLVALIVP NLMSIKSLIG RQLELTKQLP QLSDPNLLIG  120
HPEIIKIIHN DIIDVGIRQR LKSLELPSMI TLCEEIWAPD NDLLTAAMKL KRANIIKHYN  180
YDLQQMWSSL RANPEKIRLQ LKK                                          203

SEQ ID NO: 183          moltype = AA  length = 205
FEATURE                 Location/Qualifiers
REGION                  1..205
                        note = Synthetic Construct
source                  1..205
                        mol_type = protein
                        organism = synthetic construct
SEQUENCE: 183
QFSHGEVEKV ARRILGTDRT LSSYLLHYQS LVTSSDRNAP REFEQATAEI IRRVFKLEAT  60
CVGQTGREPD IVVRKPGEWR GIIDTKAYGG EYSLPSGHDR AMREYVEKYS GDGGDDLRFW  120
VFLAGSLSKN AGARARELAQ RIGCQGVVIG LSAWMKMIEL GQAGKLSGDK LGWLFSLDGE  180
LTHADIARAQ EAASFAELHA QRGLF                                        205

SEQ ID NO: 184          moltype = AA  length = 199
FEATURE                 Location/Qualifiers
REGION                  1..199
                        note = Synthetic Construct
source                  1..199
                        mol_type = protein
                        organism = synthetic construct
SEQUENCE: 184
PERQRTIHDK RKEKIMERTS LPLKFYELYD IAFDPKRSRD FEILTVELFK LATNTNARVL  60
GGSLRPDGIV YQQADGQSPG IIIDTKAYAD GYSKIKSQED EMVRYIEDNQ FRDPKRNPTK  120
WWESFPKTIS PKNTTFLWVS STFTGAFDEQ LKSTYHRTNA NGGAVAVDQL LIGVDKVCRG  180
ELTSEELFDS LKRNQIATF                                               199

SEQ ID NO: 185          moltype = AA  length = 193
FEATURE                 Location/Qualifiers
REGION                  1..193
                        note = Synthetic Construct
source                  1..193
                        mol_type = protein
                        organism = synthetic construct
```

-continued

```
SEQUENCE: 185
SKEKSNLKLK EFFISETAIP NKFITLFDLA YDGSANRDFE IITSELFRDV YKLNTKHLGG  60
TRKPDILIWN KEYGIIADTK AYSKGYKKNI SEEDKMVRYI DENIKRNKND NPNEWWKIFD  120
KSISSANYFY LWISSEFVGK FEEQLQGTAT RTNTNGASLN VYQLLMGAHL VQIEELSVNS  180
IPAYMNNMEI KFV                                                     193

SEQ ID NO: 186         moltype = AA  length = 198
FEATURE                Location/Qualifiers
REGION                 1..198
                       note = Synthetic Construct
source                 1..198
                       mol_type = protein
                       organism = synthetic construct
SEQUENCE: 186
TRRRDEIEER IVRLGARLRH VPDRYLDLVR LGFDPSRSAD FEFGVFEVFR DLLGYDALKL  60
GGGLAPDALA WYADPQFLPL SYGLIIDAKS SATAFSVDVS AADQMTRYVL EYQKELLSRH  120
IPTAYFLFVG GAFSGPLGGL RLLHERTRVA GAAITIADLI HLAEQLRERR QEVTLRSVSA  180
LFGSLQLIDA AKIDALHG                                                198

SEQ ID NO: 187         moltype = AA  length = 194
FEATURE                Location/Qualifiers
REGION                 1..194
                       note = Synthetic Construct
source                 1..194
                       mol_type = protein
                       organism = synthetic construct
SEQUENCE: 187
PVARVDWVLA QKYPSGAVDG FMNSYAQMAF ESREKATDFE KATTSIFRDV FGFEARHIGA  60
YSERPDVVIS SHEAGYGAIL DSKAYKKGYS LGVSQRNRMR DYISNFEEYA LDSNPLAFFA  120
YVVSEYKSNV ESQLRDVAEE NGVNGAAITA RDIIRMVRRH RDRPYSHEEI RAIFSGNRPV  180
VLSDLQDLSE GAFR                                                    194

SEQ ID NO: 188         moltype = AA  length = 201
FEATURE                Location/Qualifiers
REGION                 1..201
                       note = Synthetic Construct
source                 1..201
                       mol_type = protein
                       organism = synthetic construct
SEQUENCE: 188
GIDRSTVSSV LQMKFPRGAS EAFLSNYLEL SARSREKATE FEVATAEIFR KIFGFKAEHT  60
GNHGLRPDVV LSSTEAHYGA IIDNKAYKKG YSLGVSQQGR MRDYIEDFPR YRLSEDEERP  120
AFFVYVIHEG STNLTSQIQA LSEKTGVHGS AITARDILLM VRRHQEKPFT HEEIRSLFSQ  180
NQIVDLLDDG YEGLGDRVLG A                                            201

SEQ ID NO: 189         moltype = AA  length = 194
FEATURE                Location/Qualifiers
REGION                 1..194
                       note = Synthetic Construct
source                 1..194
                       mol_type = protein
                       organism = synthetic construct
SEQUENCE: 189
ASTGFSPASV SAALGRVMPD RSRTLDQFLL GYAEMARSSR ERARDFELAT TDVFKRVFEL  60
DARHVGGAGR EPDVVVDNNN SWRIIVDTKA HGNGYTLPAS DERAMKEYVA AYAQKSPKLK  120
AWVFISSSFG ASINPRLRKI VDETGVPGSA VGITAWIALI QHAQDGRVDA EMLLALLSVG  180
REVTLEDVQR VVVG                                                    194

SEQ ID NO: 190         moltype = AA  length = 191
FEATURE                Location/Qualifiers
REGION                 1..191
                       note = Synthetic Construct
source                 1..191
                       mol_type = protein
                       organism = synthetic construct
SEQUENCE: 190
REISLATGLT VSAVESGLSG WSADTLGIFE ASYVDMAFSS REKALDFELA TVDLFKQLGF  60
STRHVGASPR HPDVLIESPL CYSGIIDNKA YSAYSISNDH RNRMEQNYIP TYQSSHGDLA  120
FFMYIAGGFI NTIDNQIARI AMTSGVAGSA IKASDMIKIL QKHQNSVIDH NLLKALFRAN  180
RRITIQDIHS L                                                       191

SEQ ID NO: 191         moltype = AA  length = 185
FEATURE                Location/Qualifiers
REGION                 1..185
                       note = Synthetic Construct
source                 1..185
                       mol_type = protein
                       organism = synthetic construct
SEQUENCE: 191
```

-continued

```
SGFDEKIVEE TLLRLYPNGA VGSFMTEYFE LAFKGRDNAI EFEKATVELF KNIFGFETKH  60
IGSVGLNPDV YVLSNEGKYI GILDNKAYRR YTISNDHRNR MVHNYIEQYK SDVYPLAFFS  120
YISGGFGSNI DSQIKSISDE TQVNGSAMSV TNMIRMVEKH AQKQYSHSSI KDIFSLNRQV  180
VLSDL                                                              185

SEQ ID NO: 192          moltype = AA  length = 202
FEATURE                 Location/Qualifiers
REGION                  1..202
                        note = Synthetic Construct
source                  1..202
                        mol_type = protein
                        organism = synthetic construct
SEQUENCE: 192
ERIKKEIQKT ITYVVGKTQN LDENLIEKVI EQSFSGKKSC KEFEDSIFKL YSETIGFEGI  60
KLGGIGNREP DSLFWYKVHN DEDNYGLIVD AKAYSKGFKI NTSSSRQMND YIYKFYNKLQ  120
EEHGLNRSHY HWVTSKYIGN GDIEYFAENV RNMYSFESKG SIISISNALL IADKIQSNRD  180
FKKLESLMSI EREILETDIE VF                                           202

SEQ ID NO: 193          moltype = AA  length = 188
FEATURE                 Location/Qualifiers
REGION                  1..188
                        note = Synthetic Construct
source                  1..188
                        mol_type = protein
                        organism = synthetic construct
SEQUENCE: 193
RLVENTLIEA YPNGAISGFM TEYFEMAFKG TEEAIQFEEA TTELFSEVFG FKAKHLGQTG  60
SKSAPDVLLL SDDAGYQAII DNKAYSRYSI SGDHHNRMVH NYLNNISNYS EYQQPIGFFT  120
YISGGFGNQI DRQIQSIAEE SGIHGSGMSV SNMIKLVEKQ NEKPLTHQMI REIFSVDRQI  180
LLSDLNLV                                                           188

SEQ ID NO: 194          moltype = AA  length = 203
FEATURE                 Location/Qualifiers
REGION                  1..203
                        note = Synthetic Construct
source                  1..203
                        mol_type = protein
                        organism = synthetic construct
SEQUENCE: 194
KEIQKEIQKM VDDLKKLSLS IDDGFMEKII TEAYSGRDKC KEFEDSVFEL YRDSIGFDGI  60
KLGTIGSREP DSLFWYKVED TQDSYGLIVD AKAYSKGFKI NTNSSRQMND YIYSFTKKLE  120
ADQGVSRSHF HWVTSKYIGK NDIEDFSENV RNMYDFTSLG SIVGVGNALI MADEMKKKKD  180
FTKLENVLTT GREITVEDIR KIS                                          203

SEQ ID NO: 195          moltype = AA  length = 194
FEATURE                 Location/Qualifiers
REGION                  1..194
                        note = Synthetic Construct
source                  1..194
                        mol_type = protein
                        organism = synthetic construct
SEQUENCE: 195
ICSKTGIAEQ TVERFLLSQY PHGNIDDFFV SYREFANMGR AFAREFEKAT CEMFRKIFKM  60
RAEHVGPIGN TPDVLILSES ENFCGIIDNK AYHKGYSISG DHKRVMEDVY IPNYQAYGST  120
KLPLAFFAYI AGSFKKTVNS QLQEITRDTG ISGSAMPVDV FINFAQDYAN GSCTHRTIKD  180
LFSLNREISL SDLP                                                    194

SEQ ID NO: 196          moltype = AA  length = 184
FEATURE                 Location/Qualifiers
REGION                  1..184
                        note = Synthetic Construct
source                  1..184
                        mol_type = protein
                        organism = synthetic construct
SEQUENCE: 196
QYSVVEDCLF KIYPHGAIRI FMNEYFEMAF KGRDEATAFE KATSEIFRNV FLFQSEHIGQ  60
KGLTPDVVVI SDEFGFSGII DNKAYSKYSI NNDHKNRMIH NYIPKYKNFK KCDLAFFMYI  120
AGGFSNSFEI SIKNISRESK VNGSGISVVN LIKMIEKQIE KPYCHLSLRS IFSLNRLITP  180
EDMM                                                               184

SEQ ID NO: 197          moltype = AA  length = 181
FEATURE                 Location/Qualifiers
REGION                  1..181
                        note = Synthetic Construct
source                  1..181
                        mol_type = protein
                        organism = synthetic construct
SEQUENCE: 197
QLVEETLLRL YPRGAIGSFM TEYFDMAFRG RDDATEFELA TVELFKNAFD LRAEHIGPQG  60
```

```
LTPDVLVLSD QEGFIGIIDN KAYSKYTISN DHRNRMVHNY IPRYRSGQQY PLAFFSYISG  120
GFGSSINAQI KSIVDETHIH GSAISVSNVI TLVDLYSQRG YNHARLKDIL SLDRQVLLAD  180
L                                                                 181

SEQ ID NO: 198         moltype = AA  length = 197
FEATURE                Location/Qualifiers
REGION                 1..197
                       note = Synthetic Construct
source                 1..197
                       mol_type = protein
                       organism = synthetic construct
SEQUENCE: 198
GISMSKIRAI LQKVSKTKPS NDEIALRYLE LARGGREAAV AFEQATAEIF GPWGLGFESE  60
WIGAHPNHPD VRVLNVAQAP YYAGILDAKA YEGGYDLPRD HERRMYDEYI PAHRHMKRDE  120
HIVPLRWFGY VSSSFGANFD RKLTRIAQRG GVSGFAISAD TLLALVQRHK QRPLTEDEFC  180
DLFSVNREVM VDDFSTA                                                197

SEQ ID NO: 199         moltype = AA  length = 193
FEATURE                Location/Qualifiers
REGION                 1..193
                       note = Synthetic Construct
source                 1..193
                       mol_type = protein
                       organism = synthetic construct
SEQUENCE: 199
LVTETQFEHQ EVETAAKQIL GTDRTLETYL YNYQALVYSQ KRDAPRVFEQ ATAEILRQVF  60
GLEAVCVGQS GREPDVVVTQ PNEWRGIIDT KAYSGEYTLP SSHDRAMREY VERYSATPGE  120
TLRFWAFIAG AISRGAGAKA TSLSSQTGIP GVVVGMLAWL QLIRLGQEKR VDGEQLADYL  180
SKGGELTVAD LSQ                                                    193

SEQ ID NO: 200         moltype = AA  length = 184
FEATURE                Location/Qualifiers
REGION                 1..184
                       note = Synthetic Construct
source                 1..184
                       mol_type = protein
                       organism = synthetic construct
SEQUENCE: 200
IPSKYIEEQL DSFRIDTFSL FETNYIDMAF SGREFASEFE HTTMDVFSEL GFQTQHVGTK  60
SRQPDIFIQS HDASFSGIID NKAYHVFSIT HDYELKMINS YIPKYKKRYS DFSFFMYIAG  120
GFGKNFDKQV QTIANQSGIN GCGIRASDLM RLLKKHKQNP IDHQKLKQIF ECNRLVRIQD  180
ILSL                                                              184

SEQ ID NO: 201         moltype = AA  length = 187
FEATURE                Location/Qualifiers
REGION                 1..187
                       note = Synthetic Construct
source                 1..187
                       mol_type = protein
                       organism = synthetic construct
SEQUENCE: 201
VSLKDTERIL SAKYPKGLVD SFLSEYVQMA FESRDKATEF EKATTSIFAD IFGLYAEHIG  60
QKGIVPDVVI ASREEGWSGI LDSKAYAKGY SIGHDHRNRM VEYIERYPEY GPDFAALAFF  120
SYVVSDYKNS VTPQIRLISE KSGVPGSVIT ARDIVRMVER HKKKPYTHAE IREIFSLNRA  180
ITFEDIG                                                           187

SEQ ID NO: 202         moltype = AA  length = 189
FEATURE                Location/Qualifiers
REGION                 1..189
                       note = Synthetic Construct
source                 1..189
                       mol_type = protein
                       organism = synthetic construct
SEQUENCE: 202
TGVSAVETER ILSAKYPNGL VDSFLSEYVQ MAFESRDKAT EFEKATTSIF ADIFGLYAEH  60
IGQKGIVPDV VVASREEGWS GILDSKAYAK GYSIGHDHRN RMVEYIERYP KYGPEFATLA  120
FFSYVVSDYK NSVTPQIRTI SEKSGVPGSV ITARDIVRMV ERHQKKPYTH SEIREIFSLN  180
RAITFEDIE                                                         189

SEQ ID NO: 203         moltype = AA  length = 189
FEATURE                Location/Qualifiers
REGION                 1..189
                       note = Synthetic Construct
source                 1..189
                       mol_type = protein
                       organism = synthetic construct
SEQUENCE: 203
TGVSAVETER ILSAKYPNGF VDSFLSEYVQ MAFESRDRAT EFEKATTSIF ADIFGLYAEH  60
IGQKGIVPDV VVASREEGWS GILDSKAYAK GYSIGHDHRN RMVEYIERYP KYGPEFATLA  120
```

-continued

```
FFSYVVSDYK NSVTPQIRTI SEKSGVPGSV ITARDIVRMV ERHQKKPYAH SEIREIFSLN  180
RAITFEDIG                                                          189

SEQ ID NO: 204         moltype = AA  length = 219
FEATURE                Location/Qualifiers
REGION                 1..219
                       note = Synthetic Construct
source                 1..219
                       mol_type = protein
                       organism = synthetic construct
SEQUENCE: 204
TGVDEKTVER FLIQNYPHGN IDDFFLCYKE LAHMGTAGAR DFETATCEMF RKIFRMRAEH  60
VGPIGNTPDV FVESTDAGYC GIIDNKAYKN GYSISGDHKR VMEDVYIPNY KTYGQTEQPL  120
AFFTYIAGSF GSNINSQLAT ITRDTGVSGS AMPVDIFINL AQDYADKGYD HKFLKDIFSV  180
NREIQLSDLQ PKSKAFQYDF QSQSLGMVAE PTVPYGKKD                         219

SEQ ID NO: 205         moltype = AA  length = 195
FEATURE                Location/Qualifiers
REGION                 1..195
                       note = Synthetic Construct
source                 1..195
                       mol_type = protein
                       organism = synthetic construct
SEQUENCE: 205
DFDHSEVAKI ATNVLGTDRT LDNFLYTYQS LPHSSAKDAP RKFEQATAEI FRRVFKLDAE  60
CVGQAGREPD VVVTKPGEWR GIVDTKAYDG DYSLPSSHER AMKEYVETYQ NRDGEVLEFW  120
VFIAASVSRG AHRKAKMLAE RIETSGVVIG MFAWLEMIRK AGSGSMDSDQ MAALFQSSGE  180
LTMADVRSGE VSSSR                                                   195

SEQ ID NO: 206         moltype = AA  length = 198
FEATURE                Location/Qualifiers
REGION                 1..198
                       note = Synthetic Construct
source                 1..198
                       mol_type = protein
                       organism = synthetic construct
SEQUENCE: 206
VAVKTGISPA RVEQVLTQKY PGGSAAWFMA KYVQLAFQSR EHATQFEVAT TSIFRDVFGF  60
QAQHVGPIPR RPDIVIASLE VHYGALLDSK AYKTGYSATI GQQNRMRDYI DDFPDYALSG  120
APLAFFAYVV SGTKSTLRAQ IQDIARQNGV PGAAITAAQL AAMVERHSTT KYTHEQIRQI  180
LSVNREVEMA DLAIGDGR                                                198

SEQ ID NO: 207         moltype = AA  length = 194
FEATURE                Location/Qualifiers
REGION                 1..194
                       note = Synthetic Construct
source                 1..194
                       mol_type = protein
                       organism = synthetic construct
SEQUENCE: 207
EESETEIEKL IEKLVVQYED TIPAKLVDGL VRYGYDGSEG INFEITVAQF FRYLGYKTEY  60
FGQGRGRTAD VIARYINKIY ARSYGIIIDS KATSDKYTFP AGDIRKMKEY IDLHGRELLK  120
DSIPLHAFAF VSSCFCEDVA SPLKEISEDT GIKGTAIEVL KLLEFGCLLT KGKLYIENMY  180
PAYITNSTFD VGNL                                                    194

SEQ ID NO: 208         moltype = AA  length = 206
FEATURE                Location/Qualifiers
REGION                 1..206
                       note = Synthetic Construct
source                 1..206
                       mol_type = protein
                       organism = synthetic construct
SEQUENCE: 208
AGISAKFVEE ILQKKYPHGS IGAFMANYFE LAFNGREDCR KFEIATAEIF KNVFGFTSHH  60
IAGGAKEVPD VLLIAENAGY QAIIDTKAYN RYDLGATQRD RMIYHYLQDI QTYSSSTLPV  120
GFFSYIAGGF SNNIASPLCK IVNATGVNGS AMPVAAFIKM AERQGNSPYT KDEICQIFSV  180
NRKIELSDLD ICSSLMVAEN SIKYGK                                       206

SEQ ID NO: 209         moltype = AA  length = 186
FEATURE                Location/Qualifiers
REGION                 1..186
                       note = Synthetic Construct
source                 1..186
                       mol_type = protein
                       organism = synthetic construct
SEQUENCE: 209
PATTVEKTLA KTYPDGAVGT FMHSYAQMAF ESRDRATDFE KATASVFRDV FGFKAEHIGQ  60
RGRVPDVVIA SDTEHYGALL DSKAYAKGYS IGISQQNRMR DYITDFPTYR LTDAPLAFFA  120
YVVAEYKSTI NGQLKEIAET NGVPGSAITA RDIIRMVEHH QDTPYTHAQI RELLSVNRAV  180
```

-continued

```
TYQDLS                                                            186

SEQ ID NO: 210          moltype = AA  length = 187
FEATURE                 Location/Qualifiers
REGION                  1..187
                        note = Synthetic Construct
source                  1..187
                        mol_type = protein
                        organism = synthetic construct
SEQUENCE: 210
ITGFSNQQVE AVLQGFRPDT LSIFETSYLN MAISGTELAR EFELATNHIF ELLGFHSRHI  60
GTSPLHPDVF AASTTYNFSG IIDAKAYRTY SLTNDHRNRM INNYIPDWSN RFGNLSFFMY  120
VADGFGANID NQIQQVSNAS GKNGCVISAR DLLYLLQKHL ASPVDHSRLN NIFQYNRRLT  180
VVDIESL                                                           187

SEQ ID NO: 211          moltype = AA  length = 184
FEATURE                 Location/Qualifiers
REGION                  1..184
                        note = Synthetic Construct
source                  1..184
                        mol_type = protein
                        organism = synthetic construct
SEQUENCE: 211
ATGYTTNEVA RALDGFRPDT FSLFEATYMN MAVSGRELAT EFELATQNVF EELGFNAQHV  60
GAKPLHPDIY VESPLNYSGI IDTKAYRRYS ITNDHRNRMV RNYIPTYRDD DFTFFMYVAD  120
GFGSNISSQI QSIAEETNIN GTVITASNIM RLLQRNQVAT IDHASLRNLF TSNEVVSISD  180
INSL                                                              184

SEQ ID NO: 212          moltype = AA  length = 190
FEATURE                 Location/Qualifiers
REGION                  1..190
                        note = Synthetic Construct
source                  1..190
                        mol_type = protein
                        organism = synthetic construct
SEQUENCE: 212
QTGIDEKLVE EVLLRLYPHG AIGSFMTEYF EMSFKGRDEA TEFENVTAEL FKIVFGFDAK  60
HIGSIGLTPD VLLLSDVEGY AGIIDNKAYS KYTISNDHHN RMVHNYIRNI KNYYSGSYPL  120
AFFSYIAGGF GRNINTQIRN IAKETSVHGS AMSVSNMIKL VEFHSRTPFS HKHLRDIFSV  180
DRLILISDLE                                                        190

SEQ ID NO: 213          moltype = AA  length = 185
FEATURE                 Location/Qualifiers
REGION                  1..185
                        note = Synthetic Construct
source                  1..185
                        mol_type = protein
                        organism = synthetic construct
SEQUENCE: 213
SLGYTELQVE SALEGFPDTF SVFEAGYLNM AISGTELAKE FEIATQNIFQ QLGFISEHVG  60
NNPLHPDVFV ESSSGYSGII DNKAYRAYSI NNDHRNRMIN NYIPLYKDKH DNLEFFMYIA  120
DGFGSNIDNQ LLQISQRTQV NGCVITARNL IRLLQKHLVN PIEQSVLRDV FKCNSSITIH  180
DIDAI                                                             185

SEQ ID NO: 214          moltype = AA  length = 185
FEATURE                 Location/Qualifiers
REGION                  1..185
                        note = Synthetic Construct
source                  1..185
                        mol_type = protein
                        organism = synthetic construct
SEQUENCE: 214
STGYSNHQVE DALANFRPDT FSHFEASYLN MALSGTELAA DFEIATGGIF EELGFDSEHV  60
GNQPLHPDVF VRSPLNFSGI IDTKAYRQYT ISNDHRNRMI NNYIPTYQNG NNLEFFMYVA  120
DGFGTNIDTQ VQDIATRTNV NGSVITAQNM IRLLQRHSSN PLDHNRLRML FTQNSIIRLS  180
DINSL                                                             185

SEQ ID NO: 215          moltype = AA  length = 186
FEATURE                 Location/Qualifiers
REGION                  1..186
                        note = Synthetic Construct
source                  1..186
                        mol_type = protein
                        organism = synthetic construct
SEQUENCE: 215
LTGYTVREVE DALDGFRPDT FSQFEASYLN MAISGTELAT EFETATQAIF EQLGFRAEHV  60
GNHALHPDVF VESPLNYSGI IDTKAYVRYV INNDHRNRMV NNYIPTYQNQ HGNLEFFMYV  120
AHGFGSNIDS QVQSIADRTN VNGSVITARN VIRLLQRNYA NPIDHNTLKT LFTKNSRITM  180
ADIDSL                                                            186
```

```
SEQ ID NO: 216          moltype = AA  length = 186
FEATURE                 Location/Qualifiers
REGION                  1..186
                        note = Synthetic Construct
source                  1..186
                        mol_type = protein
                        organism = synthetic construct
SEQUENCE: 216
STGYSIREVE DALDGFRPDT FSQFEASYLN MAISGTELAT EFEIATRGIF EQLGFHAEHV  60
GNHALHPDIF VESPQNYSGI IDTKAYRTYT INNDHRNRMV NNYIPTYQNQ YGNVEFFMYV  120
ADGFGSNIAS QVQNIADRTN VNGSVITARN VIRLLQRYQA TPIDHNSLRI LFANNSVITM  180
SEIDSL                                                            186

SEQ ID NO: 217          moltype = AA  length = 189
FEATURE                 Location/Qualifiers
REGION                  1..189
                        note = Synthetic Construct
source                  1..189
                        mol_type = protein
                        organism = synthetic construct
SEQUENCE: 217
ATGYNVKEVE ESLDGFRPDT FSQFEASYLN MAISGTELAT EFEIATGEVF KQLGFCTEHV  60
GSRSLHPDLF VESPKKYSGI IDTKAYRRYT ISNDHRNRMT NNYIPNYKNI SGNLEFFMYV  120
ADGFGNNINS QLQNIADHAN TNGSVITARN VIRLLQANQA TPIDHDRLKM LFTSNSEITT  180
ADIDSCRRR                                                         189

SEQ ID NO: 218          moltype = AA  length = 191
FEATURE                 Location/Qualifiers
REGION                  1..191
                        note = Synthetic Construct
source                  1..191
                        mol_type = protein
                        organism = synthetic construct
SEQUENCE: 218
RTGINSLTVG AVLQKLYPHG AIGSFMNEYF EMAFRGREDA TDFERATQTI FQDTFGFEAT  60
HIGAAGLTPD VLVLSDSAGY QAIIDNKAYS KYSISNDHRN RMIHNYINGL ASYSKSALPL  120
AFFSYIAGGF SPSIDDQLKS IADESGVPGS AMPVSNMIKL INLHSENKFS HEQLKRIFSI  180
GRRIELKDLI H                                                      191

SEQ ID NO: 219          moltype = AA  length = 187
FEATURE                 Location/Qualifiers
REGION                  1..187
                        note = Synthetic Construct
source                  1..187
                        mol_type = protein
                        organism = synthetic construct
SEQUENCE: 219
VSGYSEKQVE HALENFHPDT YSLFEVTYLK MASSSRELDT EFEKATIDIF TQLGFSAQHV  60
GNKNLHPDGF VESPLNFSGI FDTKAYARYS ITNDHHNRMT INYIPTYQQS NPNLSFFLYV  120
AYGFKNTIDG QIQKIKRVNG VNGSAITAKD LLYLLRRHKT KAIDHADLKK LFESNKRITM  180
QEINRLP                                                           187

SEQ ID NO: 220          moltype = AA  length = 184
FEATURE                 Location/Qualifiers
REGION                  1..184
                        note = Synthetic Construct
source                  1..184
                        mol_type = protein
                        organism = synthetic construct
SEQUENCE: 220
STGITHSIIE EELANFANGA LDSFEASYFD MALKGREQCR EFEIATVELF DKAFGFDTSH  60
VGDKGKHPDI LAVSEQFSGI IDSKAYASYT ISNDHKNRMT HNYIPPYRKQ YPNLDFFMYI  120
AGGFGRNFDK QVLSVAQESN LNGCGITANN IIKLARNYKI NNWTHDNLQQ LFTLNKEIKR  180
TDFT                                                              184

SEQ ID NO: 221          moltype = AA  length = 194
FEATURE                 Location/Qualifiers
REGION                  1..194
                        note = Synthetic Construct
source                  1..194
                        mol_type = protein
                        organism = synthetic construct
SEQUENCE: 221
VTGINGKTVE NVLIETYPNG SVGAFMTRYF EMAFKGRDEA TEFEKATVEL FQDVFGYKAK  60
HVGPIGLTPD VLLLSDSDGY QAIIDNKAYH KYSISNDHYN RMVHNYIENL ANYSDSSDRL  120
AFFSYIAGGF GKNIDKQIQS VANATGVNGS AISVTNMIKM VEQHNKVPYS HKKLCEIFSV  180
NRQVLMQDLI LREE                                                   194
```

```
SEQ ID NO: 222         moltype = AA  length = 186
FEATURE                Location/Qualifiers
REGION                 1..186
                       note = Synthetic Construct
source                 1..186
                       mol_type = protein
                       organism = synthetic construct
SEQUENCE: 222
QTGIEVSIVE ETLLKLYPYG AIGSFMTEYF EMAFKGRDEA TEFEKATVEL FKSVFEFEAQ  60
HVGPIGLTPD VYILSHESRY VGIIDNKAYS KYTISNDHRN RMVHNYIKTY SAECYPLAFF  120
SYIAGGFGKN ITSQIKDIVD ETLIHGSAMS VSNMIKMVEN HQYKKYSHDE IRNIFSVDRQ  180
ILLSDL                                                            186

SEQ ID NO: 223         moltype = AA  length = 190
FEATURE                Location/Qualifiers
REGION                 1..190
                       note = Synthetic Construct
source                 1..190
                       mol_type = protein
                       organism = synthetic construct
SEQUENCE: 223
VTGIDGKTVE DVLIETYPNG SVGAFMTKYF EMAFKGRDEA TEFEKATVEL FHDVFGYKTK  60
HVGPIGLTPD VLLLSDSDGY QAILDNKAYH KYTISNDHYN RMVHNYIENL ENYSDAENRL  120
AFFSYIAGGF GKNIDKQIQS IVDATGVNGS AISVTNMIKL VEQHNKVPYS HRRLCDIFSV  180
NRQVLMQDLI                                                        190

SEQ ID NO: 224         moltype = AA  length = 190
FEATURE                Location/Qualifiers
REGION                 1..190
                       note = Synthetic Construct
source                 1..190
                       mol_type = protein
                       organism = synthetic construct
SEQUENCE: 224
RTGIDGKTVE DILIETYPNG SVGAFMTKYF EMAFKGRDEA TEFEKATVEL FQDVFGFEAK  60
HVGPIGLTPD VLLLSDESGF QAILDNKAYH KYTINNDHYN RMVHNYIGNI GNYSKSDEPL  120
AFFSYIAGGF GSNIDKQLKN IVDATDVNGS AISVSNVIKM VEQHREKPYT HQRIKDIFSV  180
NRQVLMKDIV                                                        190

SEQ ID NO: 225         moltype = AA  length = 190
FEATURE                Location/Qualifiers
REGION                 1..190
                       note = Synthetic Construct
source                 1..190
                       mol_type = protein
                       organism = synthetic construct
SEQUENCE: 225
QTGIDGKLVE EVLVEQYPTG SVGAFMTKYF EMAFKGREEA VDFEKATVEL FHDVFGFESK  60
HVGPIGLTPD VLLISDLDGY QAIIDNKAYS KYTISNDHYN RMVHNYIENL ANYSESNNNL  120
AFFSYIAGGF GSNIDGQIRN IVNTTGINGS AISVSNVIRM VDIHNSNPFN HQKIKDVFSM  180
NRQVLLKDLT                                                        190

SEQ ID NO: 226         moltype = AA  length = 190
FEATURE                Location/Qualifiers
REGION                 1..190
                       note = Synthetic Construct
source                 1..190
                       mol_type = protein
                       organism = synthetic construct
SEQUENCE: 226
RTGIDGKTVE DILIETYPHG SVGAFMTKYF EMAFKGRDEA TEFEKATVEL FQDVFGFEAK  60
HVGPIGLTPD VLLVSDSEGY QAILDNKAYH KYTINNDHHN RMVHNYIGNI HNYSKSDKPL  120
AFFSYIAGGF GSNIDKQLNN IVEATGVNGS AMSVSNMIKM VEQHECTPYS HQKIRDIFSL  180
NRQVLINDIL                                                        190

SEQ ID NO: 227         moltype = AA  length = 189
FEATURE                Location/Qualifiers
REGION                 1..189
                       note = Synthetic Construct
source                 1..189
                       mol_type = protein
                       organism = synthetic construct
SEQUENCE: 227
KTGIDGKFVE ETLLKFYPRG AIGSFMTEYF EMAFRGRDEA TEFERATTCL FKDVFNFETH  60
HVGPIGLTPD VLLISDQEGY CGIIDNKAYS KYSISNDHHN RMVHNYIEGF SRYCQSQNPL  120
AFFSYIAGGF GNNINGQIQS IVHEAGVHGC AFAVTNVIQL VEKHQVMPYS HLDLKDIFTL  180
DRQVLLSDL                                                         189

SEQ ID NO: 228         moltype = AA  length = 190
```

```
FEATURE               Location/Qualifiers
REGION                1..190
                      note = Synthetic Construct
source                1..190
                      mol_type = protein
                      organism = synthetic construct
SEQUENCE: 228
QTGIDDKTVE NILIETYPNG SIGGFMTKYF EMAFKGRDEA TEFEKATAEL FQDVFGFETK  60
HVGPIGLTPD VLLISDCAGY QAIIDNKAYH KYTINNDHYN RMVHNYIGNM NKYSSSNNAL  120
AFFSYIAGGF GSHIDSQIKS IADATGVNGS AMSVTNVIKM VEQHNKQPYS HEKIKDIFSV  180
NRQVLMNDII                                                   190

SEQ ID NO: 229        moltype = AA  length = 189
FEATURE               Location/Qualifiers
REGION                1..189
                      note = Synthetic Construct
source                1..189
                      mol_type = protein
                      organism = synthetic construct
SEQUENCE: 229
QTGFDDKLVE ETLLRLYPRG SVGAFMTEYF EMAFKGRDEA TPFEKATVEL FQDVFGFEAK  60
HVGPIGLTPD VLLVSDVEGY QAIIDNKAYS KYTISNDHHN RMVHNYIENL GRYSSSAAPL  120
AFFSYIAGGF GKNFDSQVRA IVDETGVNGS GFSVSTMIKL VECYSDKGYT HKTLRDLFSL  180
NRQVLMTDF                                                    189

SEQ ID NO: 230        moltype = AA  length = 189
FEATURE               Location/Qualifiers
REGION                1..189
                      note = Synthetic Construct
source                1..189
                      mol_type = protein
                      organism = synthetic construct
SEQUENCE: 230
ATGIDGKTVE EVLIETYPRG SIGSFMTKYF EMAFKGRDEA TEFEKATVEL FRDVFGYQTK  60
HVGPMGLTPD VLLVSPECSY QAIIDNKAYS NYSINNDHRN RMVHNYLTNI SRYSDREYPM  120
AFFTYIAGGF GTAIDKQIES IYEESGVRGS AVSVTNIIKM VEKHQESAYT HQDLRNLFGV  180
NRQILMRDL                                                    189

SEQ ID NO: 231        moltype = AA  length = 190
FEATURE               Location/Qualifiers
REGION                1..190
                      note = Synthetic Construct
source                1..190
                      mol_type = protein
                      organism = synthetic construct
SEQUENCE: 231
VTGIDGKTVE NVLVETYPNG SVGAFMTKYF EMAFKGRDEA TEFEKATVEL FQDVFGFEAR  60
HVGSIGLTPD VLVLSDEDGY QAILDNKAYH KYTISNDHFN RMVHNYIGNI SSYGDGDKSL  120
AFFSYIAGGF GTNIDKQLKN IVDATGVSGS AVSVSNMIKL VEQHNQTPYS HKRIKEIFSV  180
NRQVLLSDLA                                                   190

SEQ ID NO: 232        moltype = AA  length = 187
FEATURE               Location/Qualifiers
REGION                1..187
                      note = Synthetic Construct
source                1..187
                      mol_type = protein
                      organism = synthetic construct
SEQUENCE: 232
QTGIEAKIVE DTLQKNYSRG AIGSFMVEYF EMAFKGRDEA TEFELATAEL FKSAFGLTTE  60
HIGSKSLMPD VLVLSDQFKY IGIIDNKAYS SYSITNDHKN RMMYNYIPAY KKEQKYPLAF  120
FSYIAGGFGT NIDSQIKEIV DSTNINGSAI SVSNVINLVT NYQSKGYNHT KIKNIFSIDR  180
QVLISDL                                                      187

SEQ ID NO: 233        moltype = AA  length = 187
FEATURE               Location/Qualifiers
REGION                1..187
                      note = Synthetic Construct
source                1..187
                      mol_type = protein
                      organism = synthetic construct
SEQUENCE: 233
QTGIDARFVE ETLLKYYPHG AIGSFMTEYF EMAFRGRDDA TEFELATVEL FKSAFGFETE  60
HVGPIGLTPD VLILSNQDNY IGIIDNKAYS KYTISNDHKN RMIHNYIKTY KQEQKYPLAF  120
FSYIAGGFGK NINSQIKEIV DESKINGSAI SVTNLIKLVE YYGTKNYDHG KIRDIFSVNR  180
QVLMSDL                                                      187

SEQ ID NO: 234        moltype = AA  length = 191
FEATURE               Location/Qualifiers
```

```
REGION                 1..191
                       note = Synthetic Construct
source                 1..191
                       mol_type = protein
                       organism = synthetic construct
SEQUENCE: 234
RTGIDPRVVE EILIEKYPHG SPSAFMSEYF SMAFKGREEA ADFEKATVEL FQNVFGYEAS  60
HVGPIGRSPD VLLESKSAHY QAILDNKAYS RYTVSNDHHN RMVDNYIRDK AHYSTSPYPL  120
AFFSYIAGGF GSNIDPQIQS IVHDGGVNGS CITVSNVIQM VENSETKPYT HEKLRQIFGL  180
NRQVLISDLQ Q                                                       191

SEQ ID NO: 235         moltype = AA  length = 189
FEATURE                Location/Qualifiers
REGION                 1..189
                       note = Synthetic Construct
source                 1..189
                       mol_type = protein
                       organism = synthetic construct
SEQUENCE: 235
KTGCNAKVVE EKLCKLYPNG AVGSFMTEYF NMAFKGTEQA ADFEKATVEL FRDVFGYETE  60
HVGSIGLTPD VLLVSDSDGY QAIFDNKAYS SYSISNDHRN RMIHNYIENL GKYSKHSHPL  120
AFFSYIAGGF GNKIDSQIQS VVQETGISGS AISVSNVISL VEKHQSNPYS HKQLKDLFSL  180
ERQILLSDL                                                          189

SEQ ID NO: 236         moltype = AA  length = 189
FEATURE                Location/Qualifiers
REGION                 1..189
                       note = Synthetic Construct
source                 1..189
                       mol_type = protein
                       organism = synthetic construct
SEQUENCE: 236
QTGIDGRLVE ENLQRLYPHG AIGAFMTQYF DMATKGRDEA TEFEKATVTI FNEVFGFNSK  60
HVGPIGLTPD VLLLSDSDKY SAIIDNKAYS RYSISNDHHN RMIHNYIEGF KNYCDSPYPL  120
AFFSYIAGGF GSNIDAQLMK IVNETGVNGS AVTVSSVIQM VEKQQAEPYS HAKIRELFSL  180
NRQLVLSDL                                                          189

SEQ ID NO: 237         moltype = AA  length = 189
FEATURE                Location/Qualifiers
REGION                 1..189
                       note = Synthetic Construct
source                 1..189
                       mol_type = protein
                       organism = synthetic construct
SEQUENCE: 237
KTGFLPDLVE DCLQELYPQG AIGAFLSEYF EMAFKGREQA TDFELATVDL FQNVFGFTAR  60
HVGPKGLTPD VLLLSDDEGY SAILDNKAYS KYSITNDHHN RMVYNYIGQL NNYYNGTYPL  120
SFFSYIAGGF GSNINIQLNR VVNETGINGS AINISTMINL VYEHTSNPYT QQRIRDIFSL  180
NRRVLQADL                                                          189

SEQ ID NO: 238         moltype = AA  length = 186
FEATURE                Location/Qualifiers
REGION                 1..186
                       note = Synthetic Construct
source                 1..186
                       mol_type = protein
                       organism = synthetic construct
SEQUENCE: 238
VSGFEYRVVE QILLRKYPHG AIGSFMSNYF EMAFRGRDEA IEFETATVEI FENVFGMKAN  60
HVGPIGLTPD ILVISDDAGY LGIIDNKAYS RYSITNDHKN RMIYNYIPSY QRDEYPLAFF  120
TYIAGGFGNN INRQLNDISS ATNVHGSAIN VSNMIQLVQN FSEYSYDHFT LKDIFSLDRQ  180
ITQSDI                                                             186

SEQ ID NO: 239         moltype = AA  length = 192
FEATURE                Location/Qualifiers
REGION                 1..192
                       note = Synthetic Construct
source                 1..192
                       mol_type = protein
                       organism = synthetic construct
SEQUENCE: 239
DTGIAGNTVE EVLQKNYPHG AIGSFMTEYF EMAFKGRDEA TEFEVATRTI FEETFGFKAR  60
HVGPIGLTPD VLLLSDNAGY QAIIDNKAYS KYSISNDHRN RMVHNYINGL ANYSQSSLPL  120
AFFSYIAGGF SPSIDAQLKS ITEETGIKGS AMPVSNMIRL INQHSETPFT HEQLRGIFSL  180
NRKIELKDLI HS                                                      192

SEQ ID NO: 240         moltype = AA  length = 181
FEATURE                Location/Qualifiers
REGION                 1..181
```

```
                        note = Synthetic Construct
source                  1..181
                        mol_type = protein
                        organism = synthetic construct
SEQUENCE: 240
EQILSKKYPY GFGDLFLQKY IELSRGGRKR ATEFEKATSS IFADMFGVCA EHIGQKGSVP  60
DIVVGSRDGK WAGILDTKAY NKKYSISNDH KNRMIGYIER YSEYGFEFAN LSFFAYVVSD  120
YGKNINSQIR YISNKSGVLG SAVTARDIIR MVERHQKKPY THDEIREIFS VNRAITLKDI  180
D                                                                  181

SEQ ID NO: 241          moltype = AA  length = 189
FEATURE                 Location/Qualifiers
REGION                  1..189
                        note = Synthetic Construct
source                  1..189
                        mol_type = protein
                        organism = synthetic construct
SEQUENCE: 241
LTGIDSKLVE DTLLRWYPHG AIGSFMTEYQ EMAFKGREDA TDFEKATVAI FRDSFGFAAE  60
HVGPIGLTPD VLLLSDAAGY QAIIDNKAYS RYSISNDHRN RMVHNYICQL SSYSKSAHPL  120
AFFSYIAGGF GNNISTQIKS IADETGIAGS AVSVFNIIKL AEENQRNPYS HESIRDIFSK  180
NRLIELKDL                                                          189

SEQ ID NO: 242          moltype = AA  length = 190
FEATURE                 Location/Qualifiers
REGION                  1..190
                        note = Synthetic Construct
source                  1..190
                        mol_type = protein
                        organism = synthetic construct
SEQUENCE: 242
STGLKESFVW EILQKRFPRG SIGAFMTQYY EMAFKGREEA TEFEKATAEL FHDVFKFKTK  60
HVGPIGLTPD VLIESEDVGF VGIIDNKAYS KYSISNDHHN RMVHNYINGL GNYYKGKKNL  120
AFFSYIAGGF GINIDSQIKS IVDETEICGS CINVHNMIEL VKRNEKRAYS HEDLKKIFSV  180
NREILLSDLC                                                         190

SEQ ID NO: 243          moltype = AA  length = 194
FEATURE                 Location/Qualifiers
REGION                  1..194
                        note = Synthetic Construct
source                  1..194
                        mol_type = protein
                        organism = synthetic construct
SEQUENCE: 243
ITGADGKLVE NTLLETYPNG AISGFMTEYF EMAFKGTEEA VNFEIATTEL FKEVFGFETK  60
HLGQTGSKSA PDVLLVSNNE GYQAIIDNKA YSKYSISGDH HNRMVHNYIE NISKYSEYSH  120
PIGFFTYIAG GFGNQIDRQI QSIVAECGVH GSGMTVSNMI KLVEKQNETP LSHRDIKNIF  180
SVDRQIVLSD IEVI                                                    194

SEQ ID NO: 244          moltype = AA  length = 189
FEATURE                 Location/Qualifiers
REGION                  1..189
                        note = Synthetic Construct
source                  1..189
                        mol_type = protein
                        organism = synthetic construct
SEQUENCE: 244
QTGFEDKLVE ETLLKLYPRG SVGAFMTEYF EMAFKGRDEA TDFEKATVEL FQSVFGFQAK  60
HVGPIGLTPD VLILSDAEGY QAILDNKAYS KYTISNDHHN RMVHNYIKNL KRYSNADVSL  120
AFFSYIAGGF GNNINSQIND IVNVTGVAGS GISVSNMIKL VELYEPKNYT HKNIRDIFSV  180
NRQILLSDL                                                          189

SEQ ID NO: 245          moltype = AA  length = 191
FEATURE                 Location/Qualifiers
REGION                  1..191
                        note = Synthetic Construct
source                  1..191
                        mol_type = protein
                        organism = synthetic construct
SEQUENCE: 245
VTGVDGKLVE NVLVETYPKG ALGGFMTEYF EMAFKGTEEA IEFEKATTNL FQDVFGFNAI  60
HLGQTGSKSA PDILLLSDSE GYQAIIDNKA YHKYSISGDH RNRMIHNYIE SISNYSSFTQ  120
PIGFFSYVAG GFGNQIDKQI QDIADATGVH GSGITVSNMI ELVKQQDIKP MNHAQIRTLF  180
GVDRQIRIAD F                                                       191

SEQ ID NO: 246          moltype = AA  length = 190
FEATURE                 Location/Qualifiers
REGION                  1..190
                        note = Synthetic Construct
```

```
source                  1..190
                        mol_type = protein
                        organism = synthetic construct
SEQUENCE: 246
KSGVPFGNTE QILSKKYPYG FGDLFLQKYI ELSRGGRKRA TEFEKATSSI FADMFGVCAE  60
HIGQKGSVPD IVVGSRDGKW AGILDTKAYN KKYSISNDHK NRMIGYIERY SEYGFEFANL  120
SFFAYVVSDY GKNINSQIRY ISNKSGVLGS AVTARDIIRM VERHQKKPYT HDEIREIFSV  180
NRAITLKDID                                                        190

SEQ ID NO: 247          moltype = AA  length = 190
FEATURE                 Location/Qualifiers
REGION                  1..190
                        note = Synthetic Construct
source                  1..190
                        mol_type = protein
                        organism = synthetic construct
SEQUENCE: 247
TTGIDERFVE ETLLKFYPKG SIGAFMTEYF EMAFKGRDEA TEFEKATVNI FQDVFGFSAK  60
HVGPIGLTPD VLVLSDVDGY SAIIDNKAYS KYTINNDHHN RMVHNYIGNL SNYYDGTYSL  120
AFFSYIAGGF GTNINKQLQS ITNETGIKGS AMNVSNMIEL IKRYDTCNYN HSTIREIFSV  180
GRQILHSDFK                                                        190

SEQ ID NO: 248          moltype = AA  length = 189
FEATURE                 Location/Qualifiers
REGION                  1..189
                        note = Synthetic Construct
source                  1..189
                        mol_type = protein
                        organism = synthetic construct
SEQUENCE: 248
KTGLAFSQVE ELLLKLYPHG AVGAFMNEYF EMAFKGRDEA TDFEKATVEL FRDVFGFDAK  60
HVGPIGLTPD VLLLSDSAGY CGIIDNKAYS KYTISNDHHN RMVHNYIGGF SNYCDSENEL  120
AFFSYIAGGF GSNIDKQLLK IIDETGVHGS AVTVSNIIKM VENQQKQPYS HIQIRDIFSL  180
DRQIALSDI                                                         189

SEQ ID NO: 249          moltype = AA  length = 193
FEATURE                 Location/Qualifiers
REGION                  1..193
                        note = Synthetic Construct
source                  1..193
                        mol_type = protein
                        organism = synthetic construct
SEQUENCE: 249
KSGINEKIVE EILLKFYPRG SVGAFMTEYF EMAFRGRDNA TDFEKSTVQI FSDLFNYETI  60
HVGSIGLTPD ILILSDEDGY QAILDNKAYH SYSISNDHHN RMVHNYIAGL NKYSNSRLPL  120
AFFSYISGGF GANINSQINK IYNETNIKGS AMTVSNMIYL IENYSEKSKS HRSLRKIFSV  180
NRQILKSDID IGL                                                    193

SEQ ID NO: 250          moltype = AA  length = 190
FEATURE                 Location/Qualifiers
REGION                  1..190
                        note = Synthetic Construct
source                  1..190
                        mol_type = protein
                        organism = synthetic construct
SEQUENCE: 250
KSGVPFKDTE RILSGKYPHG FKDRFLQEYI ELSRSGRDKA TEFEKATSSI FADVFGLRAE  60
HIGQKGIVPD IVVASRGEKW AGILDTKSYK KKYSISNDHK NRMLEYIERY SEYGLEFANL  120
SFFAYVVSDY GKNINSQLEN ISNRSGLLGS VITARYLARM VERHQKNPYS HEEIRKIFSV  180
NRAITLKDID                                                        190

SEQ ID NO: 251          moltype = AA  length = 189
FEATURE                 Location/Qualifiers
REGION                  1..189
                        note = Synthetic Construct
source                  1..189
                        mol_type = protein
                        organism = synthetic construct
SEQUENCE: 251
QTGFNDKLVE EVLLKLYPSG SIGGFMTAYF EMAFKGRDKA TDFEKATVEL FKNVFGFETK  60
HVGPIGLTPD VLILSNSDGY QAIIDNKAYS KYTVSNDHRN RMIYNYIKNL KNYSNFSVPL  120
SFFSYIAGGF GNNINSQIMD IVNATNIAGS AMSVSNMIKL VELYESKNYT HKNIKDIFSV  180
NRQILLSDL                                                         189

SEQ ID NO: 252          moltype = AA  length = 189
FEATURE                 Location/Qualifiers
REGION                  1..189
                        note = Synthetic Construct
source                  1..189
```

```
                        mol_type = protein
                        organism = synthetic construct
SEQUENCE: 252
QTGFGDKLVE ETLLKLYPRG SIGAFMTEYF EMAFKGRDEA IDFEKATVEL FQNVFGFESK  60
HVGPIGLTPD VLILSDEDGY QAIIDNKAYS KYTISNDHHN RMVHNYIKNL ERYSNSDVPL  120
AFFSYVAGGF GKNINTQIND IVNVTGVSGS AMSVSNMIKL VELYESKNYT HKSIREIFSV  180
NRQILLSDL                                                         189

SEQ ID NO: 253          moltype = AA  length = 189
FEATURE                 Location/Qualifiers
REGION                  1..189
                        note = Synthetic Construct
source                  1..189
                        mol_type = protein
                        organism = synthetic construct
SEQUENCE: 253
KTGFEDKLIE ETLLKLYPRG SVGAFMTEYF EMAFKGRDEA SDFEKATVEL FQNVFGFEAK  60
HVGPIGLTPD VLILSDTDGY QAIIDNKAYS KYTISNDHHN RMVHNYIKDL NRYSSYTVPL  120
AFFSYIAGGF GKNINSQVMD IVNVTKVSGS AISVSNMIKL VELYEQKNYT NKKIRDVFSV  180
NRQILLSDL                                                         189

SEQ ID NO: 254          moltype = AA  length = 191
FEATURE                 Location/Qualifiers
REGION                  1..191
                        note = Synthetic Construct
source                  1..191
                        mol_type = protein
                        organism = synthetic construct
SEQUENCE: 254
VTGVDGKLVE NILVETYPKG ALGGFMTEYF EMAFKGTEEA VEFEKATTNL FQDVFGFNAI  60
HLGQTGSKSA PDILLLSDSE GYQAIIDNKA YSKYSITGDH KNRMIHNYIE HISNFSSFTQ  120
PIGFFSYVAG GFGNQIDKQI QDITSETGIH GSGITVSNMI ELVKQQDIKP MNHAQIRTLF  180
GVDRQIRMAD F                                                      191

SEQ ID NO: 255          moltype = AA  length = 191
FEATURE                 Location/Qualifiers
REGION                  1..191
                        note = Synthetic Construct
source                  1..191
                        mol_type = protein
                        organism = synthetic construct
SEQUENCE: 255
ITGTDRKLVE ETLLSSYPHG LVGGFLANYY EMAFKGTEEA VEFEKATTEI FNSVFGYKAI  60
HLGQTGSKSA PDILLLSDDE GYQAIIDNKA YSKYSITGDH HNRMVHNYIG KIGNYSESHY  120
PLAFFSYIAG GFISTIDKQI ASEVYESNVH GSGITVGTFI KMVEKHNATP YSHKELRNIF  180
SVDREVKLAD I                                                      191

SEQ ID NO: 256          moltype = AA  length = 190
FEATURE                 Location/Qualifiers
REGION                  1..190
                        note = Synthetic Construct
source                  1..190
                        mol_type = protein
                        organism = synthetic construct
SEQUENCE: 256
ETGVSAVETE RILSAKYPNG LVDSFLSEYV QMAFESRDRA TEFEKATTSI FADIFGLYAE  60
HIGQKGIVPD VVVASREEGW SGILDSKAYA KGYSIGHDHR NRMVEYIERY PKYGPEFATL  120
AFFSYVVSDY KNSVTPQIRT ISEKSGVPGS VITARDIVRM VERHQKKPYT HSEIREIFSL  180
NRAITFEDIE                                                        190

SEQ ID NO: 257          moltype = AA  length = 189
FEATURE                 Location/Qualifiers
REGION                  1..189
                        note = Synthetic Construct
source                  1..189
                        mol_type = protein
                        organism = synthetic construct
SEQUENCE: 257
QTGLDGKIVE ETLLKLYPKG SVGAFMTEYF EMAFKGRDEA TGFEKATVEL FKNVFGYEAK  60
HVGAIGLTPD VLILSDTDGY QAIIDNKAYS KYTISNDHHN RMVHNYIKGL NLYSTSSAPL  120
AFFSYIAGGF GKNINSQIKG IVSETTIHGS AMSVSNMIRL VENYTDKGYK HSKIKEIFSL  180
DRQILMSDI                                                         189

SEQ ID NO: 258          moltype = AA  length = 187
FEATURE                 Location/Qualifiers
REGION                  1..187
                        note = Synthetic Construct
source                  1..187
                        mol_type = protein
```

```
                         organism = synthetic construct
SEQUENCE: 258
NEVTVEKYLQ KNYPNGSIGA FMTSYFEMAF KGKDEAIDFE KATTEIFTSV FKYKAQHLGQ  60
TGSTSAPDIL LISDEDGYQS IIDNKAYSEY SINGDHHNRM VHNYIRNIKN YSSCEYPIGY  120
FSYIAGGFIK SIDKQIQAVA SESGVNGSGI TVGNFIKLIE RNQIKPFSHK ELRKIFGLNK  180
QILLEDI                                                            187

SEQ ID NO: 259           moltype = AA  length = 194
FEATURE                  Location/Qualifiers
REGION                   1..194
                         note = Synthetic Construct
source                   1..194
                         mol_type = protein
                         organism = synthetic construct
SEQUENCE: 259
RTGIDDRTVE SYLIQNHRHG SLSEFFMAYR ELAHSGRAGA TDFELATCEI FQRLFHMRAK  60
HVGPDGNTPD VFIESSECGY CGIIDNKAYH DKYSITAGHK RAMLVDYIPK YRGYGETDLP  120
LAFYTYIAGS FGTNINNQLA AITKETGING SAMPVDILID FAQDYAERGC DHEYIKNLFS  180
VNREIRLQDI ATTK                                                    194

SEQ ID NO: 260           moltype = AA  length = 196
FEATURE                  Location/Qualifiers
REGION                   1..196
                         note = Synthetic Construct
source                   1..196
                         mol_type = protein
                         organism = synthetic construct
SEQUENCE: 260
QLVKSELEEK KSELRHKLKY VPHEYIELIE IARNSTQDRI LEMKVMEFFM KVYGYRGKHL  60
GGSRKPDGAI YTVGSPIDYG VIVDTKAYSG GYNLPIGQAD EMQRYVEENQ TRNKHINPNE  120
WWKVYPSSVT EFKFLFVSGH FKGNYKAQLT RLNHITNCNG AVLSVEELLI GGEMIKAGTL  180
TLEEVRRKFN NGEINF                                                  196

SEQ ID NO: 261           moltype = AA  length = 200
FEATURE                  Location/Qualifiers
REGION                   1..200
                         note = Synthetic Construct
source                   1..200
                         mol_type = protein
                         organism = synthetic construct
SEQUENCE: 261
GEGIKSNISL LKDELRGQIS HISHEYLSLI DLAFDSKQNR LFEMKVLELL VNEYGFKGRH  60
LGGSRKPDGI VYSTTLEDNF GIIVDTKAYS EGYSLPISQA DEMERYVREN SNRDEEVNPN  120
KWWENFSEEV KKYYFVFISG SFKGKFEEQL RRLSMTTGVN GSAVNVVNLL LGAEKIRSGE  180
MTIEELERAM FNNSEFILKY                                              200

SEQ ID NO: 262           moltype = DNA  length = 21
FEATURE                  Location/Qualifiers
misc_feature             1..21
                         note = Synthetic Construct
source                   1..21
                         mol_type = other DNA
                         organism = synthetic construct
SEQUENCE: 262
gacagccacc tgctgggatc t                                            21

SEQ ID NO: 263           moltype = DNA  length = 128
FEATURE                  Location/Qualifiers
misc_feature             1..128
                         note = Synthetic Construct
source                   1..128
                         mol_type = other DNA
                         organism = synthetic construct
SEQUENCE: 263
ggatccccta agaaaaagcg gaaggtgtga aagcttctcg agtctagagg gcccgtttaa  60
acccgctgat cagcctcgac tgtgccttct agttgccagc catctgttgt ttgcccctcc  120
cccgtgcc                                                           128

SEQ ID NO: 264           moltype = DNA  length = 18
FEATURE                  Location/Qualifiers
misc_feature             1..18
                         note = Synthetic Construct
source                   1..18
                         mol_type = other DNA
                         organism = synthetic construct
SEQUENCE: 264
acccccctcc tcaccaca                                                18

SEQ ID NO: 265           moltype = DNA  length = 18
```

-continued

```
FEATURE                Location/Qualifiers
misc_feature           1..18
                       note = Synthetic Construct
source                 1..18
                       mol_type = other DNA
                       organism = synthetic construct
SEQUENCE: 265
ataaggccag tagccagc                                              18

SEQ ID NO: 266         moltype = DNA  length = 106
FEATURE                Location/Qualifiers
misc_feature           1..106
                       note = Synthetic Construct
source                 1..106
                       mol_type = other DNA
                       organism = synthetic construct
SEQUENCE: 266
ctggctaact agagaaccca ctgcttactg gcttatcgaa attaatacga ctcactatag  60
ggagtcccaa gctggctagc gtttaaactt ctgcggccgc gccacc               106

SEQ ID NO: 267         moltype = DNA  length = 51
FEATURE                Location/Qualifiers
misc_feature           1..51
                       note = Synthetic Construct
source                 1..51
                       mol_type = other DNA
                       organism = synthetic construct
SEQUENCE: 267
atgggaaaac ctattcctaa tcctctgctg ggcctggatt ctaccggagg c           51

SEQ ID NO: 268         moltype = DNA  length = 408
FEATURE                Location/Qualifiers
misc_feature           1..408
                       note = Synthetic Construct
source                 1..408
                       mol_type = other DNA
                       organism = synthetic construct
SEQUENCE: 268
gtggacctga gaacactggg atattctcag cagcagcagg agaagatcaa gcccaaggtg  60
agatctacag tggcccagca ccacgaagcc ctggtgggac acggatttac acacgcccac  120
attgtggccc tgtctcagca ccctgccgcc ctgggaacag tggccgtgaa atatcaggat  180
atgattgccg ccctgcctga ggccacacac gaagccattg tgggagtggg aaaacgaggc  240
gctggagcca gagccctgga agccctgctg acagtggccg gagaactgag aggacctcct  300
ctgcagctgg atacaggaca gctgctgaag attgccaaaa ggggcggagt gaccgcggtg  360
gaagccgtgc acgcctggag aaatgccctg acaggagccc ctctgaac               408

SEQ ID NO: 269         moltype = DNA  length = 1794
FEATURE                Location/Qualifiers
misc_feature           1..1794
                       note = Synthetic Construct
source                 1..1794
                       mol_type = other DNA
                       organism = synthetic construct
SEQUENCE: 269
ctgacccccg aacaggtggt ggccattgcc agcaacatcg gcggcaagca ggccctggaa  60
accgtgcaga gactgctgcc cgtgctgtgc caggcccatg gcctgacacc tgaacaggtg  120
gtggctatcg cctctcacga cggaggaaaa caggctctgg aaacagtgca gcggctgctg  180
cctgtgctgt gtcaggctca cggcttgact ccagaacagg tggtggctat tgcttcccac  240
gacgggggga aacaggccct ggaaactgtg cagcgcctgc tgccagtgct gtgccaggct  300
cacggactga cccccgaaca ggtggtggcc attgccagcc acgacggcgg caagcaggcc  360
ctggaaaccg tgcagagact gctgcccgtg ctgtgccagg cccatggcct gacacctgaa  420
caggtggtgg ctatcgcctc tcacgacgga ggaaaacagg ctctggaaac agtgcagcgg  480
ctgctgcctg tgctgtgtca ggctcacggc ttgactccag aacaggtggt ggctattgct  540
tcccacgacg gggggaaaca ggccctggaa actgtgcagc gcctgctgcc agtgctgtgc  600
caggctcacg ggctgacccc cgaacaggtg gtggccattg ccagccacga cggcggcaag  660
caggccctgg aaaccgtgca gagactgctg cccgtgctgt gccaggccca tggcctgaca  720
cctgaacagg tggtggctat cgcctctaac ggcggaggaa aacaggctct ggaaacagtg  780
cagcggctgc tgcctgtgct gtgtcaggct cacggcttga ctccagaaca ggtggtggct  840
attgcttccc acgacggggg gaaacaggcc ctggaaactg tgcagcgcct gctgccagtg  900
ctgtgccagg ctcacggcct cactcccgaa caggtggtgg ccattgccag ccacgacggc  960
ggcaagcagg ccctggaaac cgtgcagaga ctgctgcccg tgctgtgcca ggcccatggc  1020
ctgacacctg aacaggtggt ggctatcgcc tctaacggcg gaggaaaaca ggctctggaa  1080
acagtgcagc ggctgctgcc tgtgctgtgt caggctcacg gcttgactcc agaacaggtg  1140
gtggctattg cttcccacga cgggggggaaa caggccctgg aaactgtgca gcgcctgctg  1200
ccagtgctgt gccaggctca cggactgacc cccgaacagg tggtggccat tgccagcaac  1260
atcggcggca agcaggccct ggaaaccgtg cagagactgc tgcccgtgct gtgccaggcc  1320
catggcctga cacctgaaca ggtggtggct atcgcctctc acgacggagg aaaacaagca  1380
ctcgagacag tgcagcggct gctgcctgtg ctgtgtcagg ctcacggctt gactccagaa  1440
caggtggtgg ctattgcttc ccacgacggg gggaaacagg ccctggaaac tgtgcagcgc  1500
```

-continued

```
ctgctgccag tgctgtgcca ggctcacggc ctgacccccg aacaggtggt ggccattgcc  1560
agcaacatcg gcggcaagca ggccctggaa accgtgcaga gactgctgcc cgtgctgtgc  1620
caggcccatg gcctgacacc tgaacaggtg gtggctatcg cctctcacga cggaggaaaa  1680
caggctctgg aaacagtgca gcggctgctg cctgtgctgt gtcaggctca cggcttgact  1740
ccacagcagg tcgtggcaat tgctagcaat atcggcggac ggcccgccct ggag        1794

SEQ ID NO: 270         moltype = DNA  length = 150
FEATURE                Location/Qualifiers
misc_feature           1..150
                       note = Synthetic Construct
source                 1..150
                       mol_type = other DNA
                       organism = synthetic construct
SEQUENCE: 270
agcattgtgg cccagctgtc tagacctgat cctgccctgg ccgccctgac aaatgatcac  60
ctggtggccc tggcctgtct gggaggcaga cctgccctgg atgccgtgaa aaaaggactg  120
cctcacgccc ctgccctgat caagagaaca                                   150

SEQ ID NO: 271         moltype = DNA  length = 29
FEATURE                Location/Qualifiers
misc_feature           1..29
                       note = Synthetic Construct
source                 1..29
                       mol_type = other DNA
                       organism = synthetic construct
SEQUENCE: 271
ggatccccta agaaaaagcg gaaggtggg                                    29

SEQ ID NO: 272         moltype = DNA  length = 21
FEATURE                Location/Qualifiers
misc_feature           1..21
                       note = Synthetic Construct
source                 1..21
                       mol_type = other DNA
                       organism = synthetic construct
SEQUENCE: 272
atctgtgagc aggtgcagga g                                            21

SEQ ID NO: 273         moltype = DNA  length = 106
FEATURE                Location/Qualifiers
misc_feature           1..106
                       note = Synthetic Construct
source                 1..106
                       mol_type = other DNA
                       organism = synthetic construct
SEQUENCE: 273
ctggctaact agagaaccca ctgcttactg gcttatcgaa attaatacga ctcactatag  60
ggagtcccaa gctggctagc gtttaaactt ctgcggccgc gccacc                 106

SEQ ID NO: 274         moltype = DNA  length = 51
FEATURE                Location/Qualifiers
misc_feature           1..51
                       note = Synthetic Construct
source                 1..51
                       mol_type = other DNA
                       organism = synthetic construct
SEQUENCE: 274
atgggaaaac ctattcctaa tcctctgctg ggcctggatt ctaccggagg c           51

SEQ ID NO: 275         moltype = DNA  length = 408
FEATURE                Location/Qualifiers
misc_feature           1..408
                       note = Synthetic Construct
source                 1..408
                       mol_type = other DNA
                       organism = synthetic construct
SEQUENCE: 275
gtggacctga gaacactggg atattctcag cagcagcagg agaagatcaa gcccaaggtg  60
agatctacag tggcccagca ccacgaagcc ctggtgggac acggatttac acacgcccac  120
attgtggccc tgtctcagca ccctgccgcc ctgggaacag tggccgtgaa atatcaggat  180
atgattgccg ccctgcctga ggccacacac gaagccattg tgggagtggg aaaacgaggc  240
gctggagcca gagccctgga agccctgctg acagtggccg gagaactgag aggacctcct  300
ctgcagctgg atacaggaca gctgctgaag attgccaaaa ggggcggagt gaccgcggtg  360
gaagccgtgc acgcctggag aaatgccctg acaggagccc ctctgaac                408

SEQ ID NO: 276         moltype = DNA  length = 1794
FEATURE                Location/Qualifiers
misc_feature           1..1794
                       note = Synthetic Construct
```

```
source                  1..1794
                        mol_type = other DNA
                        organism = synthetic construct
SEQUENCE: 276
ctgacccccg aacaggtggt ggccattgcc agcaacatcg gcggcaagca ggccctggaa  60
accgtgcaga gactgctgcc cgtgctgtgc caggcccatg gcctgacacc tgaacaggtg  120
gtggctatcg cctctaacgg cggaggaaaa caggctctgg aaacagtgca gcggctgctg  180
cctgtgctgt gtcaggctca cggcttgact ccagaacagg tggtggctat tgcttccaat  240
attgggggga aacaggccct ggaaactgtg cagcgcctgc tgccagtgct gtgccaggct  300
cacggactga cccccgaaca ggtggtggcc attgccagca acatcggcgg caagcaggcc  360
ctggaaaccg tgcagagact gctgcccgtg ctgtgccagg cccatggcct gacacctgaa  420
caggtggtgg ctatcgcctc taacaacgga ggaaaacagg ctctggaaac agtgcagcgg  480
ctgctgcctg tgctgtgtca ggctcacggc ttgactccag aacaggtggt ggctattgct  540
tccaacaacg gggggaaaca ggccctggaa actgtgcagc gcctgctgcc agtgctgtgc  600
caggctcacg ggctgacccc cgaacaggtg gtggccattg ccagccacga cggcggcaag  660
caggccctgg aaaccgtgca gagactgctg cccgtgctgt gccaggccca tggcctgaca  720
cctgaacagg tggtggctat cgcctctcac gacggaggaa aacaggctct ggaaacagtg  780
cagcggctgc tgcctgtgct gtgtcaggct cacggcttga ctccagaaca ggtggtggct  840
attgcttcca atattggggg gaaacaggcc ctggaaactg tgcagcgcct gctgccagtg  900
ctgtgccagg ctcacggcct cactcccgaa caggtggtgg ccattgccag caacaacggc  960
ggcaagcagg ccctggaaac cgtgcagaga ctgctgcccg tgctgtgcca ggcccatggc  1020
ctgacacctg aacaggtggt ggctatcgcc tctaacggcg gaggaaaaca ggctctggaa  1080
acagtgcagc ggctgctgcc tgtgctgtgt caggctcacg gcttgactcc agaacaggtg  1140
gtggctattg cttccaatat tgggggggaaa caggccctgg aaactgtgca gcgcctgctg  1200
ccagtgctgt gccaggctca cggactgacc cccgaacagg tggtggccat tgccagcaac  1260
aacggcggca agcaggccct ggaaaccgtg cagagactgc tgcccgtgct gtgccaggcc  1320
catggcctga cacctgaaca ggtggtggct atcgcctctc acgacggagg aaaacaagca  1380
ctcgagacag tgcagcggct gctgcctgtg ctgtgtcagg ctcacggctt gactccagaa  1440
caggtggtgg ctattgcttc ccacgacggg gggaaacagg ccctggaaac tgtgcagcgc  1500
ctgctgccag tgctgtgcca ggctcacggc ctgacccccg aacaggtggt ggccattgcc  1560
agcaacatcg gcggcaagca ggccctggaa accgtgcaga gactgctgcc cgtgctgtgc  1620
caggcccatg gcctgacacc tgaacaggtg gtggctatcg cctctaacaa cggaggaaaa  1680
caggctctgg aaacagtgca gcggctgctg cctgtgctgt gtcaggctca cggcttgact  1740
ccacagcagg tcgtggcaat tgctagccac gacggcggac ggcccgccct ggag  1794

SEQ ID NO: 277          moltype = DNA  length = 150
FEATURE                 Location/Qualifiers
misc_feature            1..150
                        note = Synthetic Construct
source                  1..150
                        mol_type = other DNA
                        organism = synthetic construct
SEQUENCE: 277
agcattgtgg cccagctgtc tagacctgat cctgccctgg ccgccctgac aaatgatcac  60
ctggtggccc tggcctgtct gggaggcaga cctgccctgg atgccgtgaa aaaaggactg  120
cctcacgccc ctgccctgat caagagaaca  150

SEQ ID NO: 278          moltype = DNA  length = 29
FEATURE                 Location/Qualifiers
misc_feature            1..29
                        note = Synthetic Construct
source                  1..29
                        mol_type = other DNA
                        organism = synthetic construct
SEQUENCE: 278
ggatccccta agaaaaagcg gaaggtggg  29

SEQ ID NO: 279          moltype = DNA  length = 21
FEATURE                 Location/Qualifiers
misc_feature            1..21
                        note = Synthetic Construct
source                  1..21
                        mol_type = other DNA
                        organism = synthetic construct
SEQUENCE: 279
atctgtgagc aggtgcagga g  21

SEQ ID NO: 280          moltype = DNA  length = 18
FEATURE                 Location/Qualifiers
misc_feature            1..18
                        note = Synthetic Construct
source                  1..18
                        mol_type = other DNA
                        organism = synthetic construct
SEQUENCE: 280
acccccctcc tcaccaca  18

SEQ ID NO: 281          moltype = DNA  length = 18
FEATURE                 Location/Qualifiers
```

-continued

```
misc_feature          1..18
                      note = Synthetic Construct
source                1..18
                      mol_type = other DNA
                      organism = synthetic construct
SEQUENCE: 281
ataaggccag tagccagc                                              18

SEQ ID NO: 282        moltype = AA  length = 186
FEATURE               Location/Qualifiers
REGION                1..186
                      note = Synthetic Construct
source                1..186
                      mol_type = protein
                      organism = synthetic construct
SEQUENCE: 282
TGIPSKYIEE QLDSFRIDTF SLFETNYIDM AFSGREFASE FEHTTMDVFS ELGFQTQHVG  60
TKSRQPDIFI QSHDASFSGI IDNKAYHVFS ITHDYELKMI NSYIPKYKKR YSDFSFFMYI  120
AGGFGKNFDK QVQTIANQSG INGCGIRASD LMRLLKKHKQ NPIDHQKLKQ IFECNRLVRI  180
QDILSL                                                           186

SEQ ID NO: 283        moltype = DNA  length = 701
FEATURE               Location/Qualifiers
misc_feature          1..701
                      note = Synthetic Construct
source                1..701
                      mol_type = other DNA
                      organism = synthetic construct
SEQUENCE: 283
gacagccacc tgctgggatc tatccccagc aagtacatcg aggaacagct ggacagcttc  60
cggatcgaca ccttcagcct gttcgagaca aactacatcg acatggcctt cagcggcaga  120
gagttcgcca gcgagtttga gcacaccacc atggacgtgt tcagcgagct gggctttcag  180
acacagcacg tgggcaccaa gagcagacag cccgacatct tcatccagag ccacgacgcc  240
agcttctccg gcatcatcga caacaaggcc taccacgtgt tctctatcac ccacgactac  300
gagctgaaga tgatcaacag ctacatcccc aagtacaaga agcggtacag cgacttcagc  360
ttcttcatgt acattgccgg cggattcggc aagaacttcg acaaacaggt gcagacaatc  420
gccaaccaga gcggcatcaa tggctgcggc attagagcca gcgacctgat gagactgctg  480
aagaagcaca agcagaaccc catcgaccac cagaaactga agcagatctt cgagtgcaac  540
cggctcgtgc ggatccagga tattctgagc cttggatccc ctaagaaaaa gcggaaggtg  600
tgaaagcttc tcgagtctag agggcccgtt taaacccgct gatcagcctc gactgtgcct  660
tctagttgcc agccatctgt tgtttgcccc tcccccgtgc c                    701

SEQ ID NO: 284        moltype = DNA  length = 106
FEATURE               Location/Qualifiers
misc_feature          1..106
                      note = Synthetic Construct
source                1..106
                      mol_type = other DNA
                      organism = synthetic construct
SEQUENCE: 284
ctggctaact agagaaccca ctgcttactg gcttatcgaa attaatacga ctcactatag  60
ggagtcccaa gctggctagc gtttaaactt ctgcggccgc gccacc               106

SEQ ID NO: 285        moltype = DNA  length = 51
FEATURE               Location/Qualifiers
misc_feature          1..51
                      note = Synthetic Construct
source                1..51
                      mol_type = other DNA
                      organism = synthetic construct
SEQUENCE: 285
atgggaaaac ctattcctaa tcctctgctg ggcctggatt ctaccggagg c          51

SEQ ID NO: 286        moltype = DNA  length = 408
FEATURE               Location/Qualifiers
misc_feature          1..408
                      note = Synthetic Construct
source                1..408
                      mol_type = other DNA
                      organism = synthetic construct
SEQUENCE: 286
gtggacctga gaacactggg atattctcag cagcagcagg agaagatcaa gcccaaggtg  60
agatctacag tggcccagca ccacgaagcc ctggtgggac acggatttac acacgcccac  120
attgtggccc tgtctcagca ccctgccgcc ctgggaacag tggccgtgaa atatcaggat  180
atgattgccg ccctgcctga ggccacacac gaagccattg tgggagtggg aaaacgaggc  240
gctggagcca gagccctgga agccctgctg acagtggccg gagaactgag aggacctcct  300
ctgcagctgg atacaggaca gctgctgaag attgccaaaa ggggcggagt gaccgcggtg  360
gaagccgtgc acgcctggag aaatgccctg acaggagccc ctctgaac             408
```

-continued

```
SEQ ID NO: 287         moltype = DNA  length = 1794
FEATURE                Location/Qualifiers
misc_feature           1..1794
                       note = Synthetic Construct
source                 1..1794
                       mol_type = other DNA
                       organism = synthetic construct
SEQUENCE: 287
ctgacccccg aacaggtggt ggccattgcc agcaacaacg gcggcaagca ggccctggaa  60
accgtgcaga gactgctgcc cgtgctgtgc caggcccatg gcctgacacc tgaacaggtg  120
gtggctatcg cctctaatat cggaggaaaa caggctctgg aaacagtgca gcggctgctg  180
cctgtgctgt gtcaggctca cggcttgact ccagaacagg tggtggctat tgcttccaac  240
ggcgggggga aacaggccct ggaaactgtg cagcgcctgc tgccagtgct gtgccaggct  300
cacggactga cccccgaaca ggtggtggcc attgccagcc acgacggcgg caagcaggcc  360
ctggaaaccg tgcagagact gctgcccgtg ctgtgccagg cccatggcct gacacctgaa  420
caggtggtgg ctatcgcctc tcacgacgga ggaaaacagg ctctggaaac agtgcagcgg  480
ctgctgcctg tgctgtgtca ggctcacggc ttgactccag aacaggtggt ggctattgct  540
tccaacggcg gggggaaaca ggccctggaa actgtgcagc gcctgctgcc agtgctgtgc  600
caggctcacg ggctgacccc cgaacaggtg gtggccattg ccagccacga cggcggcaag  660
caggccctgg aaaccgtgca gagactgctg cccgtgctgt gccaggccca tggcctgaca  720
cctgaacagg tggtggctat cgcctctaac ggcggaggaa aacaggctct ggaaacagtg  780
cagcggctgc tgcctgtgct gtgtcaggct cacggcttga ctccagaaca ggtggtggct  840
attgcttcca acggcggggg gaaacaggcc ctggaaactg tgcagcgcct gctgccagtg  900
ctgtgccagg ctcacggcct cactcccgaa caggtggtgg ccattgccag caacaacggc  960
ggcaagcagg ccctggaaac cgtgcagaga ctgctgcccg tgctgtgcca ggcccatggc  1020
ctgacacctg aacaggtggt ggctatcgcc tctaacggcg gaggaaaaca ggctctggaa  1080
acagtgcagc ggctgctgcc tgtgctgtgt caggctcacg gcttgactcc agaacaggtg  1140
gtggctattg cttcccacga cggggggaaa caggccctgg aaactgtgca gcgcctgctg  1200
ccagtgctgt gccaggctca cggactgacc cccgaacagg tggtggccat tgccagccac  1260
gacggcggca agcaggccct ggaaaccgtg cagagactgc tgcccgtgct gtgccaggcc  1320
catggcctga cacctgaaca ggtggtggct atcgcctctc acgacggagg aaaacaagca  1380
ctcgagacag tgcagcggct gctgcctgtg ctgtgtcagg ctcacggctt gactccagaa  1440
caggtggtgg ctattgcttc caatattggg gggaaacagg ccctggaaac tgtgcagcgc  1500
ctgctgccag tgctgtgcca ggctcacggc ctgacccccg aacaggtggt ggccattgcc  1560
agccacgacg gcggcaagca ggccctggaa accgtgcaga gactgctgcc cgtgctgtgc  1620
caggcccatg gcctgacacc tgaacaggtg gtggctatcg cctctaatat cggaggaaaa  1680
caggctctgg aaacagtgca gcggctgctg cctgtgctgt gtcaggctca cggcttgact  1740
ccacagcagg tcgtggcaat tgctagcaac aacggcggac ggcccgccct ggag        1794

SEQ ID NO: 288         moltype = DNA  length = 17
FEATURE                Location/Qualifiers
misc_feature           1..17
                       note = Synthetic Construct
source                 1..17
                       mol_type = other DNA
                       organism = synthetic construct
SEQUENCE: 288
agcatgagac cccggaa                                                 17

SEQ ID NO: 289         moltype = DNA  length = 106
FEATURE                Location/Qualifiers
misc_feature           1..106
                       note = Synthetic Construct
source                 1..106
                       mol_type = other DNA
                       organism = synthetic construct
SEQUENCE: 289
ctggctaact agagaaccca ctgcttactg gcttatcgaa attaatacga ctcactatag  60
ggagtcccaa gctggctagc gtttaaactt ctgcggccgc gccacc                 106

SEQ ID NO: 290         moltype = DNA  length = 50
FEATURE                Location/Qualifiers
misc_feature           1..50
                       note = Synthetic Construct
source                 1..50
                       mol_type = other DNA
                       organism = synthetic construct
SEQUENCE: 290
atgggaaaac ctattcctaa tcctctgctg ggcctggatt ctaccggagg             50

SEQ ID NO: 291         moltype = DNA  length = 408
FEATURE                Location/Qualifiers
misc_feature           1..408
                       note = Synthetic Construct
source                 1..408
                       mol_type = other DNA
                       organism = synthetic construct
SEQUENCE: 291
gtggacctga gaacactggg atattctcag cagcagcagg agaagatcaa gcccaaggtg  60
```

-continued

```
agatctacag tggcccagca ccacgaagcc ctggtgggac acggatttac acacgcccac  120
attgtggccc tgtctcagca ccctgccgcc ctgggaacag tggccgtgaa atatcaggat  180
atgattgccg ccctgcctga ggccacacac gaagccattg tgggagtggg aaaacgaggc  240
gctggagcca gagccctgga agccctgctg acagtggccg gagaactgag aggacctcct  300
ctgcagctgg atacaggaca gctgctgaag attgccaaaa ggggcggagt gaccgcggtg  360
gaagccgtgc acgcctggag aaatgccctg acaggagccc ctctgaac              408

SEQ ID NO: 292         moltype = DNA  length = 1794
FEATURE                Location/Qualifiers
misc_feature           1..1794
                       note = Synthetic Construct
source                 1..1794
                       mol_type = other DNA
                       organism = synthetic construct
SEQUENCE: 292
ctgacccccg aacaggtggt ggccattgcc agcaacatcg gcggcaagca ggccctggaa  60
accgtgcaga gactgctgcc cgtgctgtgc caggcccatg gcctgacacc tgaacaggtg  120
gtggctatcg cctctaacaa cggaggaaaa caggctctgg aaacagtgca gcggctgctg  180
cctgtgctgt gtcaggctca cggcttgact ccagaacagg tggtggctat tgcttcccac  240
gacgggggga aacaggccct ggaaactgtg cagcgcctgc tgccagtgct gtgccaggct  300
cacggactga cccccgaaca ggtggtggcc attgccagca acggcggcgg caagcaggcc  360
ctggaaaccg tgcagagact gctgcccgtg ctgtgccagg cccatggcct gacacctgaa  420
caggtggtgg ctatcgcctc taacaacgga ggaaaacagg ctctggaaac agtgcagcgg  480
ctgctgcctg tgctgtgtca ggctcacggc ttgactccag aacaggtggt ggctattgct  540
tccaacaacg gggggaaaca ggccctggaa actgtgcagc gcctgctgcc agtgctgtgc  600
caggctcacg ggctgacccc cgaacaggtg gtggccattg ccagcaacgg cggcggcaag  660
caggccctgg aaaccgtgca gagactgctg cccgtgctgt gccaggccca tggcctgaca  720
cctgaacagg tggtggctat cgcctctaat atcggaggaa aacaggctct ggaaacagtg  780
cagcggctgc tgcctgtgct gtgtcaggct cacggcttga ctccagaaca ggtggtggct  840
attgcttccc acgacggggg gaaacaggcc ctggaaactg tgcagcgcct gctgccagtg  900
ctgtgccagg ctcacggcct cactcccgaa caggtggtgg ccattgccag caacatcggc  960
ggcaagcagg ccctggaaac cgtgcagaga ctgctgcccg tgctgtgcca ggcccatggc  1020
ctgacacctg aacaggtggt ggctatcgcc tctcacgacg gaggaaaaca ggctctggaa  1080
acagtgcagc ggctgctgcc tgtgctgtgt caggctcacg gcttgactcc agaacaggtg  1140
gtggctattg cttccaacaa cggggggaaa caggccctgg aaactgtgca gcgcctgctg  1200
ccagtgctgt gccaggctca cggactgacc cccgaacagg tggtggccat tgccagcaac  1260
aacggcggca agcaggccct ggaaaccgtg cagagactgc tgcccgtgct gtgccaggcc  1320
catggcctga cacctgaaca ggtggtggct atcgcctctc acgacggagg aaaacaagca  1380
ctcgagacag tgcagcggct gctgcctgtg ctgtgtcagg ctcacggctt gactccagaa  1440
caggtggtgg ctattgcttc caatattggg gggaaacagg ccctggaaac tgtgcagcgc  1500
ctgctgccag tgctgtgcca ggctcacggc ctgacccccg aacaggtggt ggccattgcc  1560
agcaacaacg gcggcaagca ggccctggaa accgtgcaga gactgctgcc cgtgctgtgc  1620
caggcccatg gcctgacacc tgaacaggtg gtggctatcg cctctaacaa cggaggaaaa  1680
caggctctgg aaacagtgca gcggctgctg cctgtgctgt gtcaggctca cggcttgact  1740
ccacagcagg tcgtggcaat tgctagcaac aacggcggac ggcccgccct ggag        1794

SEQ ID NO: 293         moltype = DNA  length = 17
FEATURE                Location/Qualifiers
misc_feature           1..17
                       note = Synthetic Construct
source                 1..17
                       mol_type = other DNA
                       organism = synthetic construct
SEQUENCE: 293
agcatgagac cccggaa                                                 17

SEQ ID NO: 294         moltype = DNA  length = 18
FEATURE                Location/Qualifiers
misc_feature           1..18
                       note = Synthetic Construct
source                 1..18
                       mol_type = other DNA
                       organism = synthetic construct
SEQUENCE: 294
gatcctcttg tcccacag                                                18

SEQ ID NO: 295         moltype = DNA  length = 18
FEATURE                Location/Qualifiers
misc_feature           1..18
                       note = Synthetic Construct
source                 1..18
                       mol_type = other DNA
                       organism = synthetic construct
SEQUENCE: 295
agctggtaca cggcaggg                                                18

SEQ ID NO: 296         moltype = AA  length = 185
FEATURE                Location/Qualifiers
REGION                 1..185
```

-continued

```
                        note = Synthetic Construct
source                  1..185
                        mol_type = protein
                        organism = synthetic construct
SEQUENCE: 296
GIPSKYIEEQ LDSFRIDTFS LFETNYIDMA FSGREFASEF EHTTMDVFSE LGFQTQHVGT  60
KSRQPDIFIQ SHDASFSGII DNKAYHVFSI THDYELKMIN SYIPKYKKRY SDFSFFMYIA  120
GGFGKNFDKQ VQTIANQSGI NGCGIRASDL MRLLKKHKQN PIDHQKLKQI FECNRLVRIQ  180
DILSL                                                              185

SEQ ID NO: 297          moltype = AA  length = 187
FEATURE                 Location/Qualifiers
REGION                  1..187
                        note = Synthetic Construct
source                  1..187
                        mol_type = protein
                        organism = synthetic construct
SEQUENCE: 297
KTGIPSKYIE EQLDSFRIDT FSLFETNYID MAFSGREFAS EFEHTTMDVF SELGFQTQHV  60
GTKSRQPDIF IQSHDASFSG IIDNKAYHVF SITHDYELKM INSYIPKYKK RYSDFSFFMY  120
IAGGFGKNFD KQVQTIANQS GINGCGIRAS DLMRLLKKHK QNPIDHQKLK QIFECNRLVR  180
IQDILSL                                                            187

SEQ ID NO: 298          moltype = AA  length = 188
FEATURE                 Location/Qualifiers
REGION                  1..188
                        note = Synthetic Construct
source                  1..188
                        mol_type = protein
                        organism = synthetic construct
SEQUENCE: 298
SKTGIPSKYI EEQLDSFRID TFSLFETNYI DMAFSGREFA SEFEHTTMDV FSELGFQTQH  60
VGTKSRQPDI FIQSHDASFS GIIDNKAYHV FSITHDYELK MINSYIPKYK KRYSDFSFFM  120
YIAGGFGKNF DKQVQTIANQ SGINGCGIRA SDLMRLLKKH KQNPIDHQKL KQIFECNRLV  180
RIQDILSL                                                           188

SEQ ID NO: 299          moltype = AA  length = 189
FEATURE                 Location/Qualifiers
REGION                  1..189
                        note = Synthetic Construct
source                  1..189
                        mol_type = protein
                        organism = synthetic construct
SEQUENCE: 299
ASKTGIPSKY IEEQLDSFRI DTFSLFETNY IDMAFSGREF ASEFEHTTMD VFSELGFQTQ  60
HVGTKSRQPD IFIQSHDASF SGIIDNKAYH VFSITHDYEL KMINSYIPKY KKRYSDFSFF  120
MYIAGGFGKN FDKQVQTIAN QSGINGCGIR ASDLMRLLKK HKQNPIDHQK LKQIFECNRL  180
VRIQDILSL                                                          189
```

What is claimed is:

1. A recombinant protein comprising a cleavage domain, wherein the cleavage domain comprises an amino acid sequence having at least 90% sequence identity with the amino acid sequence of any one of SEQ ID NOs: 200, 282, and 296-299, or a functional fragment thereof, wherein the cleavage domain cleaves DNA.

2. The recombinant protein of claim 1, wherein the cleavage domain comprises an amino acid sequence having at least 95% sequence identity with the amino acid sequence of any one of SEQ ID NOs: 200, 282, and 296-299, or a functional fragment thereof.

3. The recombinant protein of claim 1, further comprising a nucleic acid binding domain operably linked to the cleavage domain.

4. The recombinant protein of claim 3, wherein the cleavage domain and the nucleic acid binding domain are operably linked via a covalent linkage.

5. The recombinant protein of claim 4, wherein the recombinant protein is a fusion protein.

6. The recombinant protein of claim 3, wherein the nucleic acid binding domain is selected from the group consisting of a transcription activator-like effector (TALE) deoxyribonucleic acid binding domain (DBD) and a zinc-finger DNA binding domain.

7. The recombinant protein of claim 3, wherein the nucleic acid binding domain comprises one or more repeat units, and wherein the one or more repeat units is 30 amino acids to 45 amino acids in length, and wherein each repeat unit recognizes a nucleotide base.

8. The recombinant protein of claim 3, wherein the nucleic acid binding domain binds to a DNA target sequence and the cleavage domain cleaves DNA.

9. A nucleic acid encoding the recombinant protein of claim 1.

10. A cell comprising the recombinant protein of claim 1 or a nucleic acid encoding the recombinant protein.

11. A non-naturally occurring nucleic acid encoding an amino acid sequence having at least 90% sequence identity with the amino acid sequence of any one of SEQ ID NOs: 200, 282, and 296-299, or a functional fragment thereof, wherein the cleavage domain cleaves DNA.

12. The non-naturally occurring nucleic acid of claim 11, encoding an amino acid sequence having at least 95% sequence identity with the amino acid sequence of any one of SEQ ID NOs: 200, 282, and 296-299, or a functional fragment thereof.

13. The non-naturally occurring nucleic acid of claim 11, encoding an amino acid sequence having at least 98% sequence identity with the amino acid sequence of any one of SEQ ID NOs: 200, 282, and 296-299, or a functional fragment thereof.

14. The recombinant protein of claim 1, wherein the cleavage domain comprises an amino acid sequence having at least 98% sequence identity with the amino acid sequence of any one of SEQ ID NOs: 200, 282, and 296-299, or a functional fragment thereof.

* * * * *